(12) United States Patent
Bender et al.

(10) Patent No.: US 8,382,775 B1
(45) Date of Patent: Feb. 26, 2013

(54) METHODS, INSTRUMENTS AND DEVICES FOR EXTRAGASTRIC REDUCTION OF STOMACH VOLUME

(75) Inventors: Theodore M. Bender, San Anselmo, CA (US); Joshua Makower, Los Altos, CA (US); Brian K. Shiu, Sunnyvale, CA (US); Pablo G. Acosta, Newark, CA (US); Robert M. George, San Jose, CA (US); Lisa Serventi, Los Altos Hills, CA (US); Ed Orbeta, San Mateo, CA (US); Scott Early, Campbell, CA (US); Earl A. Bright, II, Los Altos, CA (US); Timothy A. Limon, Cupertino, CA (US)

(73) Assignee: Vibrynt, Inc., Redwood City, CA (US)

( * ) Notice: Subject to any disclaimer, the term of this patent is extended or adjusted under 35 U.S.C. 154(b) by 0 days.

(21) Appl. No.: 13/439,059

(22) Filed: Apr. 4, 2012

Related U.S. Application Data

(60) Provisional application No. 61/584,289, filed on Jan. 8, 2012.

(51) Int. Cl.
*A61B 17/04* (2006.01)
(52) U.S. Cl. .......................... 606/144; 606/148
(58) Field of Classification Search ............. 606/139, 606/144, 148, 153; 600/205, 210; 227/175.1; 604/22
See application file for complete search history.

(56) References Cited

U.S. PATENT DOCUMENTS

| | | | |
|---|---|---|---|
| 233,475 A | 10/1880 | Cook et al. | |
| 659,422 A | 10/1900 | Shidler | |
| 780,392 A | 1/1905 | Wanamaker et al. | |
| 789,467 A | 5/1905 | West | |
| 1,461,524 A | 7/1923 | Goddard | |
| 2,579,192 A | 12/1951 | Kohl et al. | |
| 2,646,298 A | 7/1953 | Leary | |
| 2,697,624 A | 12/1954 | Thomas et al. | |
| 2,734,299 A | 2/1956 | Masson | |
| 2,825,592 A | 3/1958 | Semple | |
| 3,326,586 A | 6/1967 | Frost et al. | |
| 3,470,834 A | 10/1969 | Bone | |
| 3,521,918 A | 7/1970 | Hammond | |
| 3,571,864 A | 3/1971 | Emile et al. | |
| 3,664,435 A | 5/1972 | Klessig | |
| 3,675,639 A | 7/1972 | Cimber | |
| 3,713,680 A | 1/1973 | Pagano | |
| 3,756,638 A | 9/1973 | Stockberger | |

(Continued)

FOREIGN PATENT DOCUMENTS

| | | |
|---|---|---|
| EP | 0 938 871 | 9/1999 |
| EP | 1 016 377 A2 | 7/2000 |

(Continued)

OTHER PUBLICATIONS

About the Vertical Sleeve Gastrectomy. Mar. 24, 2006, pp. 1-1. http://obesityhelp.com/forums/VSG/about.html.

(Continued)

*Primary Examiner* — Julian Woo
(74) *Attorney, Agent, or Firm* — Law Office of Alan W. Cannon

(57) ABSTRACT

Methods, instruments and systems are provided for separating opposite walls of the stomach by extragastric application of suction. Plication of the stomach can be performed between the separated walls after which the separate walls are brought back toward one another. In another aspect, methods, instruments, devices and systems are provided for reducing the effective volume of a stomach by performing one or more extragastric plications of the stomach.

15 Claims, 68 Drawing Sheets

U.S. PATENT DOCUMENTS

| | | | |
|---|---|---|---|
| 3,873,140 A | 3/1975 | Bloch |
| 3,931,667 A | 1/1976 | Merser et al. |
| 3,976,079 A | 8/1976 | Samuels et al. |
| 4,006,747 A | 2/1977 | Kronenthal et al. |
| 4,052,989 A | 10/1977 | Kline |
| 4,060,089 A | 11/1977 | Noiles |
| 4,133,315 A | 1/1979 | Berman et al. |
| 4,210,148 A | 7/1980 | Stivala |
| 4,246,893 A | 1/1981 | Berson |
| 4,291,698 A | 9/1981 | Fuchs et al. |
| 4,328,805 A | 5/1982 | Akopov et al. |
| 4,416,267 A | 11/1983 | Garren et al. |
| 4,458,681 A | 7/1984 | Hopkins |
| 4,472,226 A | 9/1984 | Redinger et al. |
| 4,485,805 A | 12/1984 | Foster, Jr. |
| 4,493,323 A | 1/1985 | Albright et al. |
| 4,558,699 A | 12/1985 | Bashour |
| 4,592,339 A | 6/1986 | Kuzmak et al. |
| 4,592,342 A | 6/1986 | Salmasian |
| 4,621,640 A | 11/1986 | Mulhollan et al. |
| 4,669,473 A | 6/1987 | Richards et al. |
| 4,694,827 A | 9/1987 | Weiner et al. |
| 4,696,288 A | 9/1987 | Kuzmak et al. |
| 4,705,040 A | 11/1987 | Mueller et al. |
| 4,714,281 A | 12/1987 | Peck |
| 4,723,547 A | 2/1988 | Kullas et al. |
| 4,738,255 A | 4/1988 | Goble et al. |
| 4,739,758 A | 4/1988 | Lai et al. |
| 4,744,364 A | 5/1988 | Kensey |
| 4,750,492 A | 6/1988 | Jacobs |
| 4,803,985 A | 2/1989 | Hill |
| 4,823,794 A | 4/1989 | Pierce |
| 4,899,747 A | 2/1990 | Garren et al. |
| 4,955,913 A | 9/1990 | Robinson |
| 5,002,550 A | 3/1991 | Li |
| 5,033,481 A | 7/1991 | Heyler, III |
| 5,041,129 A | 8/1991 | Hayhurst et al. |
| 5,084,061 A | 1/1992 | Gau et al. |
| 5,100,421 A | 3/1992 | Christoudias |
| 5,112,310 A | 5/1992 | Grobe |
| 5,123,914 A | 6/1992 | Cope |
| 5,129,912 A | 7/1992 | Noda et al. |
| RE34,021 E | 8/1992 | Mueller et al. |
| 5,151,086 A | 9/1992 | Duh et al. |
| 5,188,104 A | 2/1993 | Wernicke et al. |
| 5,217,470 A | 6/1993 | Weston |
| 5,220,928 A | 6/1993 | Oddsen et al. |
| 5,234,454 A | 8/1993 | Bangs |
| 5,246,456 A | 9/1993 | Wilkinson |
| 5,257,713 A | 11/1993 | Green et al. |
| 5,258,000 A | 11/1993 | Gianturco et al. |
| 5,258,015 A | 11/1993 | Li et al. |
| 5,259,399 A | 11/1993 | Brown |
| 5,269,809 A | 12/1993 | Hayhurst et al. |
| 5,279,551 A | 1/1994 | James |
| 5,282,832 A | 2/1994 | Toso et al. |
| 5,290,217 A | 3/1994 | Campos |
| 5,292,344 A | 3/1994 | Douglas |
| 5,334,200 A | 8/1994 | Johnson |
| 5,345,949 A | 9/1994 | Shlain |
| 5,354,271 A | 10/1994 | Voda |
| 5,364,408 A | 11/1994 | Gordon |
| 5,382,238 A | 1/1995 | Abrahamson et al. |
| 5,391,182 A | 2/1995 | Chin |
| 5,403,326 A | 4/1995 | Harrison et al. |
| 5,405,352 A | 4/1995 | Weston |
| 5,423,872 A | 6/1995 | Cigaina |
| 5,428,123 A | 6/1995 | Ward et al. |
| 5,433,723 A | 7/1995 | Lindenberg et al. |
| 5,445,608 A | 8/1995 | Chen et al. |
| 5,470,337 A | 11/1995 | Moss |
| 5,472,446 A | 12/1995 | Torre |
| 5,480,406 A | 1/1996 | Nolan et al. |
| 5,496,311 A | 3/1996 | Abele et al. |
| 5,507,754 A | 4/1996 | Green et al. |
| 5,545,171 A | 8/1996 | Sharkey et al. |
| 5,545,178 A | 8/1996 | Kensey et al. |
| 5,549,621 A | 8/1996 | Bessler et al. |
| 5,554,162 A | 9/1996 | DeLange |
| 5,571,116 A | 11/1996 | Bolanos et al. |
| 5,573,540 A | 11/1996 | Yoon |
| 5,591,177 A | 1/1997 | Lehrer |
| 5,601,604 A | 2/1997 | Vincent |
| 5,626,614 A | 5/1997 | Hart |
| 5,634,936 A | 6/1997 | Linden et al. |
| 5,647,836 A | 7/1997 | Blake, III et al. |
| 5,669,935 A | 9/1997 | Rosenman et al. |
| 5,676,674 A | 10/1997 | Bolanos et al. |
| 5,690,691 A | 11/1997 | Chen et al. |
| 5,716,368 A | 2/1998 | Torre et al. |
| 5,725,557 A | 3/1998 | Gatturna et al. |
| 5,788,715 A | 8/1998 | Watson, Jr. et al. |
| 5,792,153 A | 8/1998 | Swain et al. |
| 5,846,254 A | 12/1998 | Schulze et al. |
| 5,888,196 A | 3/1999 | Bonutti |
| 5,897,562 A | 4/1999 | Bolanos et al. |
| 5,921,978 A | 7/1999 | Thompson et al. |
| 5,931,788 A | 8/1999 | Keen et al. |
| 5,938,669 A | 8/1999 | Klaiber et al. |
| 5,947,983 A | 9/1999 | Solar et al. |
| 5,951,590 A | 9/1999 | Goldfarb |
| 5,957,939 A | 9/1999 | Heaven et al. |
| 5,961,440 A | 10/1999 | Schweich, Jr. et al. |
| 5,971,447 A | 10/1999 | Steck, III |
| 5,993,473 A | 11/1999 | Chan et al. |
| 6,006,002 A | 12/1999 | Motoki et al. |
| 6,013,053 A | 1/2000 | Bower et al. |
| 6,067,991 A | 5/2000 | Forsell |
| 6,080,160 A | 6/2000 | Chen et al. |
| 6,097,984 A | 8/2000 | Douglas |
| 6,102,922 A | 8/2000 | Jakobsson et al. |
| 6,113,609 A | 9/2000 | Adams |
| 6,143,006 A | 11/2000 | Chan |
| 6,162,234 A | 12/2000 | Freedland et al. |
| 6,174,280 B1 | 1/2001 | Oneda et al. |
| 6,186,149 B1 | 2/2001 | Pacella et al. |
| 6,270,530 B1 | 8/2001 | Eldridge et al. |
| 6,420,452 B1 | 7/2002 | Gunatillake et al. |
| 6,425,900 B1 | 7/2002 | Knodel et al. |
| 6,437,073 B1 | 8/2002 | Gunatillake et al. |
| 6,447,533 B1 | 9/2002 | Adams |
| 6,454,785 B2 | 9/2002 | De Hoyos Garza |
| 6,475,136 B1 | 11/2002 | Forsell |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,148 B1 | 12/2002 | Pinchuk et al. |
| 6,506,196 B1 | 1/2003 | Laufer |
| 6,511,490 B2 | 1/2003 | Robert |
| 6,535,764 B2 | 3/2003 | Imran et al. |
| 6,551,241 B1 | 4/2003 | Schultz |
| 6,558,400 B2 | 5/2003 | Deem et al. |
| 6,572,627 B2 | 6/2003 | Gabbay |
| 6,656,182 B1 | 12/2003 | Hayhurst |
| 6,663,639 B1 | 12/2003 | Laufer et al. |
| 6,669,713 B2 | 12/2003 | Adams |
| 6,675,809 B2 | 1/2004 | Stack et al. |
| 6,726,622 B2 * | 4/2004 | Spence et al. ............ 600/210 |
| 6,736,793 B2 | 5/2004 | Meyer et al. |
| 6,746,458 B1 | 6/2004 | Cloud |
| 6,746,460 B2 | 6/2004 | Gannoe et al. |
| 6,755,869 B2 | 6/2004 | Geitz |
| 6,773,441 B1 | 8/2004 | Laufer et al. |
| 6,790,213 B2 | 9/2004 | Cherok et al. |
| 6,821,285 B2 | 11/2004 | Laufer et al. |
| 6,835,200 B2 | 12/2004 | Laufer et al. |
| 6,869,395 B2 | 3/2005 | Page et al. |
| 6,900,055 B1 | 5/2005 | Fuller et al. |
| 6,908,487 B2 | 6/2005 | Cigaina |
| 6,981,978 B2 | 1/2006 | Gannoe |
| 6,994,715 B2 | 2/2006 | Gannoe et al. |
| 7,033,373 B2 | 4/2006 | de la Torre et al. |
| 7,037,315 B2 | 5/2006 | Sancoff et al. |
| 7,037,344 B2 | 5/2006 | Kagan et al. |
| 7,131,980 B1 | 11/2006 | Field et al. |
| 7,153,314 B2 | 12/2006 | Laufer et al. |
| 7,160,312 B2 | 1/2007 | Saadat |

| Patent/Pub No. | Date | Name |
|---|---|---|
| 7,167,750 B2 | 1/2007 | Knudson et al. |
| 7,214,233 B2 | 5/2007 | Gannoe et al. |
| 7,223,277 B2 | 5/2007 | DeLegge |
| 7,255,675 B2 | 8/2007 | Gertner et al. |
| 7,310,557 B2 | 12/2007 | Maschino et al. |
| 7,334,822 B1 | 2/2008 | Hines, Jr. |
| 7,338,433 B2 | 3/2008 | Coe |
| 7,354,454 B2 | 4/2008 | Stack et al. |
| 7,374,565 B2 | 5/2008 | Hassler et al. |
| 7,399,304 B2 | 7/2008 | Gambale et al. |
| 7,402,166 B2 | 7/2008 | Feigl |
| 7,416,554 B2 | 8/2008 | Lam et al. |
| 7,490,602 B2 | 2/2009 | Sabri |
| 7,534,248 B2 | 5/2009 | Mikkaichi et al. |
| 7,608,578 B2 | 10/2009 | Miller |
| 7,618,426 B2 | 11/2009 | Ewers et al. |
| 7,666,195 B2 | 2/2010 | Kelleher et al. |
| 7,670,279 B2 | 3/2010 | Gertner |
| 7,717,843 B2 | 5/2010 | Balbierz et al. |
| 7,753,870 B2 | 7/2010 | Demarais et al. |
| 7,775,967 B2 | 8/2010 | Gertner |
| 7,824,368 B2 | 11/2010 | Clem et al. |
| 7,841,978 B2 | 11/2010 | Gertner |
| 7,850,660 B2 | 12/2010 | Uth et al. |
| 7,862,546 B2 | 1/2011 | Conlon et al. |
| 7,862,574 B2 | 1/2011 | Deem et al. |
| 7,938,769 B2 | 5/2011 | Gertner |
| 7,947,055 B2 | 5/2011 | Gannoe et al. |
| 7,955,340 B2 | 6/2011 | Michlitsch et al. |
| 7,976,555 B2 | 7/2011 | Meade et al. |
| 7,988,617 B2 | 8/2011 | Gertner |
| 8,001,974 B2 | 8/2011 | Makower et al. |
| 8,057,490 B2 | 11/2011 | Harris et al. |
| 8,152,821 B2 | 4/2012 | Gambale et al. |
| 8,206,295 B2 | 6/2012 | Kaul |
| 2001/0010005 A1 | 7/2001 | Kammerer et al. |
| 2001/0011543 A1 | 8/2001 | Forsell |
| 2001/0044639 A1 | 11/2001 | Levinson |
| 2001/0049497 A1 | 12/2001 | Kalloo et al. |
| 2002/0055757 A1 | 5/2002 | Torre et al. |
| 2002/0077660 A1 | 6/2002 | Kayan et al. |
| 2002/0128684 A1 | 9/2002 | Foerster |
| 2002/0161382 A1 | 10/2002 | Neisz et al. |
| 2002/0161414 A1 | 10/2002 | Flesler et al. |
| 2002/0188354 A1 | 12/2002 | Peghini et al. |
| 2002/0198551 A1 | 12/2002 | Grant et al. |
| 2003/0021822 A1 | 1/2003 | Lloyd |
| 2003/0055463 A1 | 3/2003 | Gordon et al. |
| 2003/0055465 A1 | 3/2003 | Ben-Haim et al. |
| 2003/0093117 A1 | 5/2003 | Saadat |
| 2003/0114863 A1 | 6/2003 | Field et al. |
| 2003/0208212 A1 | 11/2003 | Cigaina |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0054352 A1 | 3/2004 | Adams et al. |
| 2004/0059289 A1 | 3/2004 | Garza Alvarez |
| 2004/0068224 A1 | 4/2004 | Couvillon et al. |
| 2004/0092892 A1 | 5/2004 | Kagan et al. |
| 2004/0092967 A1 | 5/2004 | Sancoff et al. |
| 2004/0097986 A1 | 5/2004 | Adams |
| 2004/0098060 A1 | 5/2004 | Ternes |
| 2004/0102804 A1 | 5/2004 | Chin |
| 2004/0116852 A1 | 6/2004 | Scopton |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0138525 A1 | 7/2004 | Saadat et al. |
| 2004/0148034 A1 | 7/2004 | Kagan et al. |
| 2004/0176785 A1 | 9/2004 | Hermann et al. |
| 2004/0186503 A1 | 9/2004 | DeLegge |
| 2004/0193194 A1 | 9/2004 | Laufer et al. |
| 2004/0194790 A1 | 10/2004 | Laufer et al. |
| 2004/0210243 A1 | 10/2004 | Gannoe et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0260345 A1 | 12/2004 | Foerster |
| 2004/0267378 A1 | 12/2004 | Gazi et al. |
| 2005/0022827 A1 | 2/2005 | Woo et al. |
| 2005/0049718 A1 | 3/2005 | Dann et al. |
| 2005/0085832 A1 | 4/2005 | Sancoff et al. |
| 2005/0096638 A1 | 5/2005 | Starkebaum et al. |
| 2005/0159769 A1 | 7/2005 | Alverdy |
| 2005/0197687 A1 | 9/2005 | Molaei et al. |
| 2005/0203344 A1 | 9/2005 | Orban, III et al. |
| 2005/0216040 A1 | 9/2005 | Gertner et al. |
| 2005/0216042 A1 | 9/2005 | Gertner et al. |
| 2005/0222638 A1 | 10/2005 | Foley et al. |
| 2005/0228415 A1 | 10/2005 | Gertner |
| 2005/0240222 A1 | 10/2005 | Shipp |
| 2005/0240279 A1 | 10/2005 | Kagan et al. |
| 2005/0250980 A1 | 11/2005 | Swanstrom et al. |
| 2005/0261712 A1 | 11/2005 | Balbierz et al. |
| 2005/0267405 A1 | 12/2005 | Shah |
| 2005/0267406 A1 | 12/2005 | Hassler, Jr. |
| 2005/0267529 A1 | 12/2005 | Crockett et al. |
| 2005/0267533 A1 | 12/2005 | Gertner |
| 2005/0267595 A1 | 12/2005 | Chen et al. |
| 2005/0267596 A1 | 12/2005 | Chen et al. |
| 2005/0273138 A1 | 12/2005 | To et al. |
| 2005/0277960 A1 | 12/2005 | Hassler, Jr. et al. |
| 2005/0277974 A1 | 12/2005 | Hassler, Jr. et al. |
| 2005/0288622 A1 | 12/2005 | Albrecht et al. |
| 2006/0009789 A1 | 1/2006 | Gambale et al. |
| 2006/0020278 A1 | 1/2006 | Burnett et al. |
| 2006/0025783 A1 | 2/2006 | Smith et al. |
| 2006/0025789 A1 | 2/2006 | Laufer et al. |
| 2006/0025819 A1 | 2/2006 | Nobis et al. |
| 2006/0030867 A1 | 2/2006 | Zadno |
| 2006/0030884 A1 | 2/2006 | Yeung et al. |
| 2006/0058829 A1 | 3/2006 | Sampson |
| 2006/0069396 A1 | 3/2006 | Meade et al. |
| 2006/0089571 A1 | 4/2006 | Gertner |
| 2006/0089646 A1 | 4/2006 | Bonutti |
| 2006/0106288 A1 | 5/2006 | Roth et al. |
| 2006/0129094 A1 | 6/2006 | Shah |
| 2006/0157067 A1 | 7/2006 | Saadat et al. |
| 2006/0161186 A1 | 7/2006 | Hassler, Jr. et al. |
| 2006/0161256 A1 | 7/2006 | Ziegler et al. |
| 2006/0195139 A1 | 8/2006 | Gertner |
| 2006/0212053 A1 | 9/2006 | Gertner |
| 2006/0229623 A1 | 10/2006 | Bonutti et al. |
| 2006/0247206 A1 | 11/2006 | Feins |
| 2006/0253131 A1 | 11/2006 | Wolniewicz |
| 2006/0264699 A1 | 11/2006 | Gertner |
| 2006/0265042 A1 | 11/2006 | Catanese, III et al. |
| 2006/0276871 A1 | 12/2006 | Lamson et al. |
| 2006/0282081 A1 | 12/2006 | Fanton et al. |
| 2007/0027358 A1 | 2/2007 | Gertner et al. |
| 2007/0049970 A1 | 3/2007 | Belef et al. |
| 2007/0055095 A1 | 3/2007 | Chu et al. |
| 2007/0060940 A1 | 3/2007 | Brazzini et al. |
| 2007/0068538 A1 | 3/2007 | Anderson et al. |
| 2007/0073318 A1 | 3/2007 | Carter et al. |
| 2007/0073323 A1 | 3/2007 | Carter et al. |
| 2007/0078439 A1 | 4/2007 | Grandt et al. |
| 2007/0088362 A1 | 4/2007 | Bonutti et al. |
| 2007/0088373 A1 | 4/2007 | Baker |
| 2007/0112363 A1 | 5/2007 | Adams |
| 2007/0112364 A1 | 5/2007 | Gerbi et al. |
| 2007/0112385 A1 | 5/2007 | Conlon |
| 2007/0129738 A1 | 6/2007 | Kraemer et al. |
| 2007/0167982 A1 | 7/2007 | Gertner et al. |
| 2007/0173869 A1 | 7/2007 | Gannoe et al. |
| 2007/0173888 A1 | 7/2007 | Gertner et al. |
| 2007/0179335 A1 | 8/2007 | Gertner et al. |
| 2007/0197896 A1 | 8/2007 | Moll et al. |
| 2007/0198038 A1 | 8/2007 | Cohen et al. |
| 2007/0198074 A1 | 8/2007 | Dann et al. |
| 2007/0203517 A1 | 8/2007 | Williams et al. |
| 2007/0233161 A1 | 10/2007 | Weller et al. |
| 2007/0233170 A1 | 10/2007 | Gertner et al. |
| 2007/0235083 A1 | 10/2007 | Dlugos |
| 2007/0239284 A1 | 10/2007 | Skerven et al. |

| | | |
|---|---|---|
| 2007/0250103 A1 | 10/2007 | Makower et al. |
| 2007/0250112 A1 | 10/2007 | Ravikumar et al. |
| 2007/0255308 A1 | 11/2007 | Williams et al. |
| 2007/0260259 A1 | 11/2007 | Fanton et al. |
| 2007/0270892 A1 | 11/2007 | Makower et al. |
| 2007/0276293 A1 | 11/2007 | Gertner |
| 2007/0276432 A1 | 11/2007 | Stack |
| 2008/0009888 A1 | 1/2008 | Ewers et al. |
| 2008/0015501 A1 | 1/2008 | Gertner |
| 2008/0033488 A1 | 2/2008 | Catanese, III et al. |
| 2008/0039894 A1 | 2/2008 | Catanese, III et al. |
| 2008/0051823 A1 | 2/2008 | Makower et al. |
| 2008/0051824 A1 | 2/2008 | Gertner |
| 2008/0051850 A1 | 2/2008 | Sparks et al. |
| 2008/0058710 A1 | 3/2008 | Wilk |
| 2008/0071306 A1 | 3/2008 | Gertner |
| 2008/0082113 A1 | 4/2008 | Bishop et al. |
| 2008/0086082 A1 | 4/2008 | Brooks |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0109027 A1 | 5/2008 | Chen et al. |
| 2008/0147002 A1 | 6/2008 | Gertner |
| 2008/0161717 A1 | 7/2008 | Gertner |
| 2008/0167519 A1 | 7/2008 | St-Germain |
| 2008/0167647 A1 | 7/2008 | Gertner |
| 2008/0167648 A1 | 7/2008 | Gertner |
| 2008/0172074 A1 | 7/2008 | Baker et al. |
| 2008/0172079 A1 | 7/2008 | Birk |
| 2008/0208240 A1 | 8/2008 | Paz |
| 2009/0005633 A9 | 1/2009 | Montpetit et al. |
| 2009/0012538 A1 | 1/2009 | Saliman et al. |
| 2009/0018552 A1 | 1/2009 | Lam et al. |
| 2009/0023984 A1 | 1/2009 | Stokes et al. |
| 2009/0024144 A1 | 1/2009 | Zeiner et al. |
| 2009/0072006 A1 | 3/2009 | Clauson et al. |
| 2009/0082792 A1 | 3/2009 | Koyfman et al. |
| 2009/0093850 A1 | 4/2009 | Richard |
| 2009/0149879 A1 | 6/2009 | Dillon |
| 2009/0192531 A1 | 7/2009 | Hsu et al. |
| 2009/0198254 A1 | 8/2009 | Laufer et al. |
| 2009/0270856 A1 | 10/2009 | Saadat et al. |
| 2009/0275942 A1 | 11/2009 | Ortiz et al. |
| 2009/0287227 A1 | 11/2009 | Newell et al. |
| 2010/0130998 A1 | 5/2010 | Alverdy |
| 2010/0145324 A1 | 6/2010 | Nihalani |
| 2010/0145370 A1 | 6/2010 | Nihalani |
| 2011/0009896 A1 | 1/2011 | Forsell |
| 2011/0172767 A1 | 7/2011 | Rathi et al. |
| 2011/0174864 A1 | 7/2011 | Cole et al. |
| 2011/0178454 A1 | 7/2011 | Gagner et al. |
| 2011/0196411 A1 | 8/2011 | Forsell |
| 2011/0208209 A1 | 8/2011 | Ewers et al. |
| 2011/0257760 A1 | 10/2011 | Waldrep |
| 2011/0295056 A1 | 12/2011 | Aldridge |
| 2011/0295057 A1 | 12/2011 | Aldridge |
| 2012/0041463 A1 | 2/2012 | Forsell |
| 2012/0059396 A1 | 3/2012 | Harris et al. |
| 2012/0143247 A1 | 6/2012 | Smith et al. |
| 2012/0149975 A1 | 6/2012 | Cohen |
| 2012/0150176 A1 | 6/2012 | Weizman |
| 2012/0165602 A1 | 6/2012 | Nissen |

FOREIGN PATENT DOCUMENTS

| | | |
|---|---|---|
| EP | 1 602 392 A1 | 7/2005 |
| EP | 1 591 140 A1 | 11/2005 |
| EP | 1 520 563 A1 | 4/2006 |
| EP | 1 547 642 B1 | 8/2007 |
| EP | 1 607 071 B1 | 8/2007 |
| EP | 1 884 198 A2 | 2/2008 |
| EP | 1 670 361 B1 | 4/2008 |
| FR | 2 907 665 | 5/2008 |
| WO | WO 87/00034 | 1/1987 |
| WO | WO 99/25418 | 5/1999 |
| WO | WO 00/09049 | 2/2000 |
| WO | WO 00/18330 | 4/2000 |
| WO | WO 00/74573 A1 | 12/2000 |
| WO | WO 01/047435 | 7/2001 |
| WO | WO 01/47435 | 7/2001 |
| WO | WO 02/35980 A2 | 5/2002 |
| WO | WO 02/071951 | 9/2002 |
| WO | WO 03/055420 | 7/2003 |
| WO | WO 03/095015 | 11/2003 |
| WO | WO 2004/004542 | 1/2004 |
| WO | WO 2004/014237 | 2/2004 |
| WO | WO 2004/019765 | 3/2004 |
| WO | WO 2004/021894 | 3/2004 |
| WO | WO 2004/037064 A2 | 5/2004 |
| WO | WO 2004096057 | 11/2004 |
| WO | WO 2005/007232 | 1/2005 |
| WO | WO 2005/009288 | 2/2005 |
| WO | WO 2005/018417 A2 | 3/2005 |
| WO | WO 2005/018417 A3 | 3/2005 |
| WO | WO 2005/020802 | 3/2005 |
| WO | WO 2005/094447 A2 | 10/2005 |
| WO | WO 2005/105003 | 11/2005 |
| WO | WO 2006002192 | 1/2006 |
| WO | WO 2006/020370 A2 | 2/2006 |
| WO | WO 2006/049725 A2 | 5/2006 |
| WO | WO 2006/063593 A2 | 6/2006 |
| WO | 2006093975 | 9/2006 |
| WO | WO 2006/108203 | 10/2006 |
| WO | WO 2006/127431 | 11/2006 |
| WO | WO 2006/134106 | 12/2006 |
| WO | WO 2007/017880 A2 | 2/2007 |
| WO | WO 2007/064906 A2 | 6/2007 |
| WO | WO 2007/067206 A2 | 6/2007 |
| WO | WO 2007/110866 A2 | 10/2007 |
| WO | WO 2008/006084 A2 | 1/2008 |
| WO | WO 2008/013814 | 1/2008 |
| WO | WO 2008/043044 A2 | 4/2008 |
| WO | 2011149882 | 12/2011 |

OTHER PUBLICATIONS

Akira., JP63277063, Japanese and English Abstract, Nov. 15, 1988, pp. 1-4.

Abhyankar et al, Use of a tissue expander and a polyglactic acid (Vicryl) mesh to reduce radiation enteritis: case report and literature view, Pediatr. Surg. Int. 21: pp. 755-757, Aug. 2005.

Buchwald, Overview of Bariatric Surgery, J. Amer. College of Surgeons,vol. 194, No. 3, Mar. 2002, pp. 367-375.

Buchwald et al., "Bariatric Surgery: A Systematic Review and Meta-analysis", JAMA 2004, vol. 292, No. 14, pp. 1724-1737.

Buchwald et al., "Evolution of Operative Procedures for the Management of Morbid Obesity 1950-2000", Obesity Surgery 2002, 12:705-717.

Burnett, et al., The Use of a Pelvic Displacement Prosthesis to Exclude the Small Intestine from the Radiation Field Following Radical Hysterectomy, Gynecologic Oncology,79, pp. 438-443, 2000. http://www.idealibrary.com.

Brolin, Robert E., Gastric Bypass. Obesity Surgery, vol. 81, No. 5, Oct. 2001, pp. 1077-1095.

Brethauer, et al. "Laparoscopic gastric plication for treatment of severe obesity", American Society for Metabolic and Bariatric Surgery, 2010, pp. 1-8.

Brethauer, et al. "Laparoscopic Greater Curvature plication in the canine: comparison of durability and tissue response using fasteners and suture", Abstracts: Poster Session 2011 / Surgery for Obesity and Related Diseases, 7 (2011) pp. 400-401.

Cheng, Splenic Epidermoid Cyst, pp. 1- 3, 1997.

Camerini et al., "Thirteen Years of Follow-up in Patients with Adjustable Silicone Gastric Banding for Obesity: Weight Loss and Constant Rate of Late Specific Complications" Obesity Surgery 2004, 14:1343-1348.

Cope et al., "Percutaneous Transgastric Technique for Creating Gastroenteric Anastomoses in Swine", Journal of Vascular and Interventional Radiology, 2004, 15:177-181.

Conroy, et al. Lubricious Coatings for Medical Devices. dds&s, vol. 3, No. 4, Jan. 2004, pp. 89-92.

Cottam, "Gastric Imbrication: The Future or Fantasy?", General Surgery News, Jul. 2011, vol. 38:7, pp. 1-5.

Cummings et al., "Genetics and Pathophysiology of Human Obesity", An Annual Review of Medicine, 2003, 54:453-471/.

DeMaria, Eric J., Laparoscopic Adjustable Silicone Gastric Banding. Obesity Surgery, vol. 81, No. 5, Oct. 2001, pp. 1129-1143.

Deitel, Mervyn., Overview of Operations for Morbid Obesity. World J. Surg., vol. 22, No. 9, Sep. 1998, pp. 913-918.

Doherty, Cornelius., Technique of Vertical Banded Gastroplasty. Obesity Surgery, vol. 81, No. 5, Oct. 2001, pp. 1097-1111.

Fried et al., Physical Principles of Available Adjustable Gastric Bands: How they Work. Obesity Surgery, 14, 2004, pp. 1118-1121.

Foglia et al., Management of giant omphalocele with rapid creation of abdominal domain, J. Ped. Surg., 41, pp. 704-709, 2006.

Geliebter et al; Extra-abdominal pressure alters food intake, intragastric pressure, and gastric emptying rate. Amer. Phys. Soc., 1986, pp. R549-R552.

Gertner, Stomach Restriction with an Extragastric Balloon, pp. 1, Abstract for 2007.

Goel et al., "Reversal of gastric plication after laparoscopic adjustable gastric banded plication" Surgery for Obesity and Related Diseases, 2011, pp. 1-2.

Hainaux et al., Laparoscopic adjustable silicone gastric banding: radiological appearances of a new surgical treatment for morbid obesity. 1999, Abdom Imaging 24: 533-537.

Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, The American Surgeon, pp. 473-483, No. 7, vol. 60, Jul. 1994.

Huang, et al., "Novel bariatric technology: laparoscopic adjustable gastric banded plication: technique and preliminary results", Surgery for Obesity and Related Diseases, 8 (2012), pp. 41-47.

Johnston et al., "The Magenstrasse and Mill Operation for Morbid Obesity", Obesity Surgery 2003, 13:10-16.

Konturek et al., Neuro-Hormonal Control of Food Intake; Basic Mechanisms and Clinical Implications, J. Phys. And Pharma., 2005, 56, Supp 6, 5-25. www.jpp.krakow.pl.

Kirk, "An Experimental Trial of Gastric Plication as a Means of Weight Reduction in the Rat", Brit. J. Surg., 1969, vol. 56, No. 12, pp. 930-933.

Lam et al., Huge Splenic Epidemoid Cyst: A Case Report, Chin Med J, 1997; 60:113-6.

Laparoscopic Duodenal Switch, Mar. 24, 2006, http://wo-pub2.med.cornell.edu/chi.bin/WebObjects/PublicA.woa/5/w . . . p. 1-1.

Lee et al.,"Laparoscopic Vertical Sleeve Gastrectomy: A Novel Bariatric Procedure-superior to Established Operations?" pp. 1- 27. 90th Annual Clinical Congress, New Orleans, LA, Oct. 10, 2004.

Lopez-Corvala, et al., "Gastric placation: Our experience in 100 patients", Abstracts: Plenary Session 2011 / Surgery for Obesity and Related Diseases, 7 (2011), pp. 350-351.

LGCP, presentation Cleveland Clinic, Oct. 22, 2011.

Med-4840, Product Profile , Mar. 30, 2007, pp. 1-2.

Malassagne, et al., "Intra-abdominal Sengstaken-Blakemore tube Placement for acute venous outflow obstruction in reduced-size Liver", British J. Surg., Nov. 1996, 83, pp. 1086.

Marceau, et al., "Malabsorptive Obesity Surgery.", Obesity Surgery, vol. 81, Oct. 2001, No. 5, pp. 1113-1127.

McMillan, et al., "Arthroscopic Knot-tying techniques", An Atlas of Shoulder Arthroscopy, pp. 81-95, 2003.

Mera, et al., Use of the Breast Implant for Liver Graft Malposition. Liver Transp. And Surg., vol. 5, No. 6, Nov. 1999, pp. 534-535.

Menchaca et al., "Gastric Plication: Preclinical study of durability of serosa-to-serosa apposition", Surgery for Obesity and Related Diseases, 7 (2011), pp. 8-14.

Morino et al., "Laparoscopic Adjustable Silicone Gastric Banding Versus Vertical Banded Gastroplasty in Morbidly Obese Patients" Analysis Obesity Surgery vol. 238, No. 6, 2003, pp. 835-842.

Obesity Surgery Including Laparoscopy and Allied Care. vol. 16, No. 1, Jan. 2006, pp. 1-2. www.obesitysurgey.com.

Ong'uti, et al., "Effective weight loss management with endoscopic gastric plication using StomaphyX device: is it achievable?", Surgery for Obesity and Related Diseases, 2011, pp. 1-5.

Ramos et al., "Laparoscopic Greater Curvature Plication: Initial Results of an Alternative Restrictive Bariatric Procedure", Obes. Surg., Apr. 21, 2010, pp. 913-918.

Pomerri et al., Adjustable Silicone Gastric Banding of Obesity. , 1992, Gastrointest Radiol 17: pp. 207-210.

Roman et al., "Intragastric Balloon of Non-Morbid Obesity: A Retrospective Evaluation of Tolerance and Efficacy", Obesity Surgery, 2004, 14:539-544.

Sallet et al., Brazilian Multicenter Study of the Intragastric Balloon; Obesity Surgery, 2004, 14, pp. 991-998.

Sharp, et al., The 4-S Modification of the Roeder Knot: How to Tie It. Obstetrics and Gyn., pp. 1004-1006, vol. 90, No. 6, Dec. 1997.

Sjostrom et al., Lifestyle, Diabetes, and Cardiovascular Risk Factors 10 years after Bariatric Surgery, New England Journal of Medicine, 2004, 351, (6) 2683-2693.

Schauer, et al., New applications for endoscopy: the emerging field of endoluminal and transgastric bariatric surgery, DOI:10.1007/s00464-006-9008-8, 2006.

Skrekas, et al., "Laparoscopic Gastric Greater Curvature Plication: Results and Complications in a Series of 135 Patients", Obes. Surg. (2011) pp. 1657-1663.

Smith et al., "Modification of the Gastric Partitioning Operation for Morbid Obesity", Am. J. Surgery 142, Dec. 1981.pp. 725-730.

Smith et al., "Results and Complications of Gastric Partitioning: Four Years Follow-Up of 300 Morbidly Obese Patients", The American Journal of Surgery, 1983, (146) pp. 815-819.

Talebpour, et al., "Laparoscopic Total Gastric Vertical Plication in Morbid Obesity", Journal of Laparoendoscopic & Advanced Surgical Techniques, vol. 17, No. 6, 2007, pp. 793-798.

The Sleeve Gastrectomy (or 2-Stage Procedure). 2006, pp. 1-2. http://surgicallyslim.com/sleeve.htm.

Trumble et al., "Method for measuring long-term function of muscle-powered implants via radiotelemetry" J. Appl. Physiol. 2001,90: pp. 1977-1985.

Tucker, Diana, Medical Device Daily. vol. 10, No. 102, pp. 1-10, May 26, 2006.

von Renteln et al., "Endoscopic full-thickness plication for the treatment of gastroesophageal reflux disease using multiple Plicator implants: 12-month multicenter study results", Surg. Endosc. (2009) 23: 1866-1875.

Walker, et al. Bladder Augmentation in Dogs Using the Tissue Capsule Formed Around a Perivesical tissue Expander, J. Urology, vol. 168, pp. 1534-1536, 2002.

Watkins, "Gastric compartment syndrome: an unusual complication of gastric plication surgery", Surgery for Obesity and Related Diseases, (2011), pp. 1-2.

Zwart et al., "Gastric Motility: Comparison of Assessment with Real-Time MR Imaging or Barostat Experience", Radiology, 224: pp. 592-597, Aug. 2002.

Akira., JP63277063, Japanese and English Abstract, Nov. 15,1988, pp. 1-4.

Conroy, et al. Lubricious Coatings for Medical Devices. dds&s,vol. 3, No. 4, Jan. 2004, pp. 89-92.

Laparoscopic Duodenal Switch, Mar. 24, 2006, http://wo-pub2.med.cornell.edu/chi.bin/WebObjects/PublicA.woa/5/w... p. 1-1.

Lee et al.,"Laparoscopic Vertical Sleeve Gastrectomy: A Novel Bariatric Procedure-superior to Established Operations?" pp. 1-27. 90th Annual Clinical Congress, New Orleans, LA, Oct. 10, 2004.

* cited by examiner

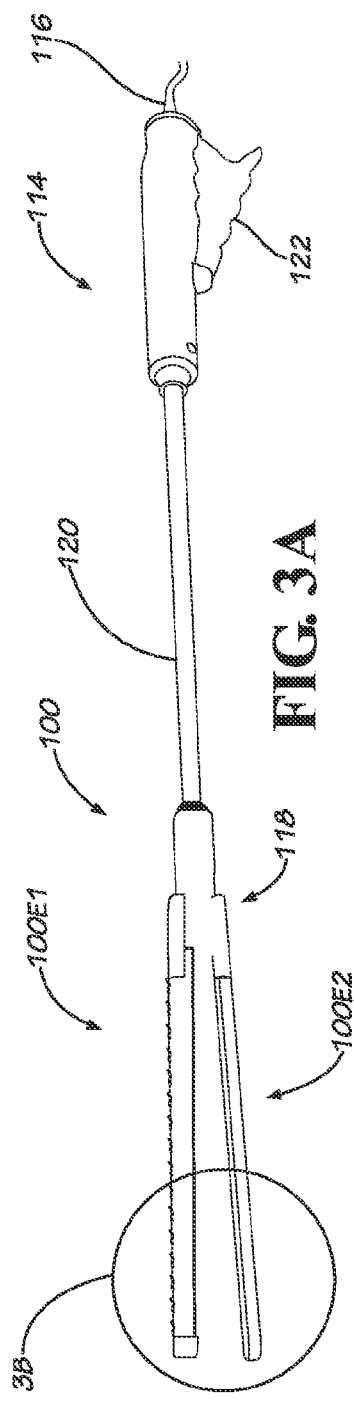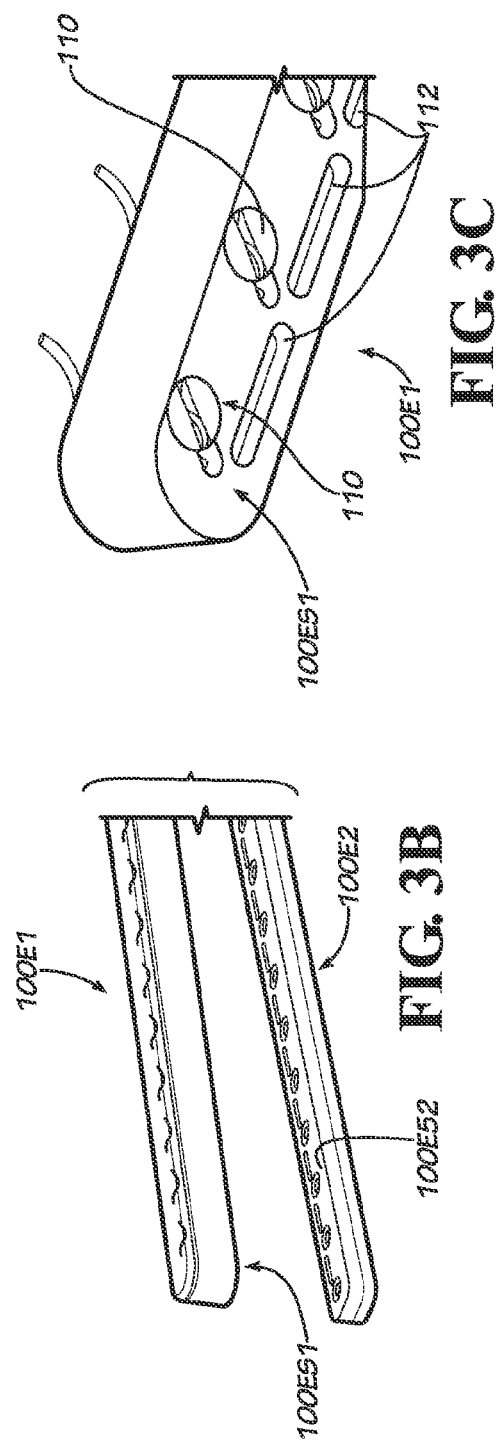

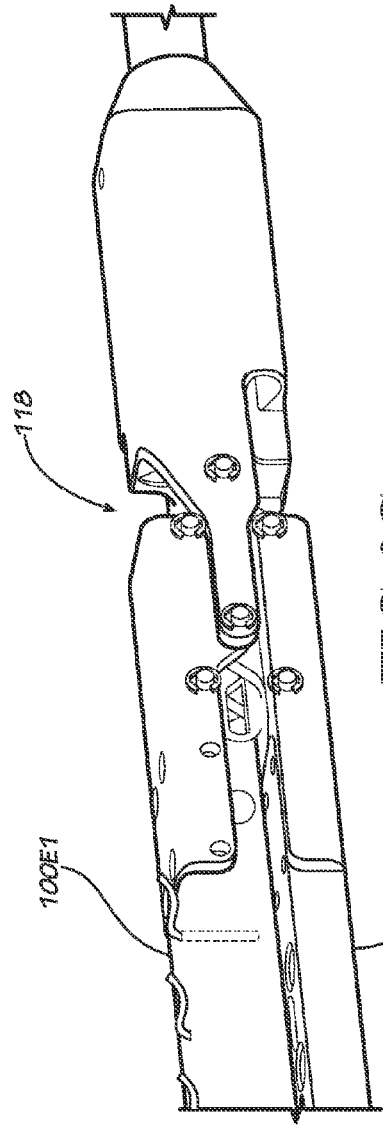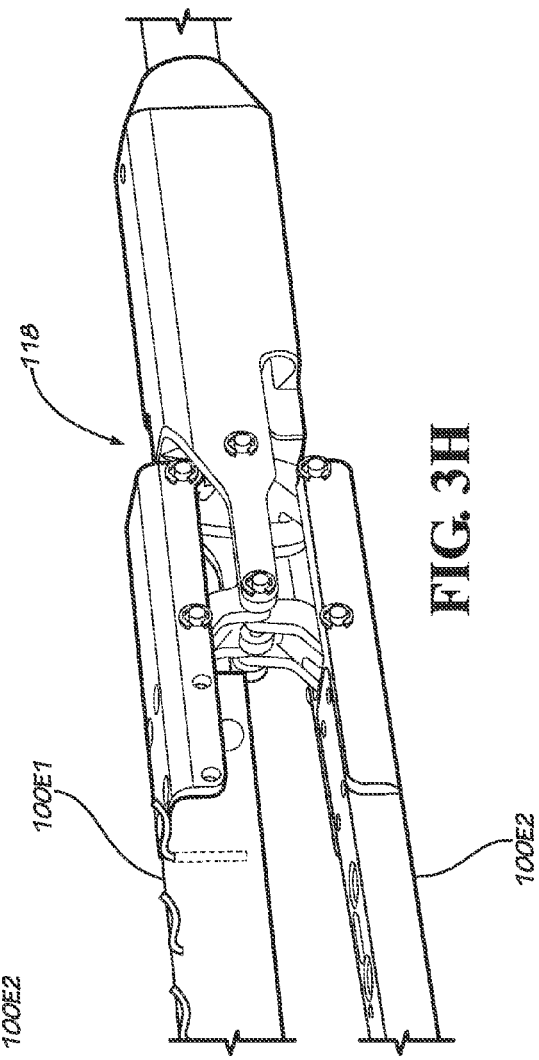

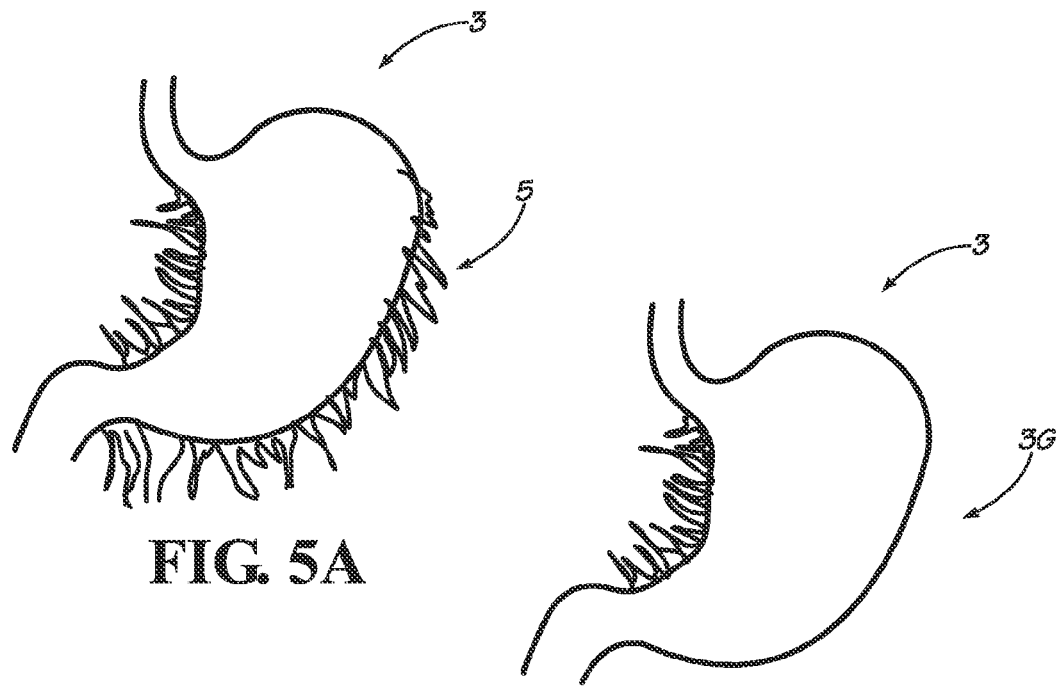
FIG. 5A
FIG. 5B
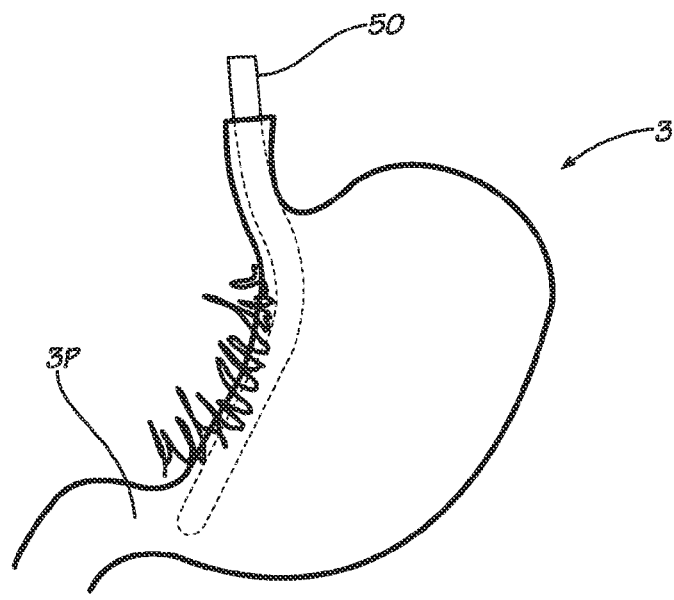
FIG. 5C

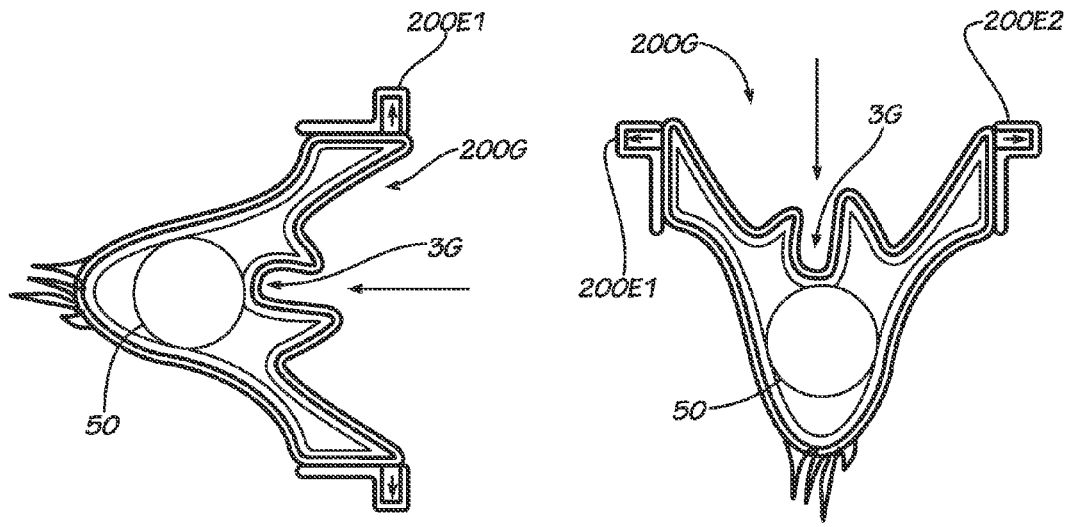
FIG. 5F
FIG. 5F'
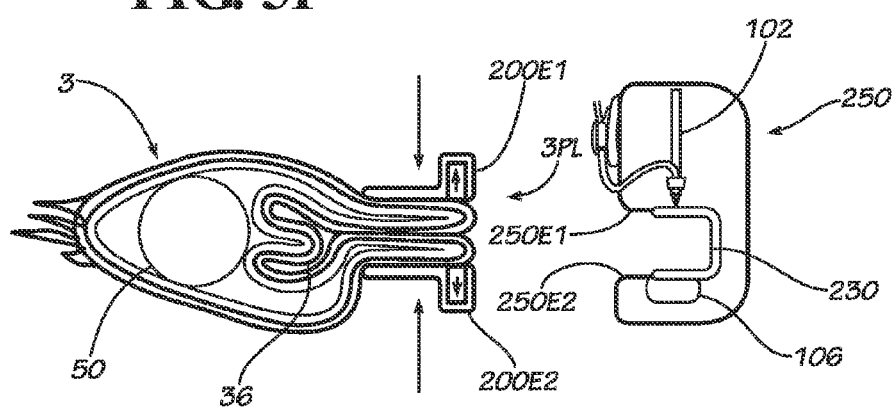
FIG. 5G
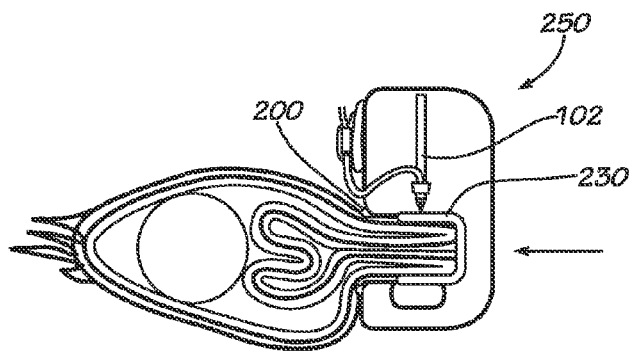
FIG. 5H

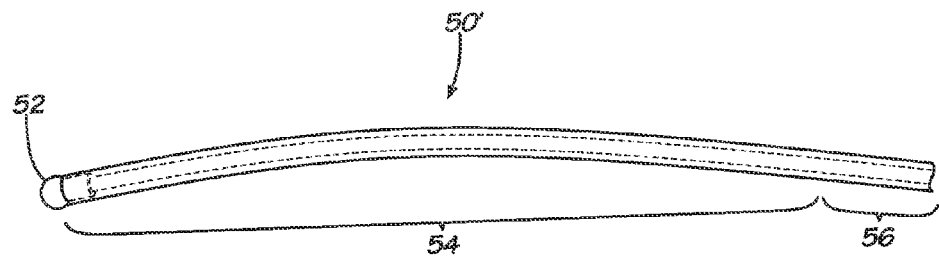
FIG. 6
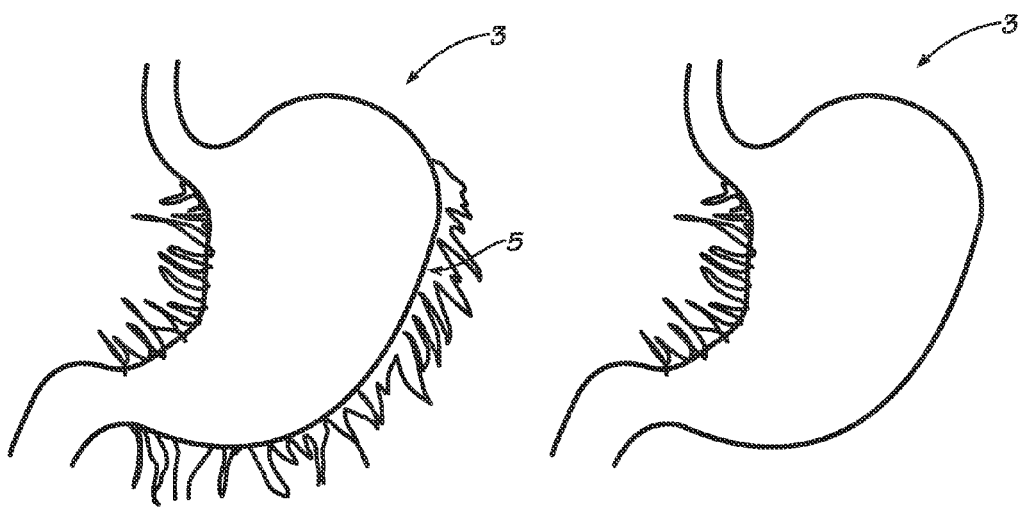
FIG. 7A  FIG. 7B

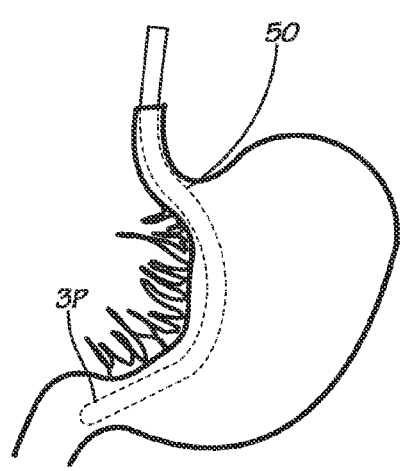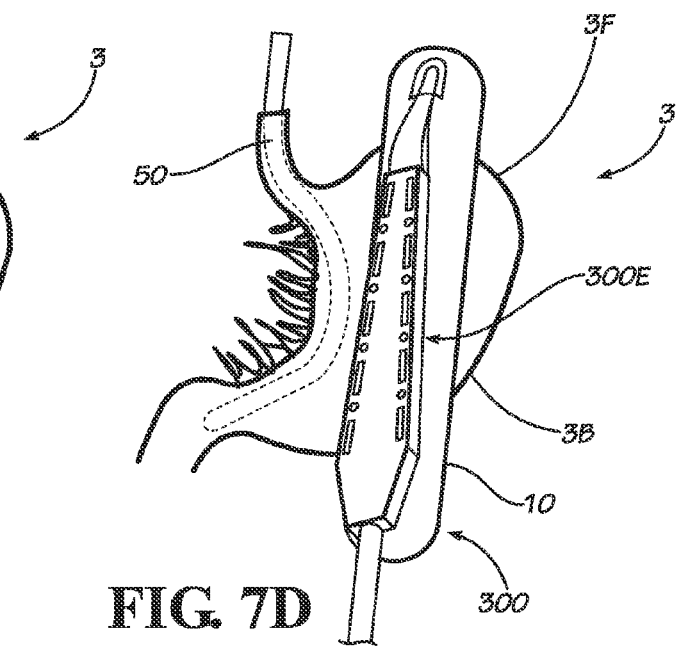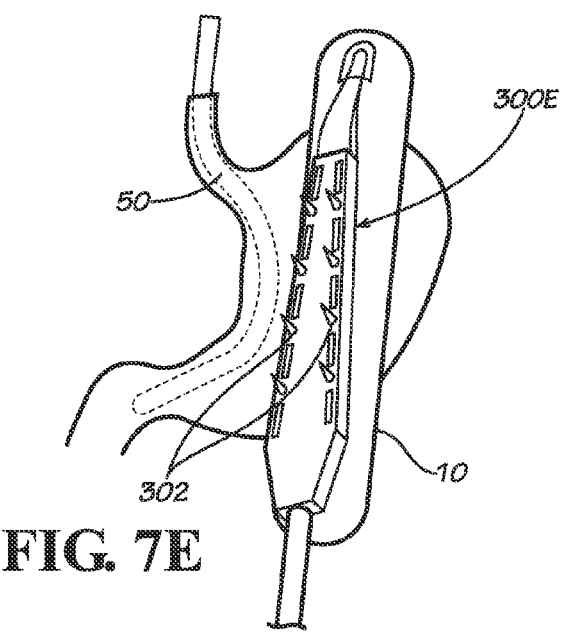
FIG. 7C  FIG. 7D
FIG. 7E

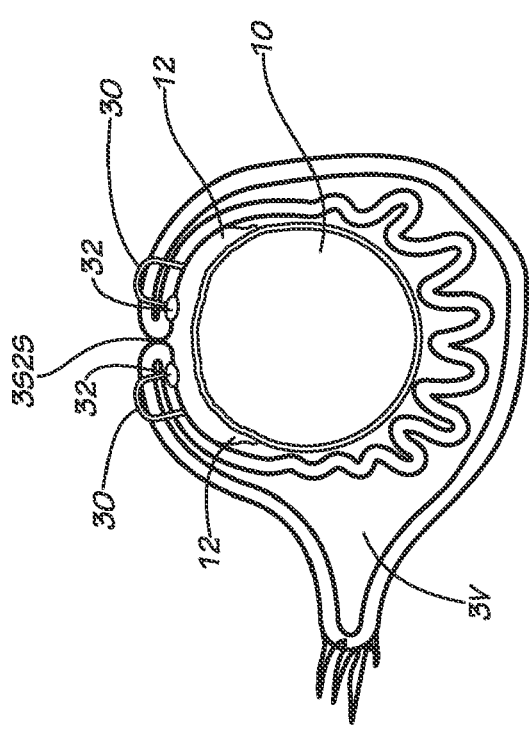
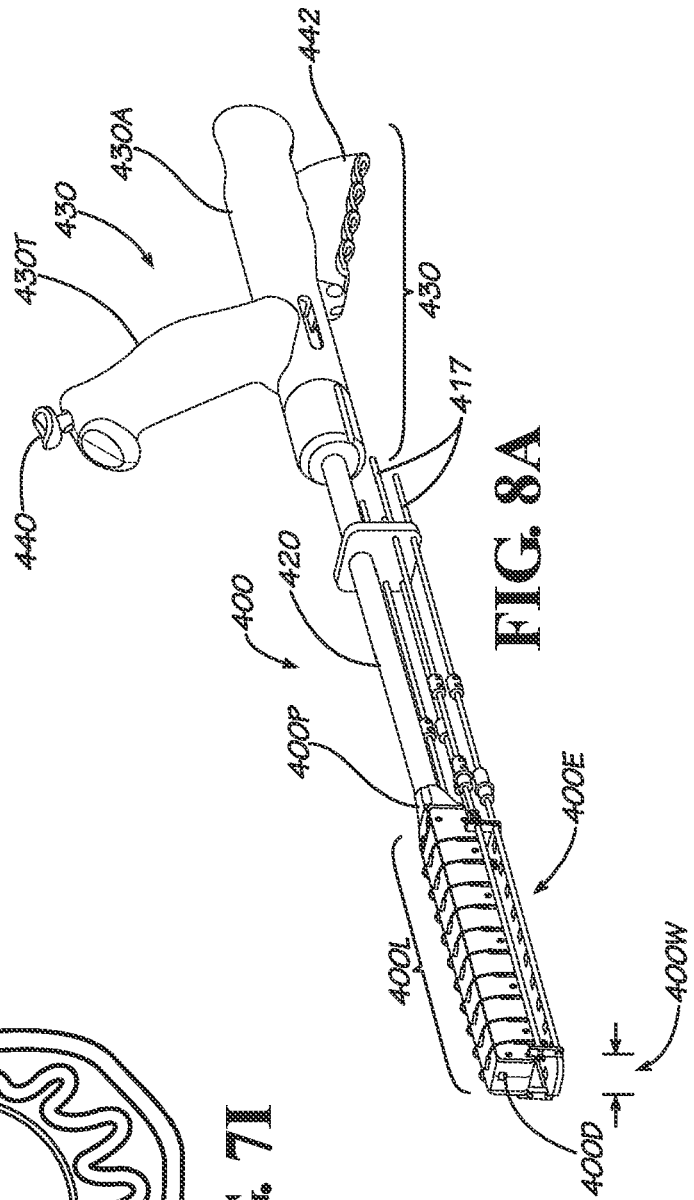

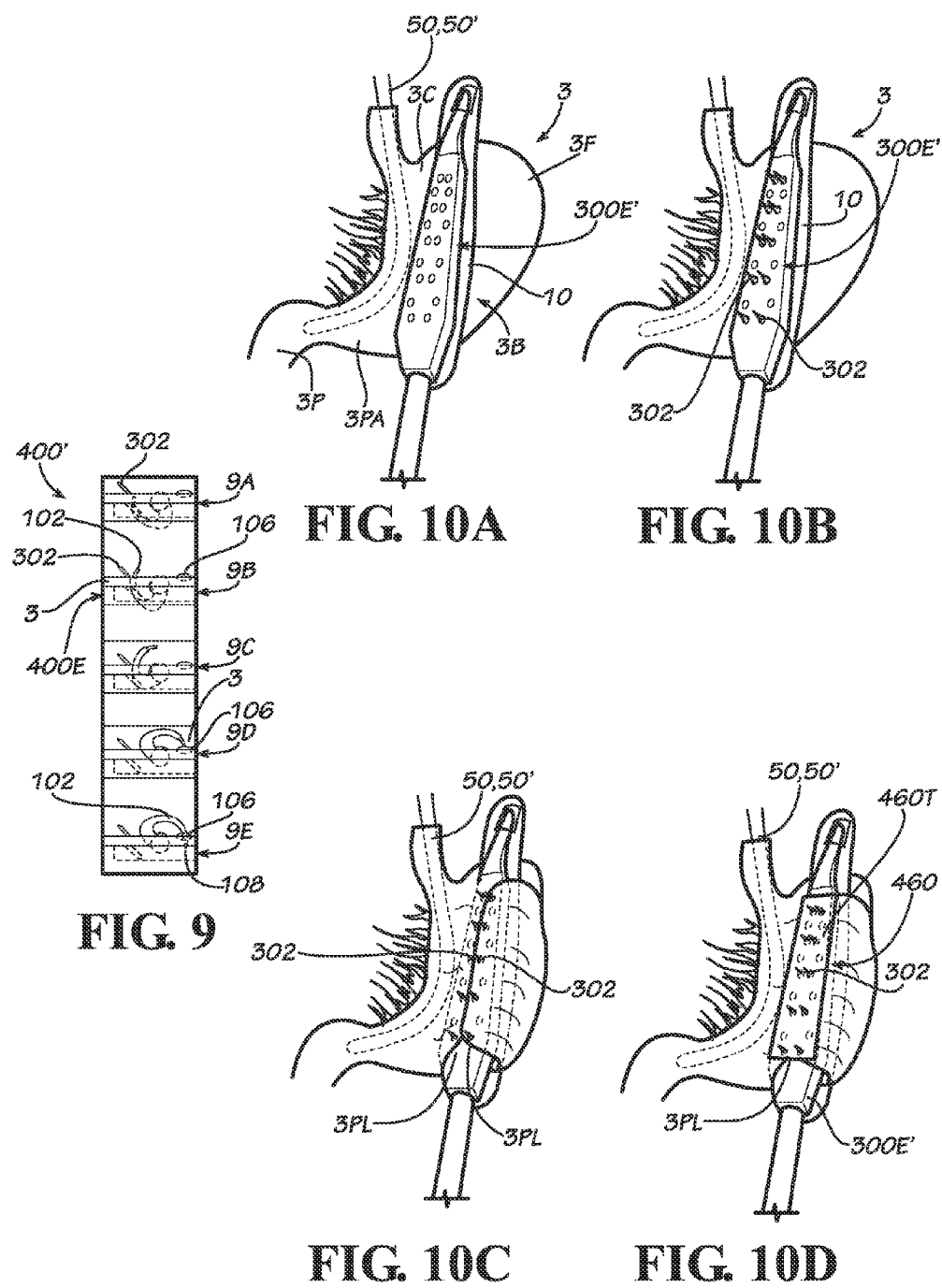

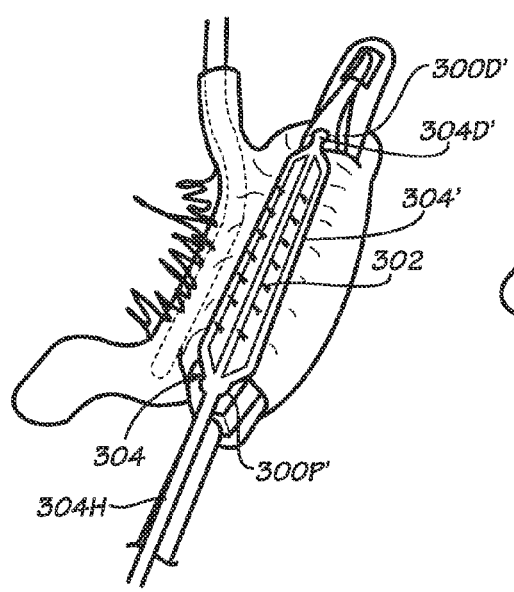
FIG. 10E
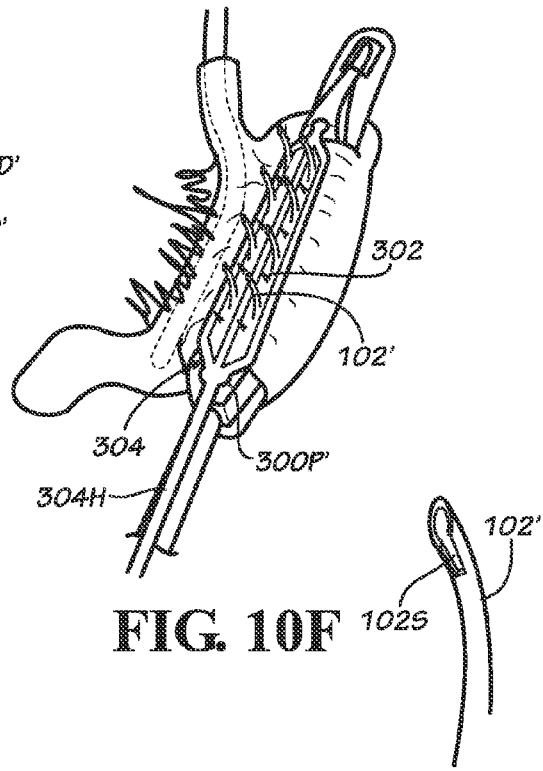
FIG. 10F
FIG. 10F'
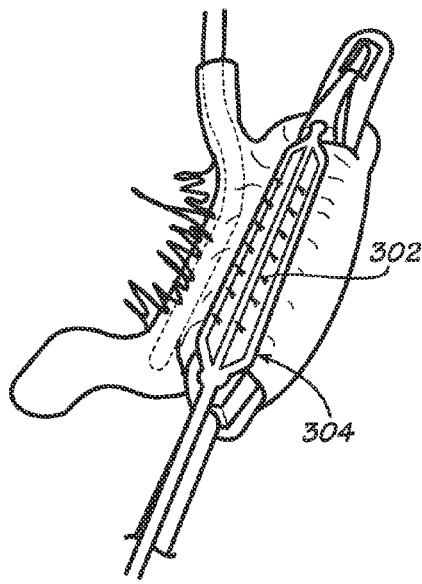
FIG. 10G
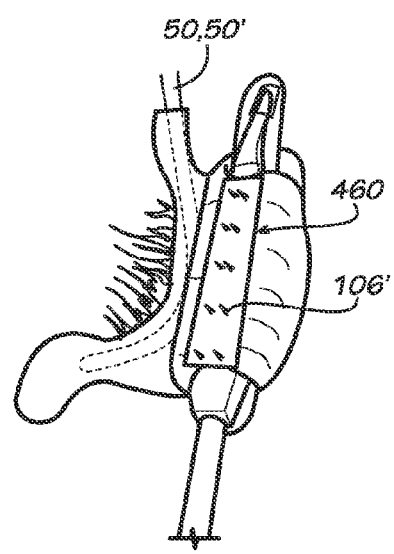
FIG. 10H

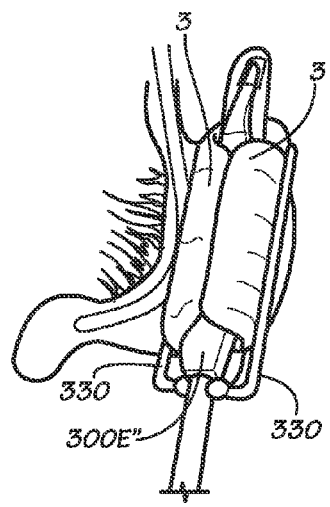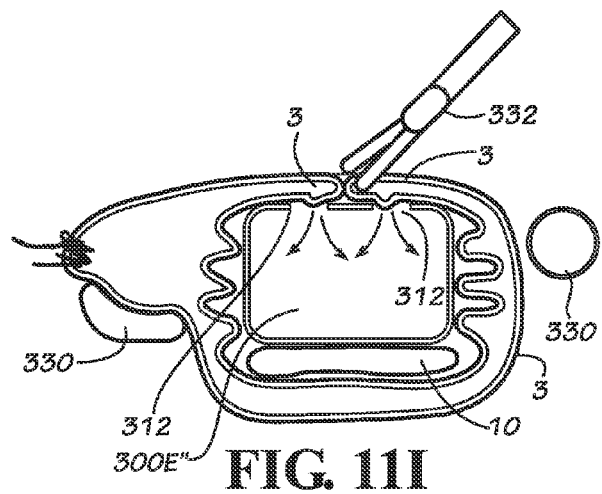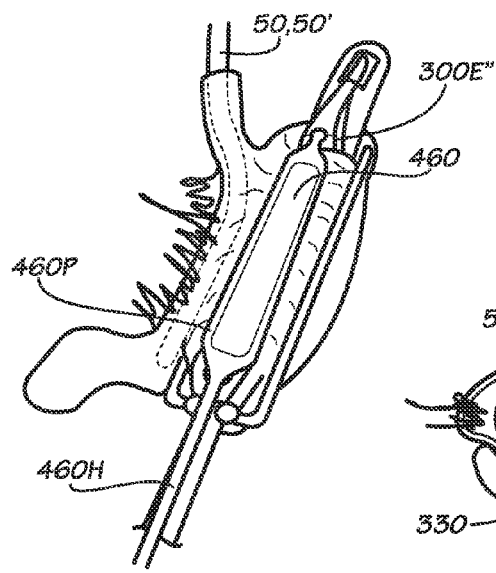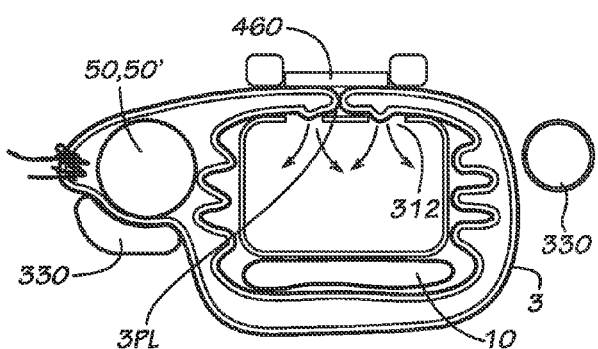
FIG. 11H
FIG. 11I
FIG. 11J
FIG. 11K

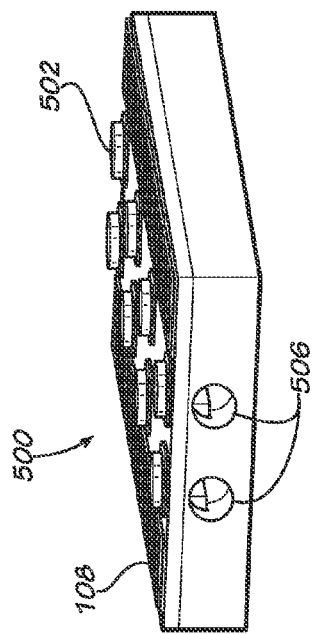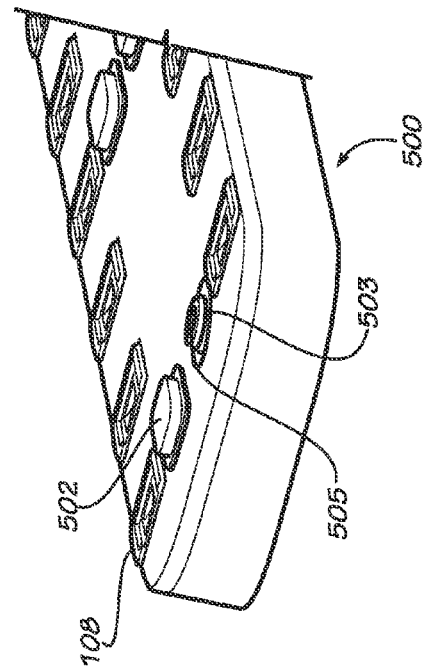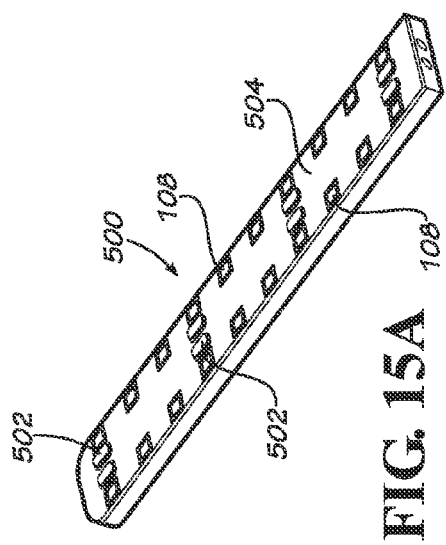

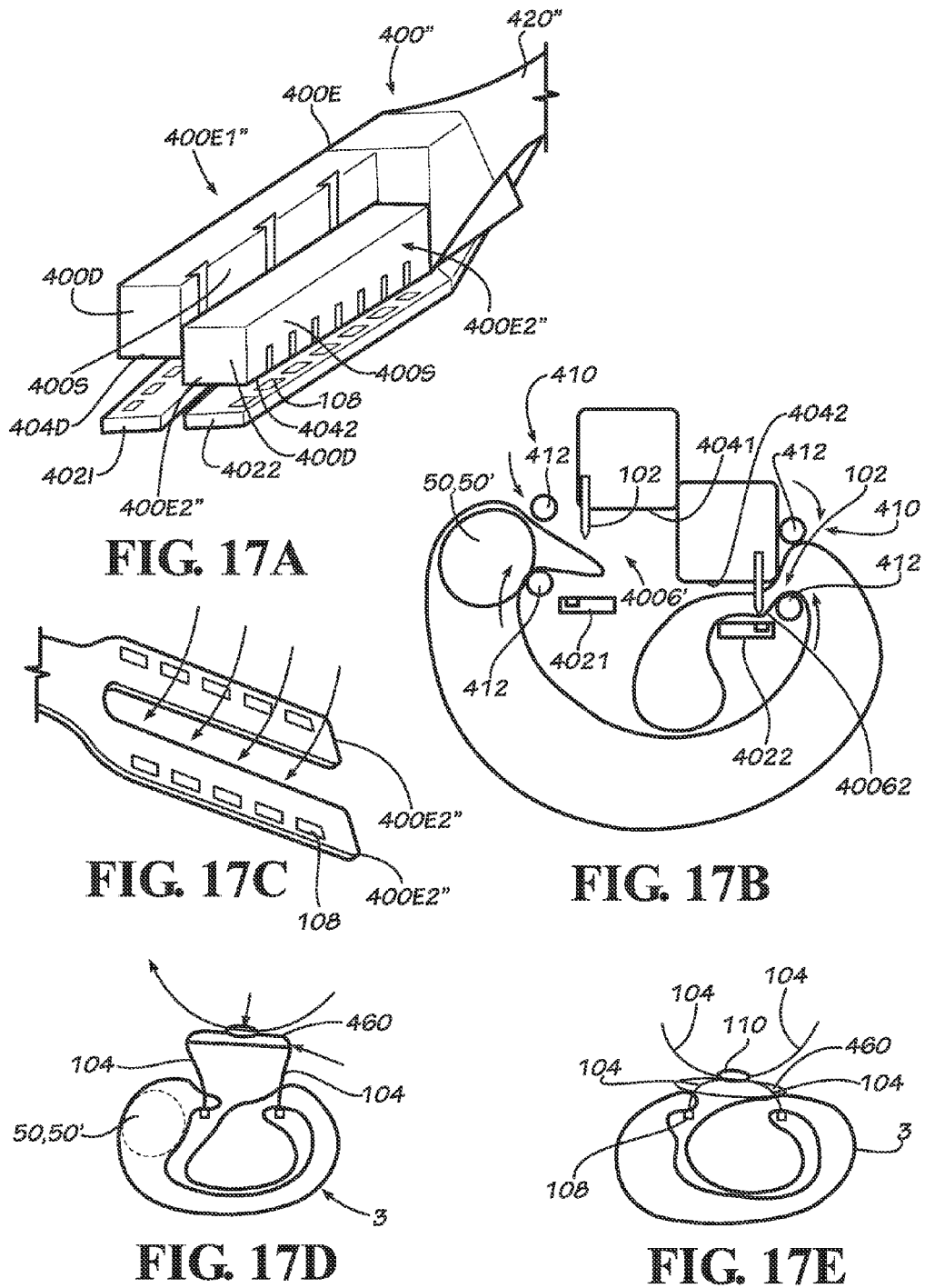

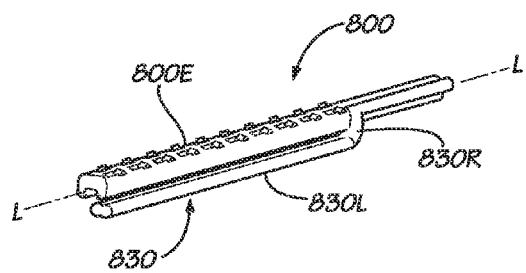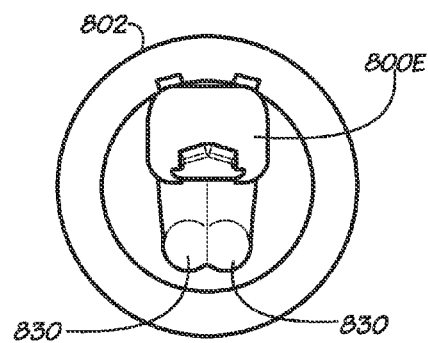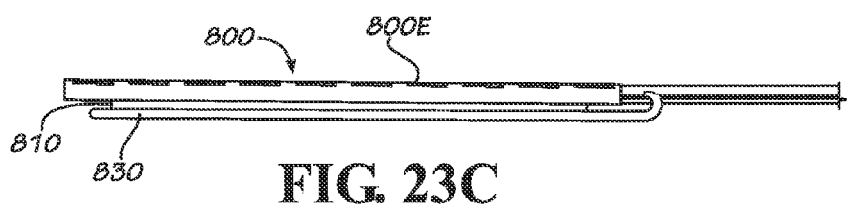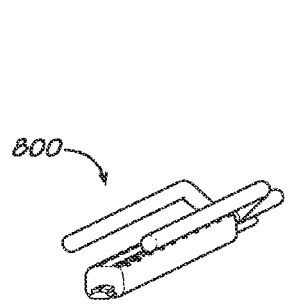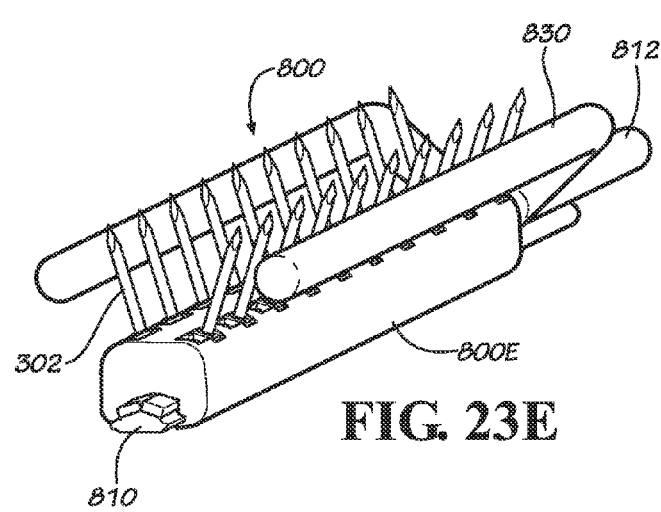

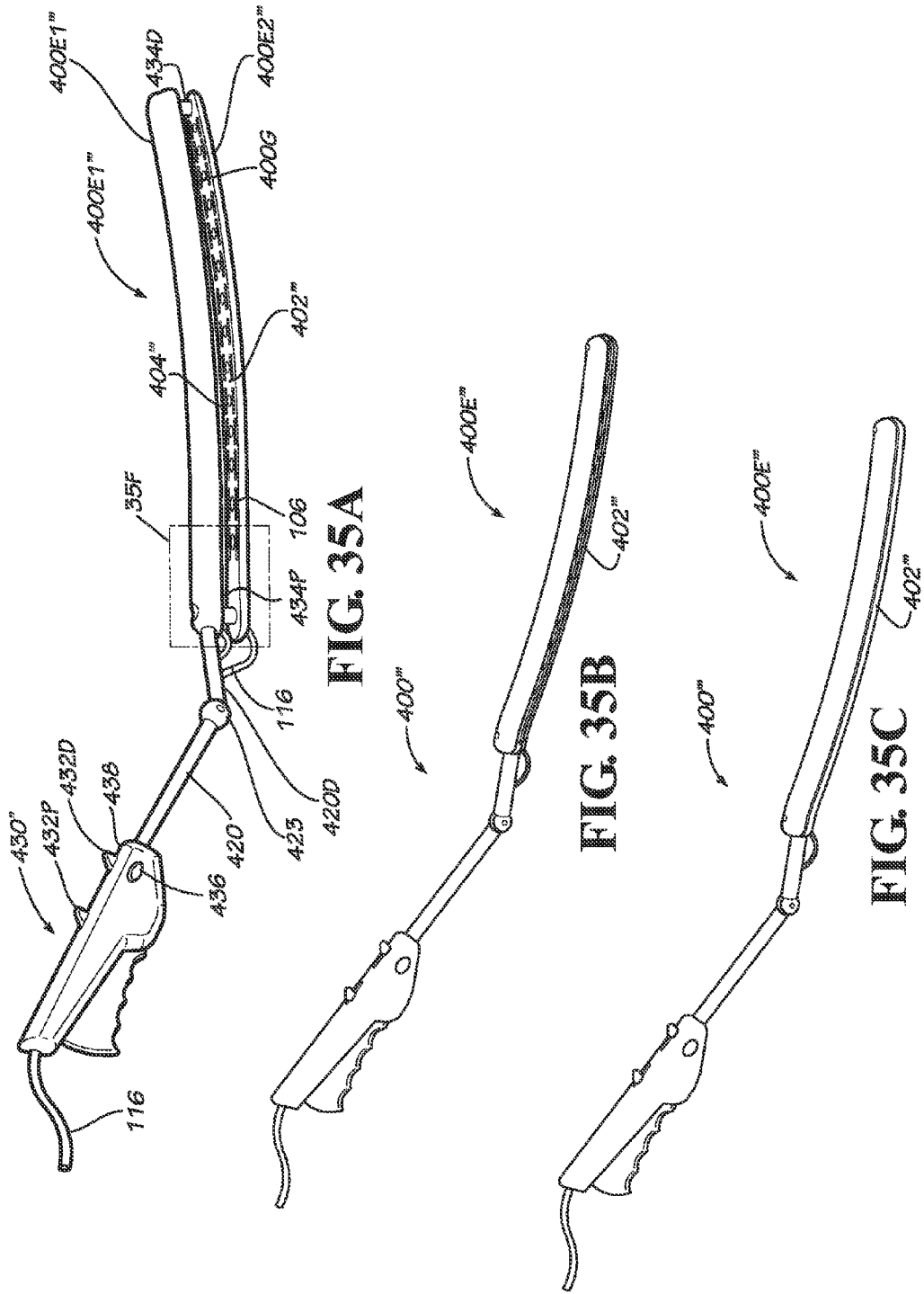

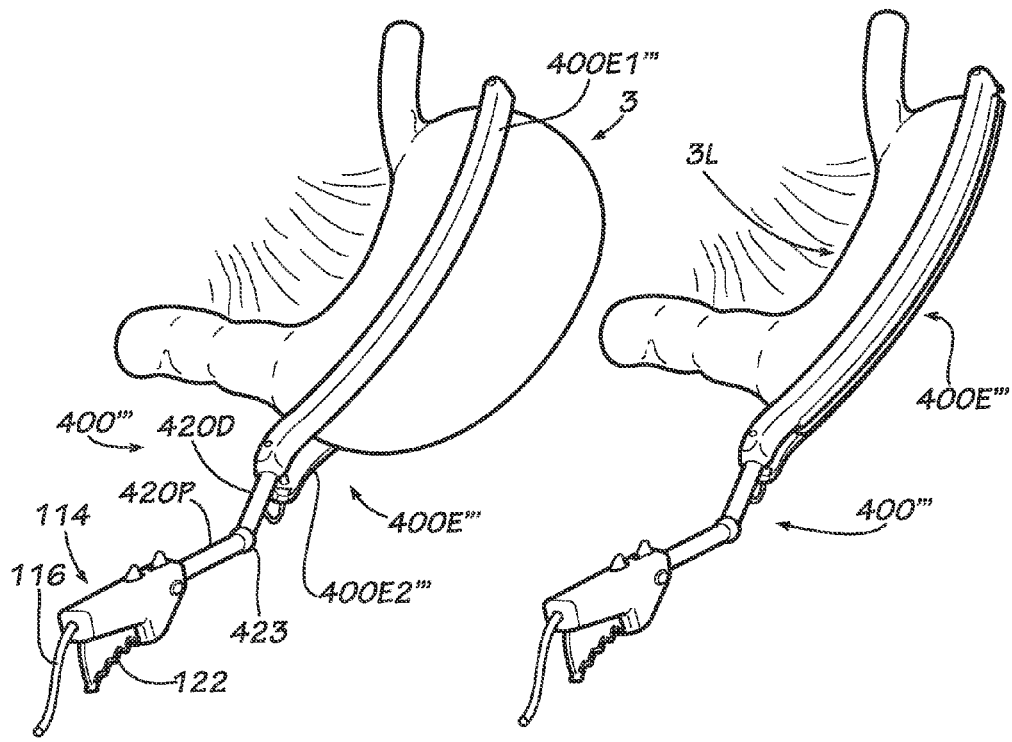
FIG. 35D  FIG. 35E
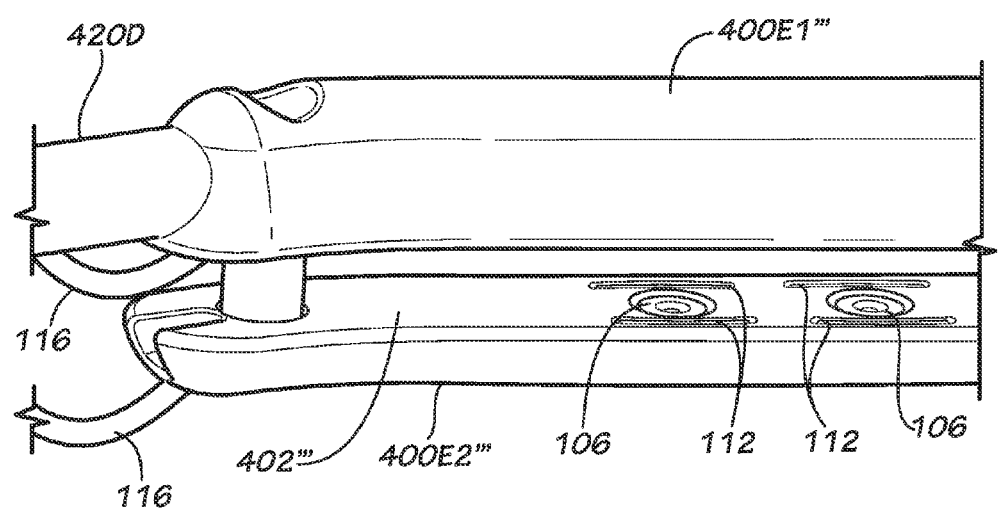
FIG. 35F

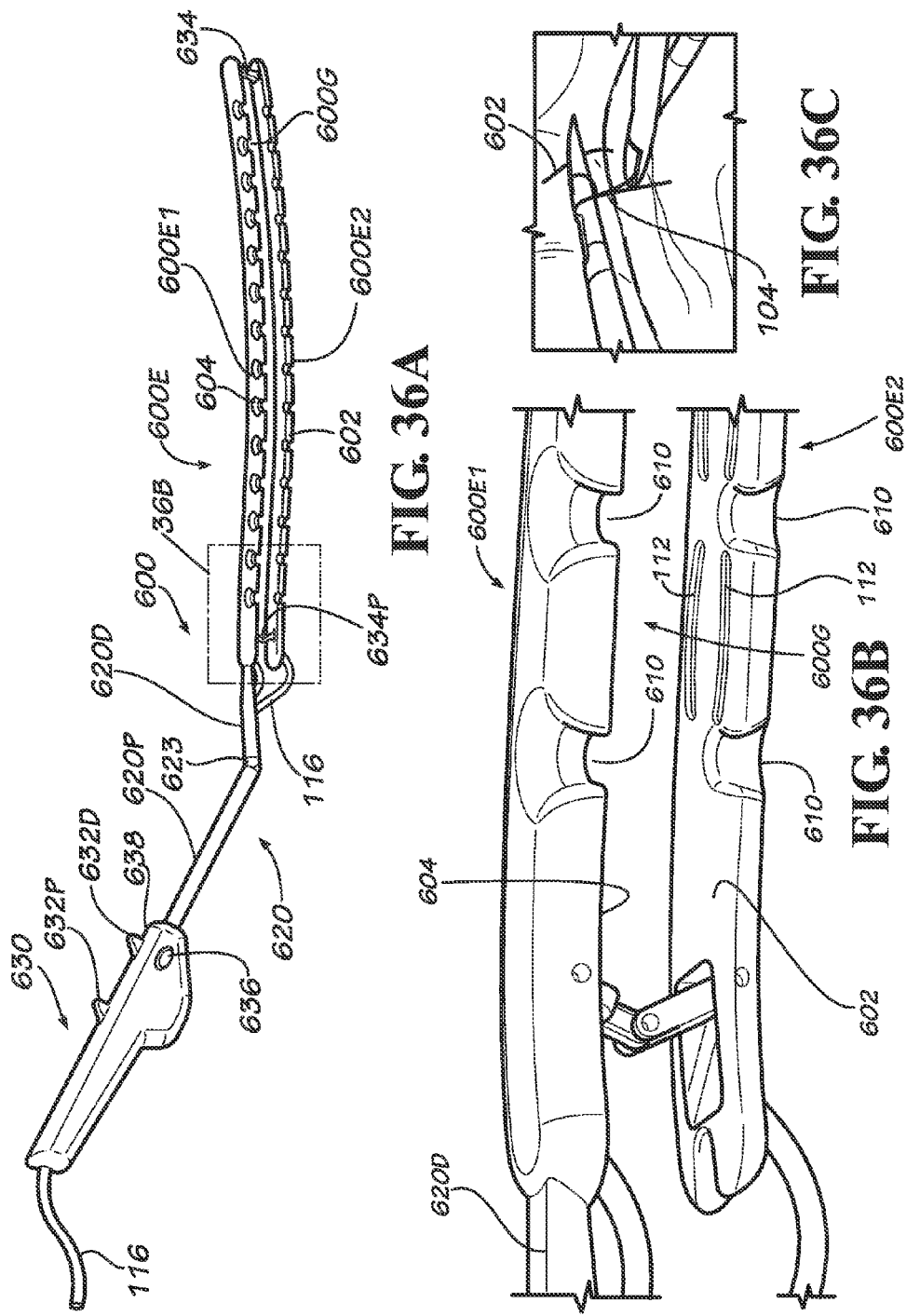

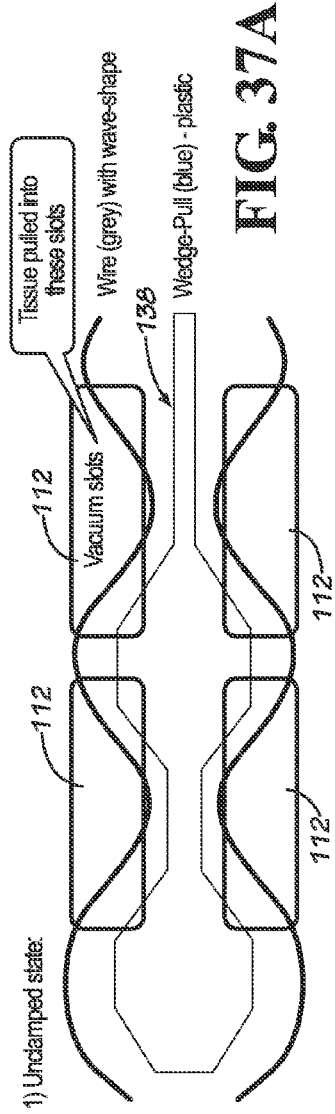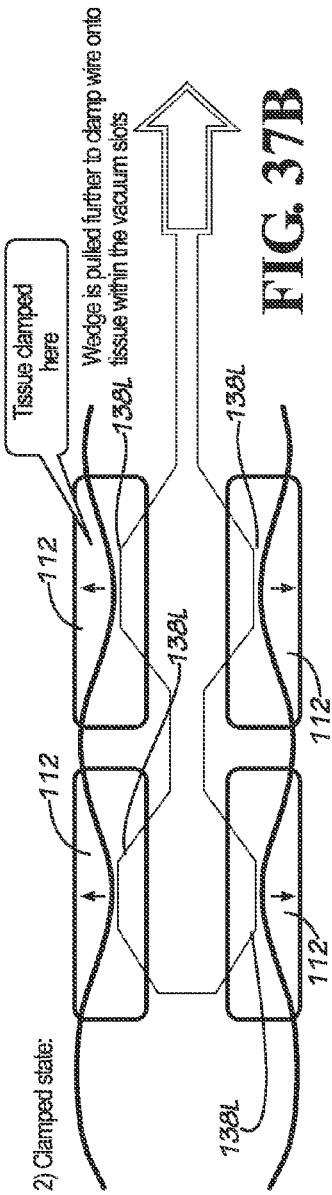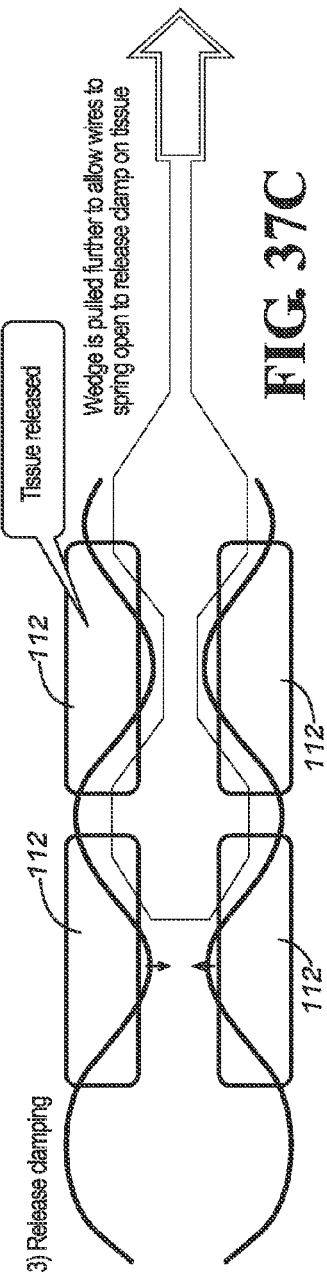

METHODS, INSTRUMENTS AND DEVICES FOR EXTRAGASTRIC REDUCTION OF STOMACH VOLUME

CROSS-REFERENCE

This application claims the benefit of U.S. Provisional Application No. 61/584,289, filed Jan. 8, 2012 and titled "Methods, Instruments and Devices for Extragastric Reduction of Stomach Tissue", which application is hereby incorporated herein, in its entirety, by reference thereto

BACKGROUND OF THE INVENTION

Obesity has become a major health concern, both nationally and internationally. The National Center for Health Statistics (NCHS) estimates that over 120 million Americans are overweight, including about 56% of the adult population. Of these, about 52 million are considered obese, as measured by a body mass index (BMI) of 30% or greater. In Europe, an estimated 77 million people are obese, as measured by the same standard. This problem is not limited to western nations, as many developing countries are reported to have obesity rates over 75% of the adult population.

Co-morbidities that are associated with obesity include, but are not limited to type II Diabetes, high blood pressure, sleep apnea, stroke and arthritis, the symptoms of which often tend to be lessened or alleviated upon loss of weight by a person so affected.

One current treatment methodology for treatment of obesity is called gastric bypass surgery and another is referred to as gastric banding (one of these techniques uses a device referred to as the LAPBAND™). These procedures are limited to only those patients with a BMI over 40 (or over 35, with co-morbidities present).

Gastric bypass procedures incur a great deal of morbidity and create a malabsorptive state in the patient by bypassing a large portion of the intestines. Serious side effects, such as liver failure have been associated with this procedure, as well as chronic diarrhea. Another surgical procedure that has a high degree of morbidity associated with it is known as the "Gastric Bypass Roux-en-Y" procedure. This procedure reduces the capacity of the stomach by creating a smaller stomach pouch. The small space holds only about one ounce of fluid. A tiny stomach outlet is also surgically created to slow the speed at which food leaves the stomach. Staples are used to create a small (15 to 20 cc) stomach pouch, with the rest of the stomach being stapled completely shut and divided from the stomach pouch. The small intestine is divided just beyond the duodenum, brought up, and connected to the newly formed stomach pouch. In addition to the considerable morbidity associated with this procedure, other disadvantages include "dumping syndrome", where stomach contents are literally "dumped" rapidly into the small intestine which may lead to nausea, weakness, sweating, faintness, and diarrhea; hernias resulting from the surgery; gallstones; leakage of the connection between the pouch and the intestine; stretching of the pouch that was formed; nutritional deficiencies; and adverse effects, including but not limited to erosion of the mucosa caused by stapling entirely through the walls of the stomach.

The LAPBAND™ is a band that, when placed, encircles the fundus-cardia junction and is inflatable to constrict the same. It does not reduce the volume of the stomach, but rather restricts passage of food into the stomach, the theory being that the patient will feel satiety with a much less volume of food than previously. Although the LAPBAND™ procedure is less invasive than a gastric bypass procedure, it also typically achieves less weight loss. Further, it is not a simple procedure and requires a substantial amount of training by a surgeon to become proficient in performing the procedure. Also, a substantial amount of dissecting and suturing is required because the pathway by which the band is introduced is not an existing pathway, and must be established by dissection. Great care is required to avoid blood vessels and nerves that may be in the intended pathway to be created by the dissection. Another potential problem is that of slipping or other displacement of the band from its intended location which often requires another procedure to reposition, replace or altogether remove the band. After placing the band around the fundus-cardia junction, the ends of the band must be connected together and then it must be cinched down into place. Additionally, complications such as erosion at the fundus-cardia junction, slippage of the band from its intended location, nausea/vomiting, gastroesophageal reflux, dysphagia and lack of effectiveness in causing weight loss have been reported.

Intra-gastric balloons have also been placed, in an attempt to fill a portion of the volume in the stomach, with the theory being that it will then require less food than previously, to give the patient a sensation of fullness or satiety. This procedure involves delivery of a balloon (typically, trans-orally) to the interior of the stomach and inflation of the balloon to take up a portion of the volume inside the stomach. However, intra-gastric balloons may also lead to complications such as obstruction, vomiting and/or mucosal erosion of the inner lining of the stomach. The balloon can break down over extended exposure to the stomach's acids, and in some cases, after breaking down, the balloon translated through the intestines and caused a bowel obstruction.

Gastrointestinal sleeves have been implanted to line the stomach and/or a portion of the small intestines to reduce the absorptive capabilities of the small intestine and/or to reduce the volume in the stomach, by reducing the available volume to the tubular structure of the graft running therethrough. Although weight loss may be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy is an operation in which the left side of the stomach is surgically removed. This results in a much reduced stomach which is substantially tubular and may take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch, the size of the stomach is reduced in similar manner to that performed in a sleeve gastrectomy. Additionally, approximately half of the small intestine is bypassed and the stomach is re-connected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves.

An inflatable gastric device is disclosed in U.S. Pat. No. 4,246,893, in which a balloon is inserted anteriorly of the stomach and posteriorly of the left lobe of the liver. The balloon is then inflated to compress the stomach so that it fills with less food that would ordinarily be possible. Not only does this device compress the stomach, but it also compresses the liver, as seen in FIG. 5 of the patent, which may cause complications with the liver function. Additionally, the balloon is simply placed into this location, and there is no assurance that it will not migrate and lose its effectiveness in compressing the stomach to the degree intended. Still further, the balloon is of a simple spherical design, and, as such, extends pressure outwardly in all directions, 360 degrees in all planes. Accordingly, the liver is compressed just as much as the stomach is. Also, the compression forces against the stomach are not ideal, as the spherical balloon conformation does not match the conformation of the expanding stomach. The stomach is not spherical when expanded, or concave with a constant radius of curvature, but expands into a designated space that allows the fundus to expand preferentially more than other parts of the stomach.

U.S. Pat. No. 7,717,843 and U.S. Patent Application Publication No. 2005/0261712 to Balbierz et al. describe capturing a device against the outer surface of the stomach wall to form a restriction that appears to function similarly to the restriction imposed by the LAPBAND™. The anchoring of the devices disclosed relies upon placement of features against the internal wall of the stomach to form an interlock with the device which is placed against the external wall of the stomach. The placement of features against the internal wall runs the risk of erosion of the mucosa, digestion and/or displacement of the features against the internal wall, and other risks associated with implanting within the stomach, as described above.

U.S. Pat. No. 6,981,978 to Gannoe discloses devices for reducing the internal cavity of the stomach to a much smaller volume, which may be used to carry out a bypass procedure. Stapling is employed to isolate the smaller volume in the stomach, and thus the same potential disadvantages are present as with other stapling procedures used to staple the stomach together in mucosa to mucosa contact as described herein.

U.S. Pat. No. 6,186,149 to Pacella et al. describes an occluder device that can be used as a dietary control device (see FIG. 8C). The occluder device is placed against the wall of the stomach and inflated to press inwardly on the stomach wall. A frame is wrapped around the stomach wall and is inflated to press against the stomach wall. However, there is no disclosure of how the frame might be adjusted to maintain a position relative to the stomach wall as the size of the stomach varies.

Gastric reduction techniques have been attempted, such as by inserting instruments trans-orally and reducing the volume of the stomach by stapling portions of it together. However, this technique also runs risks such as those described above, such as erosion of the mucosa.

Techniques referred to as gastric pacing endeavor to use electrical stimulation to simulate the normal feedback mechanisms of a patient that signal the brain that the patient is full, or satiated. While these techniques are less invasive than some of the other existing treatments, statistics to date have shown that the amount of weight lost by using such techniques is less than satisfactory.

Currently marketed drugs for weight loss, such as XENICAL®, MERIDIA® and Phen fen have largely failed, due to unacceptable side effects and complications, and sometimes to an ineffective amount of weight loss. Other drugs that are on the horizon include ACCOMPLIA® and SYMLIN®, but these are, as yet, unproven.

The risk and invasiveness factors of currently available surgeries are often too great for a patient to accept to undergo surgical treatment for his/her obesity. Accordingly, there is a need for less invasive, yet effective surgical treatment procedures for morbidly obese patients (patients having a BMI of 35 or greater). Also, since the current surgical procedures are currently indicated only for those patients having a BMI of 40 or greater, or 35 or greater when co-morbidities are present, it would be desirable to provide a surgical procedure that would be available for slightly less obese patients, e.g., patients having a BMI of 30 to 35 who are not indicated for the currently available surgical procedures. It would further be desirable to provide a surgical procedure that would be indicated for obese patients having a BMI in the range of 30-35, as well as for more obese patients.

SUMMARY OF THE INVENTION

According to one aspect of the present invention, a method for decreasing the effective volume of a patient's stomach is provided that includes: contacting and engaging a length of a first end effector to an external surface of the stomach on a first side of the stomach; contacting and engaging a length of a second end effector to an external surface of the stomach on a second side of the stomach opposite the first side; separating the first and second end effectors and opposite sides of the stomach; moving a portion of the stomach through a gap formed by separating the first and second end effectors; and moving the first and second end effectors and the opposite sides of the stomach toward one another to contact folded tissue surfaces adjacent the surfaces engaged by the end effectors into contact with one another.

In at least one embodiment, the method includes attaching the folded tissue surfaces together in serosa-to-serosa contact.

In at least one embodiment, the method includes rotating the first and second end effectors to rotate the stomach so that the portion of the stomach is superior to the gap; wherein moving a portion of the stomach through a gap is assisted by gravity as the portion is dropped through the gap between the first and second end effectors.

In at least one embodiment, the method includes counter-rotating the end effectors after moving the first and second end effectors toward one another to contact folded tissue surfaces adjacent the surfaces engaged by the end effectors into contact with one another.

In at least one embodiment, the rotating comprises rotating by about ninety degrees.

In at least one embodiment, the counter-rotating is an amount about equal to the rotation.

In at least one embodiment, the engaging is performed by applying suction to the surfaces through the end effectors.

In at least one embodiment, the first and second end effectors are distal end portions of a clamping tool.

In at least one embodiment, attaching the folded tissue surfaces together comprises driving sutures from one of the end effectors through the folded tissues and into connection with anchors on the other of the end effectors.

In at least one embodiment, the method includes placing a layer of material adjacent to or between a location where the folded tissues are connected together to discourage the stomach from herniating out between suture connections.

In at least one embodiment, the layer of material discourages ingrowth of tissue therein.

In at least one embodiment, the method includes temporarily installing a bougie in the stomach prior to moving a portion of the stomach, to provide a guide for the resulting size of the lumen through the stomach.

In at least one embodiment, at least a portion of the bougie has clear walls and the bougie is configured to receive a flexible endoscope therein, the method further comprising inserting the flexible endoscope and visualizing within the stomach through the bougie.

In at least one embodiment, the method includes inserting an expandable implant in a plication formed by moving a portion of the stomach through a gap formed by separating the first and second end effectors; and wherein moving the first and second end effectors toward one another to contact folded tissue surfaces adjacent the surfaces engaged by the end effectors into contact with one another surrounds the expandable implant.

In at least one embodiment, the method includes placing a layer of material adjacent to or between a location where the folded tissues are connected together to discourage the stomach from herniating out between connections.

In at least one embodiment, the layer of material extends from and is connected to or integral with the expandable implant.

In at least one embodiment, the layer of material discourages ingrowth of tissue therein.

In at least one embodiment, attaching the folded tissue surfaces together in serosa-to-serosa contact comprises simultaneously driving a plurality of attachment members through the folded tissue surfaces, wherein the attachment members are configured along a length direction relative to the end effectors.

In another aspect of the present invention, an instrument for use in modifying a patient's stomach by operating on the stomach extragastrically to decrease the effective volume of the patient's stomach is provided that includes: a first elongate end effector at a distal end portion of the instrument, the first elongate end effector having a first operational surface configured to contact an external surface of the patient's stomach; a second elongate end effector at a distal end portion of the instrument, the second elongate end effector having a second operational surface configured to contact an external surface of the patient's stomach on a location opposite of where the first elongate end effector is configured to contact the external surface of the stomach, and wherein the second operational surface opposes the first operational surface; a first plurality of suction ports extending along a length of the first elongate end effector and configured to deliver suction to the external surface of the stomach to engage the first elongate end effector therewith; and a second plurality of suction ports extending along a length of the second elongate end effector and configured to deliver suction to the external surface of the stomach to engage the second elongate end effector therewith.

In at least one embodiment, the first and second pluralities of suction ports are configured to apply suction in an amount sufficient to pull opposite walls of the stomach apart when the first and second elongate end effectors are engaged therewith and the first and second elongate end effectors are moved apart from one another, and wherein the opposite walls are pulled apart without losing engagement of the first and second elongate end effectors therewith.

In at least one embodiment, the first elongate end effector has a first distal end portion and a first proximal end portion and the second elongate end effector has a second distal end portion and a second proximal end portion, wherein the first and second elongate end effectors are pivotally connected at the first and second proximal end portions, and wherein the first and second distal end portions include first and second free distal ends, respectively.

In at least one embodiment, the instrument further includes means for driving a plurality of connectors from the first elongate end effector, through stomach tissue and to the second elongate end effector.

In at least one embodiment, the instrument further includes means for fixing the connectors to maintain a plication in the stomach.

In at least one embodiment, the suction ports are elongated.

In at least one embodiment, the instrument further includes an elongate shaft extending proximally from proximal end portions of the first and second elongate members.

In at least one embodiment, the instrument further includes an actuator located on a handle at a proximal end portion of the elongate shaft, the actuator being configured to actuate at least one function of the elongate end effectors.

In at least one embodiment, the instrument further includes a plurality of suture drivers extending along a length of the first elongate end effector.

In at least one embodiment, the instrument further includes a plurality of suture anchors extending along a length of the second elongate end effector and opposing the plurality of suture drivers, respectively.

In at least one embodiment, the instrument further includes a plurality of sutures releasably engaged with the plurality of suture drivers, respectively.

In at least one embodiment, each suture extends through a suture lock releasably provided on the first elongate end effector.

In at least one embodiment, each suture comprises an anchor mate mounted on a distal end portion thereof, the anchor mate being configured to engage with and connect to the anchor.

In at least one embodiment, the instrument is further provided with a layer of material configured to be placed adjacent to or between locations where the connectors from the first elongate end effector are configured to pass through the stomach tissue and to the second elongate end effector.

In at least one embodiment, the layer of material discourages ingrowth of tissue therein.

In at least one embodiment, an expandable implant is provided that is configured to be implanted in a plication created by the instrument.

In at least one embodiment, a bougie is provided that is configured to be temporarily placed in the stomach prior to forming a plication with the instrument.

In at least one embodiment, at least a portion of the bougie has clear walls and the bougie is configured to receive a flexible endoscope therein.

In at least one embodiment, a flexible endoscope is provided that is insertable into the bougie.

In another aspect of the present invention, a system for use in modifying a patient's stomach by operating on the stomach extragastrically to decrease the effective volume of the patient's stomach is provided that includes: an engagement instrument comprising: a first elongate end effector at a distal end portion of the engagement instrument, the first elongate end effector having a first operational surface configured to contact an external surface of the patient's stomach; a second elongate end effector at a distal end portion of the engagement instrument, the second elongate end effector having a second operational surface configured to contact an external surface of the patient's stomach on a location opposite of where the first elongate end effector is configured to contact the external surface of the stomach, and wherein the second operational surface opposes the first operational surface; a first plurality of suction ports extending along a length of the first elongate end effector and configured to deliver suction to the external surface of the stomach to engage the first elongate end effector therewith; and a second plurality of suction ports extending along a length of the second elongate end effector and configured to deliver suction to the external surface of the stomach to engage the second elongate end effector therewith; and a stitching instrument comprising: a third elongate end effector at a distal end portion of the stitching instrument, the third elongate end effector having a third operational surface configured to contact an external surface of the patient's stomach; a fourth elongate end effector at a distal end portion of the stitching instrument, the fourth elongate end effector having a fourth operational surface configured to contact an external surface of the patient's stomach on a location opposite of where the third elongate end effector is configured to contact the external surface of the stomach, and wherein the fourth operational surface opposes the third operational surface; a plurality of suture drivers extending along a length of the third elongate end effector; and a plurality of suture anchors extending along a length of the fourth elongate end effector and opposing the plurality of suture drivers, respectively.

In at least one embodiment, the first and second pluralities of suction ports are configured to apply suction in an amount sufficient to pull opposite walls of the stomach apart when the first and second elongate end effectors are engaged therewith and the first and second elongate end effectors are moved apart from one another, and wherein the opposite walls are pulled apart without losing engagement of the first and second elongate end effectors therewith.

In at least one embodiment, the first elongate end effector has a first distal end portion and a first proximal end portion and the second elongate end effector has a second distal end portion and a second proximal end portion, wherein the first and second elongate end effectors are pivotally connected at the first and second proximal end portions, and wherein the first and second distal end portions include first and second free distal ends, respectively.

In at least one embodiment, the suction ports are elongated.

In at least one embodiment, the system further includes an elongate shaft extending proximally from proximal end portions of the first and second elongate members.

In at least one embodiment, the system further includes an actuator located on a handle at a proximal end portion of the elongate shaft, the actuator being configured to actuate at least one function of the elongate end effectors.

In at least one embodiment, the system further includes a plurality of sutures releasably engaged with the plurality of suture drivers, respectively.

In at least one embodiment, each suture extends through a suture lock releasably provided on the third elongate end effector.

In at least one embodiment, each suture comprises an anchor mate mounted on a distal end portion thereof, the anchor mate being configured to engage with and connect to the anchor.

In at least one embodiment, the system further includes a layer of material configured to be placed adjacent to or between locations where the suture drivers from the third elongate end effector are configured to pass through the stomach tissue and to the suture anchors on the fourth elongate end effector.

In at least one embodiment, the layer of material discourages ingrowth of tissue therein.

In at least one embodiment, the system further includes expandable implant attached to or integral with the layer of material and configured to be implanted in a plication created by the instruments.

In at least one embodiment, the system further includes an expandable implant configured to be implanted in a plication created by the instruments.

In at least one embodiment, the system further includes a bougie configured to be temporarily placed in the stomach prior to forming a plication with the instruments.

In another aspect of the present invention, a method for decreasing the effective volume of a patient's stomach is provided that includes: contacting a length of an end effector to an external surface of the stomach; forming a fold in the stomach and positioning the fold over a portion of the end effector; and simultaneously driving a plurality of attachment members through the fold, wherein the attachment members are configured along a length direction relative to the end effector.

In at least one embodiment, forming a fold in the stomach comprises forming a pair of folds in the stomach, and wherein positioning the fold over a portion of the end effector comprises positioning each of the pair of folds over portions of the end effector on opposite sides of the end effector.

In at least one embodiment, the attachment members through the fold are located in the upper third of the stomach.

In at least one embodiment, the method further includes withdrawing the end effector while leaving the attachment members in place in the fold.

In at least one embodiment, the method further includes attaching a strip to the fold via the attachment members, wherein the strip is configured to encourage tissue ingrowth on a side of the strip that contacts the fold.

In at least one embodiment, a side of the strip opposite the side configured to encourage tissue ingrowth is configured to discourage tissue ingrowth.

In at least one embodiment, the method further includes installing a device between an external surface of the stomach and the fold using the end effector.

In at least one embodiment, the method further includes withdrawing the end effector and drawing down the attachment members to securely implant the device.

In at least one embodiment, the device is an expandable device, the method further comprising expanding the device to further reduce the effective volume of the stomach.

In at least one embodiment, the expandable device is fillable, and wherein the expanding is carried out by increasing an amount of fill in the device.

In at least one embodiment, the fill comprises a fluid.

In at least one embodiment, the pair of folds are positioned over the opposite sides of the end effector using a grasping device and are held in position by pushing the folds onto tissue pins on the end effector.

In at least one embodiment, the method further includes removing the end effector after driving the attachment members through the folds and tightening the attachment members to draw portions of the folds into serosa-to-serosa contact.

In at least one embodiment, the end effector engages tissue of the stomach and drives the tissue to perform the positioning of the fold.

In at least one embodiment, the end effector engages the tissue and drives the tissue to perform the forming of a fold.

In at least one embodiment, opposite side portions of the end effector engage tissue of the stomach and drive the tissue to perform the positioning of the folds.

In at least one embodiment, the opposite side portions of the end effector engage the tissue and drive the tissue to perform the forming a pair of folds.

In at least one embodiment, the method further includes: inserting a guide tool within the stomach; and aligning the length of the end effector with the stomach.

In another aspect of the present invention, a method for decreasing the effective volume of a patient's stomach is provided that includes: contacting a length of an end effector to an external surface of the stomach; forming a pair of folds in the stomach and positioning the folds over opposite side portions of the end effector; and connecting the folds to one another.

In at least one embodiment, the folds are connected in serosa-to-serosa contact.

In at least one embodiment, the method further includes removing the end effector after the connecting of the folds to one another.

In at least one embodiment, the method further includes overlaying a conjunction member on the folds to bridge the folds.

In at least one embodiment, the method further includes placing a device between an external surface of the stomach and the folds.

In at least one embodiment, the device is an expandable device, the method further comprising expanding the device to further reduce the effective volume of the stomach.

In at least one embodiment, the expandable device is fillable, and wherein the expanding is carried out by increasing an amount of fill in the device.

In at least one embodiment, the fill comprises a fluid.

In at least one embodiment, the method further includes: inserting a guide tool within the stomach; and aligning the length of the end effector with the stomach.

In another aspect of the present invention, a method for decreasing the effective volume of a patient's stomach is provided that includes: contacting an end effector carrying an implantable device to an external surface of the stomach; forming a pair of folds in the stomach and positioning the folds over opposite side portions of the end effector; and connecting the folds to one another.

In at least one embodiment, the method further includes removing the end effector while leaving the device in position between an external surface of the stomach and the pair of folds.

In at least one embodiment, the method further includes expanding the device to further reduce the effective volume of the stomach.

In another aspect of the present invention, an instrument for use in modifying a patient's stomach by operating on the stomach extragastrically is provided that includes: an elongate end effector at a distal end portion of the instrument, the end effector having a distal end, a proximal end and first and second sides; an elongate shaft extending proximally from the proximal end of the end effector, the shaft having sufficient length so that a proximal end of the shaft extends out of the patient's body when the end effector is placed on the patient's stomach; a plurality of piercing members extending lengthwise along the end effector; and a plurality of attachment members extending lengthwise along the end effector, the attachment members configured and positioned to be driven through a fold in the stomach.

In at least one embodiment, the instrument further includes an elongate strap configured and dimensioned to attach to the distal and proximal end of the end effector, to hold the fold in approximation to the end effector.

In at least one embodiment, the plurality of piercing members are arranged along both sides of the end effector.

In at least one embodiment, the attachment members are arranged along both sides of the end effector.

In at least one embodiment, the instrument further includes a driving mechanism configured to drive the fold over a side portion of the end effector.

In at least one embodiment, the driving mechanism is configured to drive tissue of the stomach into a conformation comprising the fold.

In at least one embodiment, the instrument further includes a pair of the driving mechanisms one on the first side and one on the second side, the mechanisms configured to drive a pair of folds over opposite side portions of the end effector.

In at least one embodiment, the instrument further includes receptacles configured to receive and attach to the attachment members after the attachment members are driven through the fold.

In at least one embodiment, the instrument further includes a conjunction member connected to the plurality of attachment members.

In at least one embodiment, the conjunction member is connected to the attachment members via sutures.

In at least one embodiment, the lengths of the sutures between the conjunction member and the attachments members are adjustable.

In at least one embodiment, the conjunction member is configured to encourage tissue ingrowth on a first surface and is configured to prevent tissue ingrowth on an opposite surface.

In at least one embodiment, the instrument is provided in combination with an implantable device releasably attached to the instrument.

In another aspect of the present invention, a system for use in modifying a patient's stomach by operating on the stomach extragastrically to decrease the effective volume of the patient's stomach is provided including: an instrument including: an elongate end effector at a distal end portion of the instrument, the end effector having a distal end, a proximal end and first and second sides; an elongate shaft extending proximally from the proximal end of the end effector, the shaft having sufficient length so that a proximal end of the shaft extends out of the patient's body when the end effector is placed on the patient's stomach; a plurality of piercing members extending lengthwise along the end effector; and a plurality of attachment members extending lengthwise along the end effector, the attachment members configured and positioned to be driven through a fold in the stomach; and an expandable, implantable device releasably attached to the instrument.

In at least one embodiment, the system further includes a driving mechanism configured to drive a fold of the stomach tissue over the device and a side portion of the end effector.

In at least one embodiment, the system further includes a pair of the driving mechanisms configured to drive a pair of folds of the stomach tissue over the device and opposite side portions of the end effector.

In at least one embodiment, the system further includes a conjunction member connected to the plurality of attachment members.

In at least one embodiment, the conjunction member is configured to encourage tissue ingrowth on a first surface and is configured to prevent tissue ingrowth on an opposite surface.

In another aspect of the present invention, a kit for use in modifying a patient's stomach by operating on the stomach extragastrically to decrease the effective volume of the patient's stomach is provided that includes: an implantable device comprising an elongate, tubular expandable member configured and dimensioned to be implanted between a fold created externally on the stomach and an external surface of the stomach; and a conjunction member having first and second opposite surfaces, the first surface being configured to contact the fold and encourage tissue ingrowth; the second surface being configured to prevent tissue ingrowth.

In at least one embodiment, the device is configured and dimensioned to be implanted between a pair of folds created externally on the stomach and an external surface of the stomach, and the conjunction member is configured to bridge and conjoin the two folds.

In at least one embodiment, the device further comprises a conduit in fluid communication with the expandable member, the conduit extending from an end of the expandable member.

In at least one embodiment, the kit further includes a bougie configured and dimensioned to be temporarily inserted in the stomach to function as a guide for placement of formation of the fold and placement of the device.

These and other features of the invention will become apparent to those persons skilled in the art upon reading the details of the instruments, implants, systems and methods as more fully described below.

BRIEF DESCRIPTION OF THE DRAWINGS

FIGS. 3A-3H are various views and partial views of an instrument including end effectors for operating on a stomach extragastrically to decrease the effective volume of the stomach according to an embodiment of the present invention.

FIGS. 5A-5L illustrate various events for the performance of a procedure for decreasing the effective volume of a patient's stomach that includes extragastric procedures on the stomach to create at least one plication, according to another embodiment of the present invention.

FIG. 6 illustrates an instrument that can function as a bougie, according to an embodiment of the present invention.

FIGS. 7A-7I illustrate various events for the performance of a procedure in which a device is implanted within plications formed at external locations of the stomach according to an embodiment of the present invention.

FIG. 9 is a schematic illustration of an alternative mechanism for making a stitch (or simultaneous stitches) through tissue according to an embodiment of the present invention.

FIGS. 10A-10J illustrate various events for the performance of a procedure in which a device is implanted within plications formed at external locations of the stomach according to an embodiment of the present invention.

FIGS. 15A-15E are various views showing an instrument that includes suction for holding stomach tissue in place during a plication procedure, and use thereof, according to an embodiment of the present invention.

FIGS. 17A-17E are various views of an attachment instrument and use thereof, according to another embodiment of the present invention.

FIGS. 23A-23E are various view of an instrument for performing plication according to another embodiment of the present invention.

FIGS. 35A-35F are various views of an instrument for use in performing a plication according to another embodiment of the present invention.

FIGS. 36A-36B are views of an instrument for use in performing a plication that is completed by manual suturing according to an embodiment of the present invention.

FIG. 36C illustrates manual suturing of a plication line according to an embodiment of the present invention.

FIGS. 37A-37C are schematic views illustrating a mechanism for engaging stomach tissue according to an embodiment of the present invention.

DETAILED DESCRIPTION OF THE INVENTION

Before the present systems, devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a suture" includes a plurality of such sutures and reference to "the anchor" includes reference to one or more anchors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Stomach Anatomy

Figure 1A:
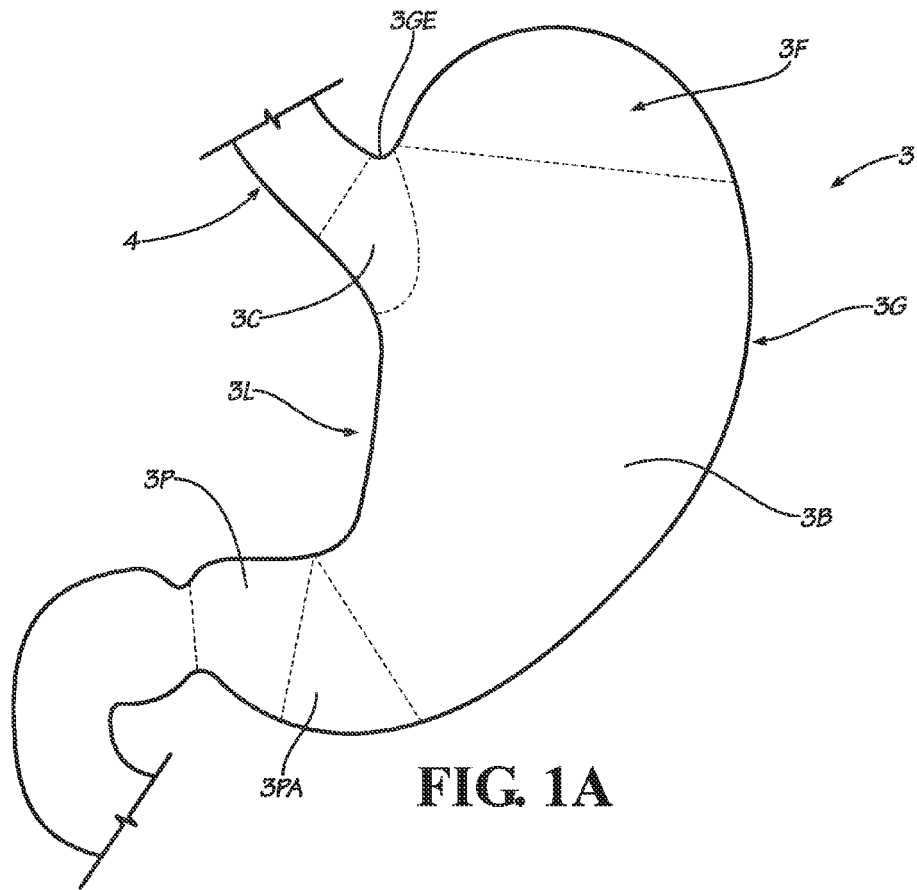
FIG. 1A illustrates basic anatomy of the human stomach.

The stomach 3 is divided into four sections, as indicated by the dashed lines on FIG. 1A. The cardia 3C (see FIG. 1A) is the section that receives the contents of the esophagus 4 to be delivered into the stomach 3. The fundus 3F is the section formed by the upper curvature of the stomach 3. The body 3F is the main, central region of the stomach, and the pylorus 3P is the lower section of the stomach 3 that facilitates emptying of the contents of the stomach 3 into the small intestine/duodenum 4. The region between the body 3B and pylorus 3P is referred to as the pyloric antrum 3PA. The greater curvature 3G of the stomach is directed mainly forward and is typically about four or five times as long as the lesser curvature 3L of the stomach, that is formed on the opposite side of the stomach 3 from the greater curvature 3G.

Figure 1B:
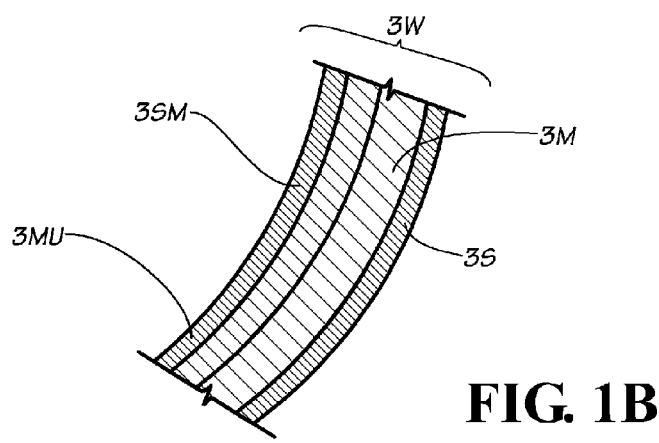
FIG. 1B is a partial, sectional illustration showing different layers of the stomach wall.

The stomach wall is made up of layers of tissues. The serosa or serosal layer 3S forms the outer layer of the stomach wall 3W, see FIG. 1B, and covers the muscularis layer 3M. The mucosa or mucosal layer 3MU forms the inner lining of the stomach, and the submucosal layer interconnects the mucosa 3MU with the muscularis 3M.

Methods, Instruments, Devices and Systems

The present invention provides methods, instruments, devices and systems for reducing the effective volume of a stomach by performing one or more extragastric plications of the stomach. As noted, the plications are performed from outside of the stomach. In some, but not all embodiments, the plication results from attachment that does not penetrate through the entire wall of the stomach. Preferably, in performing plication, the one or more plications formed place stomach tissue in serosa to serosa contact, wherein the stomach is folded in on itself and connected in place. Procedures described are repeatable to reliably form a pathway through the stomach that is substantially tube-shaped and which has a diameter which is not too small anywhere along the length thereof to raise an unacceptable risk of obstruction, but which is not too large anywhere along the length thereof to render its weight loss results less effective than expected. In one category, typically, but not necessarily performed by a laparoscopic or percutaneous procedure, only connectors are left in place at the surgical site upon formation of one or more plications. In a second category, a device is inserted within one or more plications, between external wall surfaces of the stomach 3, and is fixed in place there using connectors. Connectors are also used to maintain the plications in place. Preferably the size/volume of the device is adjustable, so that it can be adjusted, after implantation, to provide more or less reduction in the overall internal stomach space. It is noted that although certain embodiments are described with regard to practicing a procedure in the first category, and other specific embodiments are described in regard to practicing a procedure in the second category, the invention is not limited to these embodiments, and each embodiment of instrument/system described can be used to practice either category of procedure unless it would be physically impossible to do so. Also, it is noted that certain features of instruments are described with regard to a particular embodiment, but these features may be interchangeable with other embodiments described herein.

In at least one embodiment, the omentum is dissected from the greater curvature of the stomach. The stomach is rolled up, starting from the greater curvature, toward the lesser curvature, and then the rolled up portion is stitched along at least the superior portion (upper one third of the stomach) to create a pouch and narrowing near the top of the stomach. Optionally an extragastric, expandable implant may be placed in contact with the rolled up portion to provide further assurance of prevention of unrolling and to provide further adjustability of the remaining pouch and sleeve formed by the rolling and stitching.

Referring now to FIGS. 2A-2K, various events are illustrated for the performance of a procedure for decreasing the effective volume of a patient's stomach that includes extragastric procedures on the stomach to create at least one plication, typically a plication including at least a portion of the greater curve 3G of the stomach 3. Accordingly these procedures can be referred to as "greater curve plication" procedures. The procedure shown in FIGS. 2A-2K is a laparoscopic procedure in which ports are installed in a patient for access to the abdominal cavity by not only the instrument shown, but also by other instruments typically used in laparoscopic surgery, such as graspers, endoscope, etc.

Figure 2A:
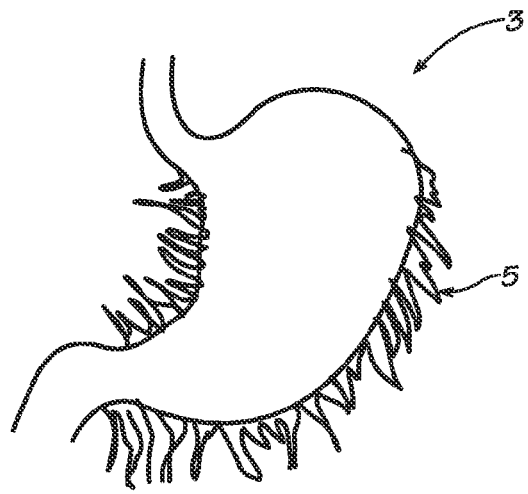
FIGS. 2A-2K illustrate various events for the performance of a procedure for decreasing the effective volume of a patient's stomach that includes extragastric procedures on the stomach to create at least one plication, according to an embodiment of the present invention.
Figure 2B:
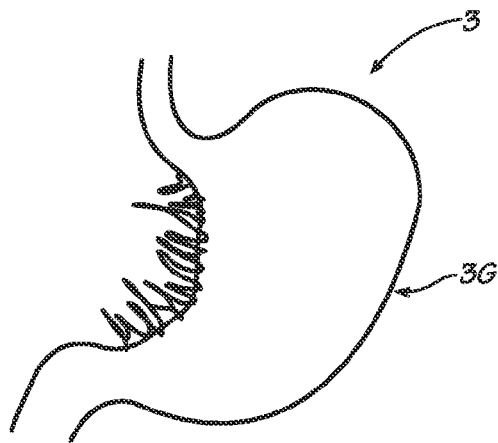
Figure 2C:
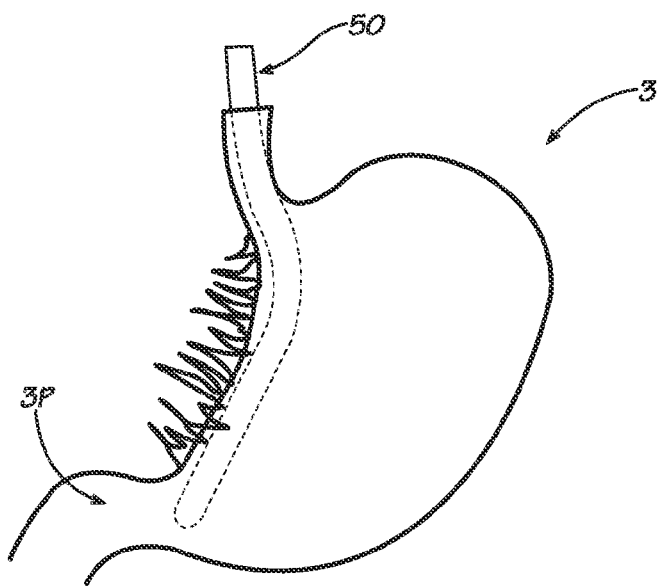
Figure 2D:
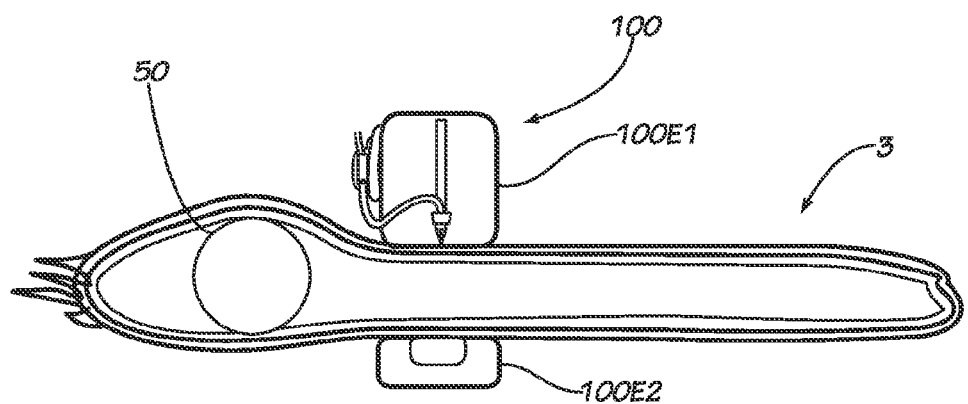

After establishing ports/pathway into the abdominal cavity from outside the patient, the omentum 5 and connective tissues are dissected at the greater curve 3G of the stomach 3 to provide access thereto, see FIGS. 2A-2B. A bougie 50 is inserted trans-esophageally and placed in the stomach 3 in a position such as shown in FIG. 2C. Typically the bougie occupies a pathway extending naturally from the esophagus, through the stomach 3 and into the pylorus 3P, so as to occupy a space similar to what is defined when a sleeve gastrectomy is performed. In one example, the bougie 50 was a size 32 French outside diameter, although this size may vary, up to and including 38 French and 40 French, for example. The bougie 50 acts as a guide so as to better standardize the size(s) and location(s) of plication(s) formed by the procedure as well as to prevent reducing the stomach too aggressively, so as to ensure no blockage locations are inadvertently formed.

An attachment instrument 100 is inserted into the abdominal cavity and a working end is positioned over a location on the stomach where a plication line is intended to be formed. The working end is the distal end portion of the instrument 100 and includes a first end effector 100E1 and a second end effector 100E2 extending alongside and opposing first end effector 100E1. One of the end effectors 100E1, 100E2 is placed on a posterior surface of the stomach and the other is placed on an anterior surface of the stomach along a line opposed to a line of the posterior surface that the first end effector contacts. In the embodiment shown in FIG. 2D, end effector 100E1 is contacted to the anterior surface, and end effector 100E2 is contacted to the posterior surface. Alternatively, end effector 100E1 could be contacted to the posterior surface, and end effector 100E2 could be contacted to the anterior surface. The end effectors 100 are positioned close to the bougie 50 so that the diameter of the bougie defines the resulting lumen in the stomach after the plication has been sutured. Optionally, the end effectors may have features that can be adjusted by the surgeon. These features would extend the width of the end effector on the side that is closest to the bougie. This would enable the surgeon to adjust how close the suturing can be placed relative to the bougie. These adjustments could be made differently at the most distal end of the end effectors, compared to the most proximal ends of the end effectors. In this manner, the surgeon could make adjustments to cause the ultimate size of the stomach's lumen to be tighter at the antrum end of the stomach, and looser at the fundus of the stomach, or vice versa. Another option if that the diameter of the bougie can be changed. With the bougie used as a guide for the initial positioning of the end effectors on the stomach's surface such that the end effectors are placed immediately adjacent to the bougie prior to gripping the stomach, the diameter or width of the bougie after gripping but prior to imbricating the stomach can be reduced to allow space between the bougie and the end effectors for the imbricated stomach tissue. This could be accomplished with a two-part bougie, one part of which is removed prior to imbrication, or with an inflatable bougie that allows its diameter to be adjusted while in place.

Figure 2E:
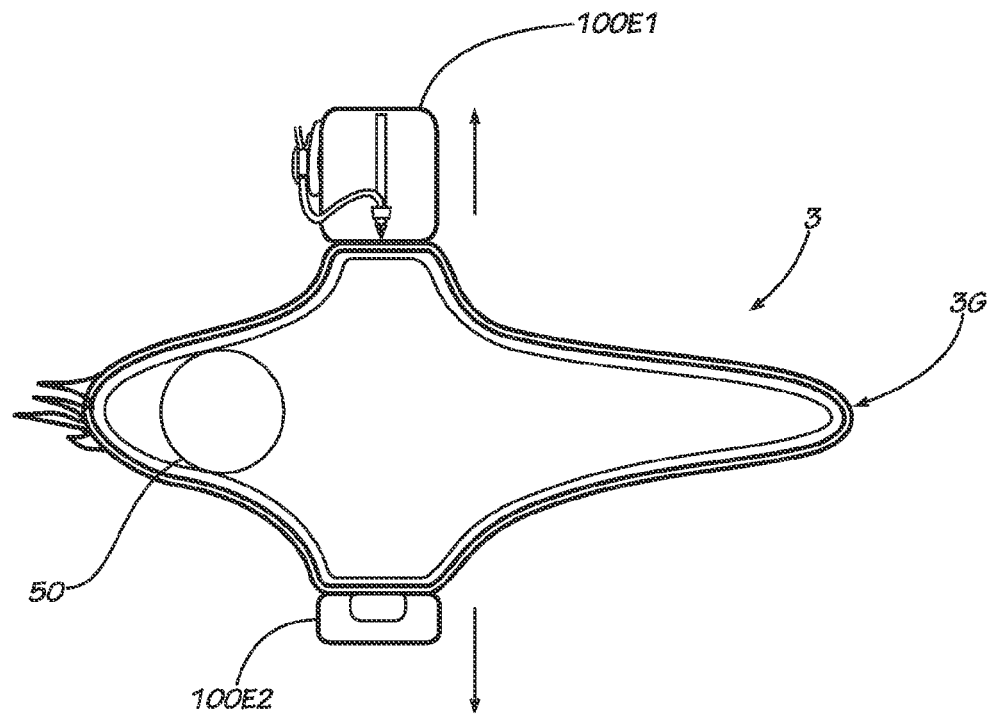

The end effectors 100E1, 100E2 engage the surfaces of the stomach that they are contacted to by application of negative pressure through suction ports defined in the contact surfaces of the end effectors, which are described in further detail below. The engagement forces are sufficiently strong so that when the end effectors 100E1, 100E2 are separated (moved away from one another) as illustrated in FIG. 2E, the portions of the stomach wall engaged by the end effectors are also drawn apart, thereby expanding the interior volume within the stomach. Alternative to moving both end effectors 100E1, 100E2 apart from each other, end effector 100E2 can be maintained stationary while end effector 100E1 is move away from it or end effector 100E1 can be maintained stationary while end effector 100E2 is moved away from it.

Figure 2F:
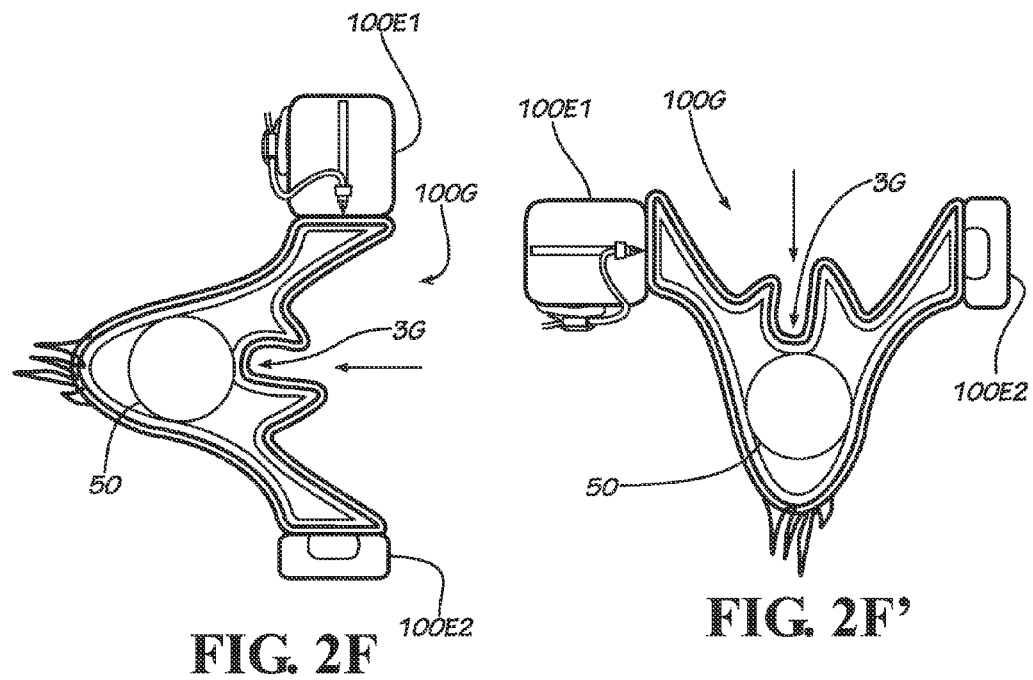

Next, a portion of the stomach forming at least a portion of the greater curvature 3G is plicated, i.e., tucked, into the gap 100G formed by separating the end effectors 100E1, 100E2 as illustrated in FIG. 2F. The plicated portion of the stomach is folded to an extent that it is located on the opposite side of the intended plication line, relative to its pre-plicated location, as can be observed by comparing FIG. 2E with FIG. 2F. Optionally, but preferably, prior to plicating the portion of the stomach, the operator of the instrument 100 may rotate the instrument by about ninety degrees (counterclockwise in the embodiment shown in optional step of FIG. 2F') about its longitudinal axis. This option positions the stomach to allow gravity to assist in plicating the portion 3G through the gap 100G, making the plicating much easier as the portion 3G "falls" in through gap 100G.

Figure 2G:
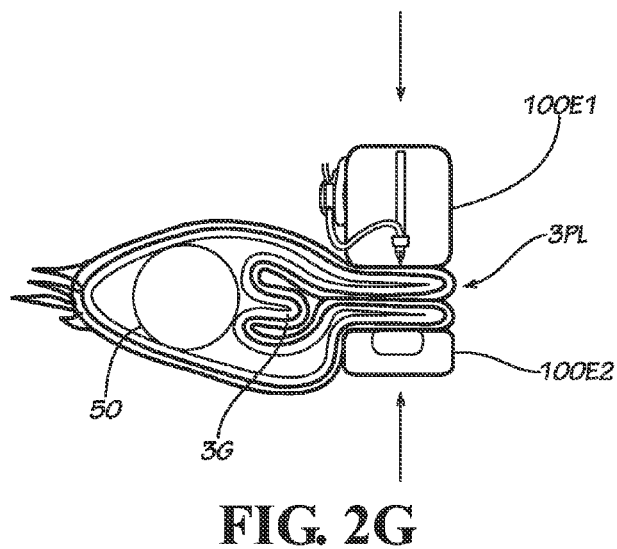
Figure 2H:
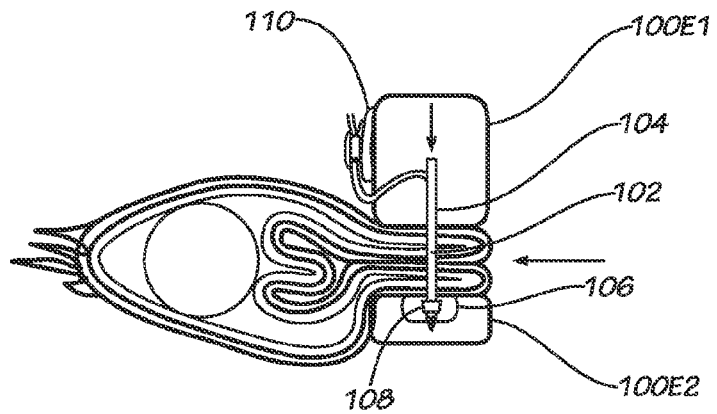
Figure 2I:
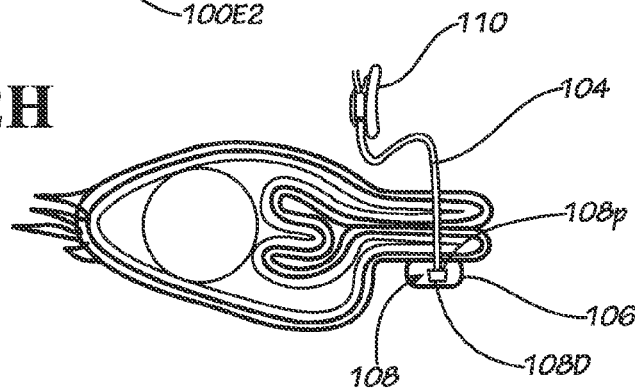
Figure 2J:
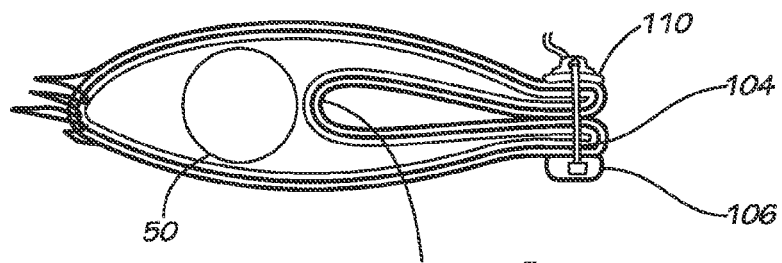

Once the portion 3G has been plicated appropriately according to either optional technique described above, the instrument 100 is then operated to move the end effectors 100E1, 100E2 together again thereby closing the plication as illustrated in FIG. 2G. During this step, and throughout the following steps, the instrument can be maintained in the rotated orientation (as shown in FIG. 2F') or it can be rotated back to the original orientation shown in FIG. 2G. Next instrument 100 is operated to attach the folded tissue surfaces of the stomach together in serosa-to-serosa contact to hold the plication. At FIG. 2H piercing members/suture drivers 102 (preferably needles, but could alternately be screw drives or other elongated members configured to temporarily attach attachment members/sutures to and to drive through the stomach tissues) are deployed from end effector 100E1 to drive attachment members/sutures 104 through the stomach tissues as shown. It should be noted that while FIG. 2G shows the needles penetrating the stomach tissue in a manner where they penetrate through four walls of tissue, the device can alternatively be configured to control the stomach tissue into a position with the location of the suction features such that the needles pierce closer to the edges of the folds. This would enable the needles and suture to transect the wall thickness of the stomach, but not breach the inner surface of the stomach. This alternative approach can be taken for all of the various embodiments described herein. Suture anchors 106 are removably held in end effector 100E2 and are aligned with the piercing member/suture drivers 102. Attachment members/sutures 104 are releasably engaged with piercing members/suture drivers 102. In the embodiment shown in FIG. 2H, attachment members/sutures 104 are each provided with an anchor mate 108 on a distal end portion thereof, preferably at the distal end thereof. Anchor mate 108 is configured to slide over the tapered distal end portion of the suture driver 102, but is prevented from sliding further proximally by the increasing diameter of the taper of the driver 102 distal end portion. The exterior of the anchor mate 108 is also tapered, so that the distal end 108D thereof is of a smaller cross-sectional dimension than the proximal end 108P thereof. This facilitates the driving of the anchor mate 108 into the anchor 106 as shown in FIG. 2H. However, upon withdrawal of the suture driver, the proximal end of the anchor mate 108P is retained by the anchor 106 and the anchor mate 108 slides off the suture driver 102, thereby leaving the anchor mate 108 and suture 104 installed through the tissues as illustrated in FIG. 2I. The end effectors 100E1, 100E2 are designed so that the suture connection elements 102, 104, 106, 108 are repeated along the length of the end effectors, spaced approximately 0.75" from center to center. These repeated elements therefore deploy the suture connection along the length of the desired plication line. It is noted here that if the optional rotation is performed in FIG. 2F', then the instrument is counter-rotated by the amount about the longitudinal axis thereof, to return the stomach to the orientation shown in FIG. 2G or FIG. 2H, either after performing the procedures described above with regard to FIG. 2G or after performing the procedures described above with regard to FIG. 2H.

Attachment members/sutures 104 are also pre-installed through suture locks 110 that are removably mounted on end effector 100E1 and are mounted on attachment members/sutures 104 proximal to the piercing members/suture drivers 102. Once the attachment members/sutures have been driven and anchored as illustrated in FIG. 2H and the stomach has been rotated back to its original orientation, if applicable, instrument 100 is removed from the patient, leaving the attachment members/sutures 104, suture locks 110, suture anchors 106 and suture anchor mates 108 in place as illustrated in FIG. 2I. Suture locks 110 have a one-way locking mechanism, such as a ratcheting type mechanism or other arrangement such as directionally oriented teeth that allow suture 104 to be pulled proximally therethrough, but which prevent attachment members/sutures 104 from backsliding distally therethrough. At FIG. 2J, the attachment members/sutures 104 are cinched by pulling them proximally relative to the suture locks 110 until a desired amount of tension is developed in the attachment members/sutures 104. The attachment members/sutures are cinched tight enough to bring the tissue surfaces into firm contact without creating tissue necrosis or overtightening. Cinching can be performed by the use of laparoscopic graspers (not shown), for example. The bougie 50 can then be removed from the patient and the patient can be closed, according to known techniques, to complete the procedure. Alternatively, the suture locks 110 can be located in end effector 100E1, but on the posterior side in contact with the stomach tissue. Alternatively, the instrument 100 can be left in place until after the sutures 104 are cinched tight and trimmed by the instrument 100, and afterwards the instrument 100 can be removed, leaving the result shown in FIG. 2J. Alternatively, staples or other fasteners could be used in place of the sutures, suture locks, suture anchors and mating anchors.

Figure 2K:
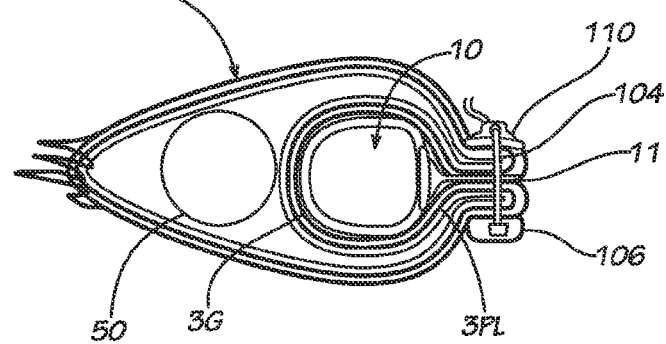
Figure 40A:
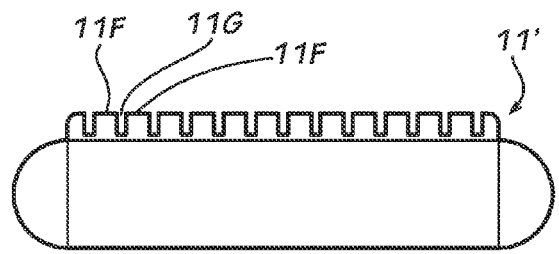
FIGS. 40A-40F illustrate various attachment tabs or fins accordance to various embodiments of the present invention.
Figure 40B:
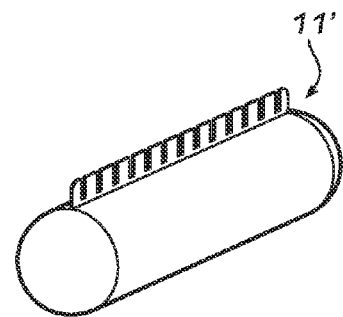
Figure 40C:
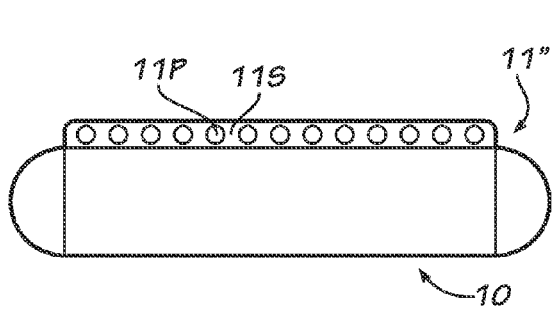
Figure 40D:
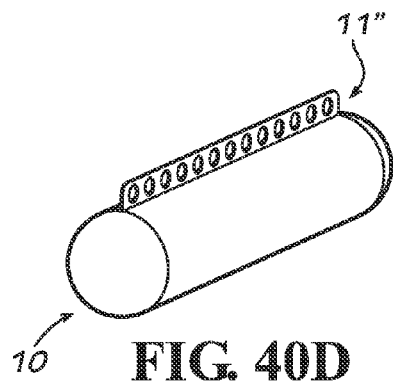
Figure 40E:
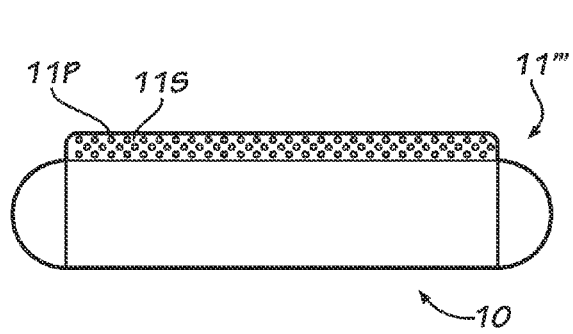
Figure 40F:
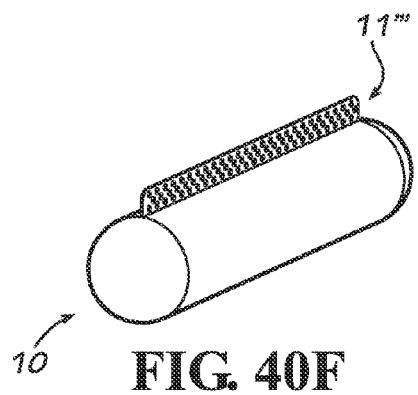

As a further option, an expandable implant 10 may be implanted to fill the inside of the plication 3PL as illustrated in FIG. 2K. The implant may be a silicone bladder, for example, capable of being inflated by biocompatible fluid such as liquid, gas, or a combination of fluids (gases, liquids, or liquids and gases). Implant 10 is connected in fluid communication to a subcutaneous fill port 80 via fill tube 12 (such as illustrated in FIG. 7H, for example, and described in detail in our previous applications which have been incorporated herein, in their entireties, by reference thereto) Subcutaneous fill port 80 can be accessed after completion of the procedure to adjust the fill volume (either increase or decrease) of implant 10. Other implants 10 may be substituted, but need to be expandable and are preferably controllable as to amount of expansion. A tab or wing 11, 11', 11", 11''' may be provided to extend from the expandable body of the implant 10 and can be inserted between the tissue folds at the plication suture line so that the attachment members/sutures 104 are also installed through the tab or wing 11, 11', 11", 11''' to thereby securely hold the implant in place, as illustrated in FIG. 2K. The tab or wing 11, 11', 11", 11''' may be made of a mesh-reinforced silicone, for example. Alternatively, all or a portion of tab or wing 11, 11', 11", 11''' may be made of a tissue ingrowth encouraging material such as DACRON or the like. Alternatively, the implant may be fixed in place by connecting only to the superior and inferior ends of the plication suture line, or by connecting to one or more of the suture locks 110 and/or suture anchors 106. By making the exteriors of the tab or wing 11, 11', 11", 11''' of silicone, this will prevent tissue ingrowth, rendering the sutured plication procedure reversible. Alternatively, by providing the mesh layers on the surface(s) of the tab or wing 11, this will encourage tissue ingrowth, thereby reinforcing the joinder of the serosa-to-serosa plication line. Alternatively, the wing 11, 11', 11", 11''' can have a shape along its length that is castellated with extensions and indentations, where the extended sections along the length engage with the sutures 104, and where the indentations between the extensions allow the serosa to serosa contact between the stomach tissues to remain and allow for adhesion and tissue ingrowth. The tab or wing 11, 11', 11", 11''' may be a fin, which may be longitudinally extending such that it has a length greater than width such as illustrated in FIGS. 40A-4F, such that it extends along the implant 10 by a greater distance than the distance that it extends from the implant 10. Alternatively, the tab 11, 11', 11", 11'" could extend from the implant 10 by a distance greater than a distance that it extends along the implant 10. The fin may be continuous, porous, or may consist of a series of fingers. The embodiments are shown as linear embodiments, but it is within the scope of the present invention that the implant and tab, wing or fin be curved or that the tab, wing or fin be curved, or that the tab, wing or fin may be discontinuous in the length direction. FIGS. 40A-40B illustrate an embodiment in which fin 11' includes a plurality of fingers 11F with gaps 11G therebetween. FIGS. 40C-40F show embodiments of fins 11" and 11'", respectively, each having pores 11P therethrough. Pores 11P may be dimensioned to allow tissue to grow between and across on either side of the fin 11", 11'" (and through pores 11P). The plication attachment devices described herein may be designed to attach within/through the pores 11P/gaps 11G or through the solid regions 11S between the pores 11P/gaps 11G. The fingers 11F may be spaced so that they traverse the space between the plication attachment locations or they may be captured in part or in full under the locations/attachment points on the instrument. The material of the fin 11, 11', 11", 11'" may be of a tissue ingrowth preventing material such as silicone or the like, or may be made partly or entirely of a mesh-like or tissue ingrowth promoting material such as DACRON or the like. The fin 11, 11', 11", 11'" should have enough flexibility to be adhered within the plication yet minimize the force imparted by the device on the attachment points. The fin 11, 11', 11", 11'" may have a coupling region that temporarily aligns it with the plication attachment instrument so that it is properly located while the plication attachments are being formed.

FIG. 3A is a perspective view of instrument 100 including end effectors 100E1 and 100E2 for operating on the stomach extragastrically to decrease the effective volume of the patient's stomach according to an embodiment of the present invention. First and second elongate end effectors 100E1, 100E2 are formed at a distal end portion of instrument 100. End effector 100E1 has an operational surface 100ES1 configured to contact an external surface of the patient's stomach 3 and end effector 100E2 has an operational surface 100ES2 configured to contact an external surface of the patient's stomach on a location opposite of where the first elongate end effector 100E1 is configured to contact the external surface of the stomach, and operational surface 100ES2 opposes operational surface 100ES1 as shown best in FIG. 3B.

A plurality of suction ports 112 are formed in both end effectors 100E1, 100E2. Suction ports 112 are oriented to extend along a length of each end effector, and are in fluid communication with a source of negative pressure (not shown) provided outside of the patient, proximal of the handle 114 on the proximal end portion of instrument 100 (see FIG. 1). For example, a suction line 116 that is in fluid communication with ports 112 may extend proximally from handle 114 and be configured for connection to a source of negative pressure, such as the suction system of an operating room or other source of negative pressure. Thus the end effectors 100E1, 100E2 are configured to deliver suction to the external surfaces of the stomach 3 to engage the surfaces.

The end effectors 100E1, 100E2 are substantially equal in length and have a length at least greater than half the length of the stomach, more preferably a length nearly as long as or even longer than the length of the stomach. The length is typically a length selected from a range of lengths of instruments. The instrument 100 may be manufactured as a plurality of models having end effectors with different lengths so as to accommodate various lengths of patient's stomachs.

As noted above and illustrated with regard to FIGS. 2D-2E, suction ports 112 are configured to apply suction in an amount sufficient to pull opposite walls of the stomach apart when the end effectors 100E1, 100E2 are engaged therewith and are moved apart from one another. This pulls the opposite walls apart without losing engagement of the end effectors with the walls.

Figure 3F:
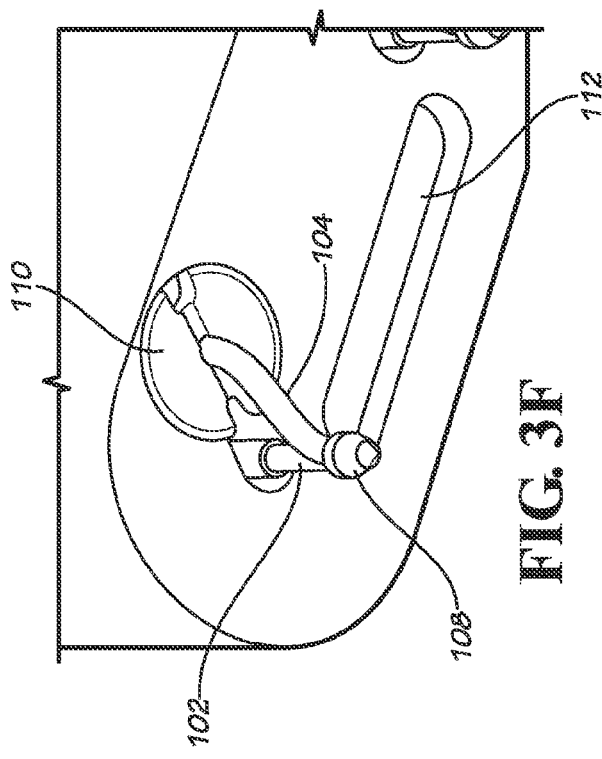
Figure 3D:
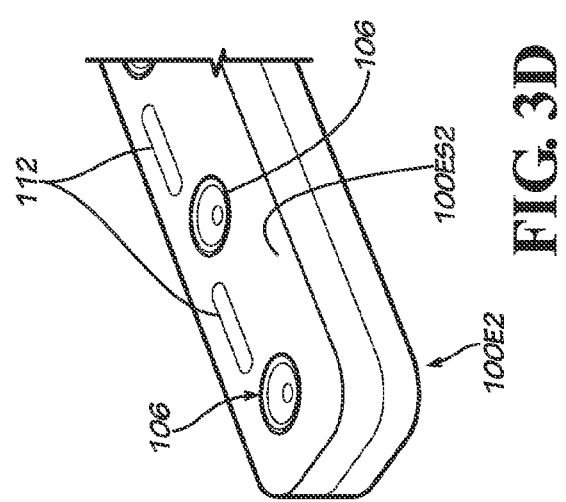
Figure 3E:
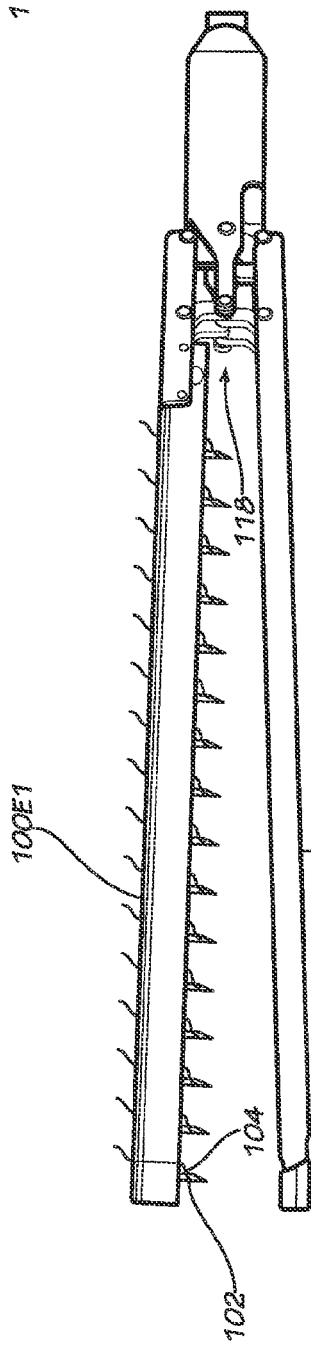

The end effectors 100E1 and 100E2 are pivotally connected at proximal end portions thereof as shown in FIGS. 3A, 3E, 3G and 3H by joint mechanism 118. Joint mechanism 118 is a complex joint mechanism that facilitates not only pivoting of the end effectors relative to one another as illustrated in FIGS. 3A and 3E, but also allows the end effectors to be moved non-rotationally, such that they remain parallel to one another over a range of motion from a closed configuration (see FIG. 3G) to and open configuration (see FIG. 3H). Accordingly, instrument 100 can be operated to place the end effectors 100E1, 100E2 into the open configuration of FIG. 3H in which the end effectors are spaced apart but parallel to one another. End effectors 100E1, 100E2 can further be pivoted relative to one another to further separate the free distal ends thereof by a separation distance greater than the distance between the proximal ends thereof, as shown in FIG. 3A. This facilitates the positioning of the end effectors over the external posterior and anterior surfaces of the stomach. Once the end effectors 100E1, 100E2 have been positioned over the intended location of the plication suture line, instrument 100 can be operated to pivot/rotate the end effectors 100E1, 100E2 in the opposite direction to return them to the open position shown in FIG. 3H so that the end effectors are once again parallel to one another. Then the end effectors 100E1, 100E2 are moved toward the closed position, but only by an amount sufficient to close the folded stomach tissues therebetween, but not so much as to risk causing necrosis or other unnecessary tissue damage. The movements of the end effectors are such that they remain parallel to one another over the entire course of this clamping action. Alternatively, the linkage can allow the end effectors 100E1, 100E2 to close so that the proximal end is slightly further apart than the distal end in order to compensate for the typically thicker stomach tissue near the antrum as compared to the thinner tissue near the fundus. The desired amount of clamping may be determined visually by the surgeon and/or feedback from one or more sensors such as a strain gauge or the like that may be provided in one or both of the end effectors (not shown). Alternatively, a linkage may be present at both the proximal end (as shown) and also at the distal end of the end effectors. If a linkage is present at both ends, it can provide improved alignment between the end effectors 100E1, 100E2, and also provide a stronger clamping force which can be advantageous when the suture connections are being deployed. Alternatively, the linkages at both ends can be replaced by a telescoping connection such as a pin that extends from a tubular hole as the end effectors 100E1, 100E2 separate. In such a configuration, the clamping together of the end effectors could be accomplished by the device pulling on cables that are connected to the pin at each end, thereby drawing the pins back into their mating tubular holes and thereby drawing the end effectors back together. This configuration can advantageously draw the ends of the end effectors to varying degrees of closeness that are adjustable to accommodate varying thicknesses of stomach 3 tissue. For example, the distal end of the end effectors could be drawn together closer to clamp around the thinner tissue in the fundus area, compared to the thicker antrum area, where the end effectors could be drawn together less.

Handle 114 is mounted on a proximal end portion of an elongated shaft 120 that connects the end effectors 100E1, 100E2 and connection mechanism 118 therewith, see FIG. 3A. Shaft 120 houses suction line 116 as well as control cables connecting actuator 122 with a mechanism for driving piercing members/suture drivers 102. Shaft 120 has a length sufficient to position handle 114 outside of the body of the patient when end effectors 100E1, 100E2 are contacted to and engaged with stomach tissue in a manner as described above. Once the end effectors 100E1, 100E2 have been clamped to close the plication by a sufficient force as described above and illustrated in FIG. 2G, actuator 122 is squeezed to actuate the driving of the piercing members/suture drivers 102 as illustrated in FIG. 2H.

As shown in FIG. 3C, the suture locks 110 are removably mounted to the operational surface 100ES1 of end effector 100E1. As shown in FIG. 3D, the suture anchors 106 are removably mounted to the operational surface 100ES2 of end effector 100E2. FIG. 3E is a partial view of the instrument 100 (distal end portion view) showing the piercing members/ suture drivers partially retracted after firing. FIG. 3F is an enlarged detail view of the distal end of the end effector 100E1 of FIG. 3F that shows the suture driver 102, suture 104, suture lock 110 and anchor mate 108. As also shown in FIGS. 3C-3D, suction ports are preferably shaped as elongated slots that are elongated in the direction of the longitudinal axes of the end effectors. FIG. 3G shows the end effectors 100E1, 100E2 in a clamped configuration. FIG. 3H shows the end effectors 100E1, 100E2 in an unclamped configuration in which they are spaced apart to provide a gap therebetween. It is noted that the joint/linkage 118 is configured to move the end effectors such that they remain substantially parallel to one another when moving between the clamped and unclamped configurations, but that it is also configured to pivot the end effectors relative to one another, as illustrated in FIGS. 3A and 3E.

Figure 4A:
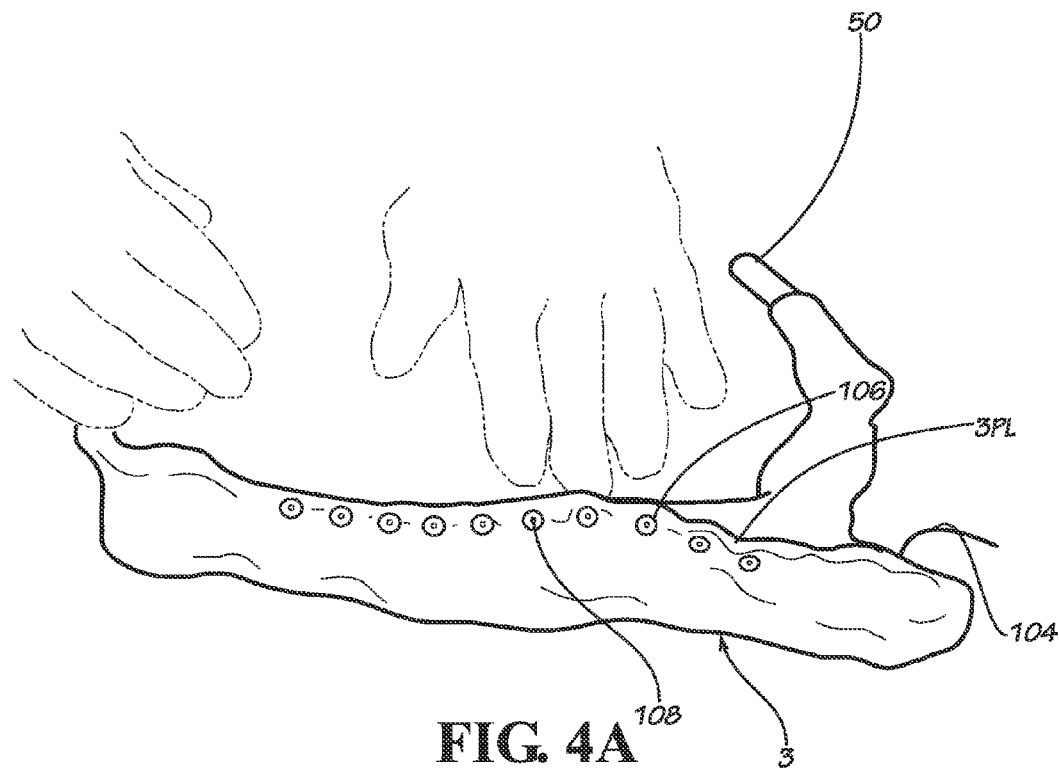
FIGS. 4A-4D are photos of a stomach that has been reduced in effective volume by a procedure according to an embodiment of the present invention.
Figure 4B:
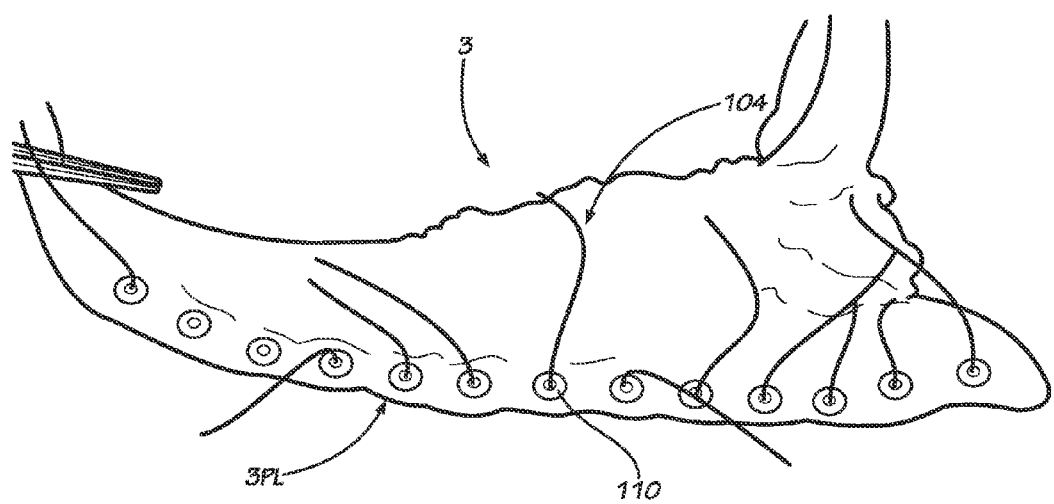
Figure 4C:
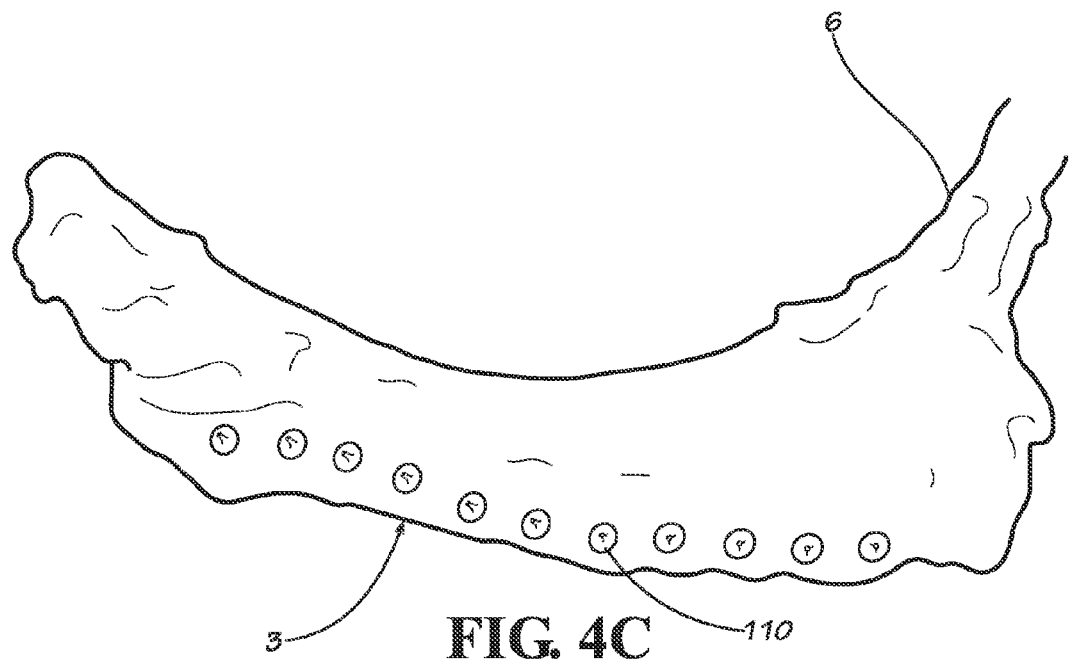
Figure 4D:
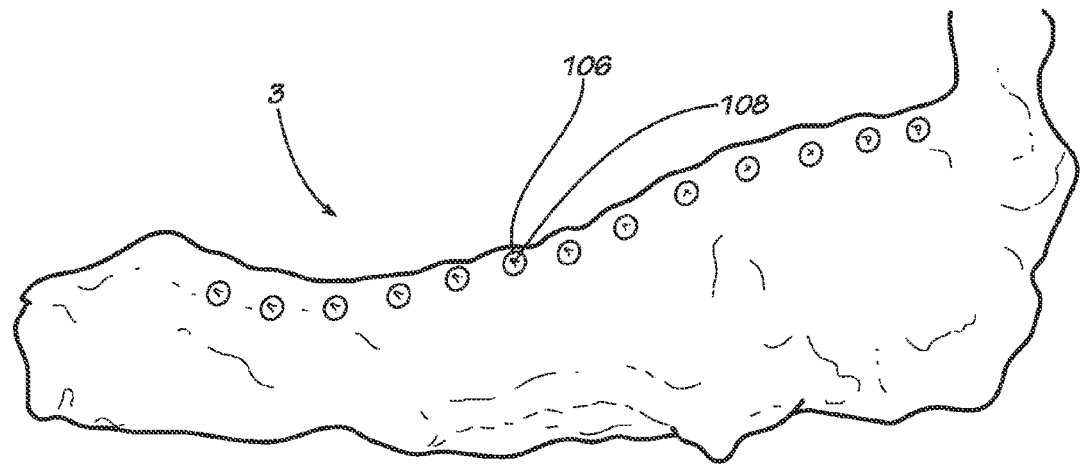

FIGS. 4A-4D are photos of a stomach 3 after performing the procedure described above with regard to FIGS. 2A-2E, 2F' and 2G-2J. With this procedure, there are no anchors or attachment mechanisms left in the stomach. As such the stomach does not have any objects or items in it that it would otherwise try to digest or expel. In FIG. 4A, the stomach 3 has been rotated 90 degrees about is longitudinal axis so to show the posterior side of the stomach 3, showing the mating anchors 108 mated with the suture anchors 106 along the posterior side of the plication line 3PL. In FIG. 4B, the stomach 3 has been counter-rotated by 90 degrees from that in FIG. 4A to show the anterior side of the stomach 3. The suture locks 10 can be seen extending along the plication line 3PL and sutures 104 have been cinched but not yet trimmed. FIG. 4C is an anterior view of the stomach, like FIG. 4B, but wherein the bougie 50 has been removed from the stomach 3 by pulling it out of the esophagus 6 and the sutures 104 have been trimmed off adjacent the suture locks. FIG. 4D is a posterior view of the stomach 3, like FIG. 4A, but where the bougie 50 has been removed from the stomach.

FIGS. 5A-5L illustrate various events for the performance of a procedure alternative to the embodiments described above with regard to FIGS. 2A-2K, for decreasing the effective volume of a patient's stomach that includes extragastric procedures on the stomach to create at least one plication, typically a plication including at least a portion of the greater curve 3G of the stomach 3. Accordingly these procedures can be referred to as "greater curve plication" procedures. The procedures shown are laparoscopic procedures in which ports are installed in a patient for access to the abdominal cavity by not only the instruments shown, but also by other instruments typically used in laparoscopic surgery, such as graspers, endoscope, etc.

After establishing ports/pathway into the abdominal cavity from outside the patient, the omentum 5 and connective tissues are dissected at the greater curve 3G of the stomach 3 to provide access thereto, see FIGS. 5A-5B. A bougie 50 is inserted trans-esophageally and placed in the stomach 3 in a position such as shown in FIG. 5C. Typically the bougie 50 occupies a pathway extending naturally from the esophagus, through the stomach 3 and into the pylorus 3P, so as to occupy a space similar to what is defined when a sleeve gastrectomy is performed. The bougie 50 acts as a guide so as to better standardize the size(s) and location(s) of plication(s) formed by the procedure as well as to prevent reducing the stomach too aggressively, so as to ensure no blockage locations are inadvertently formed.

In the embodiments of FIGS. 5D-5L the functions of instrument 100 are divided among two instruments 200 and 250. Engagement instrument 200 is configured like instrument 100, but without the piercing members/suture drivers 102, attachment members/sutures 104, anchors 106, anchor mates 108, suture locks 110 or any of the actuation mechanisms for driving and attaching attachment members/sutures. However, suction ports 112 are provided in both end effectors in the same manner and connection/joint mechanism 118 is provided and functions in the same manner. Also included are shaft 120, handle 114 and suction line 116. Stitching instrument 250 is configured like instrument 100 with the piercing members/suture drivers 102, attachment members/sutures 104, anchors 106, anchor mates 108, suture locks 110 and actuation mechanisms therefore, but without suctions ports 112 (although, optionally, suction ports may be included in the end effectors of instrument 250) or connection/joint mechanism. Also included are shaft 120, handle 114 and, optionally, suction line 116.

Engagement instrument 200 is inserted into the abdominal cavity and a working end thereof is positioned over a location on the stomach 3 where a plication line 3PL is intended to be formed. The working end is the distal end portion of the instrument 200 and includes a first end effector 200E1 and a second end effector 200E2 extending alongside and opposing first end effector 200E1. One of the end effectors 200E1, 200E2 is placed on a posterior surface of the stomach 3 and the other is placed on an anterior surface of the stomach 3 along a line opposed to a line of the posterior surface that the first end effector contacts. In the embodiment shown in FIG. 5D, end effector 200E1 is contacted to the anterior surface, and end effector 200E2 is contacted to the posterior surface. Alternatively, end effector 200E1 could be contacted to the posterior surface, and end effector 200E2 could be contacted to the anterior surface.

The end effectors 200E1, 200E2 engage the surfaces of the stomach 3 that they are contacted to by application of negative pressure through suction ports defined in the contact surfaces of the end effectors, which are described above in further detail. The engagement forces are sufficiently strong so that when the end effectors 200E1, 200E2 are separated (moved away from one another) as illustrated in FIG. 5E, the portions of the stomach wall engaged by the end effectors are also drawn apart, thereby expanding the interior volume within the stomach 3.

Next, a portion of the stomach forming at least a portion of the greater curvature 3G is plicated (i.e., tucked) into the gap 200G formed by separating the end effectors 200E1, 200E2 as illustrated in FIG. 5F. The plicated portion of the stomach 3 is folded to an extent that it is located on the opposite side of the intended plication line, relative to its pre-plicated location, as can be observed by comparing FIG. 5E with FIG. 5F. Optionally, but preferably, prior to plicating the portion of the stomach 3, the operator of the instrument 200 may rotate the instrument 200 by about ninety degrees (counterclockwise in the embodiment shown in optional step of FIG. 5F'). about its longitudinal axis. This option positions the stomach 3 to allow gravity to assist in plicating the portion 3G through the gap 200G, making the plicating much easier as the portion 3G "falls" in through gap 200G.

Once the portion 3G has been folded appropriately according to either optional technique described above, the instrument 200 is then operated to move the end effectors 200E1, 200E2 together again thereby closing the plication as illustrated in FIG. 5G. Next the surgeon can use a standard laparoscopic needle driver and needle with suture attached thereto, to suture the plication manually. Alternatively, instrument 250 is mounted over the folded tissue layers of the plication so that third end effector 250E1 and fourth end effector 250E2 contact the tissues on opposite sides thereof as shown in FIG. 5H. Instrument 250 fits in gaps in the instrument 200 between suction ports 112. Additionally, a layer of material is mounted in instrument 250 which wraps around from the operation surface of end effector 250E1 to the operational surface of end effector 250E2 (see FIG. 5G) and overlies the locations of the operational surfaces where the piercing members/suture drivers are driven out from, as well as the locations where the suture anchors are removably mounted. After mounting as described, instrument 250 is operated to attach the folded tissue surfaces of the stomach together in serosa-to-serosa contact to hold the plication. At the same time the layer of material 230 is attached to the plication. Material 230 forms a barrier layer that spans the suture line to prevent herniation of the plicated stomach in between the attachment members/sutures, thereby greatly reducing the risk of ischemia. The barrier material may be a sheet or strip of silicone, with or without mesh reinforcement, for example. Whether or not reinforced, the exterior of the strip is silicone, to prevent tissue ingrowth. By preventing tissue ingrowth, this will facilitate reversal of the procedure/plication as the silicone strip will be easily removable. At FIG. 5H piercing members/suture drivers 102 (preferably needles, but could alternately be screw drives or other elongated members configured to temporarily attach attachment members/sutures to and to drive through the stomach tissues) are deployed from end effector 250E1 to drive attachment members/sutures 104 through the material 230 and stomach tissues as shown in FIG. 5I. Suture anchors 106 are removably held in end effector 250E2 and are aligned with the piercing members/suture drivers 102. Attachment members/sutures 104 are releasably engaged with piercing members/suture drivers 102. Upon withdrawal of the piercing members/suture drivers, the proximal ends of the suture mates 108P are retained by the anchors 106 and the suture mates 108 slide off the piercing members/suture drivers 102, thereby leaving the suture mates 108 and attachment members/sutures 104 installed through the tissues and material 230 as illustrated in FIG. 5J. It is noted here that if the optional rotation is performed in FIG. 5F', then the instrument is counter-rotated by the amount about the longitudinal axis thereof, to return the stomach 3 to the orientation shown in FIG. 5G, FIG. 5H, FIG. 5I or FIG. 5J, after performing the procedures described above with regard to FIG. 5G or after performing the procedures described above with regard to FIG. 5H, or after performing the procedures described above with regard to FIG. 5I, or after performing the procedures described above with regard to FIG. 5J.

Attachment members/sutures 104 are also pre-installed through suture locks 110 that are removably mounted on end effector 250E1 and are mounted on attachment members/sutures 104 proximal to the piercing members/suture drivers 102. Once the attachment members/sutures have been driven and anchored as illustrated in FIG. 5I and the stomach 3 has been rotated back to its original orientation, if applicable, instruments 250 and 200 are removed from the patient, leaving the attachment members/sutures 104, suture locks 110, material 230, suture anchors 106 and suture anchor mates 108 in place as illustrated in FIG. 5J. Suture locks 110 have a one-way locking mechanism, such as a ratcheting type mechanism or other arrangement such as directionally oriented teeth that allow suture 104 to be pulled proximally therethrough, but which prevent attachment members/sutures 104 from backsliding distally therethrough. At FIG. 5K, the attachment members/sutures 104 are cinched by pulling them proximally relative to the suture locks 110 until a desired amount of tension is developed in the attachment members/sutures 104, as described previously. Cinching can be performed by the use of laparoscopic graspers (not shown), for example. The bougie 50 can then be removed from the patient and the patient can be closed, according to known techniques, to complete the procedure.

Figure 5D:
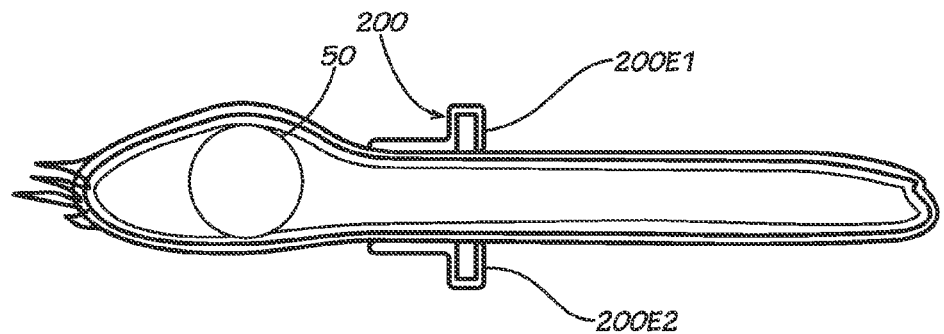
Figure 5E:
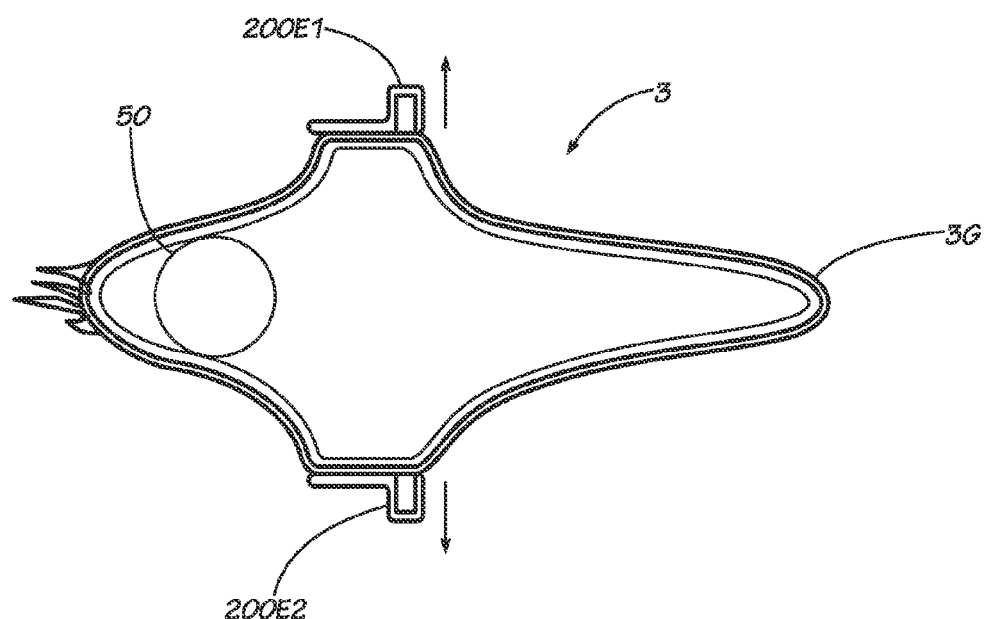
Figure 5I:
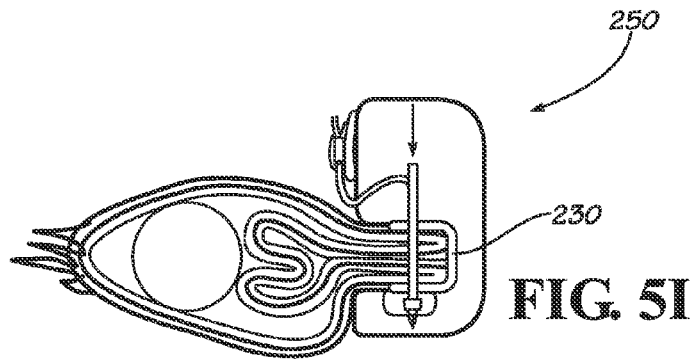
Figure 5J:
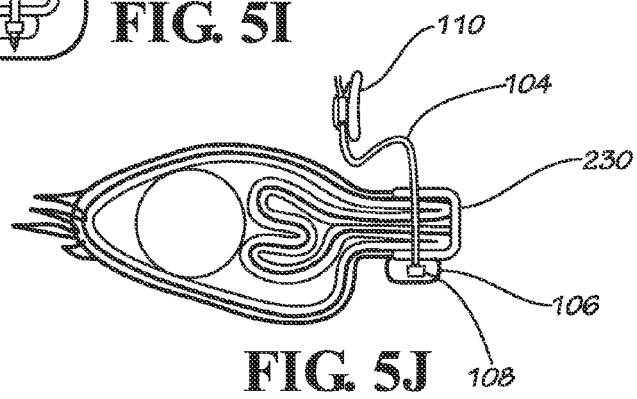
Figure 5K:
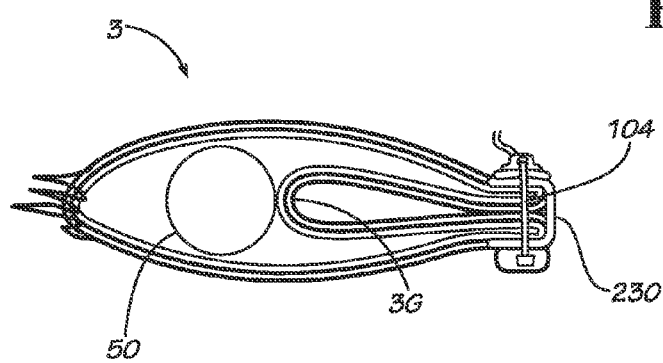
Figure 5L:
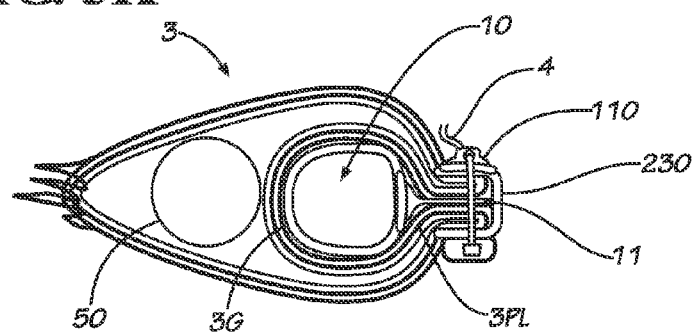

As a further option, an expandable implant 10 may be implanted to fill the inside of the plication 3PL as illustrated in FIG. 5L. The implant 10 may be a silicone bladder, for example, capable of being inflated by biocompatible fluid such as liquid, gas, or a combination of fluids (gases, liquids, or liquids and gases). Implant 10 is connected via fill tubing 12 in fluid communication with a subcutaneous fill port 80, so that the fill volume of implant 10 can be adjusted after implanting it as described from a location outside of the abdominal cavity (e.g., by an operator accessing the subcutaneous fill port 80 with a needle alone or a needle attached to a pressurized source of fluid). Other implants 10 may be substituted, but need to be expandable and are preferably controllable as to amount of expansion. A tab or wing 11, 11', 11", 11''' may be provided to extend from the expandable body of the implant 10 and can be inserted between the tissue folds at the plication suture line so that the attachment members/sutures 104 are also installed through the tab or wing 11, 11', 11", 11''' to thereby securely hold the implant in place, as illustrated in FIG. 5L. The tab or wing 11, 11', 11", 11''' may be made of a mesh-reinforced silicone, for example. Alternatively, the implant 10 may be fixed in place by connecting only to the superior and inferior ends of the plication suture line, or by connecting to one or more of the suture locks 110 and/or suture anchors 106.

FIGS. 5M-5R schematically illustrate an alternative embodiment to the instrumentation used in FIGS. 5A-5L, according to another embodiment of the present invention. In this embodiment, like the embodiment of FIGS. 5A-5L, the procedures shown are laparoscopic procedures in which ports are installed in a patient for access to the abdominal cavity by not only the instruments shown, but also by other instruments typically used in laparoscopic surgery, such as graspers, endoscope, etc. After establishing ports/pathway into the abdominal cavity from outside the patient, the omentum 5 and connective tissues are dissected at the greater curve 3G of the stomach 3 to provide access thereto, the same as in FIGS. 5A-5B. A bougie 50 is inserted trans-esophageally and placed in the stomach 3 in a position such as shown in FIG. 5C. Typically the bougie 50 occupies a pathway extending naturally from the esophagus, through the stomach 3 and into the pylorus 3P, so as to occupy a space similar to what is defined when a sleeve gastrectomy is performed. The bougie 50 acts as a guide so as to better standardize the size(s) and location(s) of plication(s) formed by the procedure as well as to prevent reducing the stomach too aggressively, so as to ensure no blockage locations are inadvertently formed.

Figure 5M:
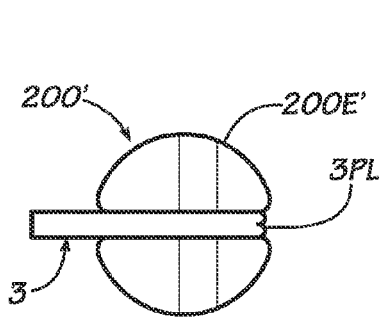
FIGS. 5M-5R schematically illustrate an alternative embodiment to the instrumentation used in FIGS. 5A-5L, according to an embodiment of the present invention.

In the embodiment of FIGS. 5M-5R, engagement instrument 200' (which, like engagement instrument 200 may optionally include secondary, mechanical clamping capability as discussed in more detail below) is configured like instrument 200, except the cross-sectional geometry of end effector 200E' is more compact than end effector 200E (when end effectors 200E1 and 200E2 are closed together), circular as shown, but could be oval, elliptical or other more compact cross-sectional geometry than that of instrument 200, as can be observed by comparing FIG. 5M with FIG. 5D. This more compact cross-sectional configuration is designed to permit the end effector 200E' to be inserted through a relatively smaller diameter port, such as a relatively smaller laparoscopic port. In one embodiment, the cross-sectional configuration of end effector 200E' is configured to enable the end effector 200E' to be passed through a laparoscopic port having a 15 mm inside diameter. The present invention is not limited to this dimension, as it is only an example, and larger or smaller end effectors 200E' may be provided.

Like instrument 200, instrument 200' does not include piercing members/suture drivers 102, attachment members/sutures 104, anchors 106, anchor mates 108, suture locks 110 or any the actuation mechanisms for driving and attaching attachment members/sutures. However, suction ports 112 are provided in both end effectors 200E1', 200E2' and may be in the same manner as in 200 and connection/joint mechanism 118 may be provided to function in the same manner. Also included are shaft 120 (not shown), handle 114 (not shown) and suction line 116 (not shown) all of which may be the same is in instrument 200.

Stitching instrument 250' is configured like instrument 250 except the cross-sectional geometry of the end effector 250E' is more compact than that of end effector 250E, circular as shown, but with a cutout region designed to be placed over the end effectors 200E1', 200E2' as described below, but could be oval, elliptical or other more compact cross-sectional geometry while still retaining the cutout region 252, as can be observed by comparing FIG. 5O with FIG. 5G. This more compact cross-sectional configuration is designed to permit the end effector 250E' to be inserted through a relatively smaller diameter trocar cannula, such as a laparoscopic trocar cannula. In one embodiment, the cross-sectional configuration of end effector 250E' is configured to enable the end effector 250E' to be passed through a laparoscopic trocar cannula having a 15 mm inside diameter. The present invention is not limited to this dimension, as it is only an example, and larger or smaller end effectors 250E' may be provided.

Engagement instrument 200' is inserted into the abdominal cavity and a working end thereof is positioned over a location on the stomach 3 where a plication line 3PL is intended to be formed, like in FIG. 5D. The working end is the distal end portion of the instrument 200' and includes a first end effector 200E1' and a second end effector 200E2' extending alongside and opposing first end effector 200E1', e.g., see FIG. 5N. One of the end effectors 200E1, 200E2 is placed on a posterior surface of the stomach 3 and the other is placed on an anterior surface of the stomach 3 along a line opposed to a line of the posterior surface that the first end effector contacts. As with instrument 200, end effector 200E1 can be contacted to the anterior surface of the stomach 3, and end effector 200E2' can be contacted to the posterior surface. Alternatively, end effector 200E1' could be contacted to the posterior surface, and end effector 200E2' could be contacted to the anterior surface.

The end effectors 200E1', 200E2' engage the surfaces of the stomach 3 that they are contacted to by application of negative pressure through suction ports defined in the contact surfaces of the end effectors, in the same manner as in instrument 200. The engagement forces are sufficiently strong so that when the end effectors 200E1', 200E2' are separated (moved away from one another, similar to what is shown in FIG. 5E), the portions of the stomach wall engaged by the end effectors are also drawn apart, thereby expanding the interior volume within the stomach 3. As already noted, instrument 200', like instrument 200 may optionally include secondary mechanical clamping of the stomach tissue 3 to reinforce the strength of engagement of the end effectors with the stomach tissues, further ensuring that the tissues do not prematurely separate from the end effectors.

Next, a portion of the stomach forming at least a portion of the greater curvature 3G is plicated (i.e., tucked) into the gap 200G formed by separating the end effectors 200E1', 200E2', like what is shown in FIG. 5F. The plicated portion of the stomach 3 is folded to an extent that it is located on the opposite side of the intended plication line, relative to its pre-plicated location, as can be observed by comparing FIG. 5E with FIG. 5F. Optionally, but preferably, prior to plicating the portion of the stomach 3, the operator of the instrument 200' may rotate the instrument 200' by about ninety degrees (counterclockwise, like the embodiment shown in the optional step of FIG. 5F') about its longitudinal axis. This option positions the stomach 3 to allow gravity to assist in plicating the portion 3G through the gap 200G, making the plicating much easier as the portion 3G "falls" in through gap 200G.

Figure 5N:
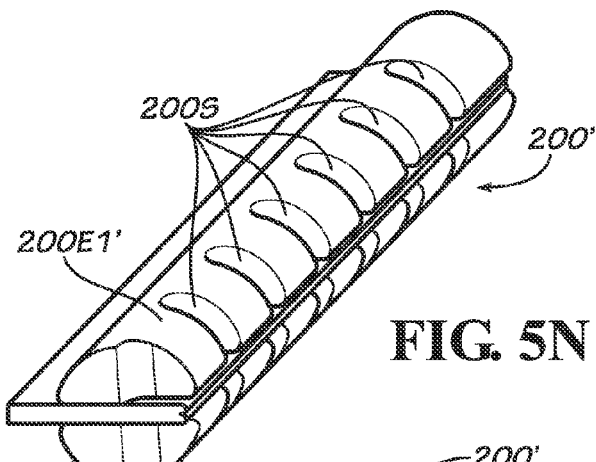
Figure 5O:
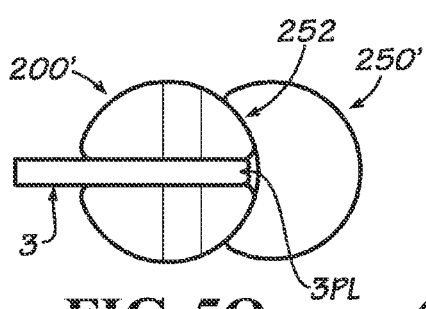
Figure 5P:
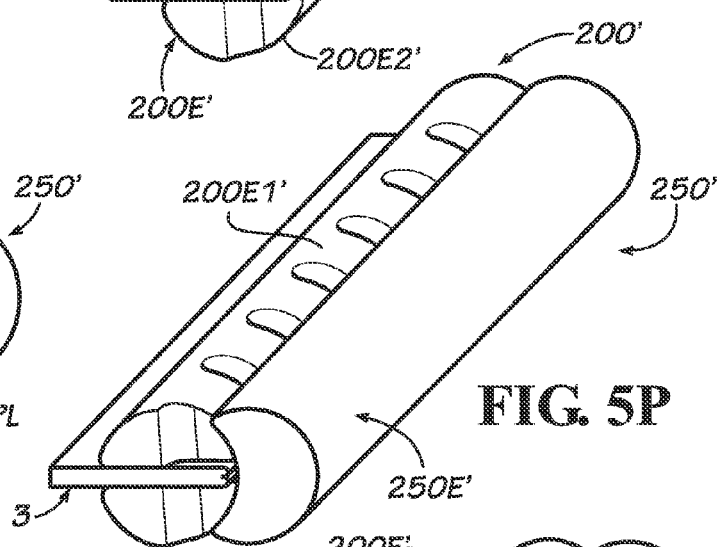
Figure 5Q:
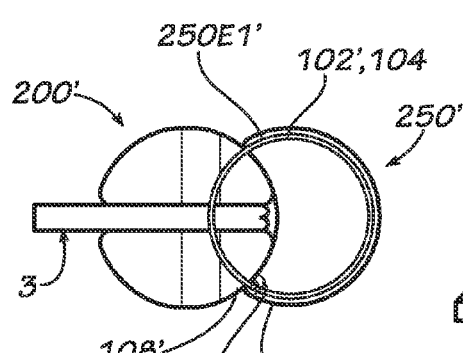
Figure 5R:
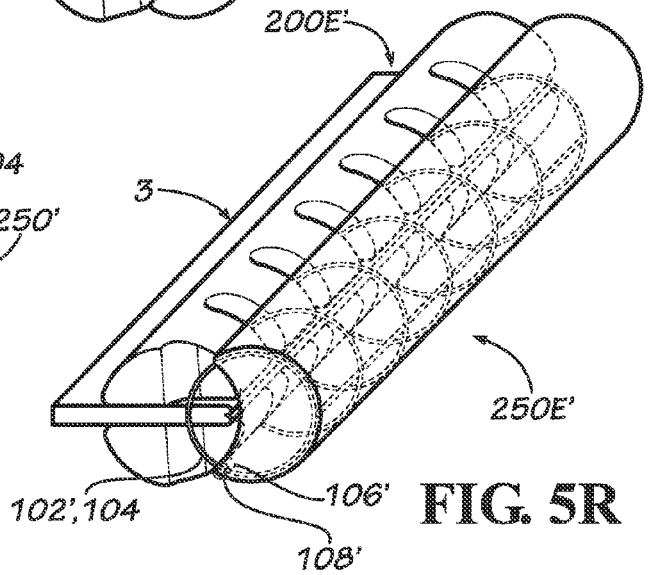

Once the portion 3G has been folded appropriately according to either optional technique described above, the instrument 200' is then operated to move the end effectors 200E1', 200E2' together again thereby closing the plication 3PL as schematically illustrated in FIGS. 5M-5N (distal end view and perspective view, respectively). Optionally the surgeon can use a standard laparoscopic needle driver and needle with suture attached thereto, to suture the plication manually by performing a line of interrupted sutures through slots 200S. Alternatively, instrument 250' is mounted over the folded tissue layers of the plication and instrument 200' as illustrated in FIGS. 5O-5P (distal end view and perspective view, respectively) so that third end effector 250E1' and fourth end effector 250E2' contact and overlie the end effectors 200E1' and 200E2', respectively. End effectors 200E1', 200E2' fit in the cutout region 252 of end effector 250E'. Optionally, a layer of material may be mounted in instrument 250' (not shown in FIGS. 5M-5R, but like that shown in FIG. 5G) to wrap around from the operational surface of end effector 250E1' to the operational surface of end effector 250E2' (see FIG. 5G) and to overlie the locations of the operational surfaces where the piercing members/suture drivers are driven out from, as well as the locations where the suture anchors are removably mounted. By mounting as described, the piercing members/suture drivers 102' are aligned with slots 200S so that they can be rotationally driven out of end effector 250E1', through tissues 3 (and optionally material 230) and into end effector 250E2' where sutures 104 are anchored to anchors 106' via suture mate 108' in much the same manner as described above with regard to FIGS. 5H-5I except that the driving is rotational rather than linear. This permits the end effectors to be made more compact and able to be delivered through relatively smaller ports. FIGS. 5Q-5R schematically illustrate (distal end schematic representation and perspective schematic representation, respectively) piercing members/suture drivers 102' (preferably curved needles, but could alternately be screw drives or other elongated members configured to temporarily attach attachment members/sutures to and to drive through the stomach tissues) are deployed from end effector 250E1' to drive attachment members/sutures 104 through the stomach tissues 3 (and, optionally, material 230). Instrument 250' is operated to attach the folded tissue surfaces of the stomach 3 together in serosa-to-serosa contact to hold the plication. At the same time the layer of material 230, if used, is loosely attached to the plication. Material 230 forms a barrier layer that spans the suture line to prevent herniation of the plicated stomach in between the attachment members/sutures, thereby greatly reducing the risk of ischemia. The barrier material may be a sheet or strip of silicone, with or without mesh reinforcement, for example. Whether or not reinforced, the exterior of the strip is silicone, to prevent tissue ingrowth. By preventing tissue ingrowth, this will facilitate reversal of the procedure/plication as the silicone strip will be easily removable.

Suture anchors 106' are removably held in end effector 250E2' and are aligned with the piercing members/suture drivers 102'. Attachment members/sutures 104 are releasably engaged with piercing members/suture drivers 102'. Upon withdrawal of the piercing members/suture drivers, the proximal ends of the suture mates are retained by the anchors 106' and the suture mates 108' slide off the piercing members/suture drivers 102, thereby leaving the suture mates 108' and attachment members/sutures 104 installed through the tissues and optionally, the material 230. It is noted here that if the optional rotation is performed in FIG. 5F', then the instrument(s) is/are counter-rotated by the amount about the longitudinal axis thereof, to return the stomach 3 to the orientation shown in FIG. 5G, FIG. 5H, FIG. 5I or FIG. 5J, after performing the procedures described above in FIG. 5N or after performing the procedures described above in FIG. 5P, or after performing the procedures described above in FIG. 5R, or after performing the procedures described above like in FIG. 5J.

Attachment members/sutures 104 are also pre-installed through suture locks 110 (like those shown in FIGS. 5I-5J) that are removably mounted on end effector 250E1' and are mounted on attachment members/sutures 104 proximal to the piercing members/suture drivers 102'. Once the attachment members/sutures have been driven and anchored as illustrated in FIG. 5R and the stomach 3 has been rotated back to its original orientation, if applicable, instruments 250' and 200' are removed from the patient, leaving the attachment members/sutures 104, suture locks 110, (optionally, material 230), suture anchors 106' and suture anchor mates 108' in place like what is shown in FIG. 5J. Suture locks 110 have a one-way locking mechanism, such as a ratcheting type mechanism or other arrangement such as directionally oriented teeth that allow suture 104 to be pulled proximally therethrough, but which prevent attachment members/sutures 104 from backsliding distally therethrough. Like shown in FIG. 5K, the attachment members/sutures 104 are cinched by pulling them proximally relative to the suture locks 110 until a desired amount of tension is developed in the attachment members/sutures 104, as described previously. Cinching can be performed by the use of laparoscopic graspers (not shown), for example. The bougie 50 can then be removed from the patient and the patient can be closed, according to known techniques, to complete the procedure.

As a further option, an expandable implant 10 may be implanted to fill the inside of the plication 3PL in a manner like that shown in FIG. 5L. The implant 10 may be a silicone bladder, for example, capable of being inflated by biocompatible fluid such as liquid, gas, or a combination of fluids (gases, liquids, or liquids and gases). Implant 10 is connected via fill tubing 12 in fluid communication with a subcutaneous fill port 80, so that the fill volume of implant 10 can be adjusted after implanting it as described from a location outside of the abdominal cavity (e.g., by an operator accessing the subcutaneous fill port 80 with a needle alone or a needle attached to a pressurized source of fluid). Other implants 10 may be substituted, but need to be expandable and are preferably controllable as to amount of expansion. A tab or wing 11, 11', 11", 11''' may be provided to extend from the expandable body of the implant 10 and can be inserted between the tissue folds at the plication suture line so that the attachment members/sutures 104 are also installed through the tab or wing 11, 11', 11", 11''' to thereby securely hold the implant in place, like that illustrated in FIG. 5L. The tab or wing 11, 11', 11", 11''' may be made of a mesh-reinforced silicone, for example. Alternatively, the implant 10 may be fixed in place by connecting only to the superior and inferior ends of the plication suture line, or by connecting to one or more of the suture locks 110 and/or suture anchors 106.

An alternative embodiment to those shown in FIGS. 5M-5R is one where the device 250' deploys a continuous suture instead of multiple interrupted sutures. In this embodiment, the device 250' would deploy a needle driver that moves from one suture slot 200S to the next, through a helical motion or through a series of alternating rotation and advancing motions. This method of suturing would result in a continuous suture that penetrated the stomach tissue at each location inside the slots 200S.

Another alternative embodiment to those shown in FIGS. 5M-5R is one where the suction and suturing functionalities of the two instruments are combined into one instrument. This embodiment would be similar to the embodiment of FIGS. 2D-2H in that the suction and suturing functionalities are provided in a single instrument. However, this embodiment may also be similar to those of FIGS. 5M-5R in that it may utilize needles that have a curved shape, rather than the straight needles shown in FIGS. 2D-2H. In this manner, the curved needles may be housed within the upper end effector, with the suture anchors 106 being housed in the lower end effector. The suction features would be present in both the upper and lower end effectors. As described for FIGS. 2D-2H, the end effectors would close onto the stomach, grip the stomach with suction, open and spread the walls of the stomach, imbricate the stomach and close. At this point, the curved needles would advance through the tissue, being driven by a cam mechanism, a gear, or another driving mechanism. The needles would rotate so that their curved shapes advance through the stomach tissue, engaging the suture anchor mates 108 with the suture anchors 106 housed in the lower end effector. This embodiment may have an advantage over that of FIGS. 2D-2H because the curved shape of the needles, with the rotating advancement, may enable the suturing functionality to be miniaturized into a smaller end effector 9 as compared to the straight needles of FIGS. 2D-2H), which can be used through a smaller surgical port. This embodiment may have an advantage over the embodiments of FIGS. 5m-5R because it can be used through a single surgical port instead of two ports.

FIG. 6 is a partial perspective view of a bougie 50' that can be used in any of the procedures described herein that employ bougie 50, alternatively to the use of bougie 50, according to an embodiment of the present invention. Bougie 50' has the same outside diameter as that of bougie 50, typically 32 French, but could vary, in the same manner described above with regard to bougie 50. Bougie 50' is provided with a round cross-section and is flexible in bending along its length, but relatively rigid under compression along its longitudinal direction which facilitated insertion through the esophagus and into the stomach. Bougie 50' is provided with a blunt, atraumatic distal tip 52 with bluntness provided by the curvature of the distal end of the tip 52. Bougie 50' includes an elongated, flexible tube 54 that has a flexible portion at at least its distal end portion (excluding distal tip 532), which flexible portion is long enough to extend out of the mouth of the patient when the bougie 50' has been placed in its intended operative location (e.g., when tip 52 is at the location of the pylorus as described above). when in an unreinforced configuration, as illustrated in FIG. 1A. Tube 54 may be formed of polyvinyl chloride (PVC) to ensure that the tube is transparent for maximizing visualization via an endoscope 33 that is insertable therein (shown in phantom in FIG. 6). Alternatively, polyethylene, polyurethane, PEBAX or MILIFLEX® (thermoplastic elastomer, thermoplastic olefin, Melitek, Dusseldorf, Germany) may be used. Optionally a proximal portion 56 that remains outside of the patient during use may be made stiff or relatively rigid to aid in manipulation of the bougie 50'.

One advantage of this embodiment is that a flexible endoscope 33 can be inserted into bougie 50' to provide visibility to a user outside the patient, through the clear walls of tube 54 and tip 52. Flexible endoscope 33 can be advanced up into the flexible distal portion of bougie 50' to provide views along a curved pathway of a tract in the stomach being formed by a procedure according to an embodiment of the present invention. Thus bougie 50' enables appropriate sizing of the stomach lumen formed during a plication procedure. Additionally, visualization can be performed through the clear side walls and tip of bougie 50' to inspect the sizing of the stomach lumen and/or various intermediate stages of performing the plication, from a location inside the stomach 30. Further details about various embodiment of bougie 50' can be found in co-pending application Ser. No. 12/474,118 filed May 28, 2009 and titled "Devices, Systems and methods for Minimally Invasive Abdominal Surgical Procedures", which application is hereby incorporated herein, in its entirety, by reference thereto.

Referring now to FIGS. 7A-7I, various events are illustrated for the performance of a procedure in which a device 10 is implanted within plications formed at external locations of the stomach. The procedure shown in FIGS. 7A-7I is a laparoscopic procedure in which ports are installed in a patient for access to the abdominal cavity by not only the instrument shown, but also by other instruments typically used in laparoscopic surgery, such as graspers, endoscope, etc.

After establishing ports/pathway into the abdominal cavity from outside the patient, the omentum 5 and connective tissues are dissected at the greater curve of the stomach to provide access thereto, see FIGS. 7A-7B. A bougie 50 is inserted trans-esophageally and placed in the stomach 3 in a position such as shown in FIG. 7C. Typically the bougie occupies a pathway extending naturally from the esophagus, through the stomach 3 and into the pylorus 3P, so as to occupy a space similar to what is defined when a sleeve gastrectomy is performed. The bougie acts as a guide so as to better standardize the sizes and locations of plications formed by the procedure as well as to prevent reducing the stomach too aggressively, so as to ensure no blockage locations are inadvertently formed.

An attachment instrument 300 is inserted into the abdominal cavity and an end effector 300E formed on a distal end of the instrument 300 and having an implantable device 10 releasably mounted thereto, is contacted to the stomach 3 in a manner as illustrated in FIG. 7D, such that the device 10 contacts the external wall of the stomach 3 and is positioned between the stomach 3 and the end effector 300E. As shown in FIG. 7D, the end effector is oriented so that the device 10 primarily contacts the body 3B and fundus 3F of the stomach, while the bougie 50 helps insure that the cardia 3C, pylorus 3P and pyloric antrum 3PA remain open so as to avoid risk of forming blockages. Once the end effector 300E has been oriented so that it is substantially aligned with the central, substantially straight section of the bougie 50 (see FIG. 7D), tissue pins 302 are deployed so as to extend from the surface of the end effector 300E as shown in FIG. 7E.

Figure 7F:
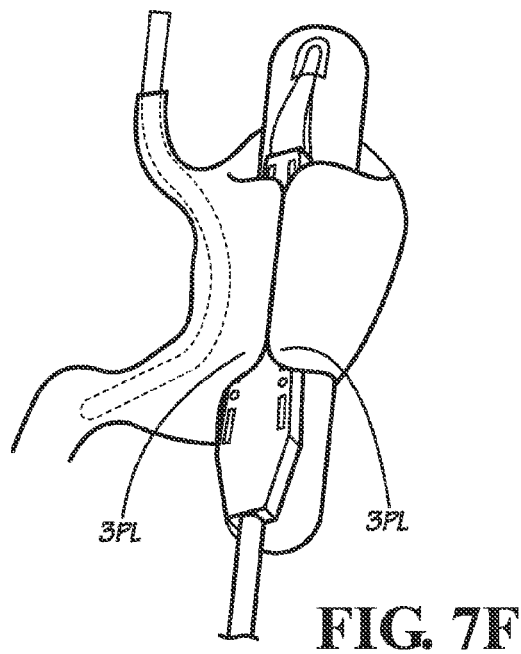
Figure 7H:
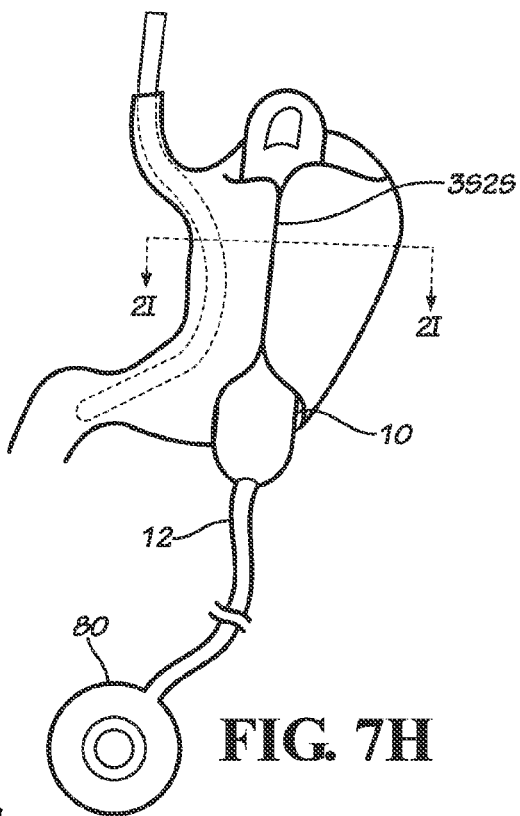
Figure 7G:
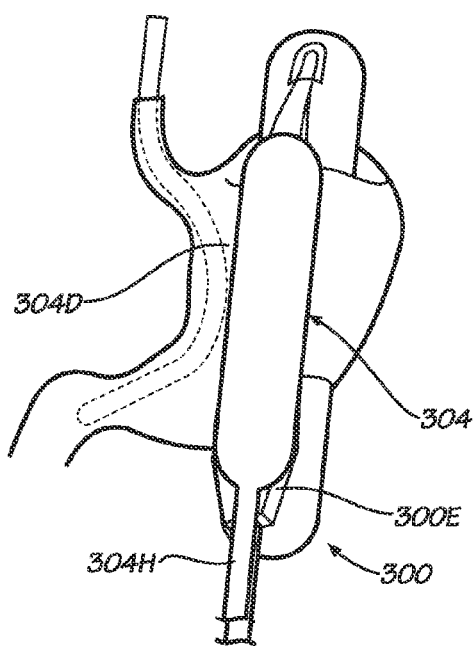

Next, at FIG. 7F, graspers are used to grasp portions of the stomach 3 and fold the portions over each side of the end effector 300E, pushing the stomach plications 3PL onto the tissue pins 302 so as to temporarily hold the plications 3PL in the positions shown in FIG. 7F. At FIG. 7G, a strap 304 of the attachment instrument 300 is inserted through the same port that the end effector 300E was inserted through. The distal end portion 304D of the strap 304 is connected to the distal and proximal ends of the end effector 300E. The strap 304 is mounted on a stiff paddle and the paddle is used to hold the strap 304 in place in compression against the stomach plications 3PL as shown. The paddle includes a proximal handle 304H that extends out of the patient and is used by the operator to manually adjust the clamping force of the strap onto the tissue so as to hold the tissue of the plications 3PL in tight approximation to the end effector 300E. Stitching needles are then deployed from the end effector 300E to penetrate the double walls of the stomach plications 3PL and connect suture bullets (described below) to anchors 32 (such as speed nuts, traps or other features that are directly connectable to the suture bullets). The opposite ends of the attachment members/sutures 30 are pre-fixed to a layer of material 12 that encourage tissue ingrowth and is also fixed to the expandable device 10, see FIG. 7I. For example, the tissue ingrowth encouraging material may be a porous mesh of biocompatible material such as DACRON® (polyester) or other fabrics that are known in the art to encourage tissue ingrowth. The attachment members/sutures are tightened and bougie 50 and attachment instrument 300 (including the strap 304 are removed, as shown in FIG. 7H, leaving the device 10 in place, maintained in positioning by the plications (see FIG. 7H) which are sutured to the device 10 via attachment members/sutures 30, see FIG. 7I. The plications 3PL preferably abut one another in serosa-to-serosa contact as illustrated by 3S2S in FIGS. 7H-7I. The space left by removal of the end effector 300E provides room for the device 10 to expand into. As shown in the cross-section illustration of FIG. 7I, device 10 can then be expanded/inflated to further reduce the amount of space in the interior cavity of the stomach 3. The sleeve volume gauged by placement of the bougie 50 during the procedure can be adjusted by adjusting the volume of the device 10. The fill tube 12 is connected to an access device which can be implanted outside the abdominal cavity, against the external abdominal wall or fascia, for example, as described in application Ser. Nos. 11/407,701; 11/881,144; 10/567,199; 11/974,444; 11/716,985; 11/716,986; 12/473,818; 12/473,881; 12/474,118; 12/474,070; 12/474,087; 12/474,158; 12/474,234; 12/474,251; 12/474,253; 12/474,226; and 13/015,086, each of which is hereby incorporated herein, in its entirety, by reference thereto.

The implantable devices described herein are preferably cylindrical shaped, so as to form a rod or hot-dog-like appearance, but could be of another shape, including, but not limited to a curved, cylindrical shape not unlike the shape of a banana. The devices are expandable, typically by input of a pressurized fluid, such as saline or other biocompatible liquid, biocompatible gas, or a combination of biocompatible gas and liquid.

FIG. 8A is a perspective view of another embodiment of an attachment instrument according to the present invention, configured to be operated from outside of a patient, with the end effector having been inserted through a laparoscopic port or percutaneous opening and into contact with the patient's stomach 3 (e.g., into the abdominal cavity of the patient), and to reduce the effective volume of the stomach 3 by performing one or more plication procedures on it.

Attachment instrument 400 includes an elongate end effector 400E having a length 400L greater than a width 400W (typically at least more than twice as great) formed at a distal end portion of instrument 400. End effector 400E includes a distal end 400D, a proximal end 400P and first and second sides 400S. An elongate shaft 420 extends proximally from the proximal end 400P of end effector 400E. Shaft 420 has sufficient length so that a proximal end of the shaft 420 extends out of the patient's body when the end effector 400E is placed on the patient's stomach in a manner described below and shown in FIG. 8D.

Figure 8B:
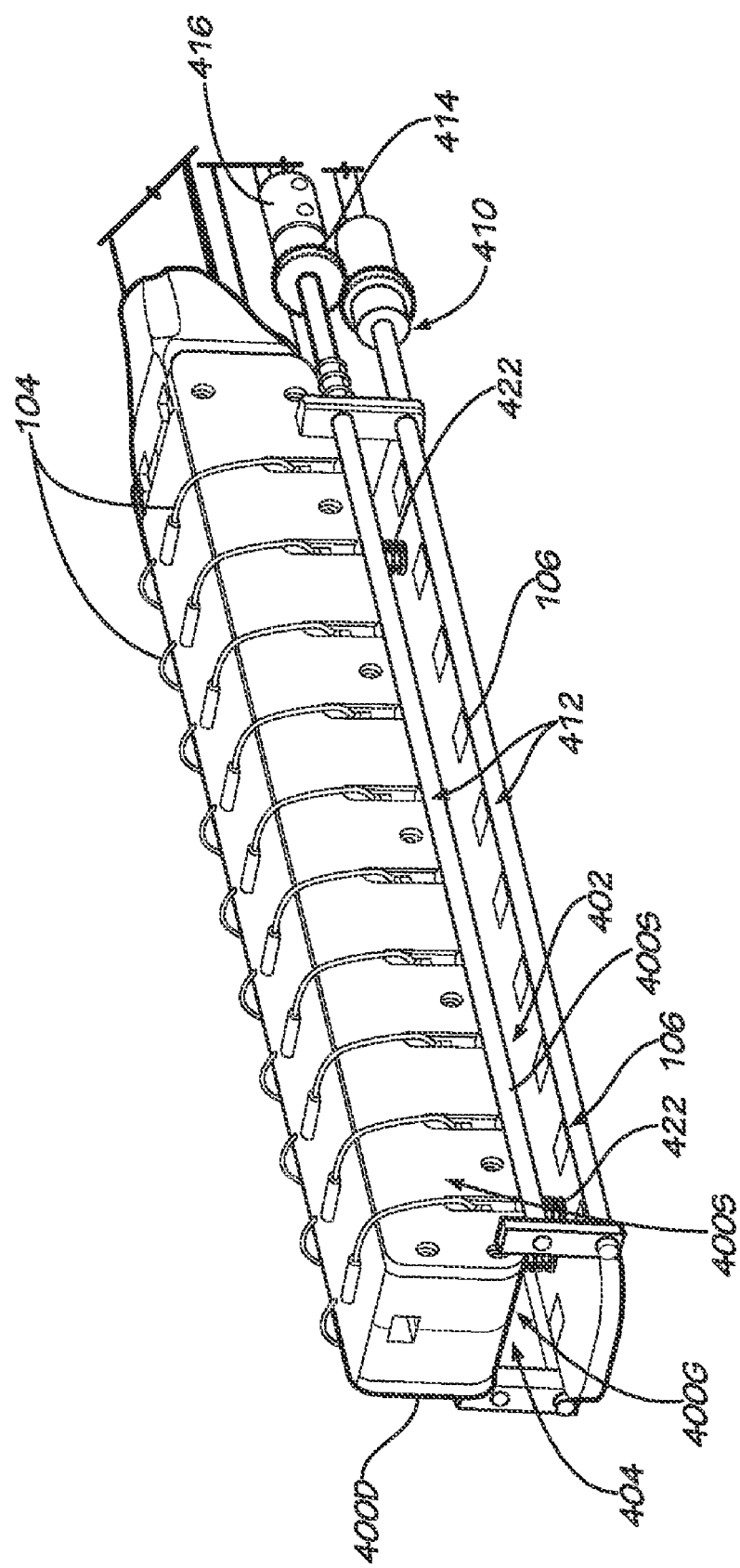
FIGS. 8A-8S are various views and partial views of an attachment instrument according to an embodiment of the present invention, and of a method of performing a plication therewith according to an embodiment of the present invention.
Figure 8C:
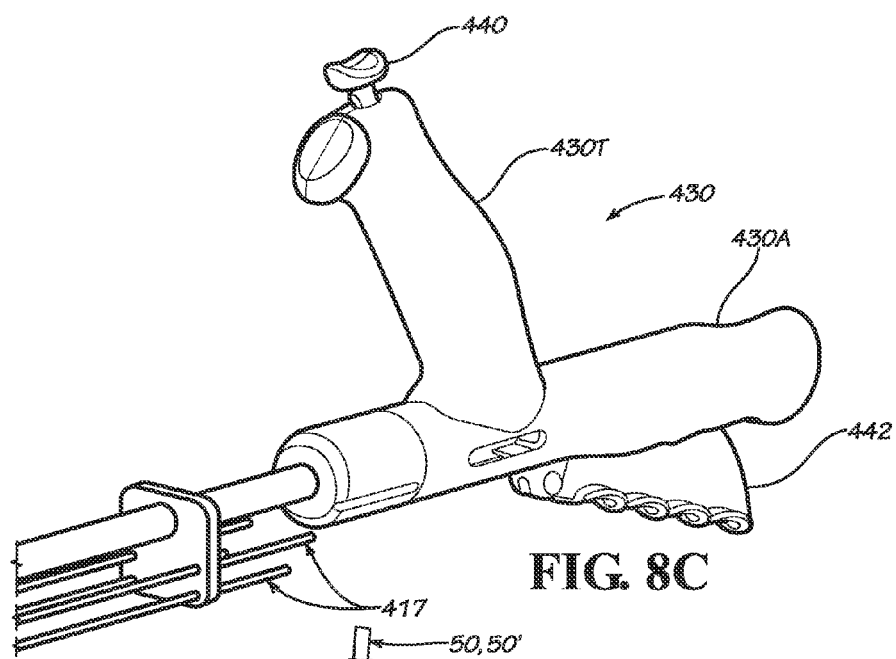
Figure 8D:
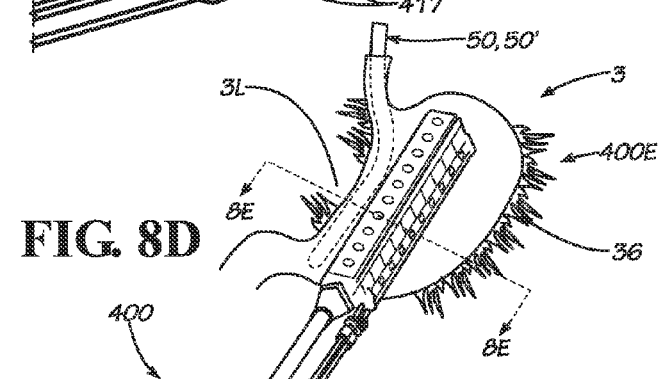
Figure 8E:
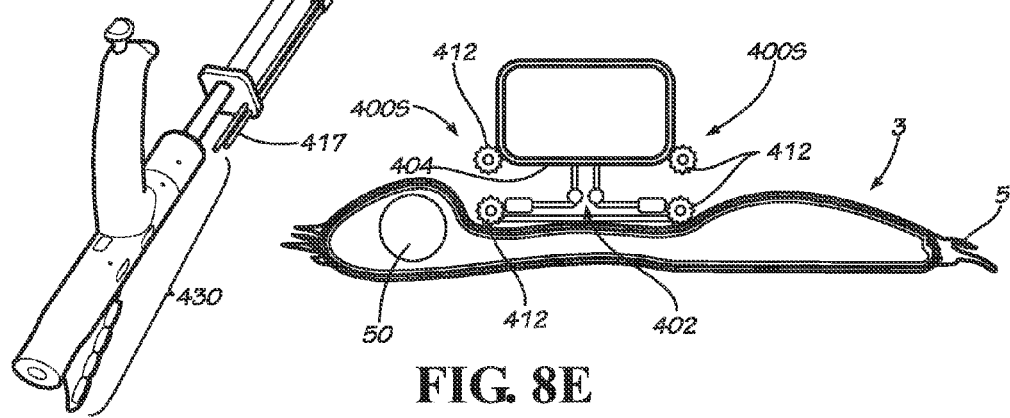
Figure 8F:
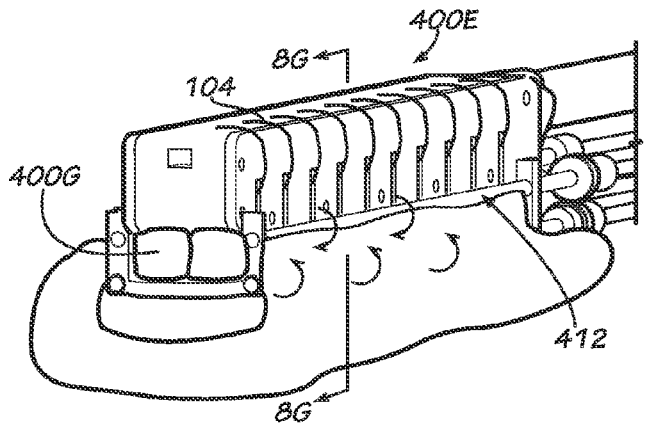
Figure 8G:
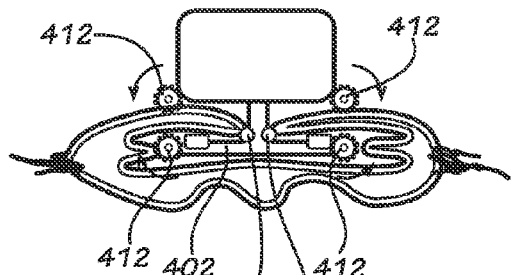
Figure 8H:
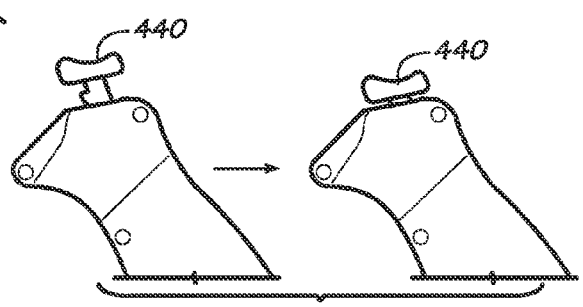
Figure 8I:
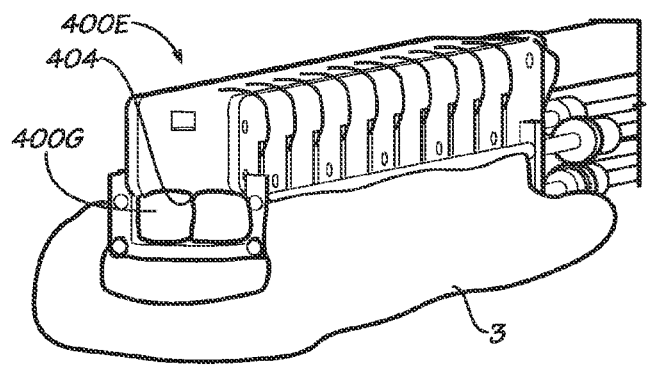
Figure 8J:
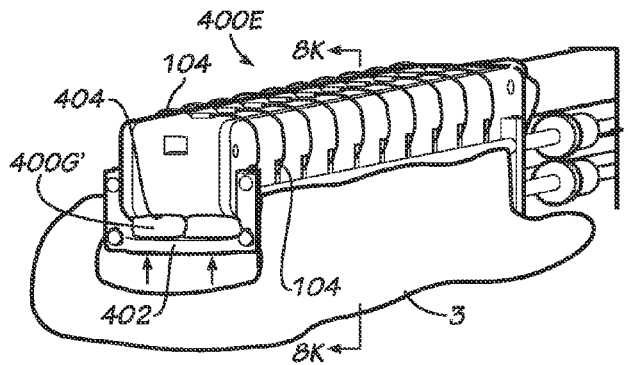
Figure 8L:
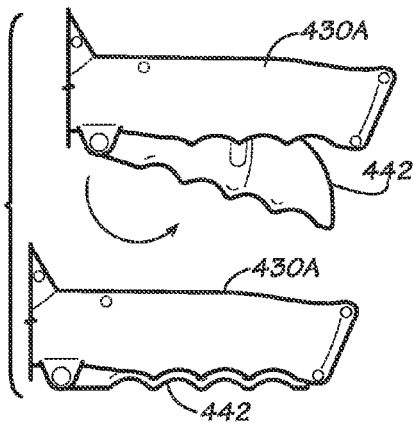
Figure 8K:
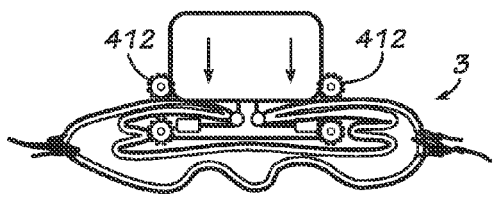
Figure 8M:
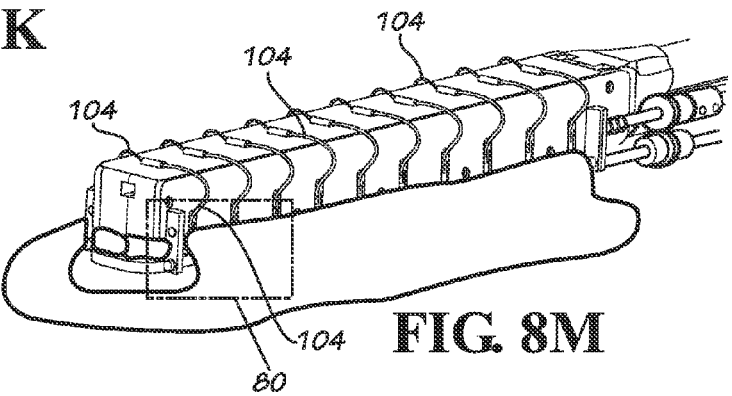
Figure 8N:
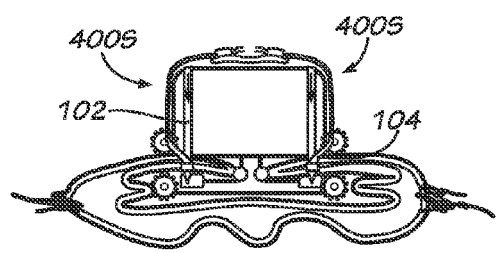

A plurality of piercing members 102 (typically suture drivers such as stitching needles or the like) are positioned along a pair of rows extending lengthwise along the end effector 400E, one row along each side 400S (e.g., see sectional illustration of FIG. 8N). A portion of a row is shown in the enlarged partial view of FIG. 8O that shows three piercing members 102.

A plurality of attachment members 104 extend along a pair of rows extending lengthwise along the end effector 400E, see FIGS. 8B, 8F, 8I, 8J, 8M and 8O. The attachment members shown in this embodiment are attachment members/sutures 104 and are arranged, configured and positioned to be driven through a fold in the stomach 3.

A lower contact plate 402 is spaced beneath and parallel with an upper tissue contact surface 404 of the end effector 400E, forming a gap 400G between plate 402 and surface 404 as shown in FIG. 8B. A driving mechanism 410 is provided which is configured to drive folds of stomach tissue into the gap 400G between plate 402 and surface 404. As shown in FIGS. 8A, 8B and 8E, driving mechanism 410 includes a pair of mechanisms, one on each side, each including a pair of textured roller bars 412, gears configured for selectively operating a single roller 412 or the pair of roller bars in linked unison, and a driver 416, which may be hand operation of one or more shafts extending proximally from the gears or one or more motors for operating the roller bars 412. The roller bars 412 extend lengthwise along the end effector 400E, one alongside surface 404 and one alongside plate 402 and, when operated, are rotated counter to each other so as to either pull tissue in between the bars 412 or eject tissue out from the gap 400G between the bars. The opposite side 400S is configured with a mechanism that is the same as that described and shown in FIG. 8B. The pair of mechanisms typically operate the pairs of rollers 412 on opposite sides independently of each other. Optionally, the mechanisms may be selectively linked to control both sets of rollers to perform the same operation simultaneously (taking tissue in or driving tissue out).

A handle 430 is connected to a proximal end portion of shaft 420. Shaft 420 has a length sufficient to allow a user to operate the controls on handle 430 (and the drive shafts 417 at least when the driver 416 is hand operation) from a location outside of an obese or overweight patient when the end effector 400E has been contacted to the stomach in a manner as shown in FIG. 8D. Handle 430 includes an axial portion 430A and a transverse portion 430T, see FIGS. 8A and 8C. These portions are configured so that the user can apply both hands to the handle 430 if desired and, by pushing on handle portion 430T and pulling up on handle portion 430A can apply a force to the end effector 400E to press it down against an external surface of the stomach 3 where the plication procedure is to be performed. Plate 402 is biased away from surface 404 such as by coil springs 422 or the like, so that gap 400G is maintained until actuator 440 is engaged (such as by pressing with the thumb, in the embodiment shown), which causes plate 402 and surface 404 to be driven closer together, so as to clamp down on stomach tissues after the stomach tissues have been drawn into the gap 400G sufficiently.

After preparing the patient, inserting a bougie 50, 50' into the stomach 3 in a manner as described above and forming either a percutaneous opening (e.g., puncture and opening leading from puncture into the abdominal cavity, for a percutaneous procedure) or a plurality of ports for a laparoscopic procedure, end effector 400E of instrument 400 is inserted through the puncture or one of the ports and delivered into the abdominal cavity, where it is placed into contact with an exterior surface of the stomach 3 as shown in FIG. 8D. Typically, the end effector is substantially aligned with the bougie 50, 50' adjacent to the bougie 50, 50' on a location of the stomach nearer to the greater curvature 3G or on the greater curvature 3G with the bougie 50, 50' being nearer the lesser curvature 3L as shown. End effector 400E preferably contacts the stomach 3 in an inferior to superior direction extending substantially over the body 3B and fundus 3F, but not over or in contact with the pylorus 3P, pyloric antrum 3PA, cardia 3C or gastro-esophageal junction 3GE.

Once the end effector 400E has been properly positioned as intended and contacted to the stomach 3, as illustrated in the schematic cross-sectional view of FIG. 8E, the bougie 50, 50' is removed from the patient and the roller bars 412 are operated by operating the driving mechanisms to draw stomach tissue into the gap 400G on both sides 400S of the end effector as illustrated in FIGS. 8F-8G. Optionally, conventional laparoscopic graspers can be used to initially feed the stomach tissue into the gap. The plications of tissue formed are pulled over the lower roller bars 412 and under the upper roller bars 412 as shown best in the schematic, cross-sectional illustration of FIG. 8G. Vacuum tubes 442 are provided that extend along the upper surface of base 402 and are provided with ports or openings at intervals along the lengths thereof. Vacuum tubes 442 extend parallel to roller bars and to each other, but are located adjacent to the central longitudinal axis of base 402 as illustrated in FIG. 8G. Preferably, a pair of vacuum tubes 442 are provided, one on each side of the central longitudinal axis as shown, although more or fewer vacuum tubes 442 may be employed. Vacuum delivered through the openings/ports of the vacuum tubes 442 hold the plicated tissues in contact therewith once the plicated tissues have been drawn/driven into contact therewith by the driving mechanism. Vacuum tubes 442 may additionally assist in drawing the tissues into the final positions shown in FIG. 8G. As noted previously, the operator can turn the roller bars 412 to draw stomach tissue into the positions shown in FIG. 8G in preparation for stitching. The bars 412 are textured or provided with other features to assist gripping the stomach tissue. The bars 412 can be rolled together or individually, in order to provide greater control over how the tissue is drawn into the gap 400G.

At this time, the operator operates actuator 440 to clamp the stomach tissue in the end effector 400E. In the unactuated position of actuator 440 shown on the left side of FIG. 8H, the gap 400G is in its biased open position as illustrated in FIG.

8*l*. Upon operating the actuator 440 to the actuated position shown on the right side of FIG. 8H, the plate 402 and surface 404 are brought closer together, thereby clamping the tissue in accordance with the force arrows shown in FIG. 8J.

Figure 8O:
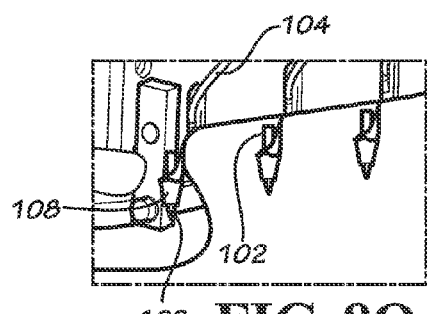
Figure 8P:
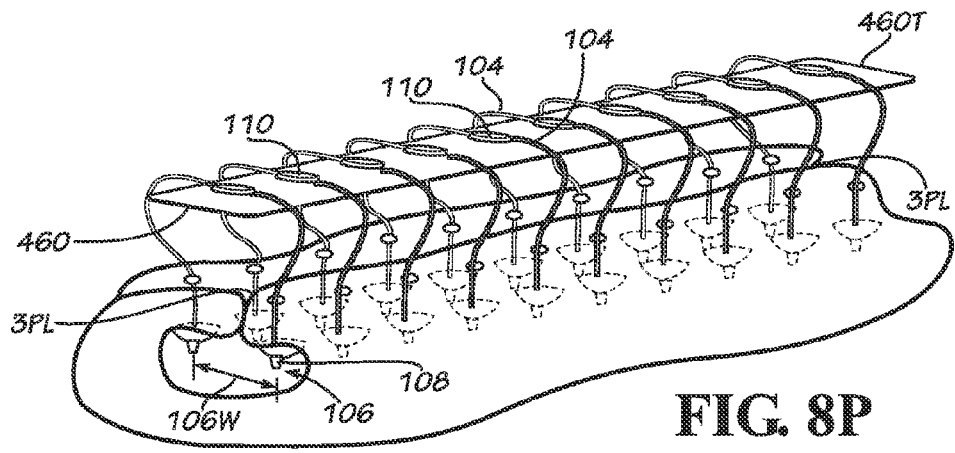

Once the stomach tissues have been clamped as described above, stitching actuator 442 is next actuated to drive piercing members 102 and attachment members 104 through the stomach tissues as illustrated in FIGS. 8M, 8N and 8O. Piercing members 102 are preferably needles, but could alternately be screw drives or other elongated members configured to temporarily attach attachment members thereto and to drive through the stomach tissues. Attachment members 104 are preferably sutures, but could alternatively be ribbons or other attachment members configured to perform as described, or hybrids thereof. Suture anchors 106 (best shown in FIG. 8B) are removably held in plate 402 and are aligned with the piercing members/suture drivers 102. Attachment members (which are sutures, in the embodiment shown) 104 are releasably engaged with piercing members 102. In the embodiment shown in FIG. 8O, attachment members/sutures 104 are each provided with an anchor mate 108 on a distal end portion thereof, preferably at the distal end thereof. Anchor mate 108 is configured to slide over the tapered distal end portion of the suture driver/stitching needle 102, but is prevented from sliding further proximally by the increasing diameter of the taper of the driver/needle 102 distal end portion. The exterior of the anchor mate 108 is also tapered, so that the distal end 108D thereof is of a smaller cross-sectional dimension than the proximal end 108P thereof. This facilitates the driving of the anchor mate 108 into the anchor 106 as shown in FIG. 8N. However, upon withdrawal of the piercing member 102, the proximal end of the anchor mate 108P is retained by the anchor 106 and the anchor mate 108 slides off the piercing member/suture driver 102, thereby leaving the anchor mate 108 and suture 104 installed through the tissues as illustrated in FIG. 8P. In the embodiment shown, actuator 442 is biased to the position shown at the top of FIG. 8L and functions as a ratchet during actuation such that cycling the actuator between the position shown at the top and the position shown at the bottom of FIG. 8*l* incrementally drives the piercing members 102, anchor mates 108 and attachment members 104 through the tissues and into the anchors 106 where anchors 106 and attachment members 104 are retained. Continued cycling retracts the piercing members 102 back into the main body of the end effector 400E into the stowed positions were they are concealed.

Figure 8Q:
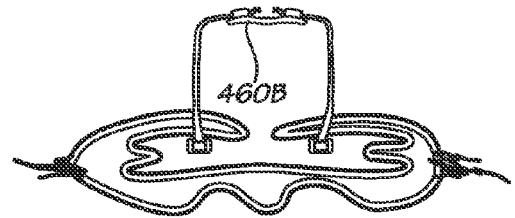

The end effector 400E is then removed by sliding it out of the attached tissues, whereby anchors 106 release from plate 402, leaving anchor mates 108, and therefore also attachment members/sutures 104 in retention by anchors 106 as shown in FIG. 8P. Attachment members/sutures 104 are also pre-installed through suture locks 110 that are attached to a conjunction member 460. In the embodiment shown in FIG. 8P, side by side pairs of sutures are preinstalled through suture locks, respectively (although other alternative arrangements may be substituted, including, but not limited to providing a suture lock 110 for each suture 104 as illustrated in the variant shown in the cross-sectional illustration of FIG. 8S) and conjunction member 460 is provided as a strip of material having sufficient length and width to cover the plication line 3PL formed by the abutment of the two tissue folds of stomach. Conjunction member 460 is configured as a porous material on the side 460B facing the plication line 3PL (see FIG. 8Q). The porous material is a tissue ingrowth material that may be made of any of the same materials mentioned above with regard to tissue ingrowth materials and/or any known biocompatible tissue ingrowth materials suitable for accomplishing the tasks described. The opposite side 460T of the conjunction member, which faces away from the plication line 3PL (see FIG. 8P) is nonporous to prevent tissue ingrowth therein. For example, the top surface 460T of 460 in FIG. 8P may be formed or coated with silicone or other nonporous biocompatible substance to prevent tissue ingrowth into the top surface of the conjunction member 460.

Figure 8R:
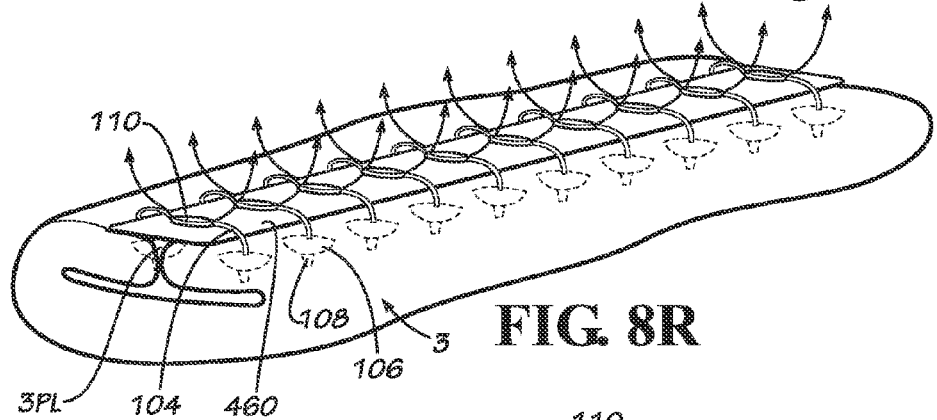
Figure 8S:
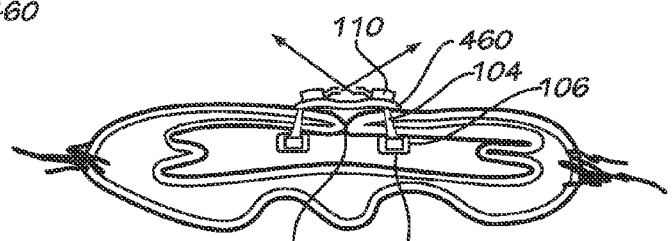

Suture locks 110 have a one-way locking mechanism per each attachment member/suture 104 inserted therethrough, such as a ratcheting type mechanism or other arrangement such as directionally oriented teeth that allow attachment member/suture 104 to be pulled proximally therethrough, but which prevent attachment members/sutures 104 from backsliding distally therethrough. FIGS. 8R and 8S illustrate the pulling of attachment members/sutures 104 in tension in the directions indicated by the arrows, so that they slide proximally relative to suture locks 110, thereby cinching the attachment members 104 tight under tension and bringing the conjunction member 460 into contact with the stomach tissues so as to overlie the plication line 3PL as illustrated in FIG. 8R. As a result, the folds of the two plications are drawn into abutment if they were not already in abutment, and the plication line 3PL is maintained with the folds in abutment, in serosa-to-serosa contact, by anchors 106 and anchor mates 108 underneath and conjunction member 460 and suture locks 110 on top, interconnected under tension by attachment members/sutures 104. Because the width of the conjunction member 460 and especially the width of the suture lock 110 or side by side pair of suture locks is less than the width 106W of the original spacing between anchors 106 (see FIG. 8P), the cinching of the attachment members/sutures 104 described above causes the stomach tissue to be drawn toward the center line, driving the opposing tissue folds together in abutment, providing serosa-to-serosa contact which eventually adhere to each other and grow together. The outer surfaces of the stomach contacting surface 460B will also grow into the tissue ingrowth material thereof. These two tissue joints (serosa-to-serosa adhesion and tissue ingrowth into the mesh 460B) provide long term attachment that maintains the plication in the configuration illustrated in FIGS. 8R and 8S.

FIG. 9 is a schematic illustration of an alternative mechanism for making a stitch (or simultaneous stitches) through tissue that is applicable to stitching a plication line PL according to another embodiment of the present invention. In this embodiment, piercing members/stitching needles 102 are rotationally driven out of the surface of the end effector 400E' through tissue and into engagement with an attachment member/suture anchor 106. Tissue pins/stabilizing pins are deployed at step 9A so as to temporarily hold the tissue in place during the stitching procedure. At 9B, deployment of the piercing members/stitching needles 102 from the surface of the end effector 400E' is begun, such as by use of an actuator like 442 described in regard to FIG. 8A, although not shown here. Further details about the structure and functioning of driving mechanisms and other components of this embodiment can be found in co-pending application Ser. No. 12/474,226, which has already been incorporated herein, in its entirety, by reference thereto above. At 9B the piercing members/stitching needles 102 are shown in an early stage of deployment of the process, e.g., after only one or two pulls of the actuator 4172. Note that the locations where the members/needles 102 pierce into the tissue 3 are substantially aligned with the locations where the corresponding stabilizing pins/tissue pins 302 pierce into the target. In the embodiment shown, the tip of the needle 102 is aligned axially (i.e., at the same length along the proximal-distal axis of the stitching instrument, i.e., the left-right direction in 9B) with the tip of the stabilizing pin 302, when both are in their starting positions, ready to pierce into tissue 5. Also, pins 302 are angled in a direction opposite to a direction toward which the stitching needles 102 are angled, relative to the surface of the tissue 3, as they enter the tissue 3. In this way, the stabilizing pins/tissue pins 302 provide counter-traction and prevent the tissue 3 from being dragged or bunched up or pushed away by the stitching needles 102 as they sweep through the tissue 3, being rotated into and then out of the tissue 3T.

At 9C, the piercing members/stitching needles 102 have been rotated about halfway through the tissue 3. Note that the pins 302 remain in position as originally deployed. The piercing members/stitching needles 102 have been rotated in 9D to the extent where the tips of the needles 102 have emerged back out of the tissue 3. Like the tissue pins/stabilizing pins, the needles 102 may pass all the way through the tissue 3 (phantom lines) or may rather be inserted into the tissue 3, rotated through the tissue 3 without ever passing through a back side of the tissue 3, and pass back out of tissue 3 at another location (exit location) different from the entry location, but located on the same surface of the target. This is preferred for serosa-to-serosa stitching where it is desirable not to pass into the mucosa or interior of the stomach, but only through the serosa 3S and muscularis 3M layers. 9E illustrates the needles 102 having been rotated to the extent where the tips of the needles 102 and the anchor mates 108 have been driven through the respective attachment member/suture anchors 106. Upon counter-rotation of the needles 102, the tips of the needles 102 slide out of contact with the anchor mates 108 and pass back out of the attachment member/suture anchors 106, while the attachment member/suture anchors 106 retain the anchor mates 108 and prevent them from passing back through, thereby securing the attachment members/sutures 104 to the attachment member/suture anchors 106.

Upon anchoring the attachment members/sutures 104 to the anchors 106 as described above and when the piercing members/stitching needles 102 have been fully returned to their concealed positions in the end effector 400E', the tissue/stabilizing pins 302 can be retracted into their concealed positions within the end effector 400E'.

Instrument 400' can therefore be used to perform a method for decreasing the effective volume of a patient's stomach, to include contacting a length end effector 400E' to an external surface of the stomach 3; forming a fold in the stomach and positioning the fold over a portion of the end effector; deploying the tissue/stabilizer pins 302 to temporarily hold the fold of tissue in place on the end effector 400E'; and simultaneously driving a plurality of attachment members 102 through the fold, wherein the attachment members are configured along a length direction relative to the end effector 400E'. Optionally, a device 10 of any of the types described above could be installed between an external surface of the stomach and the fold using the end effector 400E' and/or other instrument. The instrument 400' can be used to place a row of stitches in a single deployment as described above to make a plication and a reduced volume sleeve in the stomach, or can be used multiple times to perform multiple deployments to form a sleeve in the stomach by installing multiple lines of stitches. In this and all other embodiments employing one or more attachment members/sutures 104, the attachment members/sutures 104 may be sutures and may be connected at their distal ends to anchor mates 108 as described above, which anchor mates 108 may be made of plastic or metal. Alternatively, in addition to the alternatives already previously noted, attachment member/suture 104 may be a metal wire or lead configured to connect with anchor 106, and these metal wires or leads may be similarly connected to metal or plastic anchor mates 108. Metal wire or lead 104 may or may not be electrically conductive.

Instrument 400' may alternatively be used intralumenally to stitch a plication inside the stomach 3 by driving the needles 102 through mucosa and back out of mucosa, after passing through one or more additional layers of the stomach wall. Thus full penetration or partial penetration of the stomach wall may be performed during stitching.

FIGS. 10A-10J illustrate various events for the performance of a procedure in which a device 10 is implanted within plications formed at external locations of the stomach 3 according to an embodiment of the present invention. The procedure shown in FIGS. 10A-10J is a laparoscopic procedure in which ports are installed in a patient for access to the abdominal cavity by not only the instrument shown, but also by other instruments typically used in laparoscopic surgery, such as graspers, endoscope, etc.

After establishing ports/pathway into the abdominal cavity from outside the patient, the omentum 5 and connective tissues are dissected at the greater curve of the stomach to provide access thereto, the same as described above with regard to FIGS. 7A-7B. A bougie 50, 50' is inserted transesophageally and placed in the stomach 3 in a position such as shown in FIG. 10A. Typically the bougie 50, 50' occupies a pathway extending naturally from the esophagus, through the stomach 3 and into the pylorus 3P, so as to occupy a space similar to what is defined when a sleeve gastrectomy is performed. The bougie acts as a guide so as to better standardize the sizes and locations of plications formed by the procedure as well as to prevent reducing the stomach 3 too aggressively, so as to ensure no blockage locations are inadvertently formed.

An attachment instrument 300' is inserted into the abdominal cavity and an end effector 300E' formed on a distal end of the instrument 300' and having an implantable device 10 releasably mounted thereto, is contacted to the stomach 3 in a manner as illustrated in FIG. 10A, such that the device 10 contacts the external wall of the stomach 3 and is positioned between the stomach 3 and the end effector 300E'. As shown in FIG. 10A, the end effector 300E' is oriented so that the device 10 primarily contacts the body 3B and fundus 3F of the stomach, while the bougie 50, 50' helps insure that the cardia 3C, pylorus 3P and pyloric antrum 3PA remain open so as to avoid risk of forming blockages. Once the end effector 300E' has been oriented so that it is substantially aligned with the central, substantially straight section of the bougie 50, 50' (see FIG. 10A), tissue pins/stabilizer pins 302 are deployed so as to extend from the surface of the end effector 300E' as shown in FIG. 10B.

Next, at FIG. 10C, graspers or other instrument are used to grasp portions of the stomach 3 and fold the portions over each side of the end effector 300E', pushing the stomach plications 3PL onto the tissue pins 302 so as to temporarily hold the plications 3PL in the positions shown in FIG. 10C. At FIG. 10D, conjunction member 460 is placed over the line where the plications 3PL join one another, to cover the junction line. This placement may be performed using graspers for example, or other instrument(s). In the embodiment shown in FIG. 10D, conjunction member 460 is provided as a strip of material having sufficient length and width to cover the plication line 3PL formed by the abutment of the two tissue folds of stomach. Conjunction member 460 is configured as a porous material on the side in contact with the stomach tissues and plication line 3PL (see FIG. 10D). The porous material is a tissue ingrowth material that may be made of any of the same materials mentioned above with regard to tissue ingrowth materials and/or any known biocompatible tissue ingrowth materials suitable for accomplishing the tasks described. The opposite side 460T of the conjunction member 460, which faces away from the plication line 3PL (see FIG. 10D) is nonporous to prevent tissue ingrowth therein. For example, the top surface 460T of 460 in FIG. 10D may be formed or coated with silicone or other nonporous biocompatible substance to prevent tissue ingrowth into the top surface of the conjunction member 460.

At FIG. 10E, a strap 304' of the attachment instrument 300' is inserted through the same port that the end effector 300E' was inserted through. The distal end portion 304D' of the strap 304' is connected to the distal end portion 300D' of the end effector 300E' and the proximal end portion 304P' is connected to the proximal end portion 300P' of the end effector 300E' by means of a paddle that it is connected to. The paddle includes a proximal handle 304H that extends out of the patient and is used by the operator to manually adjust the clamping force of the strap 304 onto the tissue 3 to hold the conjunction member 460 and tissue 3 in tight approximation to the end effector 300E'. Piercing members/stitching needles 102' are then deployed from the end effector 300E' to penetrate the double walls of the stomach plications 3PL and the conjunction member 460 and to connect anchors 108' to the conjunction member 460, see FIG. 10F.

In the embodiment shown, piercing members/stitching needles 102' are configured with a slot 102S that opens to the distal end of 102' but is closed at the proximal end of the slot 102S, see FIG. 10F'. Attachment members/sutures 104 are attached distally to T-bars 108' (see FIG. 10G). T-bar 108' extends out of slot 102S when attachment member/suture 104 is preinstalled through the hollow lumen in piercing member/stitching needle 102'. When piercing members/stitching needles 102' are deployed, they carry the T-bars 106' and therefore also attachment members/sutures 104 along with them, as the T-bars stop out against the closed ends of the slots 102S. The portion of the T-bar that extends out of the slot 102S is driven through the tissue 3 and conjunction member 460. When the piercing members/stitching needles 102' are withdrawn back out of the conjunction member 460 (FIG. 10G), the extending portions of the T-bars 106' catch in the mesh of the conjunction member or other part of the conjunction member 460 and are passively deployed out of the needles 102' thereby anchoring themselves to the conjunction member 460 as illustrated in the sectional view of FIG. 10J. The opposite ends of the attachment members/sutures 104 are pre-fixed to a layer of material 12 via suture locks 110. Material 12 encourages tissue ingrowth and is also fixed to the expandable device 10, see 10J. For example, the tissue ingrowth encouraging material may be a porous mesh of biocompatible material such as DACRON® (polyester) or other fabrics that are known in the art to encourage tissue ingrowth.

Figure 10I:
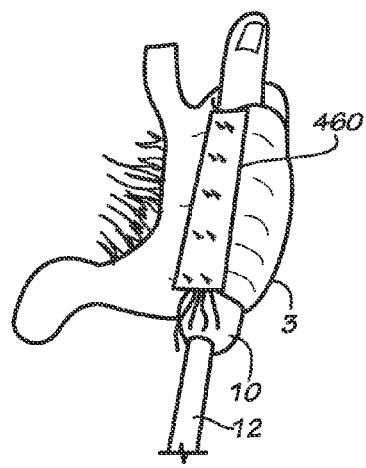

After completely retracting the needles 102' back into the end effector 300E' at FIG. 10G, the tissue pins 302 are retracted at FIG. 10H and strap 304 is detached and removed from the patient, leaving the conjunction member 460 attached to the tissues 3 as shown in FIG. 10H. Next, the bougie 50, 50' is removed from the stomach 3 and the patient at FIG. 10I. The sutures 104 can then be cinched down under tension by pulling them through suture locks 110, and excess suture material can then be trimmed, such as by using a suturing/stitching device as described in application Ser. No. 12/474,226 or by use of graspers, for example. The remaining instruments are then removed and the implant 10 is inflated via inflation tubing 12. Inflation tubing is then connected in fluid communication with an inflation port that allows changing the volume of the implant from outside of the patient.

Figure 10J:
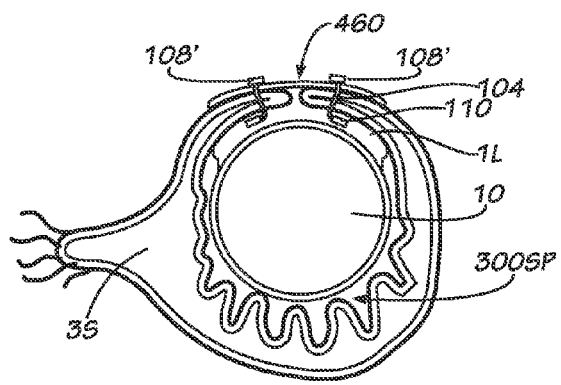

FIG. 10J is a cross-sectional illustration of the result of the procedure described above, with implant 10 having been inflated. The sleeve volume 3S can be adjusted by adjusting the volume of the implant 10. The space 300SP left upon removal of the end effector 300E' allows for room for the implant 10 to expand into upon further adjustment.

Figure 11A:
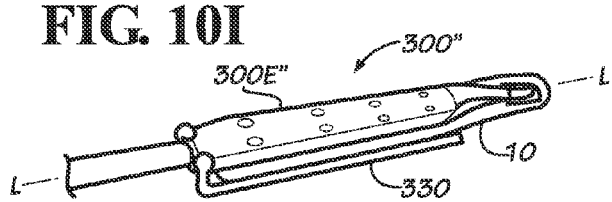
FIGS. 11A-11S illustrate various events for the performance of a procedure in which a device is implanted within plications formed at external locations of the stomach according to an embodiment of the present invention.
Figure 11B:
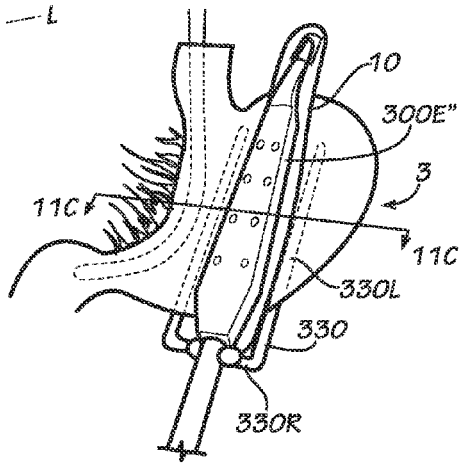
Figure 11C:
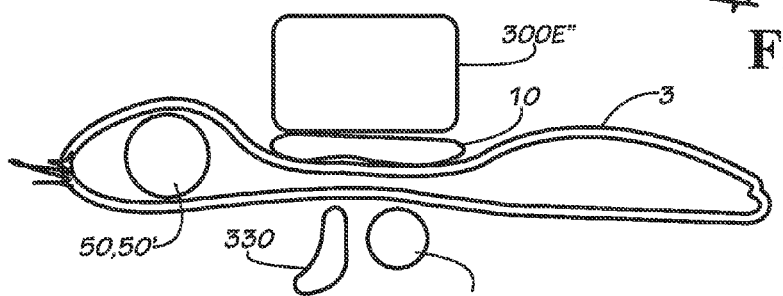
Figure 11D:
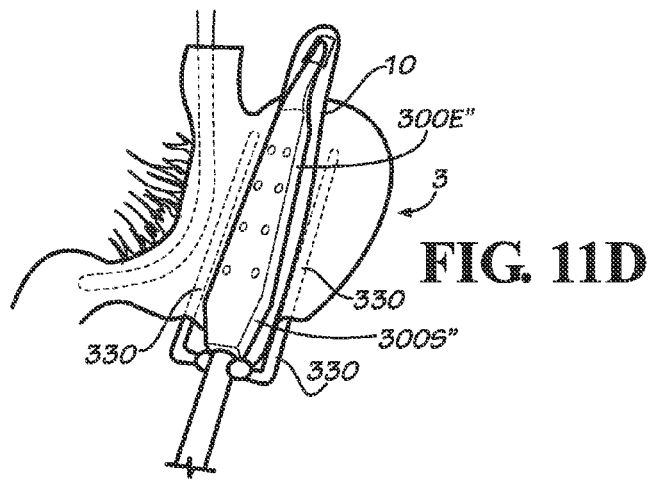
Figure 11E:
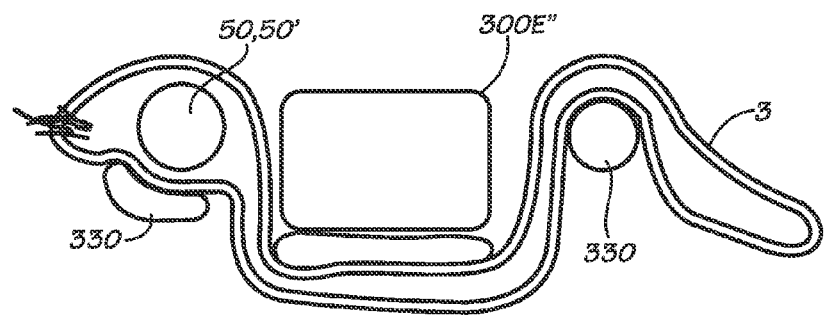
Figure 11F:
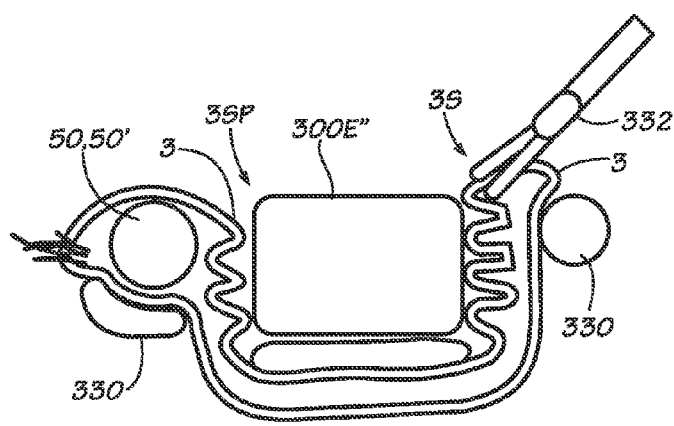
Figure 11G:
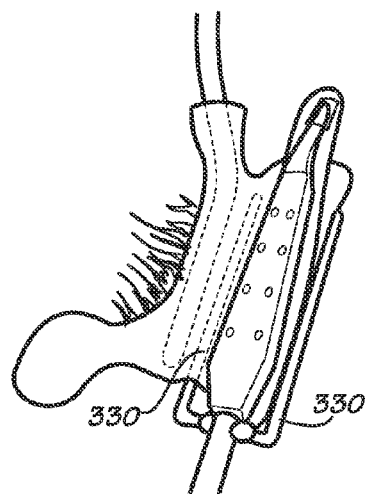
Figure 11L:
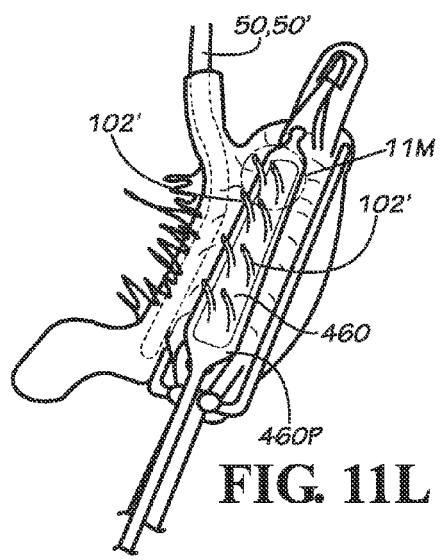
Figure 11M:
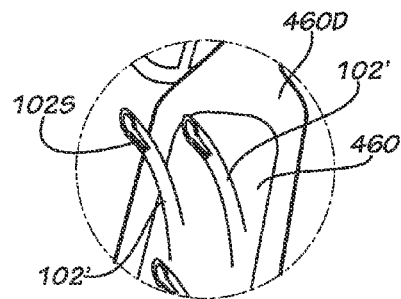
Figure 11N:
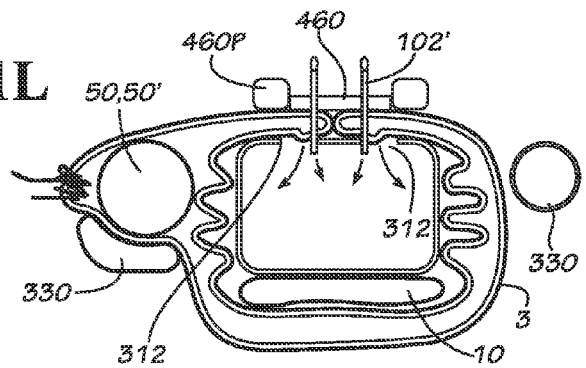
Figure 11O:
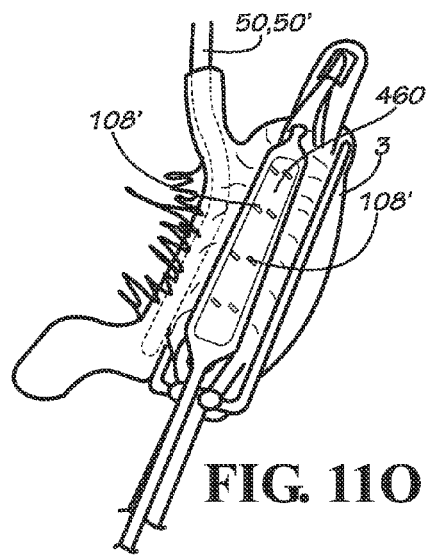
Figure 11P:
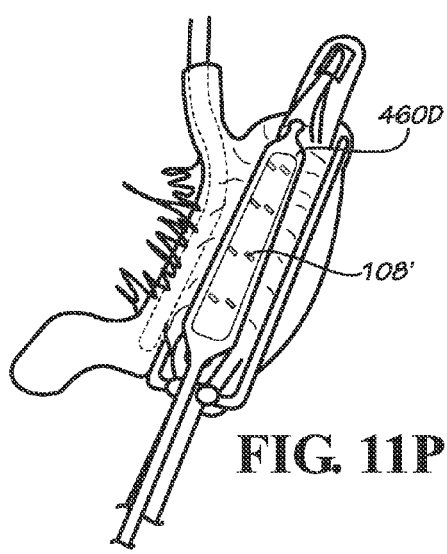
Figure 11Q:
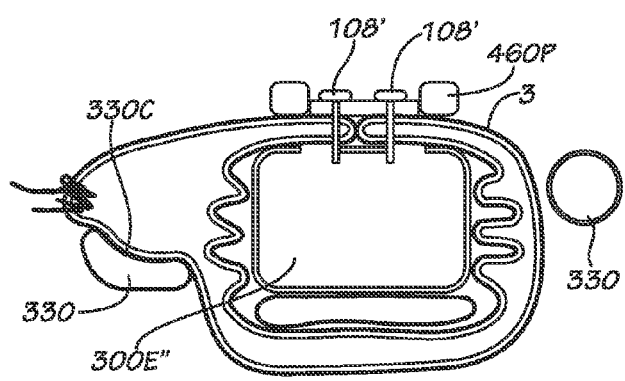
Figure 11R:
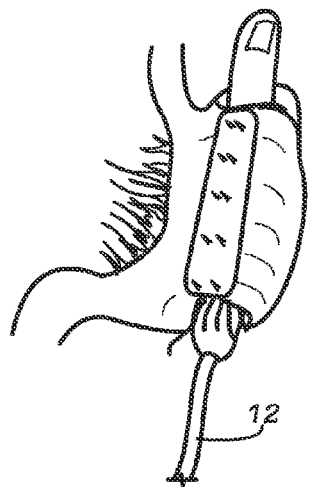
Figure 11S:
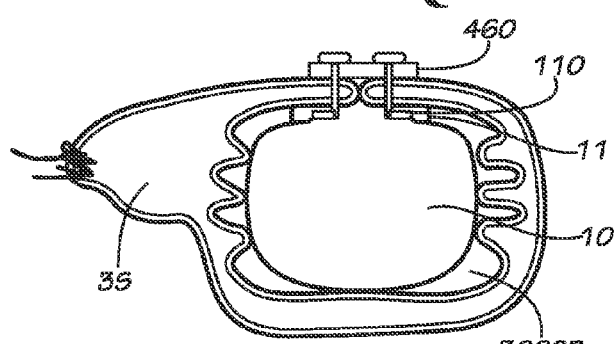

FIGS. 11A-11S illustrate various events for the performance of a procedure in which a device 10 is implanted within plications formed at external locations of the stomach 3 according to an embodiment of the present invention. The procedure shown in FIGS. 11A-11S is a laparoscopic procedure in which ports are installed in a patient for access to the abdominal cavity by not only the instrument shown, but also by other instruments typically used in laparoscopic surgery, such as graspers, endoscope, etc.

After establishing ports/pathway into the abdominal cavity from outside the patient, the omentum 5 and connective tissues are dissected at the greater curve of the stomach to provide access thereto, the same as described above with regard to FIGS. 7A-7B. A bougie 50, 50' is inserted transesophageally and placed in the stomach 3 in a position such as shown and described above with regard to FIG. 7C, for example. Typically the bougie 50, 50' occupies a pathway extending naturally from the esophagus, through the stomach 3 and into the pylorus 3P, so as to occupy a space similar to what is defined when a sleeve gastrectomy is performed. The bougie acts as a guide so as to better standardize the sizes and locations of plications formed by the procedure as well as to prevent reducing the stomach 3 too aggressively, so as to ensure no blockage locations are inadvertently formed.

An attachment instrument 300", a distal end portion of which is shown in the isolated view of FIG. 11A, is inserted into the abdominal cavity and an end effector 300E" formed on a distal end of the instrument 300" and having an implantable device 10 releasably mounted thereto, is contacted to the stomach 3 in a manner as illustrated in FIG. 11B, such that the implantable device 10 contacts the external wall of the stomach 3 and is positioned between the stomach 3 and the end effector 300E". In this embodiment, instrument 300" is provided with folding bars 330 that are elongated along the lengthwise direction of end effector 300E" and preferably extend substantially parallel to the longitudinal axis of the L-L of end effector 300E". Folding bars are rotationally mounted to instrument 300E", each bar having a radially extending portion 330R that is rotationally mounted to the instrument 300" and from which the main longitudinal portion 330L extends, as shown in FIGS. 11A-11B. This arrangement allows the longitudinal portions 330L of the bars 330 to be rotated relative to end effector 300E" and implant 10 along arcs that are at predetermined distances from the end effector 300E". As shown in FIG. 11B and the cross-sectional view of FIG. 11C, the instrument 300" and implant 10 are inserted such that folding bars 330 slide under (posterior to) the stomach 3 and implant 10 and end effector 300E" are contacted to the stomach on top (anterior to) of the stomach. Once the instrument 300" and implant 10 are contacted to the stomach in the manner desired, with the end effector 300E" and left folding bar adjacent the bougie 50, 50' as illustrated in FIG. 11C, the folding bars 330 are rotated in opposite directions relative to one another to a level about the same as the level of the end effector 300E", such that they are side by side with the sides 300S" of the end effector 300E", see FIG. 11D, rather than below the end effector as they were in FIG. 11C. Alternatively, one bar 330 can be rotated while the other bar 300 remains stationary. The cross-sectional view of FIG. 11E better illustrates the side by side positioning of the folding bars 330 and end effector 300E".

The surgeon next uses laparoscopic graspers 332 to manipulate tissue of the stomach 3 by grasping the stomach wall and plicating it into the spaces between the end effector 300E" and the folding bars 330, as illustrated in the cross-sectional view of FIG. 11F. This plicating procedure allows the irregular shape of the stomach to be compensated for, where more plicating is provided at locations that extend further out from the bars 33 and relatively less plicating is performed in regions that extend out less far from the bars 330. For example, near the fundus 3F, where there is more stomach tissue, more tissue is plicated into the space 3SP then the amount that is plicated at the lower main body, nearer the antrum. The goal is to plicate as much stomach tissue inside each gap 3SP as possible, so that the resulting plications formed will make the outside wall resulting tight. FIG. 11G illustrates the stomach tissue having been plicated as desired.

At FIG. 11H the surgeon uses laparoscopic graspers 332 to grasp the stomach wall tissue and pull the outside wall 3 tight around the end effector 300E" as illustrated in FIG. 11H and the cross-sectional illustration of FIG. 11I. A plurality of suction holes or ports 312 are formed in both end effectors 100E1, 100E2. Suction holes/ports 312 are oriented in a pair of rows extending along a length of end effector 300E", and are in fluid communication with a source of negative pressure (not shown) provided outside of the patient. For example, a suction line that is in fluid communication with holes/ports 312 may extend proximally therefrom and be configured for connection to a source of negative pressure, such as the suction system of an operating room or other source of negative pressure. These suction holes/ports 312, upon application of suction therethrough and when tissue 3 is in contact therewith, engaged the end effector 300E" with the stomach tissue 3 and hold the stomach walls in the folded configurations shown in FIG. 11H-11I, in a pair of plications ready to be finalized by fixing their positions.

Next, a conjunction member (e.g., mesh layer or other tissue ingrowth encouraging material) 460 is placed against the stomach tissue 3 in contact therewith, and spanning the plication line 3PL between the plications as illustrated in FIGS. 11J-11K. In this embodiment, conjunction member 460 is temporarily mounted in a paddle 460P. Paddle 460P has a handle 460H extending proximally therefrom that a user can operate from outside the patient to engage the paddle 460P with end effector 300E" in the manner shown, so as to contact the conjunction member 460 to the stomach 3 tissue as described above. The conjunction member 460 will become attached to the stomach 3, and the paddle 460P will release the conjunction member 460 before the paddle 460P is removed.

At FIG. 11L piercing members/stitching needles 102' are deployed from the end effector 300E" to penetrate the double walls of the stomach plications and the conjunction member 460, see also, the detail view of FIG. 11M. As noted above, the application of suction through suction holes/ports 312 maintains the stomach 3 tissues engaged with the end effector 300E" as the piercing members/stitching needles 102' penetrate the stomach tissues and conjunction member, as shown in the cross-sectional view of FIG. 11N.

In the embodiment shown, piercing members/stitching needles 102' are configured with a slot 102S (see FIG. 11M) that opens to the distal end of 102' but is closed at the proximal end of the slot 102S. Attachment members/sutures 104 are attached distally to T-bars 108' (although the T-bars could alternatively be replaced by umbrella-shaped members, grappling hooks, other hook-shaped members, or the like). T-bar 108' extends out of slot 102S when attachment member/suture 104 is preinstalled through the hollow lumen in piercing member/stitching needle 102'. When piercing members/stitching needles 102' are deployed, they carry the T-bars 108' and therefore also attachment members/sutures 104 along with them, as the T-bars stop out against the closed ends of the slots 102S. The portion of the T-bar that extends out of the slot 102S is driven through the tissue 3 and conjunction member 460. When the piercing members/stitching needles 102' are withdrawn back out of the conjunction member 460 (FIG. 11O), the extending portions of the T-bars 108' catch in the mesh of the conjunction member 460 or other part of the conjunction member 460 and are passively deployed out of the needles 102' thereby anchoring themselves to the conjunction member 460 (see also, the sectional view of FIG. 11Q). At FIG. 11P, the attachment members/sutures are cinched using a suture tightening device of the instrument 300" and this pulls the T-bars 108' tight against the conjunction member 460 as illustrated in FIGS. 11P-11Q.

Next, the bougie 50, 50' is removed from the stomach 3 and the patient. The paddle 460P is detached from the conjunction member 460 and removed from the patient, the attachment portion of instrument 300E" is removed from the patient, and attachment members/sutures 104 can be cinched again at this time, using the suture tightening device of instrument 300E" and the excess of the attachment member/sutures 104 resulting from cinching are also trimmed, using the suture tightening portion of instrument 300". The suture tightening portion is also removed, and the implant 10 is inflated leaving the result shown in FIGS. 11R-11S. Inflation tubing 12 is then connected in fluid communication with an inflation port that allows changing the volume of the implant 10 from outside of the patient.

FIG. 11S is a cross-sectional illustration of the result of the procedure described above, with implant 10 having been inflated. The sleeve volume 3S can be adjusted by adjusting the volume of the implant 10. The space 300SP left upon removal of the end effector 300E" allows for room for the implant 10 to expand into upon further adjustment. The ends of the attachment members/sutures 104 opposite the ends fixed to 108' are pre-fixed to a layer of material 11, 11', 11", 11'" via suture locks 110. Tab 11, 11', 11", 11'" encourages tissue ingrowth and is also fixed to the expandable device 10, see FIG. 11S. For example, the tissue ingrowth encouraging material may be a porous mesh of biocompatible material such as DACRON® (polyester) or other fabrics that are known in the art to encourage tissue ingrowth.

The folding bars 330 of this embodiment are shaped to nest tightly with the bougie 50, 50' (e.g., see FIG. 11Q). In at least one embodiment, the folding bar adjacent the bougie 50, 50' has a concave surface 330C to better conform to the bougie 50, 50' for tighter nesting therewith, so that the resulting plication can be as tight against the bougie 50, 50' as possible. The use of suction to hold the plications in position until they are more permanently attached with the attachment members 104' avoids potential injury and/or damage to the tissues that may result with alternative features such as needles or clamps.

Figure 12A:
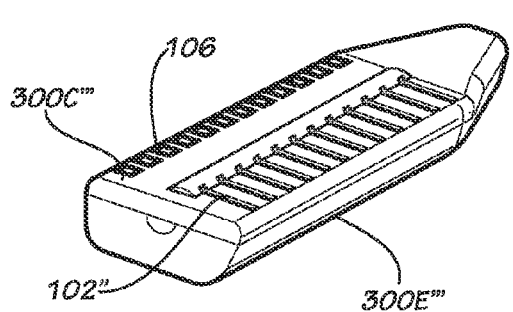
FIGS. 12A and 12G-12I are various views of an end effector according to an embodiment of the present invention.
Figure 12B:
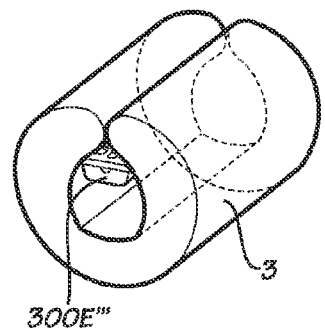
FIGS. 12B-12F illustrate a method of using the end effector of FIGS. 12A and 12G-12I according to an embodiment of the present invention.

FIG. 12A is a perspective view of an end effector 300E' according to another embodiment of the present invention. End effector 300E'" can be used alternatively to end effector 300E, 300E' or 300E" in the instruments described above. In this embodiment, piercing members/stitching needles 102" are rotated about ninety degrees upon storage in the end effector 300E'", relative to the storage positions of the previous embodiments. Thus, piercing members/stitching needles 102" are stored such that the sharp distal ends thereof point in a direction substantially parallel to the place of the contact surface 300C''' (or arranged more nearly parallel than perpendicular), rather than substantially perpendicular to it (or more nearly perpendicular than parallel), as in the previous embodiments. This allows closer arrangement of piercing members/stitching needles, thereby providing a tighter stitching pattern relative to the previous embodiments. Piercing members/'stitching needles 102" can be driven by a drive shaft which can apply more torque than the rack and pinion drive system used in the previous embodiments. FIG. 12B schematically illustrates the stomach 3 tissue being wrapped around the end effector 300E''', and this can be performed according to any of the applicable techniques described above.

Figure 12C:
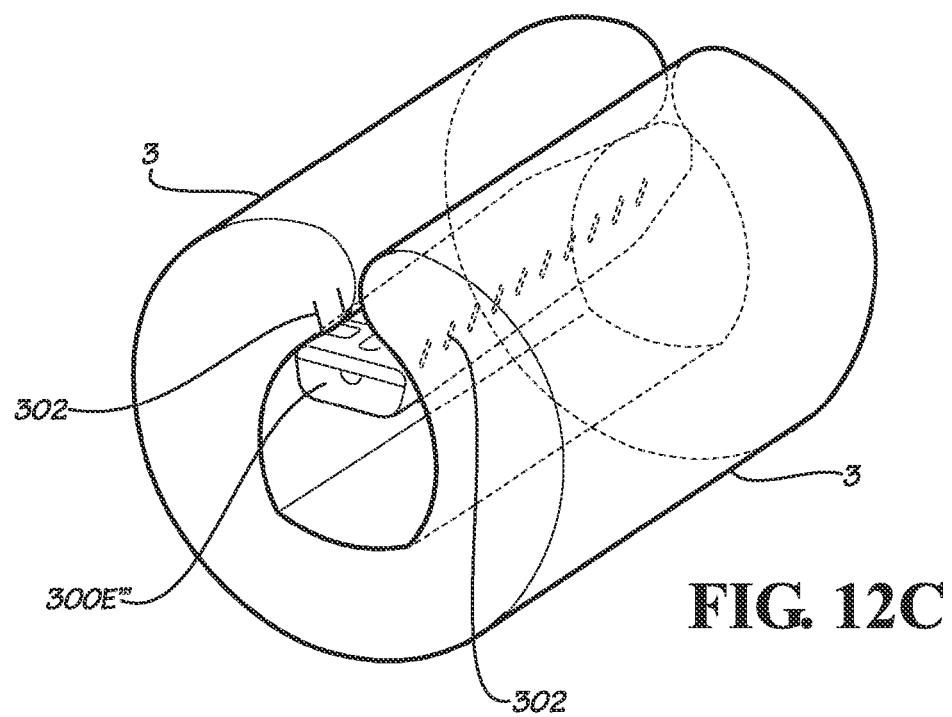
Figure 12D:
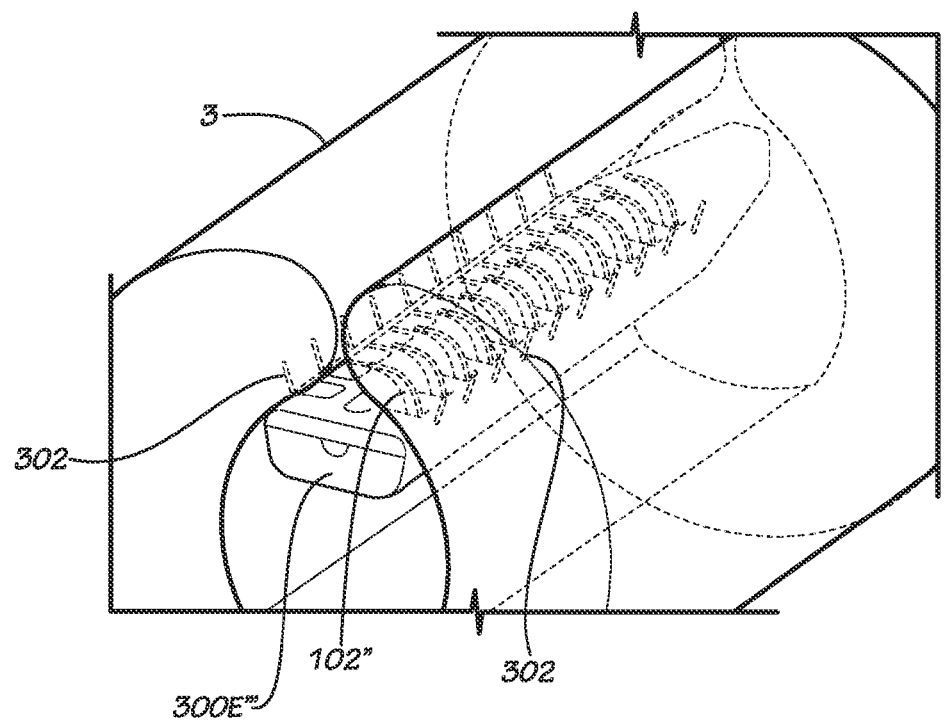

Next, at FIG. 12C, tissue pins/stabilizing pins 302 are deployed so as to temporarily hold the tissue in place during the stitching procedure. At FIG. 12D, piercing members/stitching needles 102" are deployed 9B, from the surface of the end effector 300E''' is begun, such as by use of an actuator like 442 described in regard to FIG. 8A, although not shown here. At FIG. 12D the piercing members/stitching needles 102" are shown in an early stage of deployment of the process, e.g., after only one or two pulls of the actuator, or after otherwise driving the drive shaft for only a short time. Note that the locations where the members/needles 102" pierce into the tissue 3 are substantially aligned with the locations where the corresponding stabilizing pins/tissue pins 302 pierce into the target. In the embodiment shown, the tip of the needle 102 is aligned axially (i.e., at the same length along the proximal-distal axis of the stitching instrument, i.e., the left-right direction in FIG. 12D) with the tip of the stabilizing pin 302, when both are in their starting positions, ready to pierce into tissue 3. Also, pins 302 are angled in a direction opposite to a direction toward which the stitching needles 102 are angled, relative to the surface of the tissue 3, as they enter the tissue 3. In this way, the stabilizing pins/tissue pins 302 provide counter-traction and prevent the tissue 3 from being dragged or bunched up or pushed away by the stitching needles 102 as they sweep through the tissue 3, being rotated into and then out of the tissue.

Figure 12E:
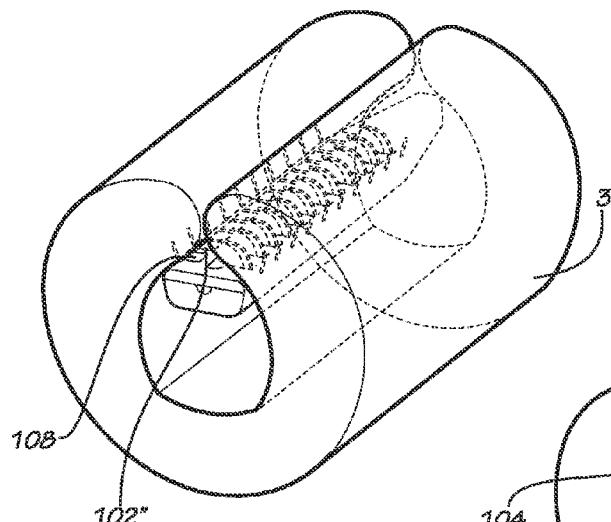
Figure 12F:
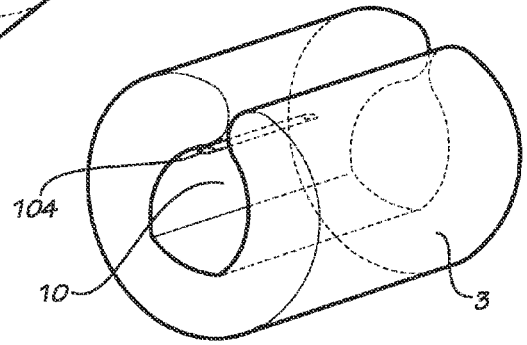

At FIG. 12E, the piercing members/stitching needles 102" have been deployed into the anchors 108, followed by retraction of the piercing members/stitching needles 102", leaving the anchor mates 106 mated with the anchors 108 and the attachment members/sutures therefore also attached to the anchors 106 via anchor mates 108. The stabilizing/tissue pins 302 are then retracted, and the sutures are tightened, instruments are removed and the implant is inflated, as in any of the applicable manners discussed above, leaving the final result schematically represented in FIG. 12F.

Figure 12G:
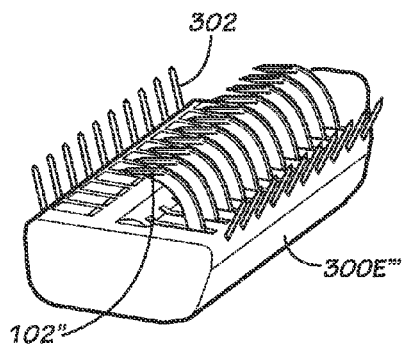
Figure 12H:
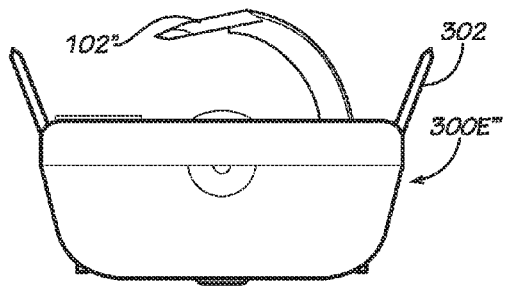
Figure 12I:
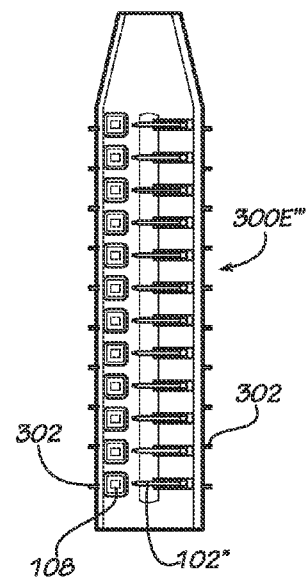

FIG. 12G shows an isolated perspective view of end effector 300E''' without the stomach 3 being shown, for clarity of illustration of the tissue/stabilizer pins (shown deployed) and piercing members/stitching needles 102" (shown partially deployed. FIG. 12H is an end view of the embodiment of FIG. 12G and FIG. 12I is a top view of the embodiment of FIG. 12G.

Figure 13A:
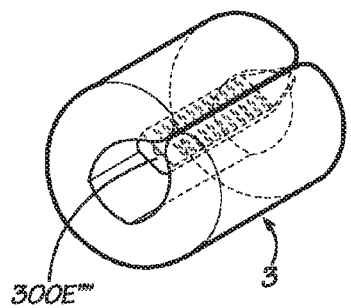
FIGS. 13A-13G show various views of an end effector according to another embodiment of the present invention and a method of using it according to another embodiment of the present invention.

FIG. 13A is a perspective view of an end effector 300E' according to another embodiment of the present invention. End effector 300E''' can be used alternatively to end effector 300E, 300E', 300E'' or 300E''' in the instruments described above. In this embodiment, piercing members/stitching needles 102" are rotated about ninety degrees upon storage in the end effector 300E', like that described above with regard to end effector 300'. Additionally, this embodiment is provide with a platform 300ER that is a separate component of the instrument that slides into place as shown in FIG. 13D, and on which anchors 108 are temporarily held.

FIG. 13A schematically illustrates the stomach 3 tissue having been wrapped around the end effector 300E''', and this can be performed according to any of the applicable techniques described above.

Figure 13B:
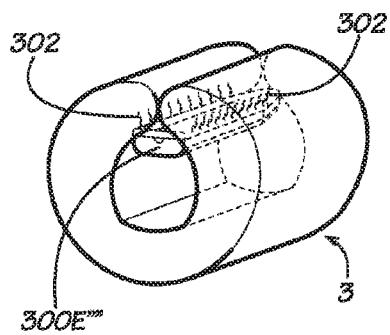
Figure 13C:
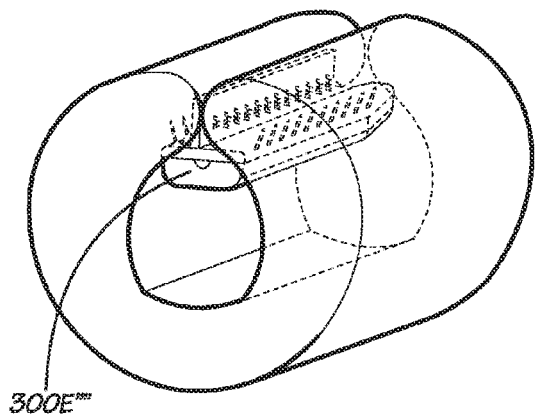
Figure 13D:
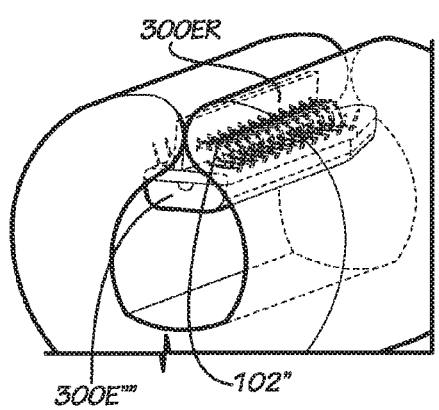
Figure 13E:
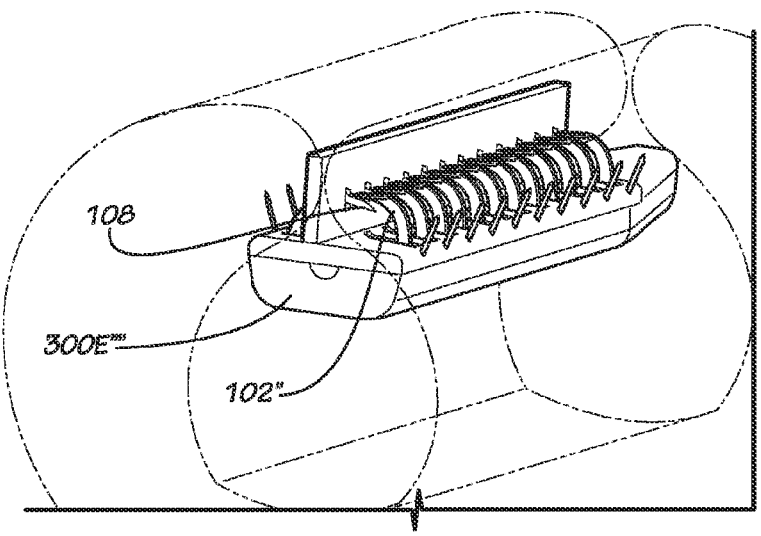
Figure 13F:
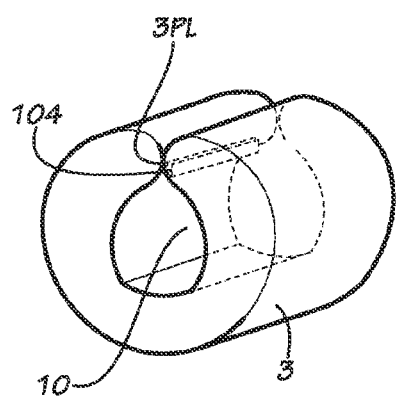
Figure 13G:
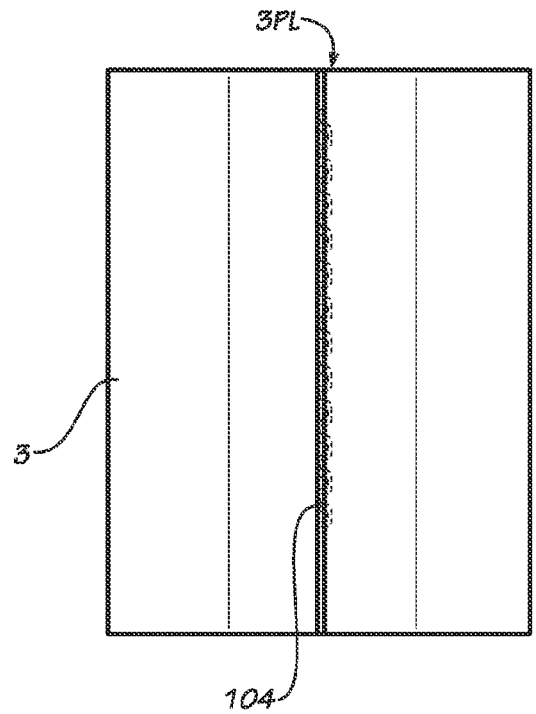

Next, at FIG. 13B, tissue pins/stabilizing pins 302 are deployed so as to temporarily hold the tissue in place during the stitching procedure. At FIG. 13C, platform 300ER is slid to its operational position. In the operational position, the operation surface of platform 300ER is substantially normal to the remainder of the top surface of the end effector 300E', including the locations from which the piercing members/stitching needles 102" are deployed, as can be seen in FIGS. 13C-13D. At FIG. 13D, deployment of piercing members/stitching needles 102" from the surface of the end effector 300E''' is begun, such as by use of an actuator like 442 described in regard to FIG. 8A, although not shown here. At FIG. 13E, the piercing members/stitching needles 102" have been deployed into the anchors 108. Next, the piercing members/stitching needles 102" are retracted, leaving the anchor mates 106 mated with the anchors 108 and the attachment members/sutures therefore also attached to the anchors 106 via anchor mates 108. The plate 300ER is withdrawn back to its non-operational/starting position so that end effector 300E' again appears as shown in FIG. 13A. The stabilizing/tissue pins 302 are then retracted, and the sutures are tightened, instruments are removed and the implant 10 is inflated, as in any of the applicable manners discussed above, leaving the final result schematically represented in FIGS. 13F-13G. FIG. 13F is a perspective schematic view and FIG. 13G is a schematic top view, showing the attachment members/sutures 104 along the plication line 3PL.

Figure 14A:
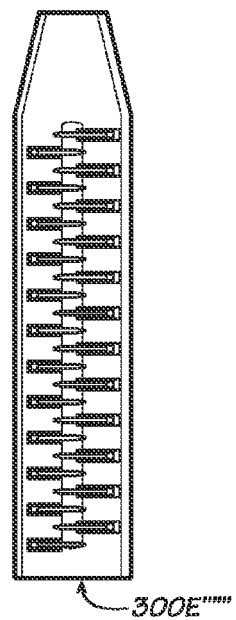
FIGS. 14A-14B are a top view and perspective view, respectively, of an end effector according to another embodiment of the present invention.
Figure 14B:
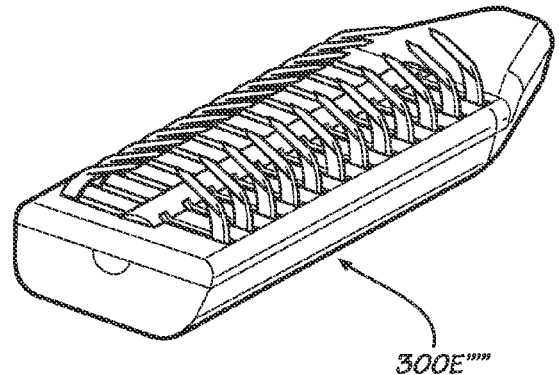

FIG. 14A is a perspective view of an end effector 300E'''' according to another embodiment of the present invention. End effector 300E'''' can be used alternatively to end effector 300E, 300E', 300E'', 300E''' or 300E'''' in the instruments described above. In this embodiment, two sets of piercing members/stitching needles 102", are provided, and are rotated about ninety degrees upon storage in the end effector 300E'''', like those of end effectors 300E''' and 300E''''. In this embodiment, one set of piercing members/stitching needles 102" is deployed from a top (contact) surface of the end effector 300E'''', while the second set of piercing members/stitching needles 102" are deployed from the opposite side of the top (contact) surface of the end effector, see FIG. 14B. In this way, stabilizer/tissue pins 302 are not needed because the forces of the two sets of piercing members/stitching needles 102" on the tissues oppose each other and drive the plications together, thereby maintaining the plication as desired during the stitching process.

Alternatively to making a greater curvature plication, or an anterior plication, a plication can be formed posteriorly, or one plication can be formed on the anterior side and another plication can be formed on the posterior side of the stomach 3. In an embodiment where a plication is formed on the anterior surface and a plication is formed on the posterior surface, this can create a sufficient restriction of the stomach 3 to be effective for weight loss without the need to dissect the blood vessels and connective tissues along the greater curvature 3G of the stomach 3, which could reduce the risk of ischemia in the stomach tissues. At least the following embodiment is useful for these alternative procedures. Alternatively, the following embodiment can be used in performing a greater curvature plication, where the blood vessels and connective tissues (e.g., omentum 5) are dissected to allow for a single, larger plication to be performed.

FIG. 15A illustrates an instrument 500 that includes suction for holding stomach 3 tissue in place during a plication procedure. Air poppets 502 are aligned inwardly of temporarily held anchors 108 with similar relative positioning to the anchors and suction provided in the embodiment of FIGS. 8A-8N. In the embodiment of FIG. 15A however, air poppets 502 can be used to individually capture stomach tissue during a plication procedure without losing suction from any of the other poppets 502. When suction is applied to the poppets 502, the poppets 502 normally remain closed and therefore do not lose any suction. As can be seen in FIGS. 15A, 15B and 15C, poppets 502 are raised above the main contact surface 504 of instrument 500 and also above the level of the anchors 108.

Figure 15D:
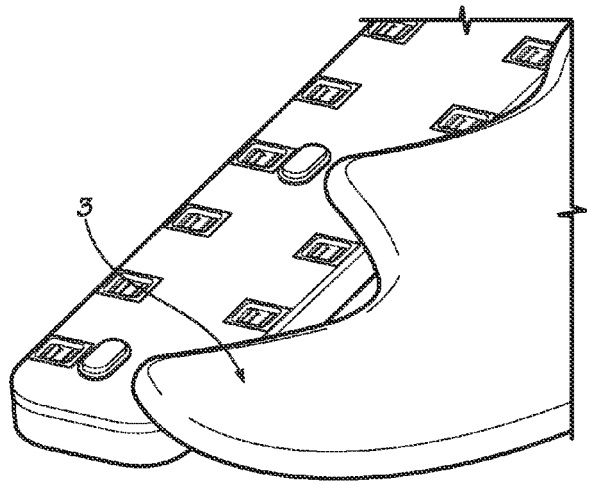

Suction is applied through the back ports 506 of the instrument 500. Back ports 506 are in fluid communication with poppets 502 via conduits (not shown) that extend through the instrument 500. The poppets are spring loaded to the normal, closed position shown in FIGS. 15A-15C. As stomach 3 wall tissue is pushed down on a poppet 502, this moves the top part of the poppet downward, thereby opening its suction port. The spring that biases the poppet 502 to the raised, off position is just strong enough to overcome the force of the suction. Therefore when additional force is applied to it, such as the stomach tissue contacting the top of the poppet 502, this compresses the spring and opens the suction port of the poppet 502. FIG. 15C illustrates one of the poppet tops having been removed to show the underlying spring 503 and suction port 505. As stomach wall tissue 3 is pushed down on a poppet, like shown in FIG. 15D, suction is applied to the stomach tissue thereby holding it in place. In the meantime, the other poppets 502 that have not been contacted with tissue stay closed, keeping the suction level constant with no significant loss of suction in the system.

Figure 15E:
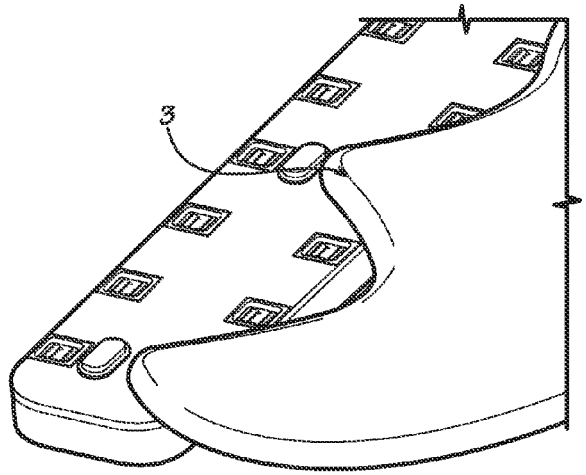

At FIG. 15E, another portion of stomach wall is pushed down against the next poppet in sequence, thereby attaching that portion of the stomach wall 3. Again, the poppets 502 that have not been contacted remain closed. Also, the previously attached stomach wall tissue remains engaged by the previously contacted poppet 502. The process can be repeated in the same manner for all remaining poppet, at which time the stomach plications can be more permanently fixed in placed, such as by suturing or the like.

Figure 16A:
FIGS. 16A-16D illustrate use of vacuum to ascertain proper placement of plicated tissue according to embodiments of the present invention.
Figure 16B:
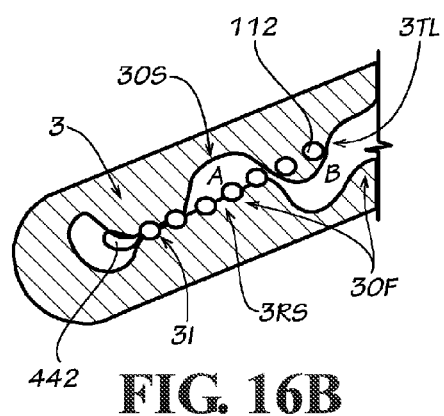

When performing a stomach plication, a method for maintaining the external wall portions being joined in serosa to serosa contact is important as the healing of the serosa to itself is a means of supporting, strengthening and maintaining the plication in the desired geometry. FIGS. 16A-16D illustrate vacuum tubes 442 that can be employed as a mechanical means of ensuring that the stomach tissue is folded into a desired configuration, and which may be used in embodiment such as that shown in FIG. 8G or the like. Vacuum tube 442 can be connected to a gauge such as a ball gauge or other type of gauge 443 outside of the patient so that when all of the suction ports of the suction tube are covered by stomach 3 tissue, the pressure in the gauge drops to a suction pressure indicative of such, but if the tissue breaks loose at one or more suction ports, the pressure level rises, indicating that the plication is not in proper position to be sutured. However, with only one vacuum tube 442 and gauge 443, it is possible that only one side of the plication may be covering the suction ports of the tube 442 thus leading to a false indication that the plication is ready to be sutured when, in reality, one side/fold of the stomach tissue is not properly positioned, and therefore serosa to serosa contact would not result if the plication were to be sutured under these conditions. For example, FIG. 16A illustrates use of only one tube 442 and gauge 443. FIG. 16B shows a possibility, using the arrangement of FIG. 16A, where the top left side of the stomach 3TL covers the vacuum holes/ports 112 but it is not in contact with the opposing fold 30F of the stomach 3. Likewise the right side fold at 3RS covers vacuum holes 112 but it is not in contact with the tissue fold on the opposing side at 3OS. 3I shows the ideal positioning of the stomach folds such that the opposing folds both cover the ports 112 and are in the correct positions for being joined in serosa to serosa contact.

Figure 16C:
Figure 16D:
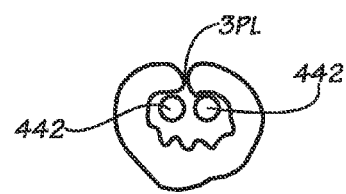

By providing two side-by-side vacuum tubes as illustrated in FIG. 16C, one vacuum tube 442 and its ports 112 can be dedicated to monitoring the positioning of one fold of stomach tissue, and the adjacent vacuum tube 442 and its ports can be dedicated to monitoring the positioning of the opposite fold of stomach tissue. To further ensure serosa to serosa contact of the opposing folds the vacuum tubes 442 can be provided to be movable relative to on another. Accordingly, in a first, relatively spaced apart position shown in FIG. 16C, the folds of stomach tissue can be placed over the suction tube 442 and engaged thereby. Once the gauges 443 register that the folds of tissue are properly covering the suction holes/ports 112, the tubes 442 can then be brought closer together, as illustrated at FIG. 16D, all the while maintaining the tissue folds in engagement with the tubes 442 via the applied suction force and bringing the tissue folds into serosa to serosa contact at the plication line 3PL.

FIG. 17A is a perspective view of another embodiment of an attachment instrument 400" according to the present invention, configured to be operated from outside of a patient, with the end effector having been inserted through a laparoscopic port or percutaneous opening and into contact with the patient's stomach 3 (e.g., into the abdominal cavity of the patient), and to reduce the effective volume of the stomach 3 by performing one or more plication procedures on it.

Attachment instrument 400" includes a pair of offset, elongate end effectors 400E", one being positioned higher than other, but substantially parallel therewith in both length and pitch aspects, each having a length greater than a width (typically at least more than twice as great) formed at a distal end portion of instrument 400". End effectors 400E1", 400E2" each include a distal end 400D, a proximal end 400E and first and second sides 400S. An elongate shaft 420 extends proximally from the proximal ends 400P of end effectors 400E1", 400E2". Shaft 420 has sufficient length so that a proximal end of the shaft 420 extends out of the patient's body when the end effectors are placed on the patient's stomach in a manner described below and illustrated in FIG. 17B.

A plurality of piercing members 102 (typically suture drivers such as stitching needles or the like) are positioned along a pair of rows extending lengthwise along the end effectors 400E1", 400E2", see FIG. 17B. Lower contact plates 4021, 4022 are spaced beneath and parallel with an upper tissue contact surface 4041, 4042 of the end effectors 400E1", 400E2", respectively, forming a gap 400G1, 400G2 therebetween as shown in FIG. 17B. A driving mechanism 410 is provided which is configured to drive folds of stomach tissue into the gaps 400G1, 400G2 as shown in FIG. 17B. The driving mechanism can be the same as that described above with regard to the embodiment of FIGS. 8A-8B.

After preparing the patient, inserting a bougie 50, 50' into the stomach 3 in a manner as described above and forming either a percutaneous opening (e.g., puncture and opening leading from puncture into the abdominal cavity, for a percutaneous procedure) or a plurality of ports for a laparoscopic procedure, end effectors 400E1", 400E2" of instrument 400" are inserted through the puncture or one of the ports and delivered into the abdominal cavity, where they are placed into contact with an exterior surface of the stomach 3. Typically, the end effectors are substantially aligned with the bougie 50, 50' adjacent to the bougie 50, 50' on a location of the stomach nearer to the greater curvature 3G or on the greater curvature 3G with the bougie 50, 50' being nearer the lesser curvature 3L. End effectors 400E1", 400E2" preferably contact the stomach 3 in an inferior to superior direction extending substantially over the body 3B and fundus 3F, but not over or in contact with the pylorus 3P, pyloric antrum 3PA, cardia 3C or gastro-esophageal junction 3GE.

Once the end effectors 400E1", 400E2" have been properly positioned as intended and contacted to the stomach 3, the roller bars 412 are operated by operating the driving mechanisms to draw stomach tissue into the gaps 400G1, 400G2 as illustrated in FIG. 17B. The plications of tissue formed are pulled over the lower roller bars 412 and under the upper roller bars 412. After the first stitch is completed, rollers 410 gather stomach tissue until a desired amount has been driven through the gap 400G2, see FIG. 17B. The first stitch is formed along the first side of the instrument, along end effector 400E1 and fixes the first fold of tissue, but then the rollers adjacent end effector 400E2" can continue to be operated to increase the amount of stomach tissue rolled through the gap 400G2, see FIGS. 17B-17C. The stitches are performed one at a time. A wedge can be pulled proximally with the instrument to push down one suture needle at a time as the wedge passes over them.

Once a satisfactory amount of stomach tissue has been drawn through gap 400G2, the stitches are driven on the second side 400E2" of instrument 400" to fix the other fold of tissue. A conjunction member 460 can be installed and sutures 104 cinched in the same manner as described above with regard to FIGS. 8P-8S. FIG. 17D shows instrument 400" having been removed but sutures 104 not yet having been cinched. FIG. 17E shows the procedure at the stage where the sutures 104 have been cinched, but not yet trimmed, and where the bougie 50, 50' has been removed.

Figure 18A:
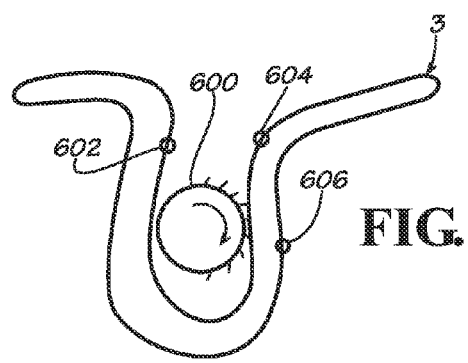
FIGS. 18A-18H are various views illustrating an instrument and use thereof to perform a plication according to embodiments of the present invention.
Figure 18B:
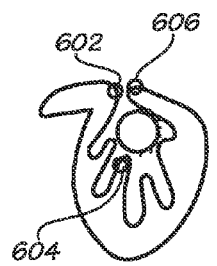
Figure 18D:
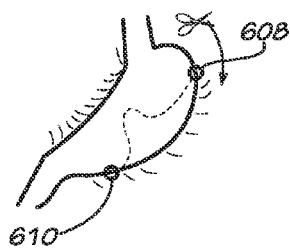
Figure 18C:
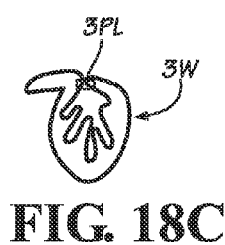

FIGS. 18A-18C illustrate use of a wrapping plication tool 600 used to leave a minimal amount of outer wall of the stomach 3 on the outside of the plication 3PL. The portion of the stomach wall 3W that was not collected into the center of the plication determines the final geometry of the plicated stomach. The more wall that is collected into the center, the less there is on the outer perimeter and the more restricted is the stomach lumen capacity internally. FIG. 18B illustrates how the rolling action moves an outer wall surface location 604 into the center of the plication, when location 606 is brought into apposition with location 602.

Figure 18F:
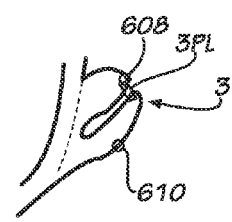
Figure 18G:
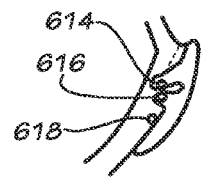
Figure 18E:
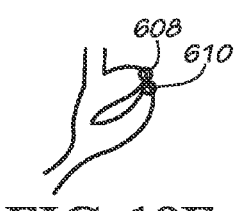
Figure 18H:
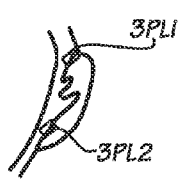

The method of FIGS. 18A-18C leaves a shorter stomach while also creating a smaller lumen so that the overall pathway for food mimics that of a gastric bypass. FIGS. 18D-18F show anterior view of a greater curvature plication performed using wrapping plication tool 600. By joining location 608 with 610, the stomach is effectively shortened, and a smaller lumen 612 is formed in the stomach 3, so that the effects of a gastric bypass are mimicked. FIG. 18G illustrate use of wrapping tool 600 to move locations 614, 616, 618 to together to join the stomach 3 tissue in two plications 3PL1, 3PL2.

Figure 19A:
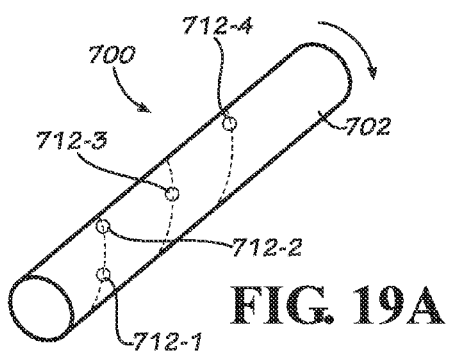
FIGS. 19A-19B are views of an instrument and stomach illustrating use of the instrument to perform a plication according to another embodiment of the present invention.
Figure 19B:
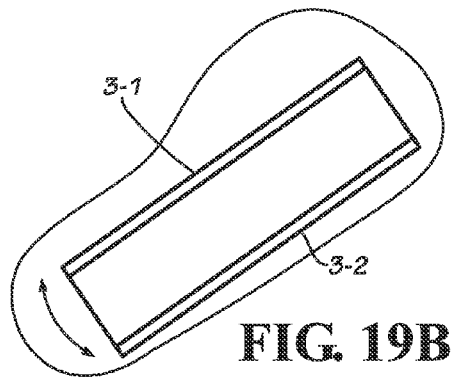

FIG. 19A illustrates an instrument 700 used in performing a plication of the stomach 3 according to another embodiment of the present invention. In this embodiment, suction ports/holes 712 are spirally positioned along roller body 702 as illustrated in FIG. 19A. FIG. 19B is an illustration of the stomach 3 with two lines or "rails" identifying locations of the stomach 3 intended to be joined in a plication 3PL. Instrument 700 is applied to rail location 3-1 with suction port 712-1 engaging the stomach tissue there. Tube 702 can be rotated to open a specific port, or to attach it to the stomach tissue. By selectively attaching and detaching ports, this separates the management of folding the stomach tissue and connecting the folds of tissue together. Instrument 700 is used to gather up the stomach tissue to be joined and then the plication is manually stitched with conventional suture and needle and laparoscopic tools.

Figure 20A:
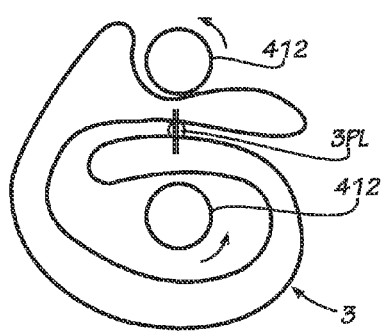
FIGS. 20A-20B illustrate use of an instrument to perform a plication according to another embodiment of the present invention.
Figure 20B:
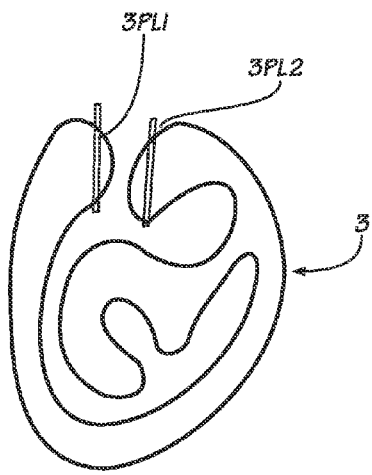

FIG. 20A illustrates a method in which both of the opposing folds of tissue are passed in opposite directions between rollers 412, after which they are connected at 3PL in serosa-to-serosa contact. FIG. 20B illustrates a method in which a first fold of stomach 3 tissue is secured such as by suturing. Subsequently, the stomach on the opposing side is rolled up further to gather more of the stomach 3 within the plication prior to fixing the opposing side at 3PL2.

Figure 21A:
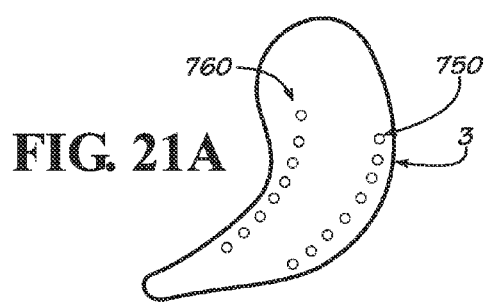
FIGS. 21A-21C illustrate a method of performing a plication according to another embodiment of the present invention.
Figure 21B:
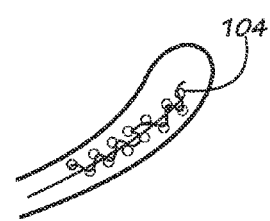
Figure 21C:
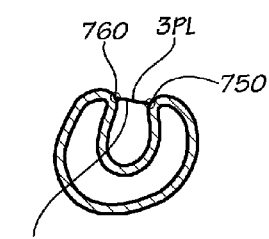

In FIGS. 21A-21B a first line of anchors 750 is installed on the surface of the stomach, such as in a location generally following the greater curve 3G and adjacent thereto, and a second line of anchors 760 is installed adjacent the lesser curve 3L and generally following the curvature thereof. Then, an attachment member/suture 104 is laced around the anchors 750, 760 and cinched down as shown in FIG. 21B. This draws the two sets of anchors 750, 760 up toward each other, thereby forming a fold/plication in the stomach tissue and reducing the volume of the stomach 3, as shown in the cross-sectional illustration of FIG. 21C.

Figure 22A:
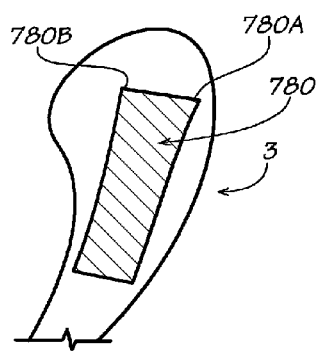
FIGS. 22A-22B illustrate a device and a method of performing a plication according to another embodiment of the present invention.
Figure 22B:
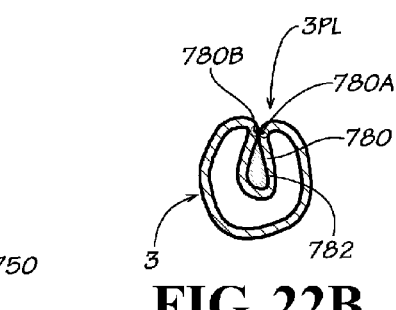

FIG. 22A illustrates an embodiment in which a mesh sheet 780 is attached to the stomach 3 on a location where a plication is intended to be formed. Sheet 780 includes rails or other connectors 780A and 780B (e.g., male/female connectors or the like) on opposite sides thereof. Once sheet 780 is securely fixed to the stomach 3, the connectors 780A and 780B are joined to one another, resulting in the plication 3PL shown in FIG. 22B. Mesh 780 is preferably formed of a material that encourages tissue ingrowth, such as any of the materials identified above as tissue ingrowth encouraging materials. This then encourages tissue to grow into the location 782.

FIG. 23A is a perspective view of a distal end portion of an instrument 800 that is useful for folding the stomach in the performance of a plication procedure, to position the folded stomach tissues for manual stitching by a surgeon. Instrument 800 can be inserted through a laparoscopic port 802 when in a compact configuration in which folding bars 830 are retracted to the compact configuration beneath the end effector 800E as shown in FIG. 23B. FIG. 23C show a side view of instrument 800 in the compact configuration. Shaft 810 is a fixed shaft that extends proximally of the end effector 800E and 812 is a rotational shaft that extends proximally form end effector 800E and is linked to bars 830 so that an operator can rotate the shaft 812 from outside the patient to rotate the bars 830 when they are in the abdominal cavity.

After establishing ports/pathway or other opening leading into the abdominal cavity from outside the patient, the omentum 5 and connective tissues are dissected at the greater curve of the stomach to provide access thereto, the same as described above with regard to FIGS. 7A-7B. A bougie 50, 50' may be inserted trans-esophageally and placed in the stomach 3 in a position such as shown and described above with regard to FIG. 7C, for example.

Once the end effector 800E and folding bars 830 have been inserted through the laparoscopic port 802 (or through a percutaneous opening for a percutaneous procedure or through a large opening if the procedure is an open surgical procedure) and have entered the abdominal cavity, the instrument 800 is installed on the stomach such that the end effector 800E is against one external wall of the stomach and the folding bars 830 are in contact with the opposite external wall of the stomach, similar to what is shown in FIG. 11D with regard to instrument 300". Folding bars 830 are elongated along the lengthwise direction of end effector 800E and preferably extend substantially parallel to the longitudinal axis L-L of end effector 800E. Folding bars 830 are rotationally mounted to instrument 800, each bar 830 having a radially extending portion 830R that is rotationally mounted to the instrument 800 and from which the main longitudinal portion 830L extends, as shown in FIGS. 23A and 23C-23E. This arrangement allows the longitudinal portions 830L of the bars 830 to be rotated relative to end effector 800E along arcs that are at predetermined distances from the end effector 800E. Once the instrument 800 end effector 800E and folding arms 830 are contacted to the stomach 3 and appropriately positioned in the manner described above, the folding bars 830 are rotated in opposite directions relative to one another, upwards to fold the stomach into a "U-shape". The stomach 3 is not shown in FIGS. 23D-23E for clarity, to view the actions and components of the instrument 800.

Next, at FIG. 23E, tissue pins/stabilizing pins 302 are deployed from end effector 800E into the folds of stomach tissue (not shown) to temporarily maintain the stomach folds in the desired positions/orientations for performing the plication. The surgeon may assist in pushing or further pushing the stomach tissue folds down on the pins 302 on both sides. This accurately positions the fold for a very tight, precise plication. Sutures are then manually placed by the surgeon to attached the two folds of stomach in serosa-to-serosa contact, like illustrated in FIG. 12F, for example, after which the pins 302 are retracted and the instrument 800 is removed. Optionally instrument 800 can be used along the greater curve 3G of the stomach to perform a plication after the omentum has been dissected. Optionally an implant may also be placed during the procedure in a manner also similar to that described in regard to FIG. 12F, as well as in other previous embodiments.

Figure 24A:
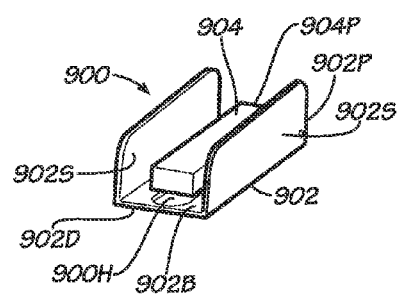
FIGS. 24A-24D are various views of another instrument for use in performing plication, according to an embodiment of the present invention.
Figure 24B:
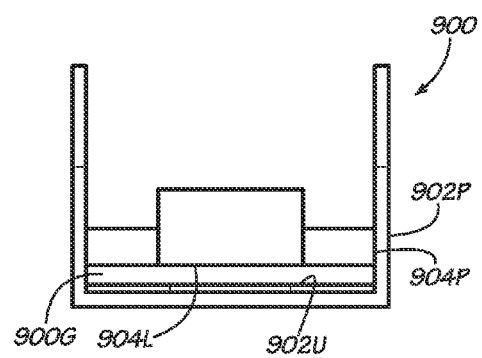
Figure 24C:
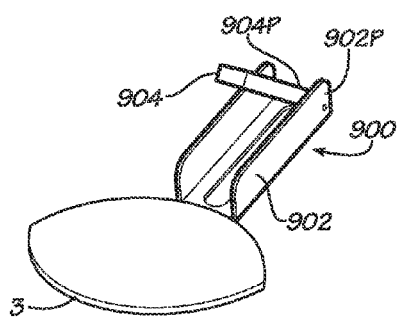

FIGS. 24A-24D illustrate another instrument 900 and use of instrument 900 on the stomach 3 to created folds in the stomach 3 for performing a plication according to another embodiment of the present invention. Instrument 900 includes an elongated, channel-shaped base jaw 902 and a mating jaw 904 that cooperates with base jaw 902. Base jaw 902 forms an open channel at a distal end 902D thereof and has sides 902S that extend upwardly from base 902B to form the channel. Mating jaw 904 is hinged to base jaw 902 at their proximal end portions as shown in FIGS. 24A and 24C. In the end view of FIG. 24B, it is shown that when the jaws 902, 904 are in a closed configuration, the mating jaw 904 is mounted such that the lower surface 904L is parallel to the upper surface 902U of base 902B and substantially parallel thereto, to form a gap 900G therebetween to provide a space for the stomach 3 so as to avoid overly compressing the stomach tissue, thereby avoiding tissue damage, necrosis, etc. Additionally the base 902B may be provided with an opening 900H to further relieve stress on the stomach 3 tissue between the jaws in the closed position, as a portion of the stomach 3 tissue therebetween may be forced out through the opening 900H, thereby reducing the pressure on the tissues.

Figure 24D:
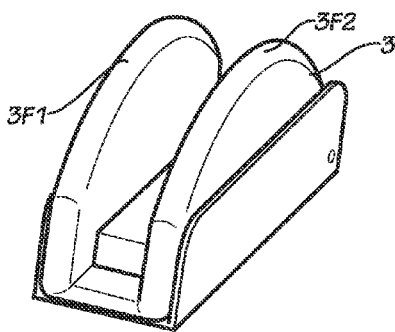

FIG. 24C illustrates the instrument 900 in an open position, in which mating jaw 904 is pivoted away from base 902. Instrument 900 is then installed over the stomach 3 so that base 902 is on one side of the stomach 3 and mating jaw 904 is positioned on the opposite side of the stomach 3. After such placement, the upper jaw 904 and base 902 are brought back together, to or at least toward the closed position, thereby forcing the stomach tissue 3 to conform into the channel, and shaping the stomach into a substantial "U-shape" as illustrated in FIG. 24D. At this time, a surgeon can complete the plication by manually suturing the two folds of stomach tissue 3F1, 3F2 together, after which the instrument 900 can be at least partially opened to remove it off the stomach, and then closed again to make it as compact a possible for removal from the abdominal cavity and patient. Optionally instrument 900 can be used along the greater curve 3G of the stomach to perform a plication after the omentum has been dissected.

Figure 25A:
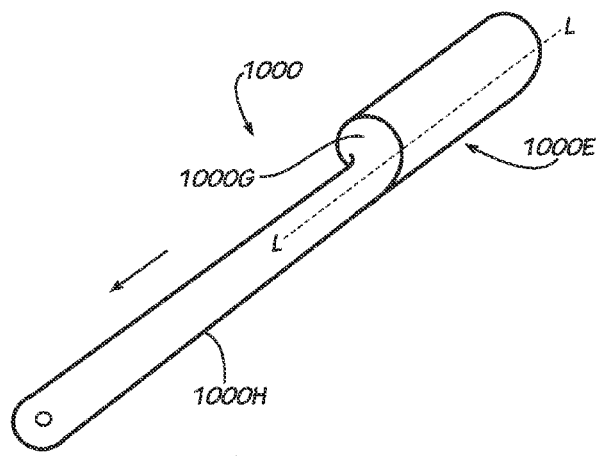
FIGS. 25A-25B are views of another instrument for use in performing plication, according to an embodiment of the present invention.
Figure 25B:
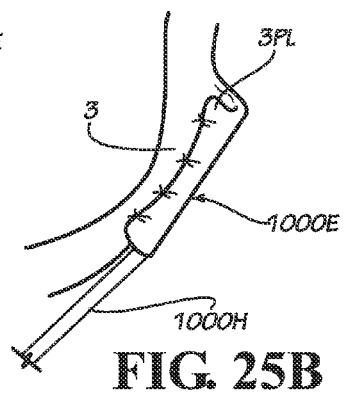

FIGS. 25A-25B illustrate instrument 1000 and use of instrument 1000 on the stomach 3 to maintain the stomach in the desired folded conformation while sutures are being placed to hold the plication. After establishing ports/pathway or other opening leading into the abdominal cavity from outside the patient, the omentum 5 and connective tissues are dissected at the greater curve of the stomach to provide access thereto, the same as described above with regard to FIGS. 7A-7B. A bougie 50, 50' may be inserted trans-esophageally and placed in the stomach 3 in a position such as shown and described above with regard to FIG. 7C, for example.

Instrument 1000 has a distal end effector 1000E and a handle 1000H that extends proximally therefrom. Handle 1000H has a length sufficient so that a proximal end portion of the handle can be grasped and operated from outside the patient even when the end effector is in its operative position on the target stomach 3 tissue, such as illustrated in FIG. 25B, for example. The end effector 1000E is curved about the longitudinal axis L-L of the end effector 1000E such that the inner walls of the end effector extend lengthwise, substantially parallel to the longitudinal axis L-L. Thus end effector 1000E forms a partial cylinder, with a gap 1000G that extends the entire length of the end effector 1000E so as to permit folded stomach tissue to enter in through the gap 100G and be held by the walls of the partial cylinder body of the end effector 1000E during the suturing of the plication. End effector 1000E may be made of a spring-like material, such as spring steel, Nitinol, or the like. After preparation of the surgical site as described above, the stomach is folded over into the configuration intended to be maintained by the plication, so as to reduce the effective volume of the stomach and thereby effect weight loss. Instrument 1000 is then inserted and end effector 1000E is slid over the fold of the stomach 3 tissue is then performed while end effector 100E remains in place to ensure that the stomach 3 remains folded in the manner desired, so as to ensure serosa-to-serosa contact of the stomach tissues being sutured together. As noted above, the end effector 1000E has a gap 1000G that is sized to allow the outside wall of the stomach 3 to remain in contact with one another, without being over compressed or damaged. Once the suturing has been completed, the end effector 1000E is slid off of the folded stomach tissues and instrument 1000 is removed from the patient.

Alternatively instrument 1000 could be formed of wire. Further alternatively, instrument 1000 could be formed of two pieces of curved metal with a hinge and a spring to provided clamping action over the folded stomach 3 tissues.

FIGS. 26A-26D illustrate a method of performing a plication of the stomach according to another embodiment of the present invention. After preparing the surgical site, such as by the techniques described above with regard to FIGS. 7A-7C, for example, the greater curvature portion of the stomach 3G has been cleared of omentum and vasculature to the extent that it is ready to be folded in a manner desired, see FIG. 26A. The stomach is then folded, such as by using laparoscopic instruments (graspers or the like) and/or other instruments for a percutaneous or open surgical procedure. Optionally, instrument 1000 may then be used to maintain the stomach in the desired folded configuration with end effector 1000E. Alternatively, the folded orientation can be maintained using graspers or other instruments.

Figure 26A:
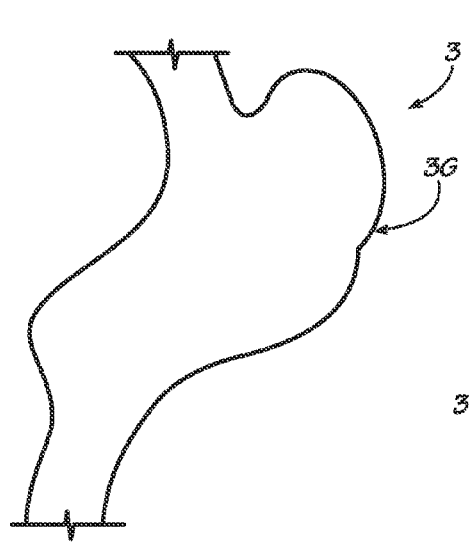
FIGS. 26A-26D illustrate various events in performing a plication according to another embodiment of the present invention.
Figure 26B:
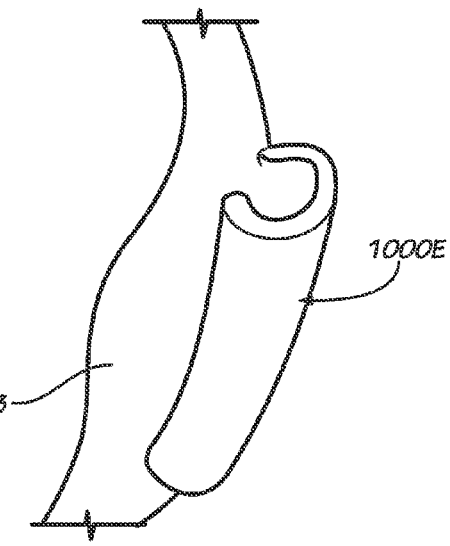
Figure 26C:
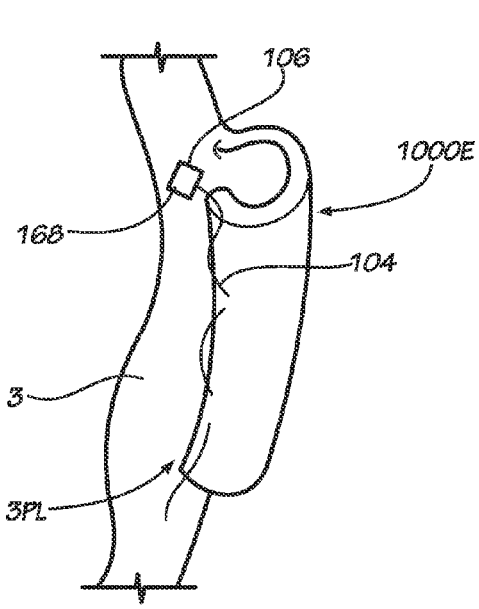
Figure 26D:
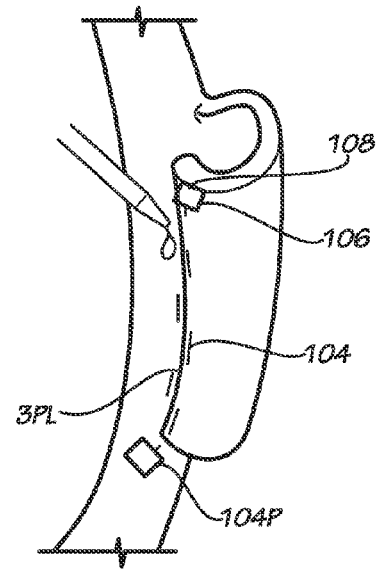

At FIG. 26C a needle is used to advance an attachment member/suture 104 through the edges of the fold at the plication line 3PL to fasten the fold in place. Attachment member 104 has an anchor mate 108 on a distal end portion thereof that interacts with the needle in the same manner as described above with regard to piercing members/suture drivers 102, as the needle also functions as a piercing member/suture driver 102. Also, anchor mate 108 mates with anchor 106 at the distal end of the plication line 3PL as shown in FIG. 26C. The attachment member/suture 104 is then pulled tight and tied at the proximal end of the stitch 104P. Optionally, bioglue (e.g., cyanoacrylate glue or other biocompatible adhesive suitable for this purpose) may be applied to the stitch line and plication line (fold seam) for added strength of the attachment.

Figure 27A:
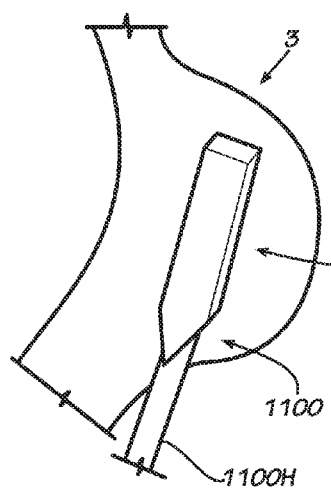
FIGS. 27A-27B illustrate an instrument and performance of a plication according to another embodiment of the present invention.
Figure 27B:
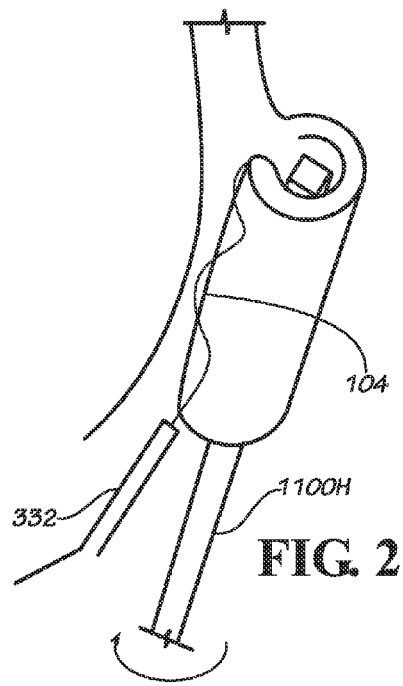
Figure 29A:
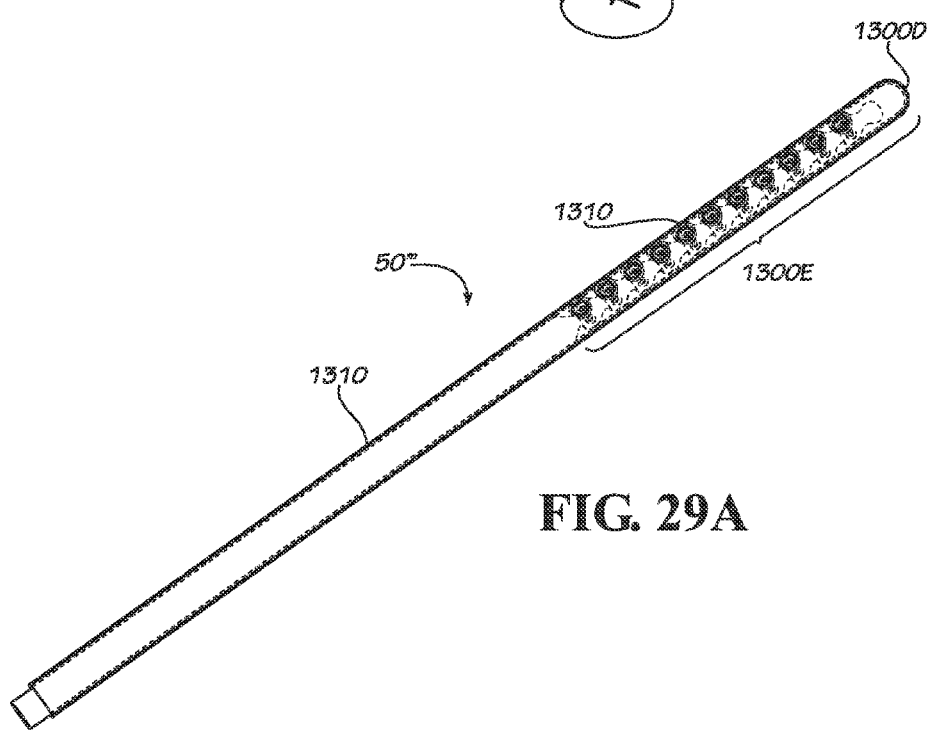
FIGS. 29A-29D illustrate an instrument and use thereof for forming a plication as well as functioning as a bougie according an embodiment of the present invention.

FIGS. 27A-27B illustrate instrument 1100 and use of instrument 1100 on the stomach 3 to form a plication by rolling according to an embodiment of the present invention. After establishing ports/pathway or other opening leading into the abdominal cavity from outside the patient, the omentum 5 and connective tissues are dissected at the greater curve of the stomach to provide access thereto, the same as described above with regard to FIGS. 7A-7B. A bougie 50, 50' may be inserted trans-esophageally and placed in the stomach 3 in a position such as shown and described above with regard to FIG. 7C, for example.

Instrument 1100 has a distal end effector 1100E and a handle 1100H that extends proximally therefrom. Handle 1100H has a length sufficient so that a proximal end portion of the handle can be grasped and operated from outside the patient even when the end effector 1100E is in its operative position on the target stomach 3 tissue, such as illustrated in FIG. 27A, for example.

After preparation as noted above, end effector 1100E is inserted into the abdominal cavity and contacted to the stomach 3 as illustrate in FIG. 27A. Tissue pins/stabilizer pins 302 (not shown) are next deployed from the surface of end effector 1100E that contacts the stomach, so as to better mechanically engaged the stomach tissues. The operator then rotates the handle 27B (counterclockwise in the embodiment shown in FIG. 27B). This rotates the end effector 1100E which is temporarily attached to the stomach tissue via pins 302, resulting in a rolling up of the stomach into a plication fold as illustrated in FIG. 27B. The instrument is held in place as shown in FIG. 27B. The stomach can be held in the rotated configuration by means of a clamp affixed to the shaft extra-corporally, while the plication line 3PL is fixed, such as by suturing. Once the suturing has been securely performed, pins 302 are retracted back into the end effector 1100E, the end effector 1100E is rotated is the opposite direction and slid out from within the stomach tissues and instrument 1100 is removed from the abdominal cavity and the patient. Alternative to pins 302, piercing members or needles such as 102, 102', 102" could be deployed from end effector 1100E.

FIGS. 28A-28G illustrate instrument 50" and use of instrument 50" within the stomach to function as a bougie and optionally, to make a plication in the stomach 3 by drawing on the stomach tissues from inside the stomach 3, although the attachment of the folds is preferably still performed by connecting the outside portions of the folds in serosa-to-serosa contact as described in previous embodiments.

Instrument 50" comprises an elongate flexible tube 1210 having at least two lumens therein. A first lumen 1212 is in fluid communication with suction ports 1218, and is connectable, at a proximal end portion thereof, to a source of suction so as to apply suction to suction ports 1218. A second lumen 1214 is in fluid communication with and inflatable anchor 1220 formed at a distal end portion of the instrument 50". A proximal end portion of the tubing forming lumen 1214 is connectable to a source of pressure, so as to fill the anchor 1220 with a pressurized fluid to expand it to the configuration shown in FIG. 28A. By disconnecting lumen 1214 from the source of pressure (or discontinuing the fluid communication with the pressurized fluid source such as by use of a valve and venting the portion of the lumen 1214 leading to the inflatable anchor 1220, the inflatable anchor can then be deflated to substantially the size of the tubing 1210 for easier installation or removal from the patient. Optionally, a third lumen 1216 may be provided as a main lumen sized and configured to allow instruments such as, but not limited to, an endoscope to be passed therethrough.

As noted above, a tube having known outside diameter can be used as a calibration tube for a plication procedure to adequately size the residual lumen left in the stomach by the plication procedure. Accordingly, instrument 50" can be used in any of the embodiments described herein that use bougie 50 or 50', as an alternative to such use.

In this embodiment, instrument 50" is useful not only as a bougie, but is operable as a tissue manipulator, utilizing suction through ports 1218 to engage mucosal tissue and draw the entire stomach wall into a fold, as described in more detail below.

Figure 28A:
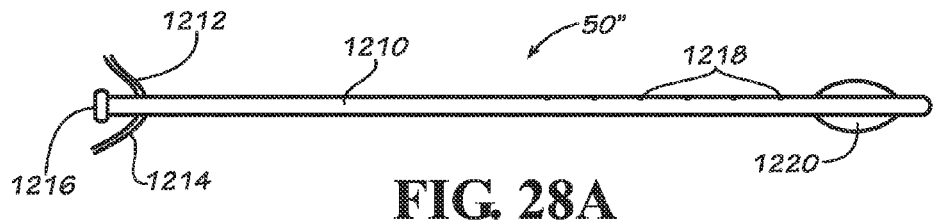
FIGS. 28A-28G illustrate an instrument and use thereof for forming a plication as well as functioning as a bougie according an embodiment of the present invention.
Figure 28B:
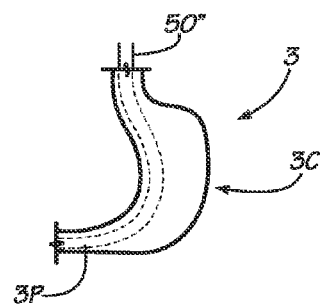
Figure 28C:
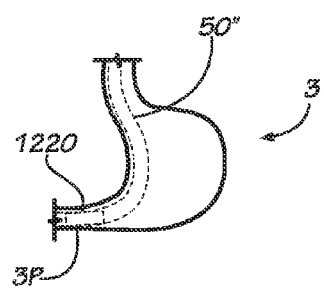

At FIG. 28B instrument 50" is placed transesophageally, down into the stomach 3, with the inflatable anchor 1220 placed towards the pylorus 3P. At FIG. 28C the anchor 1220 is inflated by delivering pressurized fluid thereto via lumen 1214. The anchor 1220 expands against the walls of the pylorus 3P thereby anchoring the distal end of the instrument 50".

Figure 28D:
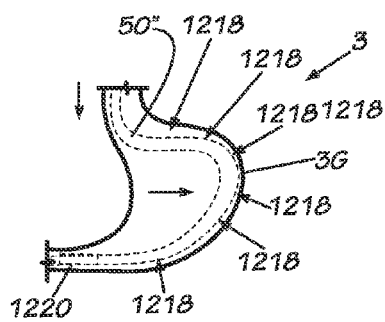
Figure 28E:
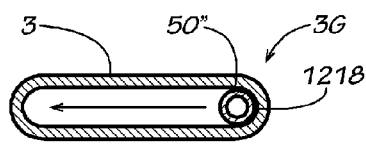

At FIG. 28D, the proximal end portion of instrument 50" extending out of the patient is pushed on to deliver more of the tubing 1210 into the stomach. Because the tubing 1210 if flexible and the instrument is anchored at 1220, the tubing snakes around and into contact with the mucosa of the greater curvature 3G of the stomach 3. Vacuum is applied through suction holes 1218 via lumen 1212 and this attaches the tubing 1210 to mucosa along the greater curvature as illustrated in FIG. 18D and the cross-sectional view of FIG. 28E.

Figure 28F:
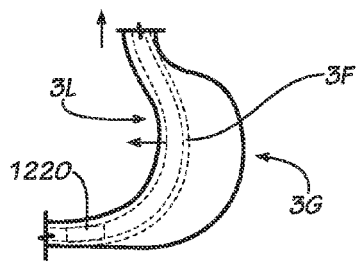
Figure 28G:
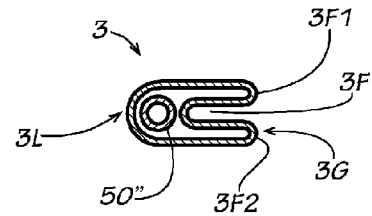

At FIG. 28F, the proximal portion of the tubing 1210 extending outside of the patient is pulled on, to pull some of the tubing 1210 out of the stomach and thus shorten the length of the tubing 1210 that remains inside the stomach. This causes the anchored tube to move toward the lesser curvature 3L (to the left in FIG. 28F) thereby pulling a fold 3F of stomach tissue from the greater curvature 3G inward, as indicated in phantom in FIG. 28F and as shown more clearly in the cross-sectional illustration of FIG. 28G. Thus, this procedure actively sizes the lumen that will remain in the stomach after completion of the procedure, as the fold 3F is actively pulled by the instrument 50" into place against the bougie 50" thereby accurately sizing the lumen all through the stomach 3. The plication shape is formed and the folds 3F1, 3F2 can be fixated, joined by suturing, staples or other attachment features, including, but not limited to automated suturing as described herein, automated stapling, etc.

FIGS. 29A-29D illustrate instrument 50''' and use of instrument 50''' within the stomach, according to another embodiment of the present invention, to function as a bougie and optionally, to make a plication in the stomach 3 by drawing on the stomach tissues from inside the stomach 3, although the attachment of the folds is preferably still performed by connecting the outside portions of the folds in serosa-to-serosa contact as described in previous embodiments.

Figure 29B:
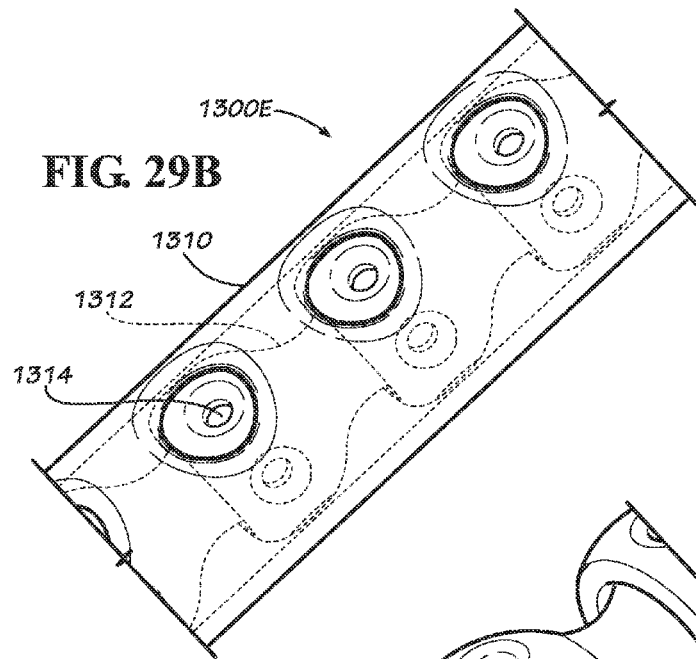
Figure 29C:
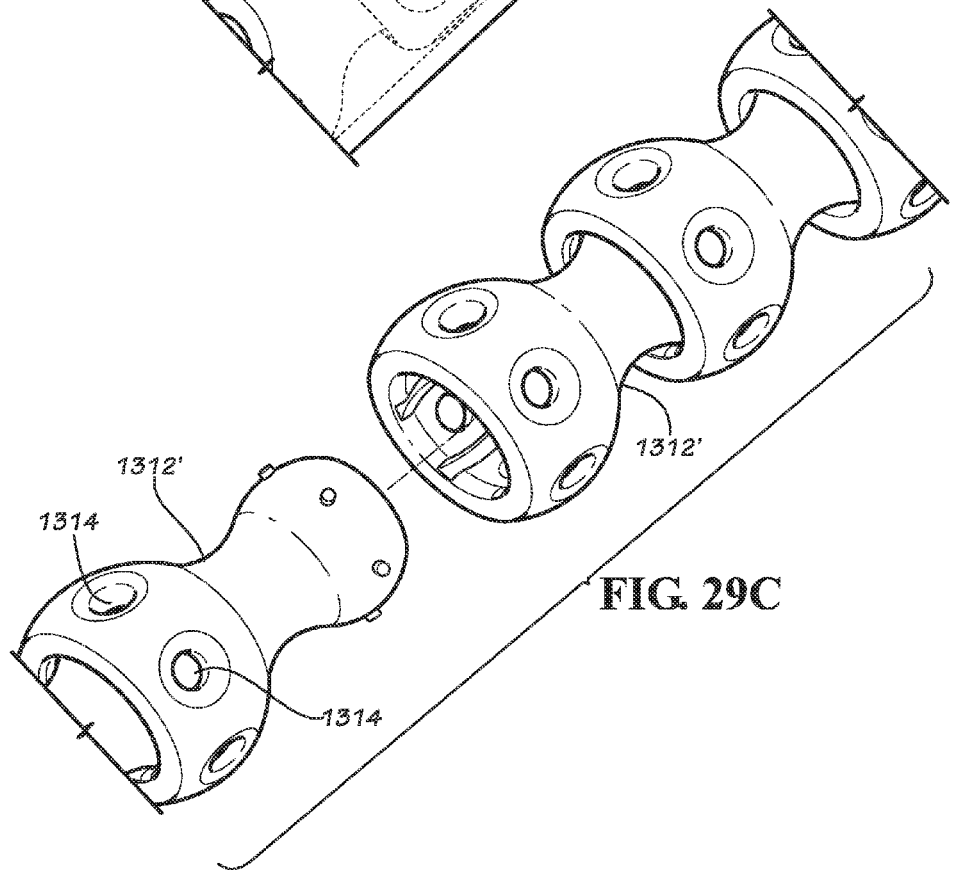
Figure 29D:
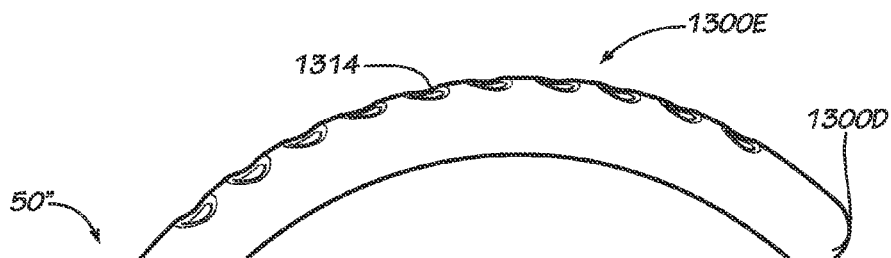

Instrument 50''' comprises an elongate flexible tube 1310 and an end effector 1300E formed in a distal end portion of tube 1310. FIG. 29B illustrates a plurality of members 112 interconnected by joints so render the end effector 1300E flexible. Each member 112 includes at least one suction port 1314 that opens through tubing 1310 for application of suction to the inner stomach wall (mucosa). The suction ports are in fluid communication with a lumen (not shown) in tubing 1310 that is connectable to a source of suction proximal of instrument 5''' and outside of the patient. FIG. 29C shows a variation of the end effector of FIG. 29C, in which members 1312' are individually separable and snap together. Like the variation in FIG. 29B, the members 1312' are formed to fit together to form ball and socket joints therebetween, and each has at least one (multiple in the embodiments shown) suction port 1314 that opens to the outside of the instrument 50'''. FIG. 29D illustrates the flexibility provided by the members 1312, 1312' in the end effector 1300E. The portion of the tubing 1310 proximal of end effector 1300E is flexible but somewhat stiff, similar to the consistency of a garden hose, such that it can be pushed without buckling, but it is still flexible enough to curve to conform to tortuosity of the pathway that it is inserted through, such as curvature of the esophagus, stomach, etc., while still being capable of being advanced by pushing on it from a proximal location outside the mouth of the patient.

Although instrument 50'' is flexible in bending, as illustrated in FIG. 29D, it is rigid when axially torqued about its longitudinal axis.

In this embodiment, instrument 50''' is useful not only as a bougie, but is operable as a tissue manipulator, utilizing suction through ports 1314 to engage mucosal tissue and torque the entire stomach wall to roll it into a fold, as described in more detail below.

After connecting instrument 50''' to a vacuum source, instrument 50''' is inserted into the patient's esophagus until it enters the stomach 3. The distal tip 1300D of instrument 50''' is blunt and finds its way toward the pylorus 3P. The end effector 1300E is flexible, as noted, and so as more of the instrument if fed into the stomach after contacting the tip 1300D in the pylorus 3P, the end effector 1300E curves into contact with the greater curvature of the stomach 3 inside the stomach, much like instrument 50'' does in FIG. 28D. The vacuum source is turned on and the mucosa of the greater curvature 3G is thereby attached to the suction ports 1314. A proximal portion of instrument 50''' that extends out of the patient is than axially torqued. Since the instrument 50''' is rigid under axial torqueing, this rotates the end effector 1300E, thereby rolling up the stomach to a folded configuration suitable for plication. When multiple suction ports 1314 are provide in each member 1312, 1312', this is advantageous as the members attach to multiple locations of the mucosa upon rotating and thereby more securely hold the plication during suturing. The plication line can be sutures via conventional laparoscopic techniques. Once the plication line has been securely sutured, the vacuum can be turned off and instrument 50''' can be withdrawn from the stomach 3 and the patient. Alternatively, each member 1312, 1312' could be provided with a large suction slot rather than a plurality of suction ports. Instrument 50''' can be used alternatively to the use of 50, 50' or 50'' in any of the other embodiments described herein that refer to use of bougie 50 or 50'. Alternatively, the stiffness of 50, 50' or 50''' can be adjustable by means of a tapered mandrel inserted into an axial lumen. Since the thinner portions of the mandrel are lower in stiffness than the proximal portions, the mandrel can be advance or retracted inside the lumen to adjust the stiffness to the appropriate level for apposition to the greater curvature of the stomach.

Figure 30A:
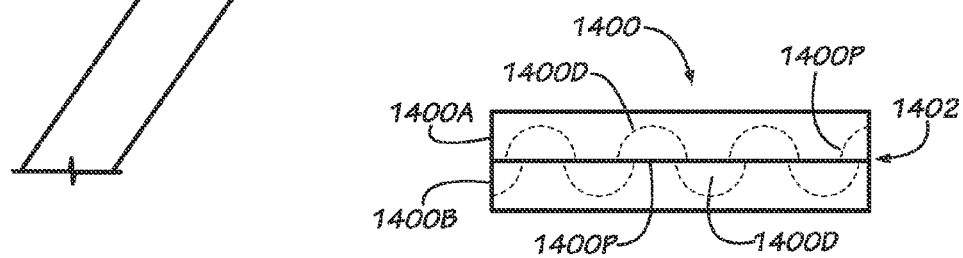
FIGS. 30A-30D illustrate an instrument for deforming tissues to be sutured and suturing the tissues, according to an embodiment of the present invention.
Figure 30B:
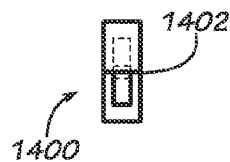
Figure 30C:
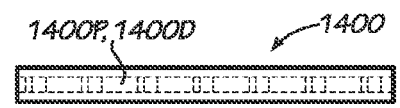
Figure 30D:
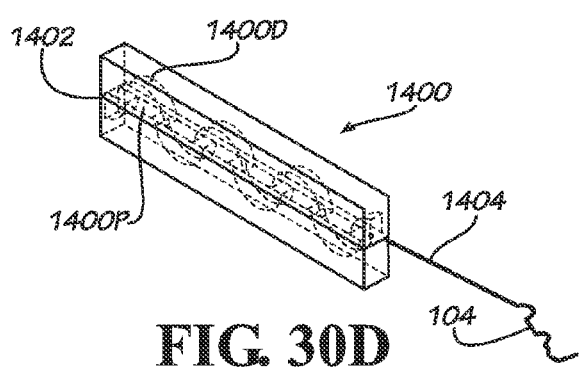

FIGS. 30A-30D are plan, end, top and perspective view of an instrument 1400 useable to create a suture line for joining stomach tissues together in a plication. Instrument 1400 includes first and second base members 1400A and 1400B each having a contact surface configured to contact stomach 3 tissues to be attached, and to sandwich those tissues therebetween. The contact surfaces each have a plurality of alternating depressions 1400D and 1400P that are configured to mate with the depressions 1400D and protrusions 1400P of the other base member when the base members are brought together. Accordingly, the sequence of depressions and protrusions of one base 1400A are offset from that of the other base 1400B as shown in FIGS. 30A and 30B, so that the opposing protrusions 1400P mate with depressions 1400D and the opposing depressions 1400D mate with protrusions. When these bases 1400A, 1400B are separated, the stomach tissues to be sutured are placed between the bases at 1402. When the bases are pressed together, the mating protrusions 1400P and depressions 1400D deform the stomach 3 tissues accordingly, forming an undulating shape in the tissues. Once the bases 1400A, 1400B are fitted together (FIG. 38C, 38D) with the stomach tissues therebetween, a wire 1404 is inserted into a predefined pathway between the bases 1400A,1400B. This wire passes through both layers of stomach tissue 3 that are to be joined, entering and exiting the many undulations of the tissue pair. An attachment member/suture 104 is fixed to the proximal end of the wire 1404. Once the distal end of the wire 1404 emerges from between the bases 1400A, 1400B at the opposite end from which it was inserted, it can be pulled out from between the bases, 1400A, 1400B, thereby dragging the suture through the same pathway that the wire had taken thorough the undulations of the tissue layers. The suture 104 can then be secured to the stomach 3 tissue near both proximal and distal ends of the bases 1400A, 1400B. Then the bases 1400A, 1400B can be separated and removed, leaving the tissues sewn together by suture 104.

Figure 31A:
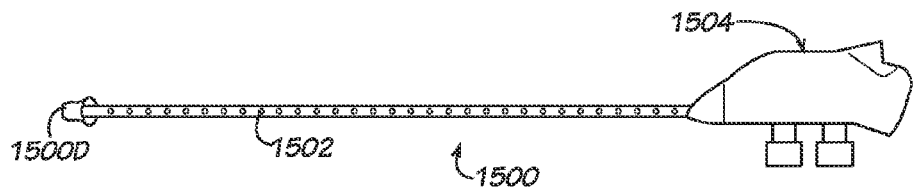
FIGS. 31A-31B illustrate a plan view and a partial view, respectively, of a view of an instrument that can be used to manipulate stomach tissue in furtherance of a plication procedure according to an embodiment of the present invention.
Figure 31B:
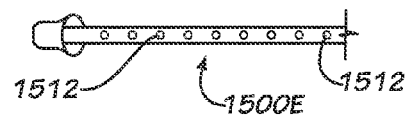

FIG. 31A is a plan view of an instrument 1500 that can be used to manipulate stomach tissue in furtherance of a plication procedure according to an embodiment of the present invention. Instrument 1500 includes an elongate shaft 1502 and a handle 1504 formed at a proximal end portion thereof. At least one suction hole (preferably a plurality of suction holes 1512, as shown) is formed in the end effector 1500E formed at the distal end portion of the shaft 1502, see FIG. 31B. A source of suction can be connected to instrument 1500 at port 1506 in handle 1504. Port 1504 is in fluid communication with holes/ports 1512 via shaft 1502. The distal end of the shaft is closed. Upon placement of end effector 1500E in contact with stomach 3 tissue and actuation of vacuum applied to suction holes 1512, the suction holes, in contact with the stomach 3 tissue, engage the stomach tissue with sufficient force such that movement of the instrument 1500, such as by an operator moving the handle 1504 from outside the patient to effect movement of the end effector 1500E, in turn moves the stomach 3 tissue. The suction openings 1512 can be designed so that a collection of instruments 1500 having different sizes and/or numbers of openings 1512 can be provided to allow for the appropriate length of tissue to be grasped. Alternatively, instrument 1500 may be provided with the ability to close off one or more openings. A relatively smaller opening or single opening 1512 could be used to attached to tissue at a single point location, whereas longer or multiple openings 1512 can be used to manipulate longer lengths of tissue 3. For suturing tissues together, two or more instruments 1500 may be used to manipulate the tissues to be joined to move them into the desired locations for suturing.

For plication, different parts of the stomach 3 can be grasped using vacuum, lifted, and then placed close together.

Figure 32A:
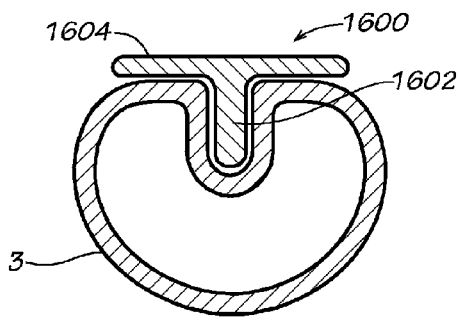
FIGS. 32A-32C illustrate an instrument for use in performing a plication according to another embodiment of the present invention.
Figure 32B:
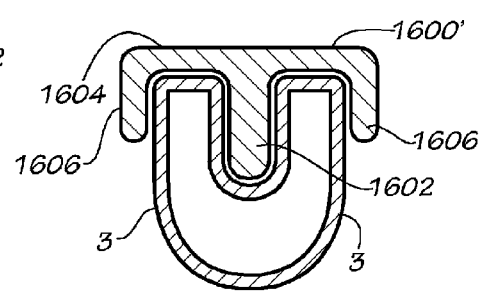
Figure 32C:
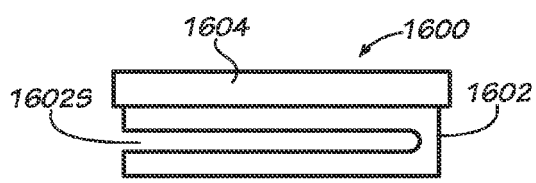

FIGS. 32A-32C illustrates variations of an instrument 1600, 1600' that can be used in the performance of a plication procedure on the stomach, according to an embodiment of the present invention. Instrument 1600 is rigid and formed as a T-shaped spine, having a deformation spine 1602 and a cross member 1604. Instrument 1600 can be made of biocompatible metal or rigid plastic. In use, instrument 1600 is pressed against the stomach so as to trap and plicate the stomach 3 tissue as shown. The deformation spine 1602 causes folding of the stomach tissue and the cross member maintains the outer folds of the plication evenly and up against the deformation spine in preparation for joining them together, such as by suturing or the like. The deformation spine 1602 may be provided with a slot 1602S (see FIG. 32C) or other opening or openings that allow suturing therethrough, but still permits the instrument 1600 to be removed after suturing has been performed. In the variation of FIG. 32C, side guides 1606 extend from the edges of cross member 1604 in substantially the same direction that deformation spine 1602 extends in, thereby better channeling the tissue folds between the deformation spine and the respective side guides 1606. Once the folds of the stomach have been connected together, instrument 1600 can be slid out and removed from the patient.

Further alternatively deformation spine 1602 may contain a mechanism that automatically holds and/or seals the plicated stomach together.

Figure 33:
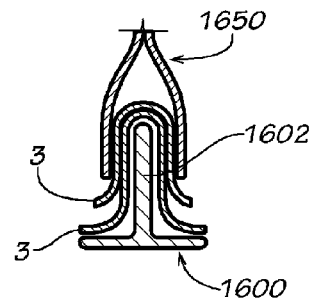
FIG. 33 illustrates instruments for use in performing a plication according to another embodiment of the present invention.

FIG. 33 illustrates an embodiment that employs an instrument 1600 together with a forked clip 1650. The empty, relaxed stomach 3 is draped over the instrument 1600 and deformation spine 1602 deforms the stomach 3 tissues, creating the plication. The forked clip 1650 is then applied over the folded stomach 3 tissues to hold them in place against the deformation spine 1602 of instrument 1600. Instrument 1600 is then removed, sliding the deformation spine 1602 out from between the folded tissues and leaving the folds of the stomach clipped together by instrument 1650, thereby reducing the volume of the stomach. Additionally the clamped, folded tissues can be sutured, stapled or otherwise further connected, and instrument 1650 can be left in place or removed.

Figure 34:
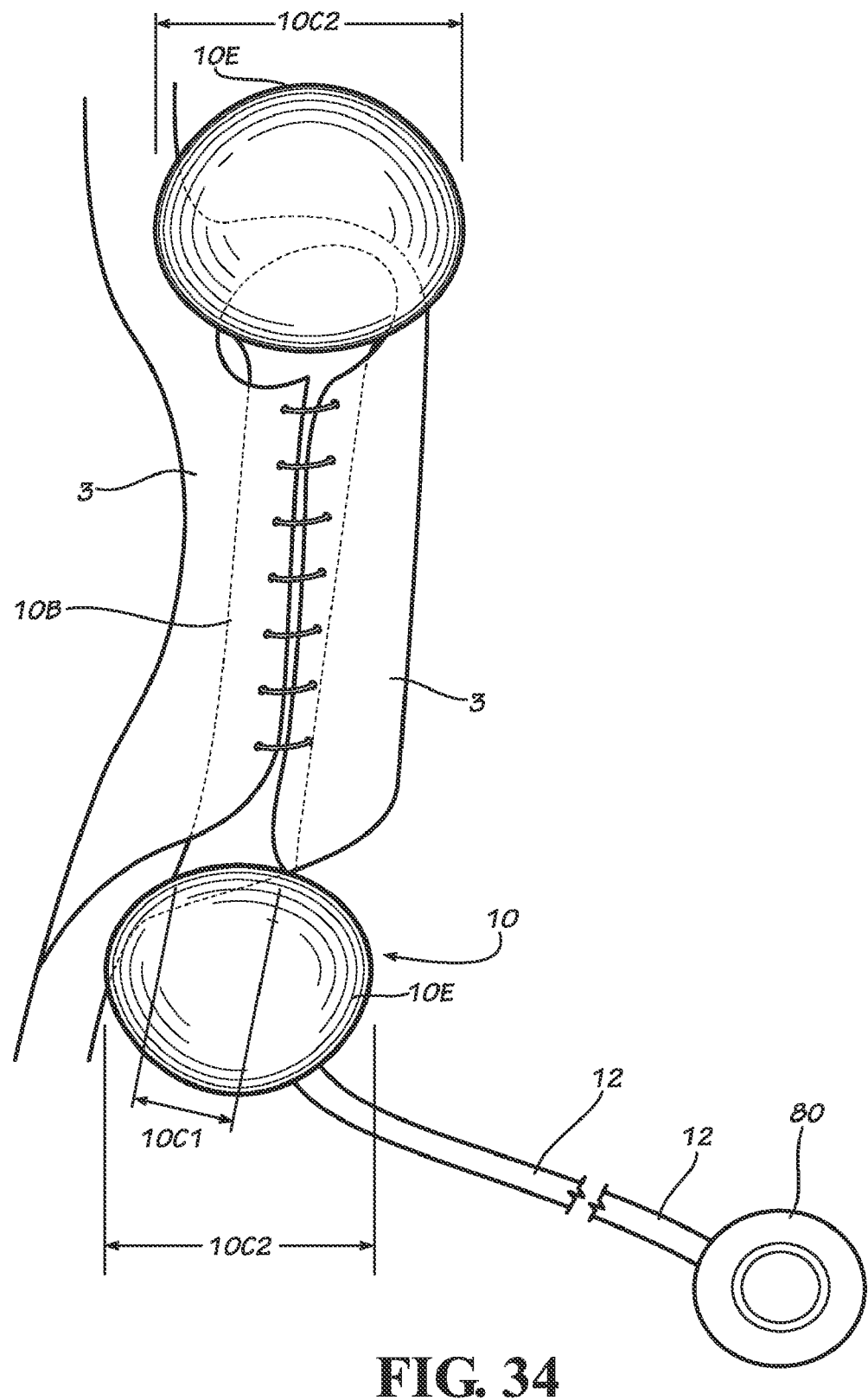
FIG. 34 illustrates an implant according to an embodiment of the present invention.

FIG. 34 illustrates a dumbbell-shaped implant 10 that can be implanted in a plication according to procedures described herein. Implant 10 includes an elongate, substantially cylindrical, central body portion 10B having a first cross-sectional dimension (diameter) with enlarged portions 10E formed at both ends of the central body portion 10B. Then enlarged portions are bulbous and have a cross-sectional dimension larger than the cross-sectional dimension of the central body. In the embodiment shown, each enlarged portion is substantially spherical and has a cross-sectional dimension (diameter) 10C2 that is greater than the cross-sectional diameter 10C1 of the central body 10B.

A plicated stomach can expand over time. By attaching an inflatable implant 10 in the folded stomach 3 as illustrated in FIG. 34, this allows adjustment of the compression on the stomach, and thus compensation for expansion of the stomach, by expanding the implant 10 further, without the need for further surgery. The main body (narrow section) of the implant 10 is attached inside the plicated stomach, while the enlarged portions 10E extend out towards the fundus end of the stomach 3 as well as the antrum. The implant is inflatable via a subcutaneous port 80 in fluid communication with an inflation tube 12 which we have already described in detail previously. By making the implant 10 dumbbell-shaped, the size can be made universal. In patients with a relatively shorter length of the plicated stomach 3, the enlarged ends 10E of the dumbbell-shaped implant 10 will occupy space and prevent the motion of the implant 10 out of its intended location. In plicated stomachs 3 that are relatively long, the dumbbell-shaped implant 10 will still function by providing adequate restriction while one or both of the enlarged portions are inflated inside of the plicated area. The dumbbell shape of the implant 10 can reduce the number of attachments required since additional anchoring is provided by the enlarged ends 10E. This can result in smaller instruments being used to perform the attachment procedures and enable linearity of the attachment locations, thus overcoming challenges in stitching along the curvature of the stomach. Alternative shapes for implant 10 include, but are not limited to: substantially cylindrical (already described above), disc-shaped or cube-shaped.

FIGS. 35A-35C are perspective views of an attachment instrument 400''' according to another embodiment of the present invention, configured to be operated from outside of a patient, with the end effector having been inserted through a laparoscopic port or percutaneous opening and into contact with the patient's stomach 3 (e.g., into the abdominal cavity of the patient), and to reduce the effective volume of the stomach 3 by performing one or more plication procedures on it. Of course instrument 400''' could also be used during open surgery.

Attachment instrument 400''' includes an elongate end effector 400E''' comprising first and second end effector portions 400E1''' and 400E2''' and operates similarly to attachment instrument 400 with notable differences described hereafter. A joint 423 is provided intermediate of shaft 420''' that permits the operator, after inserting the end effector 400E''' into the abdominal cavity to operate the handle 430''' from outside of the patient to articulate the end effector 400''' and distal end portion 420D of shaft 420''' relative to the proximal end portion 420P of shaft 420''' and handle 430'''. This can assist in orienting the end effector 400E''' more tangentially to the stomach 3 before contacting it, than what otherwise might be possible in embodiments where the end effector has to remain aligned with the entire shaft and handle, the angle of which is sometimes not optimum in view of the angle of approach needed to be taken when inserting the instrument from outside the patient and into the abdominal cavity. An example of this is illustrated in FIG. 3I.

FIG. 35A illustrates instrument 400''' in a configuration where lower contact plate 402''' on end effector portion 400E2''' is spaced beneath and parallel with an upper tissue contact surface 404''' on the end effector portion 400E1''' of the end effector 400E''', forming a gap 400G between plate 402''' and surface 404''' as shown. Actuators 432D and 432P are cyclically actuatable to operate distal ratchet driving mechanism 434D and proximal ratchet driving mechanism 434P respectively, to vary the distances between the plate 402''' and surface 404''' at 434D and 434P and locations therebetween. The independently operable ratchet systems 434D, 434P are independently controllable to better account for varied thicknesses of the stomach 3 along the plication line.

Optionally the end effector 400E''' may be slightly curved relative to its longitudinal axis, as shown, to better match the curvature of the bougie 50, 50', 50'', 50''''' and/or lesser curvature 3L of the stomach 3, so as to achieve a plication line 3PL that better conforms to the lesser curvature 3L resulting in a more consistent cross-sectional size and shape of the lumen that is left in the reduced stomach, see FIGS. 35D and 35E. Alternatively, the end effectors 400E''' could be designed to have linkages along their length to allow the user to adjust the overall curvature to match the curvature of the bougie 50, 50', 50'', 50''' and inner curvature of the stomach 3 (i.e., lesser curvature 3L).

Actuator/button 436 when pressed/actuated, activates a suction system supplied with suction via suction line 116 and which functions like previously described suction ports used to help ensure that tissue to be plicated is properly positioned. Actuator/button 438 has an appearance like actuator/button 436 but is positioned on the opposite side of handle 430'''. When pressed/actuated, actuator/button 438 activates the tissue clamping system of instrument 430''', which actuates small clamping features along the end effectors 400E''' that clamp onto the stomach tissue at locations near the locations where the tissue contacts the suction features. This tissue clamping thereby complements the engagement of the tissue by the suction system. Upon properly positioning the stomach tissue 3 between the surfaces 404''' and 402''', the drivers 434P, 434D are driven as necessary to contact the tissues all along the plication line and adjust the gap 400G so that the surfaces will apply pressure evenly along the plication line during clamping. Upon actuating the clamping system using actuator 438, the contact surfaces 402''', 404''' clamp the tissues to be attached, as illustrated in FIG. 35B. Further adjustment of the ratchet drivers 434P, 434D may be performed at this time to achieve a more even distribution of clamping force, if needed. FIG. 35C illustrates the ability of the drivers 434P, 434D to completely close the end effector 400E''' so that there is no gap 400G between 402''' and 404'''. FIG. 35F is an enlarged, detail view of the portion of FIG. 35A outlined by box 35F. FIG. 35F better shows the suture anchors 106 and suction ports 112 in end effector 400E2''' that are open to surface 402'''.

FIG. 36A is a side view of an attachment instrument 600 according to another embodiment of the present invention. Instrument 600 is configured to engage stomach tissue via suction (and optionally, additional mechanical clamping force as described after this embodiment) like instruments 100, 200, 400, 400', 400'', 400''', etc., but unlike instrument 100, 400, 400', 400'' and 400''', instrument 600 is not configured to perform suturing/fixation of the serosal tissues together (other than temporarily by clamping action until something more permanent is installed). In this embodiment, instrument 600 is used to engage the stomach tissues by suction or by suction and mechanical clamping.

Instrument 600 can be inserted into the abdominal cavity and a working end thereof is positioned over a location on the stomach 3 where a plication line 3PL is intended to be formed. The working end is the distal end portion of the instrument 600 and includes a first end effector 600E1 and a second end effector 600E2 extending alongside and opposing first end effector 600E1. These end effector 600E (600E1, 600E2) can be straight, or can be slightly curved relative to its longitudinal axis, as shown in FIG. 36A, to better match the curvature of the bougie 50, 50', 50'', 50''' and/or lesser curvature 3L of the stomach 3, so as to achieve a plication line 3PL that better conforms to the lesser curvature 3L resulting in a more consistent cross-sectional size and shape of the lumen that is left in the reduced stomach. Alternatively, the end effectors 600E could be designed to have linkages along their length to allow the user to adjust the overall curvature to match the curvature of the bougie 50, 50', 50'', 50''' and inner curvature of the stomach 3 (i.e., lesser curvature 3L).

One of end effectors 600E1, 600E2 can be placed on a posterior surface of the stomach 3 and the other can be placed on an anterior surface of the stomach 3 along a line opposed to a line of the posterior surface that the first end effector contacts, like that described above with regard to instrument 200 in FIG. 5D. The end effectors 600E1, 600E2 engage the surfaces of the stomach 3 that they are contacted to by application of negative pressure through suction ports 112 (see FIG. 36B) defined in the contact surfaces 602, 604 of the end effectors 600E2, 600E1 (and optionally, additional mechanical clamping force as described in more detail below), respectively. The engagement forces are sufficiently strong so that when the end effectors 600E1, 600E2 are separated (moved away from one another) as the portions of the stomach wall engaged by the end effectors are also drawn apart, thereby expanding the interior volume within the stomach 3 (like shown in FIG. 5E when using instrument 200).

Next, a portion of the stomach forming at least a portion of the greater curvature 3G is plicated (i.e., tucked) into the gap 600G formed by separating the end effectors 600E1, 600E2 (like shown in FIG. 5F when using instrument 200). The plicated portion of the stomach 3 is folded to an extent that it is located on the opposite side of the intended plication line, relative to its pre-plicated location, as can be observed by comparing FIG. 5E with FIG. 5F. Optionally, but preferably, prior to plicating the portion of the stomach 3, the operator of the instrument 600 may rotate the instrument 600 by about ninety degrees (counterclockwise in the embodiment shown in optional step of FIG. 5F') about its longitudinal axis. This option positions the stomach 3 to allow gravity to assist in plicating the portion 3G through the gap 600G, making the plicating much easier as the portion 3G "falls" in through gap 600G.

Figure 36F:
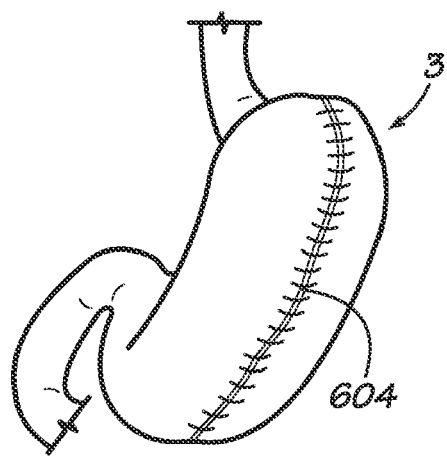
FIGS. 36F-36G are perspective and cross-sectional illustrations, respectively, of a stomach having a plication with one suture line installed according to an embodiment of the present invention.
Figure 36G:
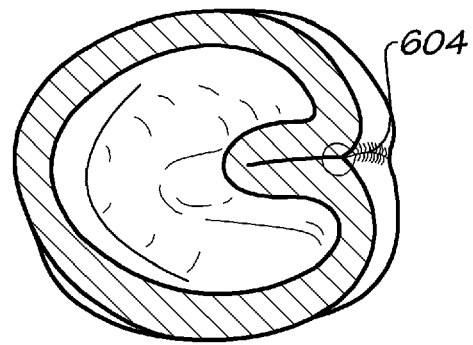
Figure 36D:
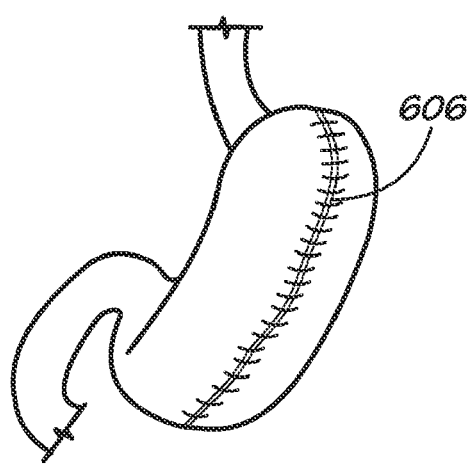
FIGS. 36D-36E are perspective and cross-sectional illustrations, respectively, of a stomach having a plication with two suture lines installed according to an embodiment of the present invention.
Figure 36E:
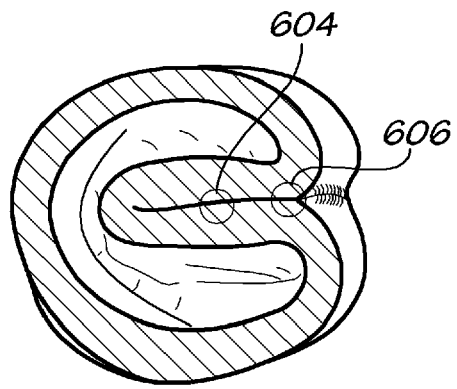

Once the portion 3G has been folded appropriately according to either optional technique described above, the instrument 600 is then operated to move the end effectors 600E1, 600E2 together again thereby closing the plication (like shown in FIG. 5G when using instrument 200). At this time, a surgeon sutures the plication so as to more permanently attached the stomach tissues together in serosal to serosal contact so as to maintain the configuration shown in FIG. 5G. Thus, rather than using an instrument to perform the suturing via an automated instrument like in FIGS. 5G-5L, instrument 600 is configured for manual suturing of the plication. The surgeon will typically manually sew, via needle 602 and suture 104 (FIG. 36C) a set of interrupted sutures 604 along the plication line, followed by a second suture line 606 (see FIGS. 36D-36E), which may be a continuous running stitch or a second set of interrupted sutures. Further alternatively, only one row of sutures 604, typically a set of interrupted sutures, may be employed, as illustrated in FIGS. 36F-36G.

As a further option, an expandable implant 10 may be implanted (manually sutured in place by a surgeon, like descried above with regard to FIG. 5L except using instrument 600 and replacing instrument 150 by manual suturing) to fill the inside of the plication 3PL. The implant 10 may be a silicone bladder, for example, capable of being inflated by biocompatible fluid such as liquid, gas, or a combination of fluids (gases, liquids, or liquids and gases). Implant 10 is connected via fill tubing 12 in fluid communication with a subcutaneous fill port 80, so that the fill volume of implant 10 can be adjusted after implanting it as described from a location outside of the abdominal cavity (e.g., by an operator accessing the subcutaneous fill port 80 with a needle alone or a needle attached to a pressurized source of fluid). Other implants 10 may be substituted, but need to be expandable and are preferably controllable as to amount of expansion. A tab or wing 11, 11', 11'', 11''' may be provided to extend from the expandable body of the implant 10 and can be inserted between the tissue folds at the plication suture line so that the attachment members/sutures 104 are also installed through the tab or wing 11, 11', 11'', 11''' to thereby securely hold the implant in place, as illustrated in FIG. 5L. The tab or wing 11, 11', 11", 11'" may be made of a mesh-reinforced silicone, for example. Alternatively, the implant 10 may be fixed in place by connecting only to the superior and inferior ends of the plication suture line, or by connecting to one or more of the interrupted sutures.

Instrument 600 includes an elongate end effector 600E comprising first and second end effector portions 600E1 and 600E2 and operates similarly to attachment instrument 400'" with regard to tissue attachment, separation and clamping functions. As already noted however, instrument 600, unlike instrument 400'" does not perform suturing of the plication. A joint 623 is provided intermediate of shaft 620 that permits the operator, after inserting the end effector 600E into the abdominal cavity to operate the handle 630 from outside of the patient to articulate the end effector 600E and distal end portion 620D of shaft 620 relative to the proximal end portion 620P of shaft 620 and handle 630. This can assist in orienting the end effector 600E more tangentially to the stomach 3 before contacting it, than what otherwise might be possible in embodiments where the end effector has to remain aligned with the entire shaft and handle, the angle of which is sometimes not optimum in view of the angle of approach needed to be taken when inserting the instrument from outside the patient and into the abdominal cavity.

FIG. 36A illustrates instrument 600 in a configuration where lower contact plate 602 on end effector portion 600E2 is spaced beneath and parallel with an upper tissue contact surface 604 on the end effector portion 600E1 of the end effector 600E, forming a gap 600G between plate 602 and surface 604 as shown. Actuators 632D and 632P are cyclically actuatable to operate distal ratchet driving mechanism 634D and proximal ratchet driving mechanism 634P respectively, to vary the distances between the plate 602 and surface 604 at 634D and 634P and locations therebetween. The independently operable ratchet systems 634D, 634P are independently controllable to better account for varied thicknesses of the stomach 3 along the plication line.

Actuator/button 636 when pressed/actuated, activates a suction system supplied with suction via suction line 116 and which functions like previously described suction ports used to help ensure that tissue to be plicated is properly positioned. Actuator/button 638 has an appearance like actuator/button 636 but is positioned on the opposite side of handle 630. When pressed/actuated, actuator/button 638 activates the tissue clamping system of instrument 630, which actuates small clamping features along the end effectors 600E that clamp onto the stomach tissue at locations near the locations where the tissue contacts the suction features. This tissue clamping feature is described in greater detail below. This tissue clamping thereby complements the engagement of the tissue by the suction system. Upon properly positioning the stomach tissue 3 between the surfaces 604 and 602, the drivers 634P, 634D are driven as necessary to contact the tissues all along the plication line and adjust the gap 600G so that the surfaces will apply pressure evenly along the plication line during clamping. Upon actuating the clamping system using actuator 638, the contact surfaces 602, 604 clamp the tissues to be attached, similarly to what is shown in FIG. 35B with regard to instrument 400'". Further adjustment of the ratchet drivers 634P, 634D may be performed at this time to achieve a more even distribution of clamping force, if needed. The drivers can be configured with the ability to completely close the end effector 600E, if desired, so that there is no gap 600G between 602 and 604. FIG. 36B is an enlarged, detail view of the portion of FIG. 36A outlined by box 36B. FIG. 36B better shows the suction ports 112 in end effector 600E2'" that are open to surface 602. Additionally, FIG. 36B better shows the recesses or scallops 610 formed in the end effectors 600E1 and 600E2 all the way through the thicknesses thereof, including the contact surfaces 604 and 602. The recesses/scallops 610 in end effector 600E1 are aligned with the recesses/scallops 610 in end effector 600E2 and are configured and dimensioned to facilitate manually installing/sewing sutures 104 therethrough by the surgeon. By installing interrupted sutures through a plurality of the recesses/scallops 610 (typically all recesses/scallops that sandwich stomach tissue are sutured, although fewer could be sutured) this fixes the plication line 3PL independently of the instrument 600, so that the stomach tissue are held in serosa-to-serosa approximation after completion of the suturing, and unclamping and removal of the instrument 100. The interrupted sutures do not constrain the end effectors 600E1, 600E2 in any way, so that the end effectors 600E1, 600E2 can be maintained clamping the tissues until at least the first line of interrupted sutures have been completed. Removal of the end effectors and instrument 600 can be readily accomplished without affecting tensioning of the sutures or the condition of the plication line.

FIGS. 37A-37C are schematic representations illustrating functioning of a tissue engagement arrangement for engaging stomach tissue during procedures discussed above. Alternative to the use of suction only, this approach uses secondary mechanical clamping, in addition to suction to engage the stomach tissues. In the schematics shown, the surface of the page represents contact surface 404'". The distal end of the instrument is to the left in the schematics and the proximal direction is to the right. With the secondary mechanical clamping non-actuated as shown in FIG. 37A, stomach tissue is pulled into the slots 112 by application of suction through the slots 112. Secondary clamp actuator 138, which is operable by the user of the instrument from outside of the patient, for example, by actuating actuator/button 438, is in its non-actuated position as shown in FIG. 37A.

By drawing the actuator 138 proximally relative to the remainder of the instrument, actuator lobes 138L of actuator 138 drive clamping wires 139 against the stomach tissues engaged by the slots 112 and wedge the tissues against the inside surface of the slots 112. This tissue clamping complements the engagement and grasping of the stomach 3 tissue by the suction system, and provides a stronger grip on the stomach 3 tissue so that the instrument does not prematurely release its grip on the stomach 3 tissue. To release the secondary clamping, the operator can pull the actuator 138 further proximally so that the lobes 138L are positioned in between the slots 112 as illustrated in FIG. 37C, allowing clamping wires 139 to resiliently return to positions away from the tissues so that they no longer clamp the tissues. Alternatively, the operator can push the actuator 138 back distally, allowing the camping wires to resiliently return to positions away from the tissues so that they no longer clamp the tissue in the slots 112.

Figure 38A:
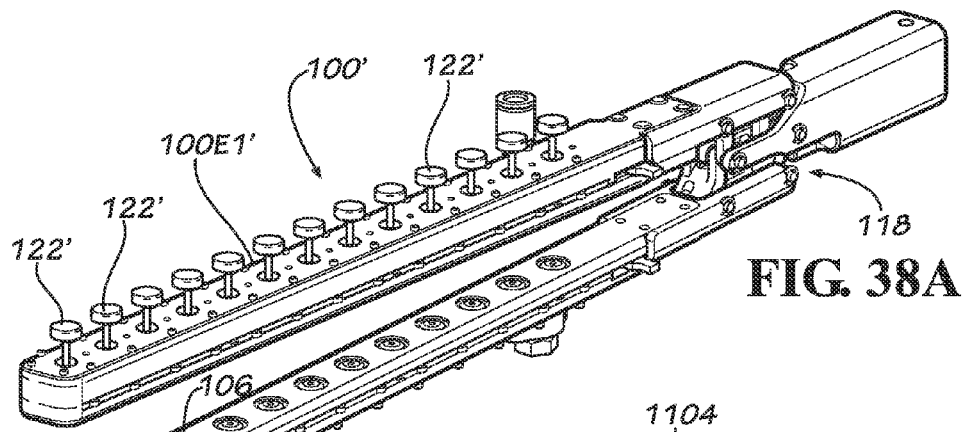
FIGS. 38A-38H provide various partial views of an instrument that employs suction as a primary clamping feature and a mechanical secondary clamping feature according to an embodiment of the present invention.
Figure 38B:
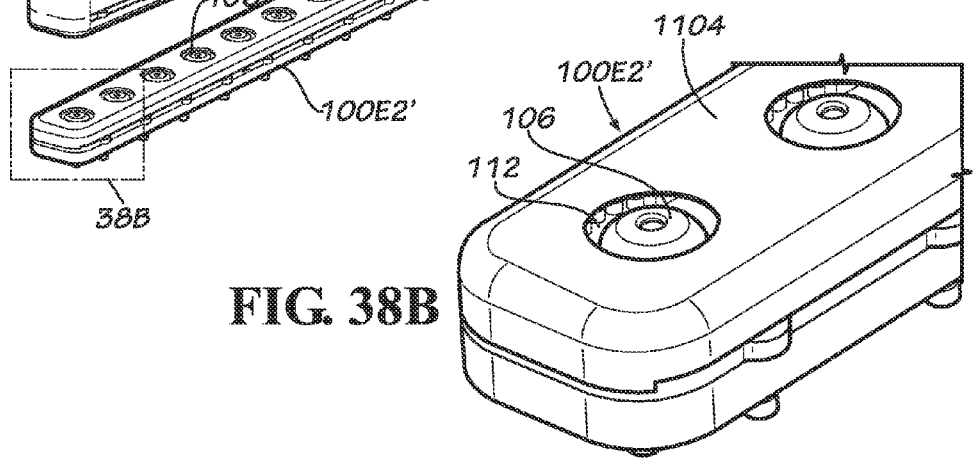
Figure 38C:
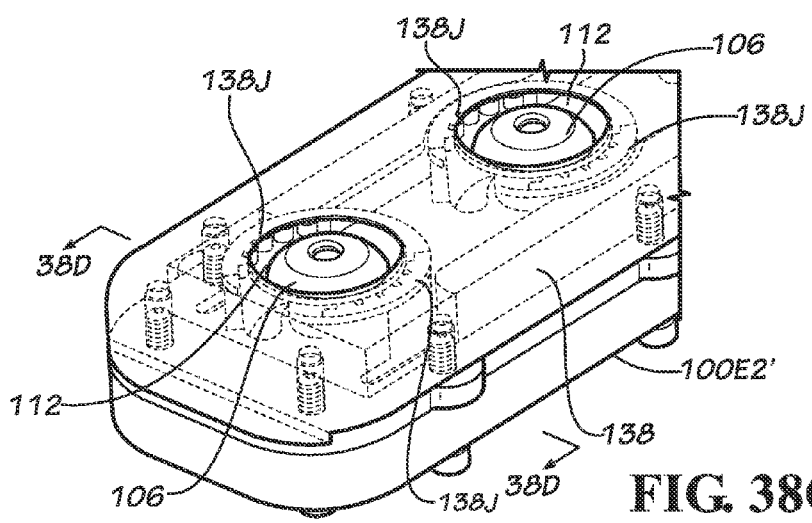
Figure 38D:
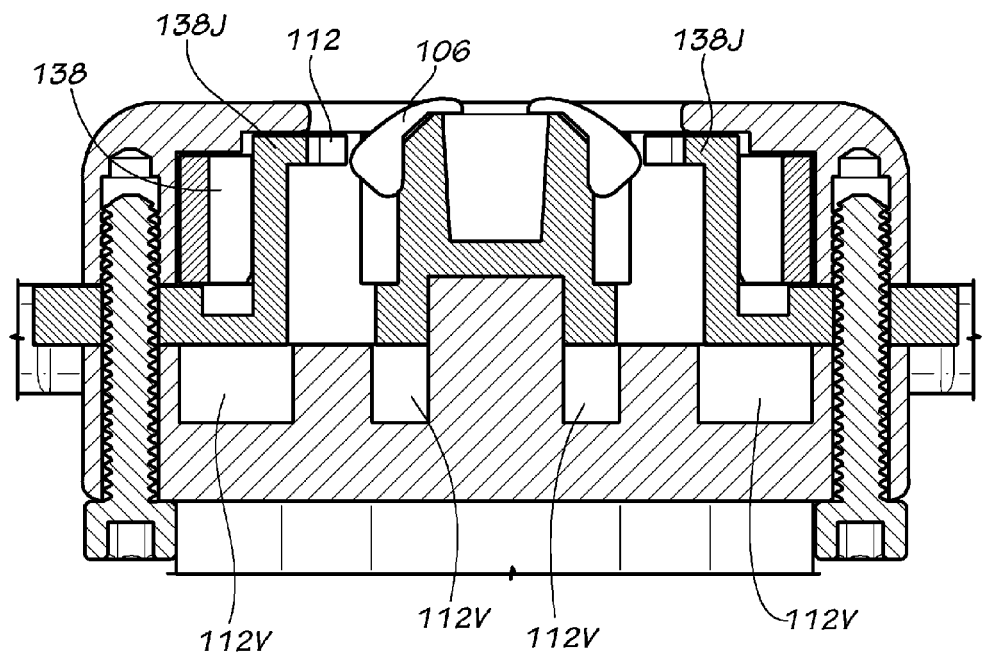
Figure 41A:
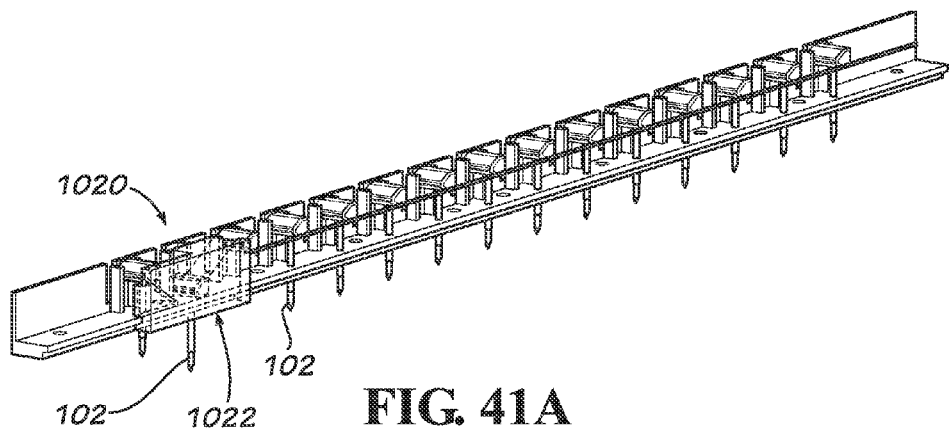
FIGS. 41A-41E illustrate various schematic views and partial views of a driving mechanism according to an embodiment of the present invention.
Figure 41B:
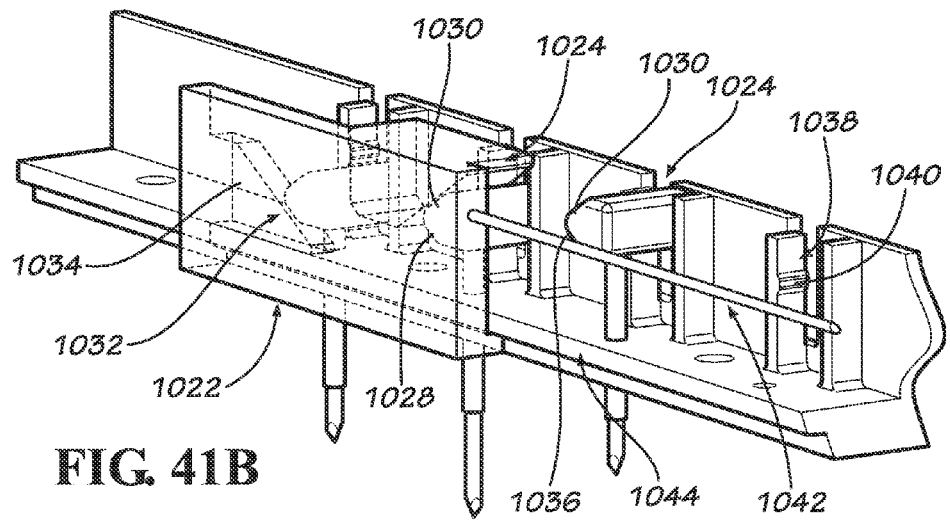

FIGS. 38A-38H provide various partial views of an instrument 100' that employs suction as a primary clamping feature and a mechanical secondary clamping feature according to an embodiment of the present invention. It is noted here that although the instrument 100' is similar to the construction and function of instrument 100 shown in FIG. 3A, that the secondary mechanical clamping features shown and described in this embodiment are not limited to instruments 100 and 100', but can be employed in any of the instruments described herein that use suction to engage the stomach tissue, as additional securement of the stomach. These features are also not limited to those instruments that both engage the stomach tissue and attach the tissues in serosa-to-serosa contact, as they can also be employed in instrument that engage by suction, but do not perform suturing (such as instruments 200 and 600, for example). It is further noted that although the embodiment 100' in FIG. 38A provides a series of individual actuators 122' for individually driving piercing members/suture drivers 102 into suture anchors 106, that typically instruments described herein use a sled pulled along by a cable to automatically press the piercing members/suture drivers 102 through the stomach tissues and into the suture anchors 106, as described above. The piercing members/suture drivers 102 can be pressed/driven into the tissues all at once simultaneously, in any of the manners described previously and below. Alternatively, the piercing members/suture drivers 102 may be driven individually, as noted above. FIGS. 41A-41E are various partial views illustrating an alternative driving arrangement for an attachment instrument, which is alternatively available for instrument 100' but can also be readily adapted for use in other attachment instruments described herein. An actuation mechanism 1020 is provided for individually driving piercing members/suture drivers 102 into suture anchors 106. Actuation mechanism 1020 includes a sled 1022 that pulled along by a cable (or, alternatively, pulled or pushed by a screw drive mechanism or other driving mechanism) to press the piercing members/suture drivers 102 through the stomach tissues and into the suture anchors 106, as described above. A driver head 1024 is mounted on top of each piercing member/suture driver 102 as shown. As illustrated in the enlarged partial view of FIG. 41B, a leading ramp or cam 1026 mounted on a proximal end portion (but could be on the distal end portion for embodiments wherein the sled is pushed rather than pulled) of sled 1022 and is provided with a cam surface 1028 configured to cooperate with cam surface 1030 of driver head 1024 to drive the piercing member/suture driver 102 further out of the instrument as shown by the second to the leftmost piercing member/suture driver 102 in FIG. 41A. As the sled 1022 advances further and the leading ramp 1030 clears the drive head 1024 that it has just depressed, a trailing ramp or cam surface 1032 of a trailing ramp 1034 that is mounted on a distal end portion (but could be on the proximal end portion for embodiments wherein the sled is pushed rather than pulled) of sled 1022 cooperates with cam surface 1036 of driver head 1024 to drive the piercing member/suture driver 102 in the opposite direction, further into the instrument, back to its undeployed, starting position as shown by the leftmost piercing member/suture driver 102 in FIG. 41A. At the same time, the leading ramp 1030 engages the next driver head to deploy the next piercing member/suture driver 102. This process continues to sequentially and individually deploy each piercing member/suture driver 102 until all of them have been deployed. Flexure arms 1038 with stops 1040 are provided both proximally and distally of each piercing member/suture driver 102 to guide the placement and travel of each piercing member/suture driver 102 and to provide an end stop to the return travel as the piercing member/suture driver 102 returns to its undeployed position. A pull cable 1042 is illustrated in FIG. 41B to pull the sled 1022 proximally relative to the end effector. Alternatively, a pulley could be employed so that when the cable 1042 is pulled proximally, it would pull the sled 1022 distally. As noted earlier, alternative drivers, including, but not limited to a screw drive, could be employed to pull or push the sled 1022. A rail 1044 is provided to guide the travel of the sled in a lengthwise direction along the end effector and to help maintain alignment of the ramps 1030 and 1034 with the driver heads 1024. The sled 1022 is further secured and guided by the roof and side wall of the end effector, which are not shown in FIGS. 41A-41B.

Figure 41C:
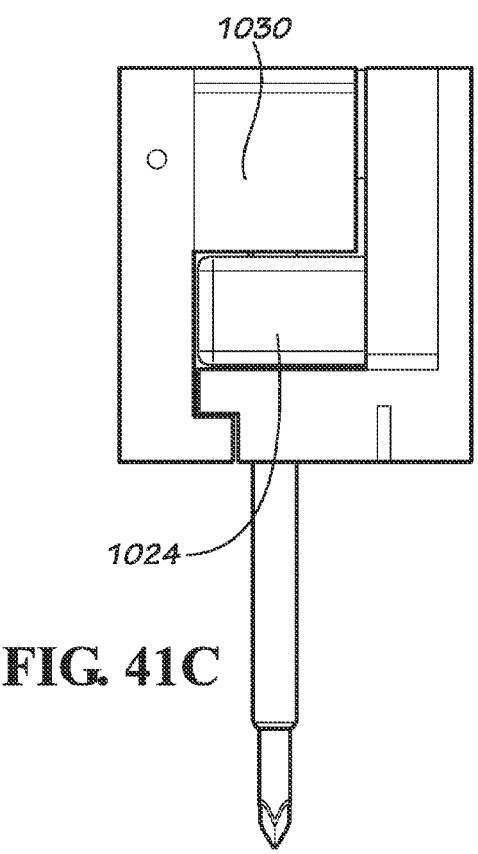
Figure 41D:
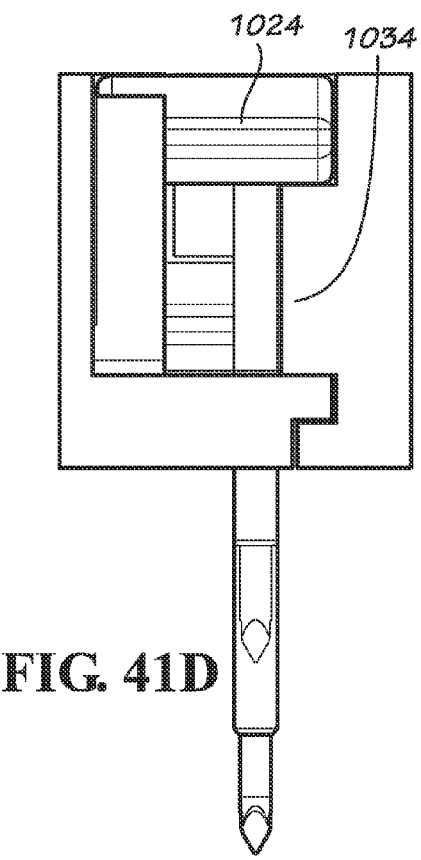
Figure 41E:
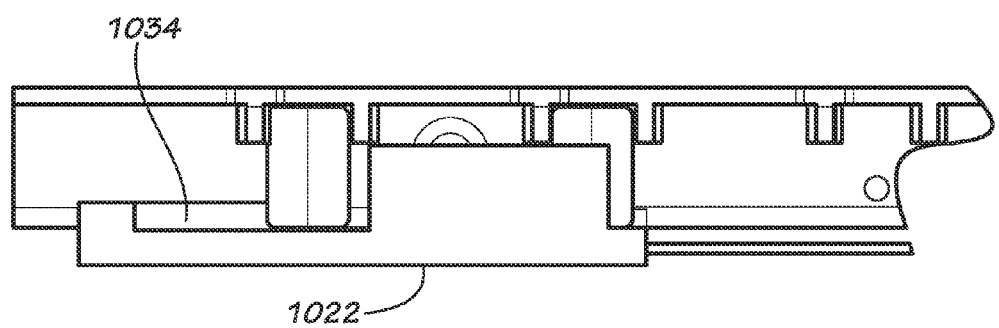

FIG. 41C is a schematic front view (looking toward the distal end of the end effector) showing the piercing member/suture driver 102 being driven out of the end effector to its furthest extent by the driving action of the leading ramp 130 against the driver head 1024. FIG. 41D is a schematic rear view (looking toward the proximal end of the end effector) showing the piercing member/suture driver 102 being retracted fully to the undeployed position in the end effector by the driving action of the trailing ramp 134 against the driver head 1024. FIG. 1022 illustrates a top view of the distal end portion of FIG. 41A.

Figure 42A:
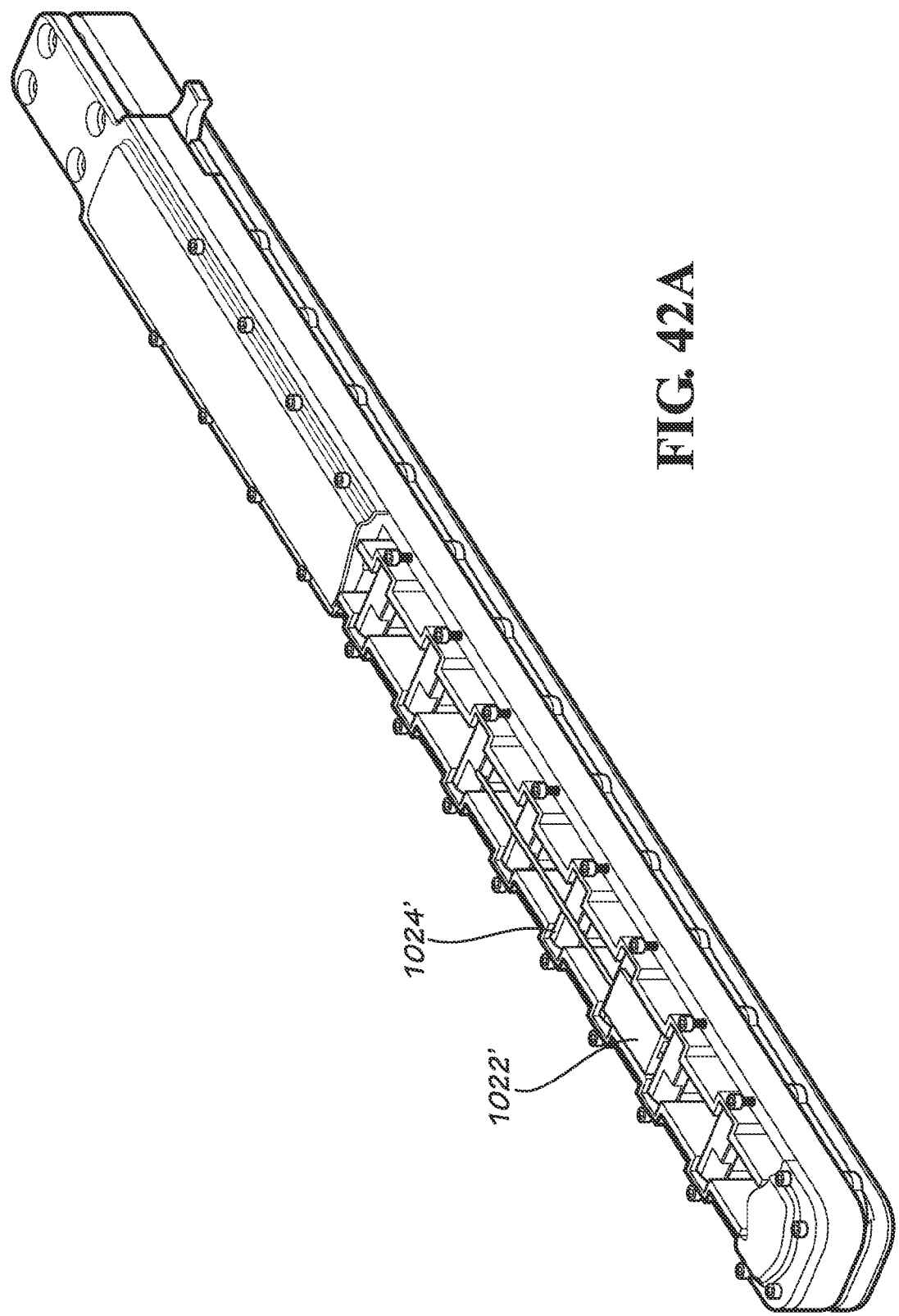
FIGS. 42A-42B illustrate partial schematic views of an end effector having a driving mechanism according to another embodiment of the present invention.
Figure 42B:
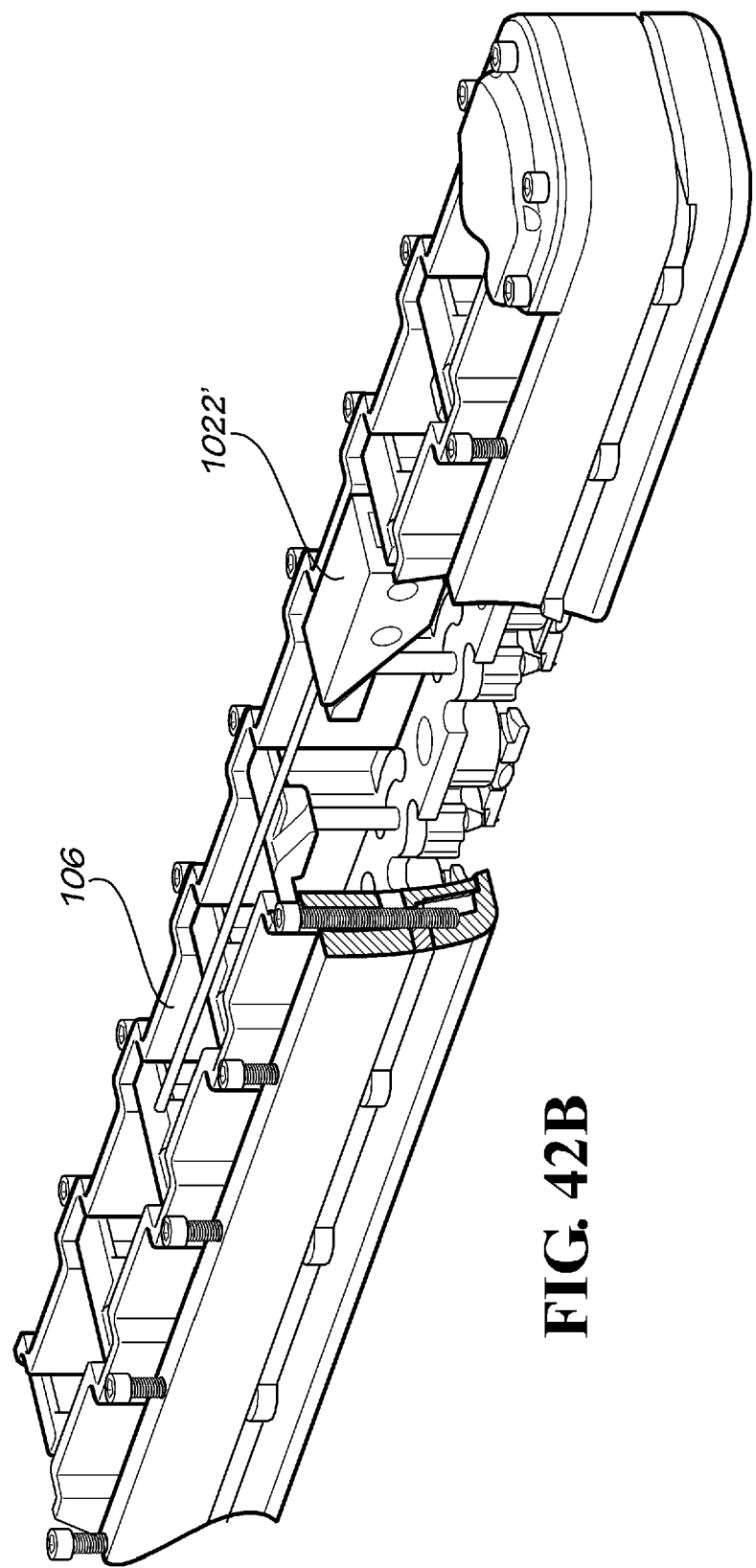

FIG. 42A illustrates an alternative embodiment of an individual driver mechanism in which the sled 1022' rides over the top of the drive head 1024' and FIG. 42B illustrates the compact construction of this embodiment as the sled 1022' travels between the tissue clamps 106.

Figure 43A:
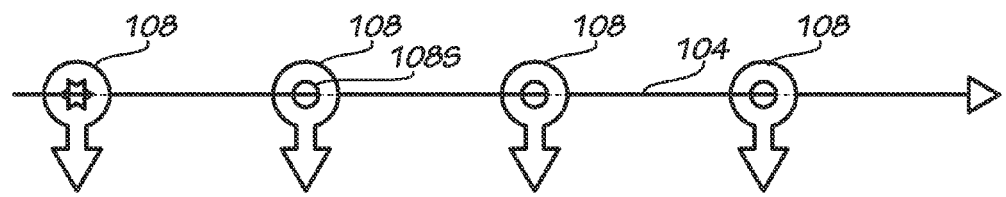
FIGS. 43A-43C illustrate arrangements and methods for installing a running stitch using an attachment instrument according to various embodiments of the present invention.
Figure 43B:
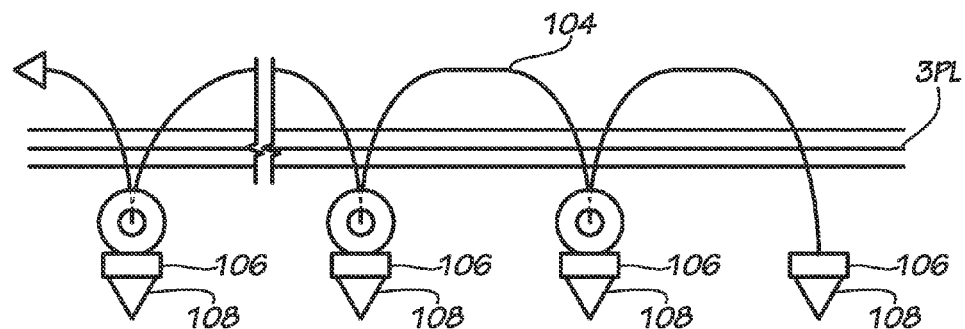
Figure 43C:
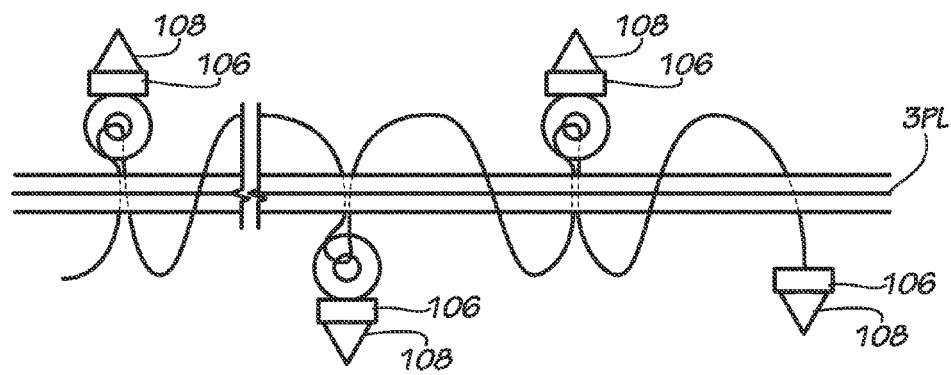

FIGS. 43A-43C illustrate arrangements and methods for installing a running stitch using an attachment instrument according to various embodiments of the present invention. A running stitch may be preferable to the interrupted stitches described thus far in regard to the attachment instruments above, in at least some situations, such as to provide a second line of suturing (additional to a primary line of suturing that may be interrupted sutures or a running stitch) to prevent herniation of a gastric plication. As described above, the instruments create single stitches, which can be utilized as interrupted stitches. Each anchor mate 108 is molded or otherwise fixed to a suture, and each anchor mate 108 is placed through the tissue desired to be stitched, into the anchor 106 on the other side of the tissue to create the stitch. A suture lock may be utilized to tighten and lock the suture in place. Each individual or interrupted suture is created in this fashion.

In the embodiments of FIGS. 43A-43C, to create a running stitch, the first anchor mate 108 (leftmost anchor mate 108 in FIG. 43A, rightmost anchor mate 108 in FIGS. 43B-43C) on the distal end of the suture 104 is also permanently fixed to the suture 104. The suture 104 then is loaded with multiple anchor mates 108 bullets that are free to move along the length of the suture 104 similar to beads on a string. The first anchor mate 108 is placed through the tissue desired to be stitched into an anchor 108. This creates one anchoring point of the suture 104. Each subsequent anchor mate 108 is fired through the tissue into each subsequent anchor 106, respectively. This can be accomplished singularly at the discretion of the physician, or can be preloaded in multiple sequence so that all the intended anchor mates 108 are fired in a predetermined configuration (i.e. predetermined number of anchor mates 108, spacing between anchor mates 108, using straight suture drivers 102 or curved suture drivers 102, etc.). Since the distal end of the suture 104 is anchored by the fixed anchor mate 108/anchor 106 connection and each subsequent anchor mate 108 allows the suture 104 to move freely, once all connections are made, the suture 104 can be pulled from the proximal end to tighten through a suture lock mechanism. The suture lock can additionally or alternatively be incorporated into one or more sliding anchor mates 108 by creating locking teeth within the sliding ring 108S of the anchor mate 108. The physician can control the tension on the suture 104 as desired. FIG. 43B illustrate an arrangement where all anchor mates 108 are driven through the tissues from the same side of the tissues being joined. To create a more spiral shaped running suture the pattern of the anchor mates 108/anchors 106 can be alternated from one side of the tissue to the other, as illustrated in FIG. 43C.

Figure 38E:
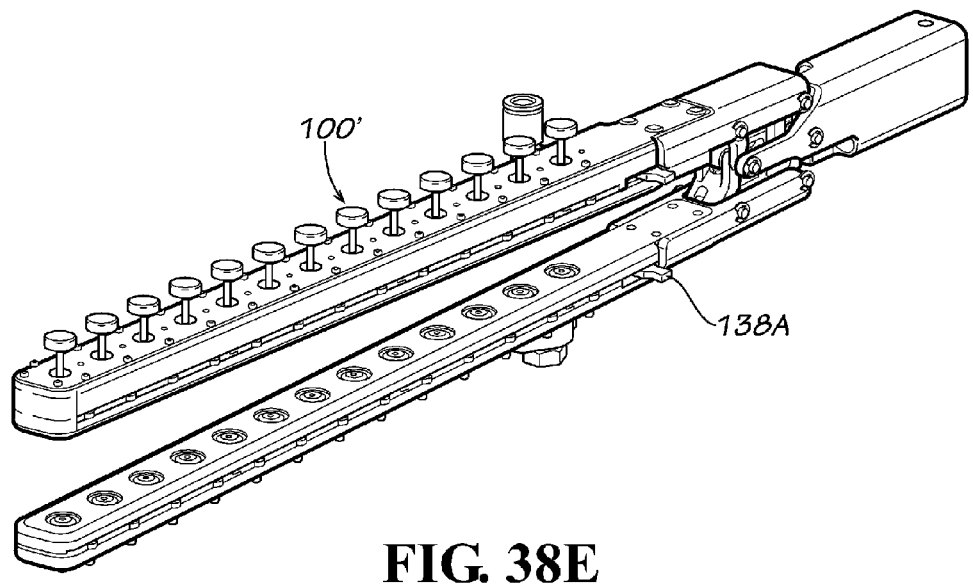
Figure 38F:
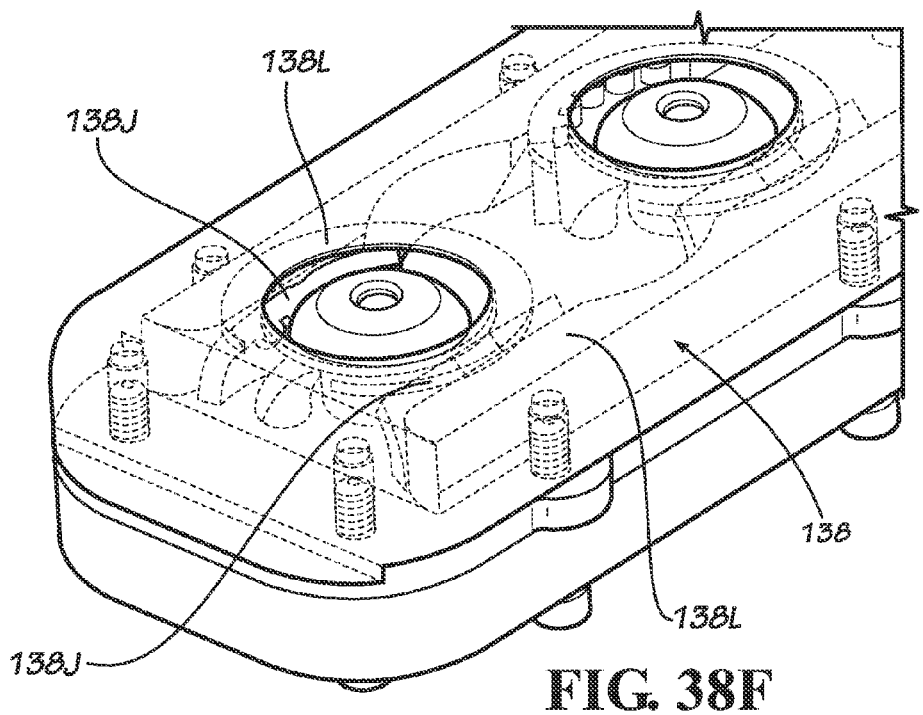

Referring back again to the embodiment of FIGS. 38A-38H, the suction ports 112 are annular, surrounding the suture anchors 106 and located between the suture anchors 106 and tissue contacting surface 1104 of end effector 100E2', as shown in the detailed view of FIG. 38B. As illustrated in FIG. 38E, a clamp actuator feature 138A is provided for each end effector (upper and lower) that is slidable by the operator of instrument 100' to effect mechanical clamping and unclamping as described in more detail below.

FIG. 38C illustrates the positions/orientations of clamping jaws 138J relative to the suture anchors 106, wherein a gap is maintained therebetween in which the suction ports 112 are located. It should be noted here, that although the clamping mechanism is descried here with particularity with regard to the lower end effector, that the upper end effector contains the same mechanism, except a stationary is provided to surround each suture driver 102, through which suture driver 102 is slidable, and the stationary feature has tissue clamped against it in the same way the tissue is clamped against the anchor 106 in the lower actuator. The clamp actuator 138 that is drivable by actuator feature 138A is in an unclamped position in FIG. 38C. The cross-sectional view in FIG. 38D taken along line 38D-38D of FIG. 38C better illustrates the gap between unclamped jaw 138J and suture anchor 106 that permits air flow and stomach tissue (drawn by suction applied via vacuum chambers 112V).

Figure 38G:
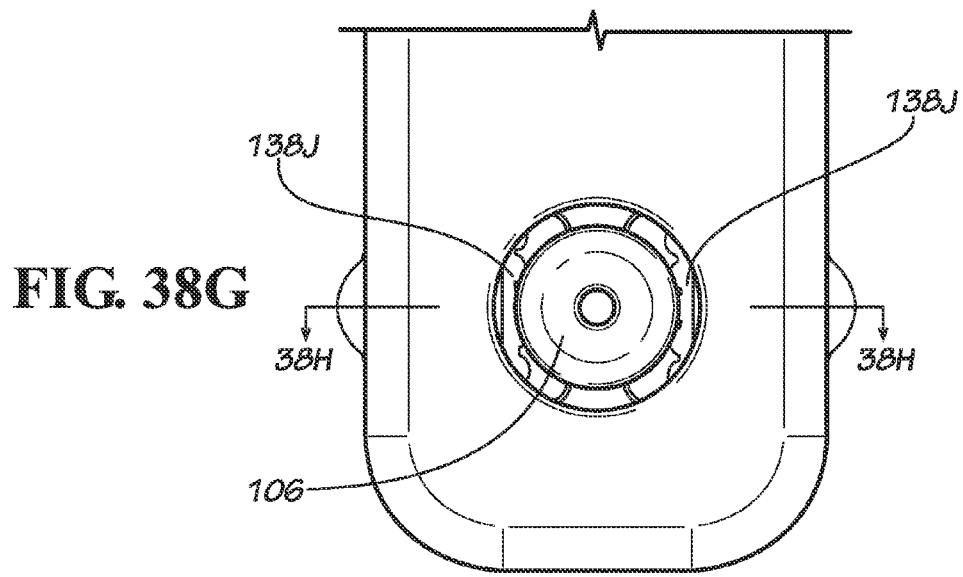

With the secondary mechanical clamping non-actuated as shown in FIGS. 38A-38D, stomach tissue is pulled into the gaps between the jaws 138J and suture anchors 106 by application of suction through the suction ports 112. Upon advancing (sliding) the actuator feature 138A as illustrated in FIG. 38E, this drives the actuator 138 distally relative to the end effector and drives the actuator lobes 138L into contact against clamping jaws 138J. This drives the clamping jaws 138J towards the suture anchor 106, thereby mechanically clamping stomach tissues that were drawn into the gaps, between jaws 138J and suture anchor 106, see FIG. 38F. FIG. 38G is a top view of FIG. 38F which more clearly shows the clamping jaws 138J in the clamping position relative to the suture anchor 106, such that tissues between these features would be securely mechanically clamped.

Figure 38H:
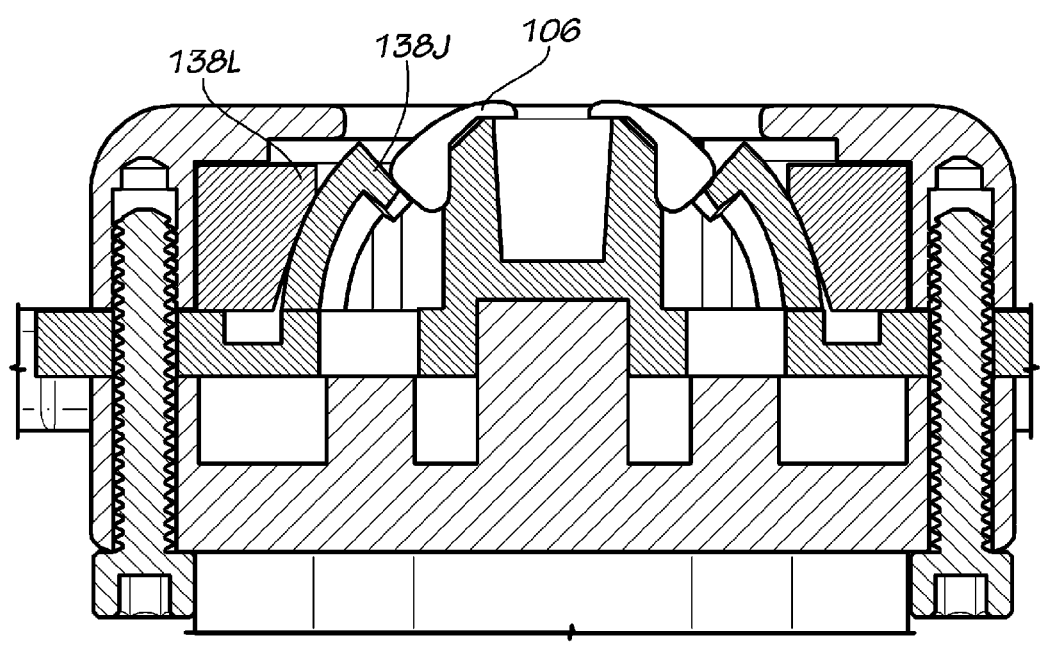

FIG. 38H is a cross-sectional view of FIG. 38G taken along line 38H-38H that better shows the contact between the actuator lobes 138L and clamping jaws 138J, as well as showing the jaws 138J having been driven toward (and in this case in contact with, although that is not always absolutely necessary) suture anchor 106 in the clamping configuration.

This tissue clamping complements the engagement and grasping of the stomach 3 tissue by the suction system, and provides a stronger grip on the stomach 3 tissue so that the instrument does not prematurely release its grip on the stomach 3 tissue. To release the secondary clamping, the operator can pull the actuator 138 proximally so that the lobes 138L no longer contact the clamping jaws 138J, like shown in FIG. 38A, whereupon the clamping jaws 138J resiliently return to their unclamped positions shown in FIG. 38C, thereby allowing tissue to be released upon deactivation of the suction.

Figure 39A:
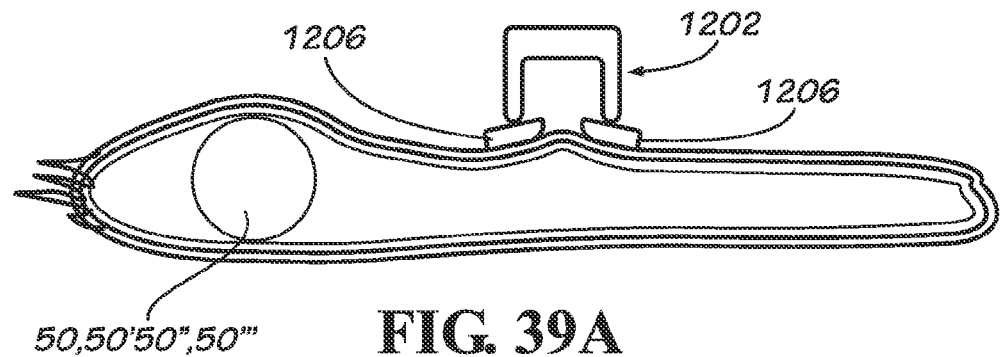
FIGS. 39A-39K illustrate various events for the performance of a procedure for decreasing the effective volume of a patient's stomach that includes extragastric procedures on the stomach to create at least one plication, according to another embodiment of the present invention.

FIGS. 39A-39 illustrate various events for the performance of a procedure for decreasing the effective volume of a patient's stomach that includes extragastric procedures on the stomach to create at least one plication, according to another embodiment of the present invention. After establishing ports/pathway into the abdominal cavity from outside the patient, the omentum 5 and connective tissues are dissected at the greater curve of the stomach to provide access thereto, the same as described above with regard to FIGS. 7A-7B. A bougie 50, 50', 50", 50''' is inserted trans-esophageally and placed in the stomach 3 in a position like shown in FIG. 7C and the cross-sectional schematic representations in FIGS. 39A-39K. Typically the bougie 50, 50' 50", 50''' occupies a pathway extending naturally from the esophagus, through the stomach 3 and into the pylorus 3P, so as to occupy a space similar to what is defined when a sleeve gastrectomy is performed. The bougie acts as a guide so as to better standardize the sizes and locations of plications formed by the procedure as well as to prevent reducing the stomach 3 too aggressively, so as to ensure no blockage locations are inadvertently formed.

In the embodiments of FIGS. 39A-39K the functions of the instruments performing the procedure are divided among at least two instruments. Engagement and manipulation of the stomach tissue are performed using and engagement instrument 1200 or two or more laparoscopic grasper instruments 1202, 1204 as described below. Engagement instrument 1200 is configured like instrument 200 or could be configured like instrument 200', but in each case, engagement is performed by graspers jaws 1206 or other clamping mechanism that are included in instrument 1200 instead of the suction ports of instrument 200, 200'. In the same manner the instrument 200, 200' or any other instrument described herein may employ suction ports in only one end effector, while providing the contact surface of the opposite end effector with enhanced friction capability (e.g., by knurling, or providing some other surface treatment and/or coating to increase friction), instrument 1200 may optionally be provided with grasper jaws 1206 on only one of end effectors 1200E1 or 1200E2, while providing the other end effector with a contact surface exhibiting enhanced friction, but without grasper jaws. In this optional case, as well as with engaging with a suction instrument having suction on only one end effector, the procedures described can still be carried out effectively, except for the optional rotation step like that shown in FIGS. 2F', 5F' and 39E'. Other features of instrument 1200, such as shaft, handle and optional shaft joint can be the same as or similar to those of instruments 200, 200' and others of those described above. Stitching instrument 1250 is configured like instrument 250 (or can be configured like 250' when 1200 is configured like 200') with the piercing members/suture drivers 102, attachment members/sutures 104, anchors 106, anchor mates 108, suture locks 110 and actuation mechanisms therefore, but without suction ports 112 (although, optionally, suction ports may be included in the end effectors of instrument 1250) or connection/joint mechanism. Also included are shaft 120, handle 114 and, optionally, suction line 116.

Engagement instrument 1200 is inserted into the abdominal cavity and a working end thereof is positioned over locations on the stomach 3 where a plication line is intended to be formed. The working end is the distal end portion of the instrument 1200 and includes a first end effector 1200E1 and a second end effector 1200E2 (cross-sectional illustrations of end effectors 1200E1 and 1200E2 are schematically represented in FIGS. 39C-39H) extending alongside and opposing first end effector 200E1. One of the end effectors 1200E1, 1200E2 is placed on a posterior surface of the stomach 3 and the other is placed on an anterior surface of the stomach 3 along a line opposed to a line of the posterior surface that the first end effector contacts. In the embodiment shown in FIG. 39C, end effector 1200E1 is contacted to the anterior surface, and end effector 1200E2 is contacted to the posterior surface. Alternatively, end effector 1200E1 could be contacted to the posterior surface, and end effector 1200E2 could be contacted to the anterior surface.

Figure 39B:
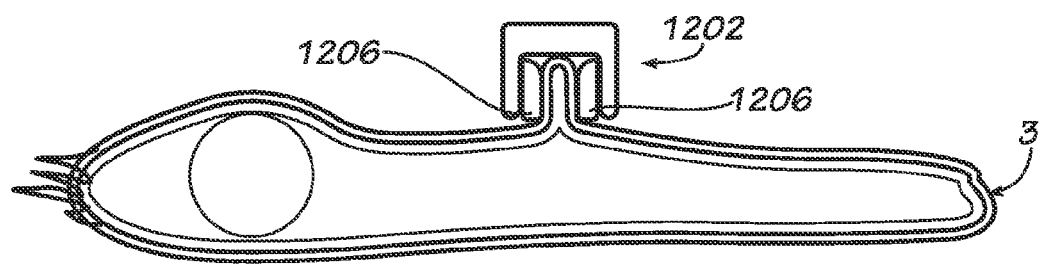
Figure 39C:
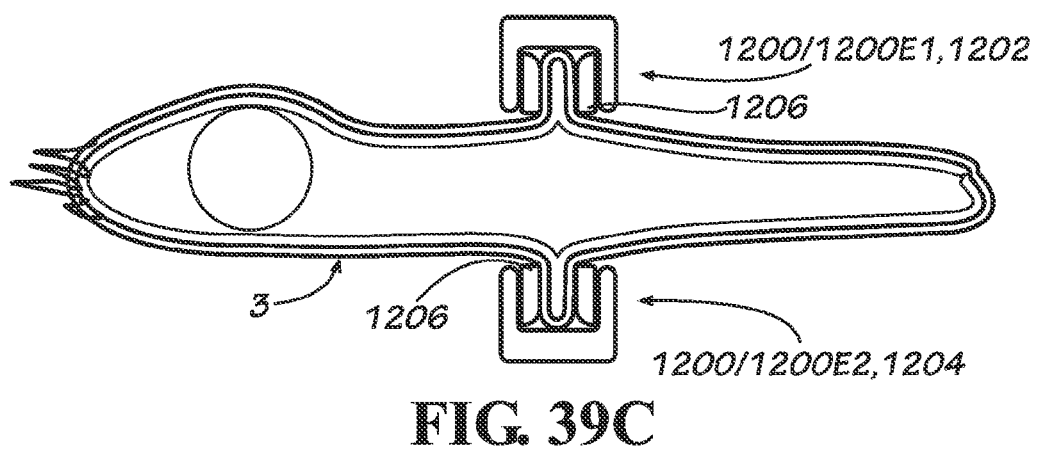

The operator of instrument 1200 then actuates end effectors 1200E1, 1200E2 to engage the surfaces of the stomach 3 that they are contacted to with grasping jaws 1206 as illustrated in FIG. 39C. Alternative to use of instrument 1200, grasper instruments can be used to carry out the functions of instrument 1200. In this case, the working end (end effector) 1202 of a first grasper is inserted into the abdominal cavity and positioned over locations on the stomach 3 where a plication line is intended to be formed, see FIG. 39A. The operator then actuates the grasper to engage the surfaces of the stomach 3 that the grasping jaws of grasper distal end 1202 as illustrated in FIG. 39B. Optionally, but preferably, the graspers include a locking feature that allows the user to lock the grasper jaws in the configuration shown in FIG. 39B. Alternatively, the grasping of the tissue may be performed with a different type of mechanism, such as providing 1206 as rollers that rotate to pinch and grasp the tissue, or multiple small rotating needles that pierce into the tissue to grasp the tissue wall. The steps of FIGS. 39A-39B are repeated with a second graspers instrument so that a location on the stomach opposite the location where graspers (end effector) 1202 grasps the stomach is grasped by the working end/end effector 1204/grasper jaws 1206 of the second grasper instrument as illustrated in FIG. 39C. From FIG. 39C forward, the procedures conducted as described with reference to FIGS. 39C through 39H can be carried out using instrument 1200 or, alternatively, two or more grasper instruments 1202, 1204.

Figure 39D:
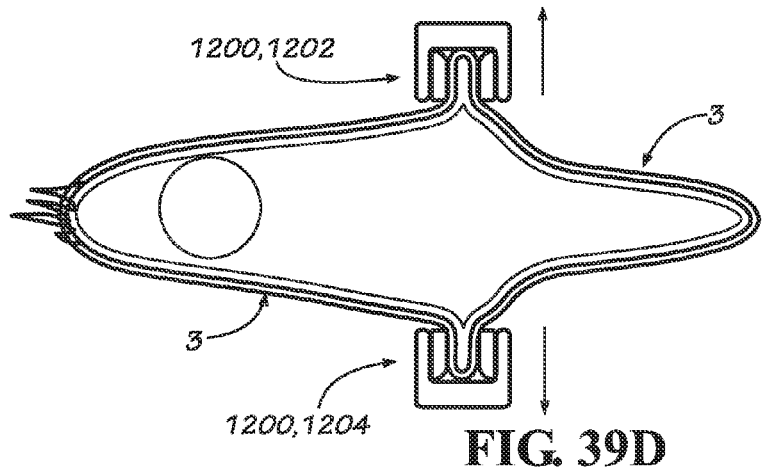

The working end of instrument 1200 is the distal end portion of the instrument 1200 and includes a first end effector 1200E1 and a second end effector 1200E2 (cross-sectional illustrations of end effectors 1200E1 and 1200E2 are schematically represented in FIGS. 39C-39H) extending alongside and opposing first end effector 200E1. One of the end effectors 1200E1, 1200E2 is placed on a posterior surface of the stomach 3 and the other is placed on an anterior surface of the stomach 3 along a line opposed to a line of the posterior surface that the first end effector contacts. In the embodiment shown in FIG. 39C, end effector 1200E1 is contacted to the anterior surface, and end effector 1200E2 is contacted to the posterior surface. Alternatively, end effector 1200E1 could be contacted to the posterior surface, and end effector 1200E2 could be contacted to the anterior surface. Whether using instrument 1200 or graspers 1202, 1204, the engagement forces are sufficiently strong so that when the end effectors 1200E1, 1200E2 (or 1202, 1204) are separated (moved away from one another) as illustrated in FIG. 39D, the portions of the stomach wall engaged by the end effectors are also drawn apart, thereby expanding the interior volume within the stomach 3. It is noted here that separation of the end effectors 1200E1, 1200E2 or graspers 1202, 1204 to expand the interior volume within the stomach does not require that both end effectors 1200E1 and 1200E2 be moved, or that both graspers 1202 and 1204 be moved. Rather, only relative movement between the two is required. Therefore, alternatively, end effector 1200E1 can be moved while holding end effector 1200E2 stationary or end effector 1200E2 can be moved while holding end effector 1200E1 stationary. Likewise graspers instrument 1202 can be moved while holding graspers instrument 1204 stationary or graspers instrument 1204 can be moved while holding graspers instrument 1202 stationary. Likewise, all other procedures described herein to separate the stomach walls apart so as to increase the interior volume of the stomach can be performed by moving both of the engaged members apart, or moving only one or the other of the engaged members away from the other while holding the other stationary.

Figure 39E:
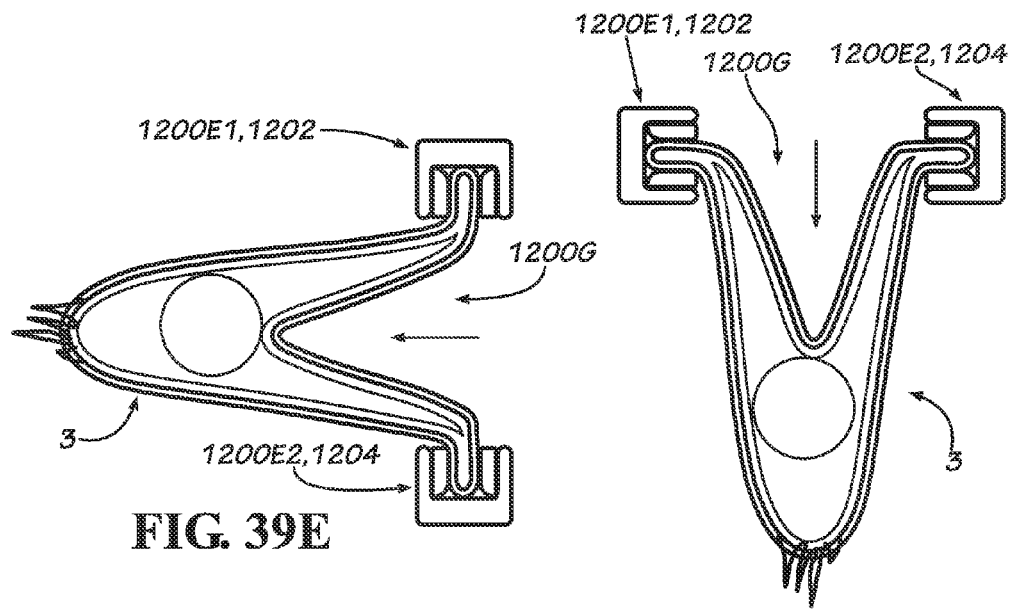
Figure 39E:
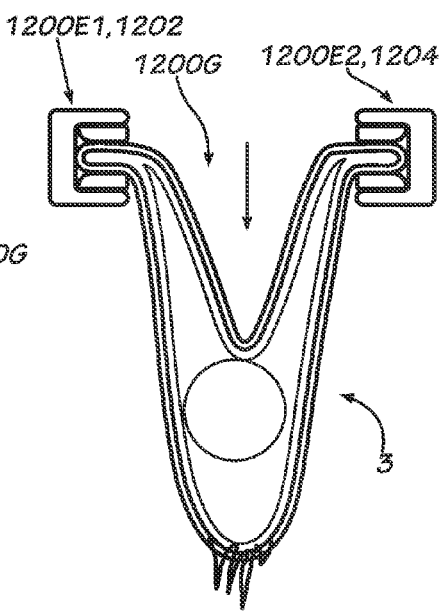

Next, a portion of the stomach forming at least a portion of the greater curvature 3G is plicated, i.e., tucked, into the gap 1200G formed by separating the end effectors 1200E1, 1200E2 (or 1202, 1204) as illustrated in FIG. 39E. The plicated portion of the stomach is folded to an extent that it is located on the opposite side of the intended plication line, relative to its pre-plicated location, as can be observed by comparing FIG. 39D with FIG. 39E. Optionally, but only in variants in which both sides of the stomach are grasped in this procedural embodiment, prior to plicating the portion of the stomach, the operator of the instrument 1200 (or graspers 1202, 1204) may rotate the instrument 1200 (or graspers, 1202, 1204 in concert) to rotate the stomach 3 by about ninety degrees (counterclockwise in the embodiment shown in optional step of FIG. 39E'). This option positions the stomach to allow gravity to assist in plicating the portion 3G through the gap 1200G, making the plicating much easier as the portion 3G "falls" in through gap 1200G.

Figure 39F:
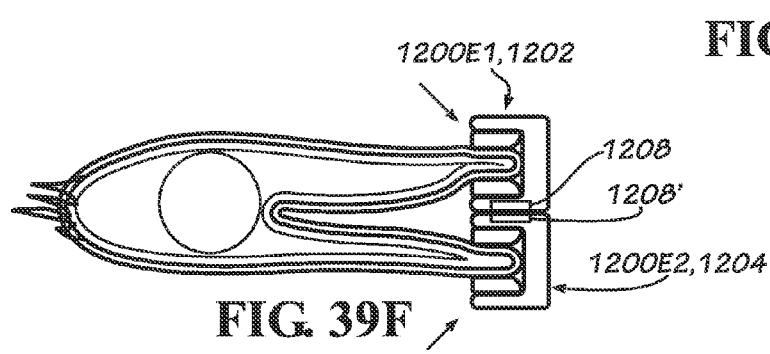

Once the portion 3G has been plicated appropriately according to either optional technique described above, the instrument 1200/graspers 1202, 1204 is/are then operated to rotate the grasping jaws 1206/end effectors 1200E1, 1200E2/ graspers 1202, 1204 and move them together, into contact with one another, as illustrated in FIG. 39F. During this step, and throughout the following steps, the instrument(s) and stomach 3 can be maintained in the rotated orientation (as shown in FIG. 39E') or can be rotated back to the original orientation shown in FIG. 39F. The end effectors 1200E1, 1200E2 or working ends 1202, 1204 of the graspers when joined as in FIG. 39F can optionally be provided with joining features 1208, 1208', respectively, to facilitate joining and or strengthen the joint once it has been made. Such joining features may include one or more of, but are not limited to: mating magnets, mating snap elements; mating hook and loop type fasteners, etc.

Figure 39G:
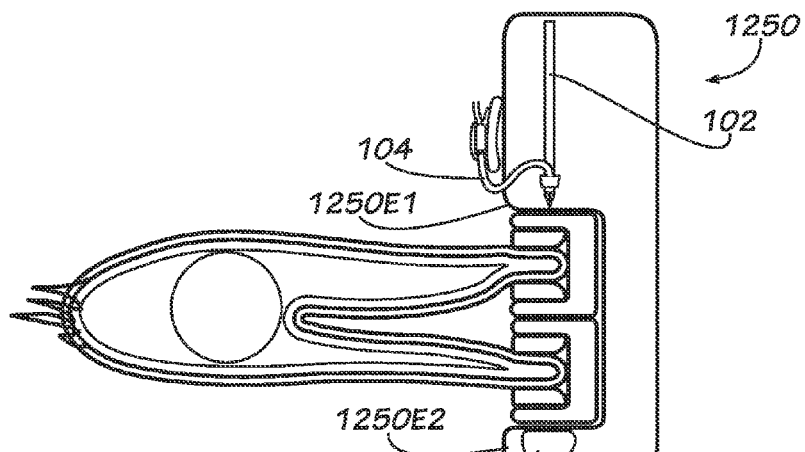

Next, the surgeon can use a standard laparoscopic needle driver and needle with suture attached thereto, to suture the plication manually. Alternatively, instrument 1250 is mounted over the folded tissue layers of the plication so that third end effector 1250E1 and fourth end effector 1250E2 are positioned on opposite sides of the tissues as shown in FIG. 39G. Instrument 1250 can be configured to fit in gaps in the instrument 1200 (or between, distal to, or proximal of grasping jaws of graspers 1202, 1204) between sets of grasping jaws 1206. Although not shown in FIGS. 39G-39K, a layer of material 230 may optionally be mounted in instrument 1250, like shown and described with regard to FIG. 5G, which wraps around from the operational surface of end effector 1250E1 to the operational surface of end effector 1250E2 and overlies the locations of the operational surfaces where the piercing members/suture drivers are driven out from, as well as the locations where the suture anchors are removably mounted. After mounting as described, instrument 1250 is operated to attach the folded tissue surfaces of the stomach together in serosa-to-serosa contact to hold the plication. At the same time the layer of material 230, when used, is attached to the plication. Material 230 forms a barrier layer that spans the suture line to prevent herniation of the plicated stomach in between the attachment members/sutures, thereby greatly reducing the risk of ischemia. The barrier material may be a sheet or strip of silicone, with or without mesh reinforcement, for example. Whether or not reinforced, the exterior of the strip is silicone, to prevent tissue ingrowth. By preventing tissue ingrowth, this will facilitate reversal of the procedure/plication as the silicone strip will be easily removable.

Figure 39H:
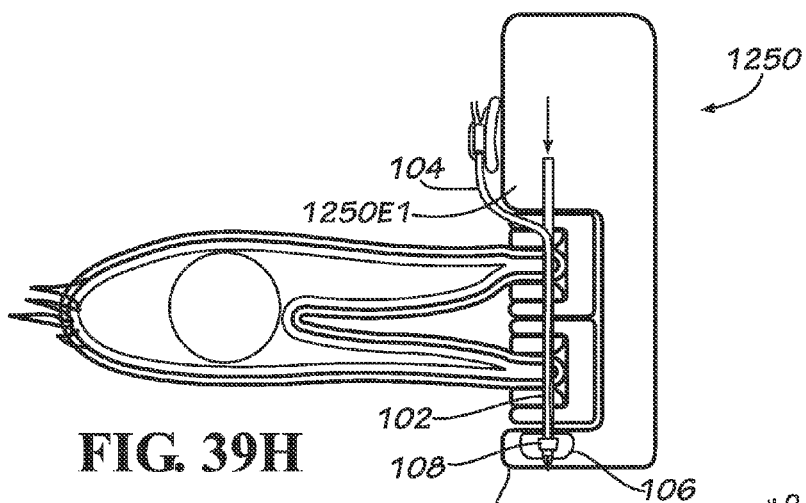
Figure 39I:
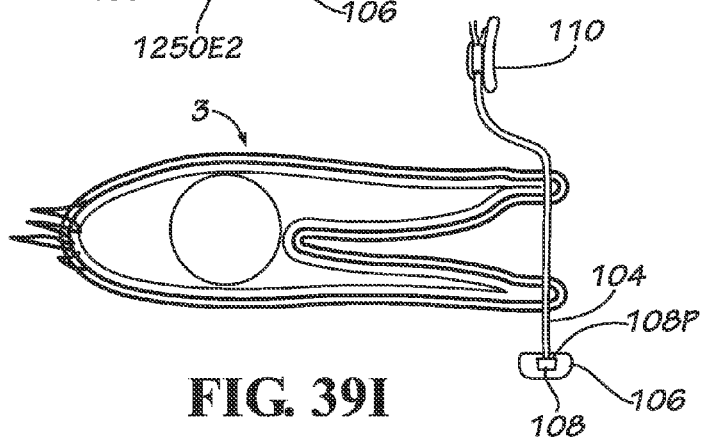
Figure 39J:
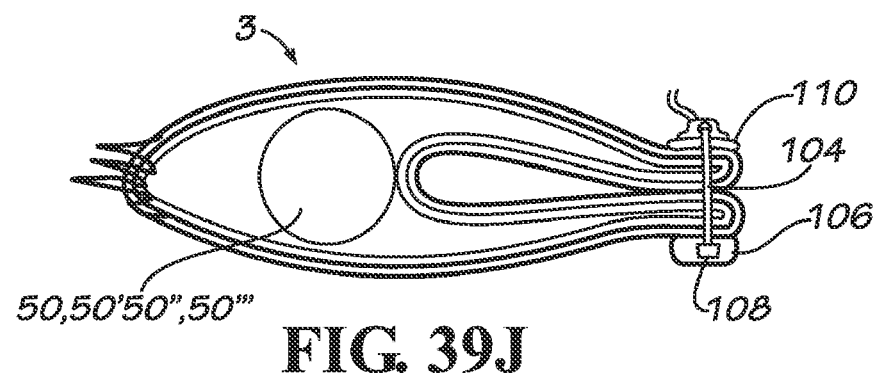

At FIG. 39H piercing members/suture drivers 102 (preferably needles, but could alternately be screw drives or other elongated members configured to temporarily attach attachment members/sutures to and to drive through the stomach tissues) are deployed from end effector 1250E1 to drive attachment members/sutures 104 through stomach tissues (and material 230, when used). Suture anchors 106 are removably held in end effector 1250E2 and are aligned with the piercing members/suture drivers 102. Attachment members/sutures 104 are releasably engaged with piercing members/suture drivers 102. Upon withdrawal of the piercing members/suture drivers, the proximal ends of the suture mates 108P are retained by the anchors 106 and the suture mates 108 slide off the piercing members/suture drivers 102, thereby leaving the suture mates 108 and attachment members/sutures 104 installed through the tissues (and, optionally, material 230) as illustrated in FIG. 39I. It is noted here that if the optional rotation is performed in FIG. 39E', then the instrument(s) is/are counter-rotated to return the stomach 3 to the orientation shown in FIG. 39F, 39G, 39H, or 39I, after performing the procedures described above with regard to FIG. 39E' or after performing the procedures described above with regard to FIG. 39F, or after performing the procedures described above with regard to FIG. 39G, or after performing the procedures described above with regard to FIG. 39H.

Attachment members/sutures 104 are also pre-installed through suture locks 110 that are removably mounted on end effector 1250E1 and are mounted on attachment members/sutures 104 proximal to the piercing members/suture drivers 102. Once the attachment members/sutures have been driven and anchored as illustrated in FIG. 39H1 and the stomach 3 has been rotated back to its original orientation, if applicable, instruments 1250 and 1200/1202,1204 are removed from the patient, leaving the attachment members/sutures 104, suture locks 110, (optionally, material 230,) suture anchors 106 and suture anchor mates 108 in place as illustrated in FIG. 39I. Suture locks 110 have a one-way locking mechanism, such as a ratcheting type mechanism or other arrangement such as directionally oriented teeth that allow suture 104 to be pulled proximally therethrough, but which prevent attachment members/sutures 104 from backsliding distally therethrough. At FIG. 39J, the attachment members/sutures 104 are cinched by pulling them proximally relative to the suture locks 110 until a desired amount of tension is developed in the attachment members/sutures 104, as described previously. Cinching can be performed by the use of laparoscopic graspers, for example. The bougie 50,50',50",50''' can then be removed from the patient and the patient can be closed, according to known techniques, to complete the procedure.

Figure 39K:
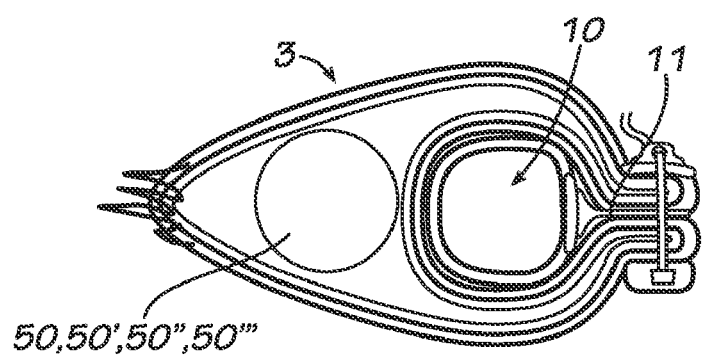

As a further option, an expandable implant 10 may be implanted to fill the inside of the plication 3PL as illustrated in FIG. 39K. The implant 10 may be a silicone bladder, for example, capable of being inflated by biocompatible fluid such as liquid, gas, or a combination of fluids (gases, liquids, or liquids and gases). Implant 10 is connected via fill tubing 12 in fluid communication with a subcutaneous fill port 80, so that the fill volume of implant 10 can be adjusted after implanting it as described from a location outside of the abdominal cavity (e.g., by an operator accessing the subcutaneous fill port 80 with a needle alone or a needle attached to a pressurized source of fluid). Other implants 10 may be substituted, but need to be expandable and are preferably controllable as to amount of expansion. A tab or wing 11, 11', 11", 11''' may be provided to extend from the expandable body of the implant 10 and can be inserted between the tissue folds at the plication suture line so that the attachment members/sutures 104 are also installed through the tab or wing 11, 11', 11", 11''' to thereby securely hold the implant in place, as illustrated in FIG. 39K. The tab or wing 11, 11', 11", 11''' may be made of a mesh-reinforced silicone, for example. Alternatively, the implant 10 may be fixed in place by connecting only to the superior and inferior ends of the plication suture line, or by connecting to one or more of the suture locks 110 and/or suture anchors 106.

While the present invention has been described with reference to the specific embodiments thereof, it should be understood by those skilled in the art that various changes may be made and equivalents may be substituted without departing from the true spirit and scope of the invention. For example, an instrument as described herein may employ suction on one end effector to engage tissue, while providing grasping jaws on an opposite end effector to engage tissue or vice versa. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An instrument for use in modifying a patient's stomach by operating on the stomach extragastrically to decrease the effective volume of the patient's stomach, said instrument comprising:
   a first elongate end effector formed at a distal end portion of said instrument, said first elongate end effector having a first operational surface configured to contact an external surface of the patient's stomach;
   a second elongate end effector formed at a distal end portion of said instrument, said second elongate end effector having a second operational surface configured to contact an external surface of the patient's stomach on a location opposite of where the first elongate end effector is configured to contact the external surface of the stomach, and wherein said second operational surface opposes said first operational surface;
   a first plurality of suction ports extending along a length of said first elongate end effector from a distal portion of said first end effector to a proximal portion of said first end effector and configured to deliver suction to the external surface of the stomach to engage said first elongate end effector therewith; and
   a second plurality of suction ports extending along a length of said second elongate end effector from a distal portion of said second end effector to a proximal portion of said second end effector and configured to deliver suction to the external surface of the stomach to engage said second elongate end effector therewith and wherein said first end effector and said second end effector are movable by actuating a joint mechanism connecting said first and second end effectors.

2. The instrument of claim 1, wherein said first and second pluralities of suction ports are configured to apply suction in an amount sufficient to pull opposite walls of the stomach apart when said first and second elongate end effectors are engaged therewith and said first and second elongate end effectors are moved apart from one another, and wherein the opposite walls are pulled apart without losing engagement of said first and second elongate end effectors therewith.

3. The instrument of claim 2, wherein at least one of said first elongate end effector and said second elongate end effector comprises a clamping mechanism including at least one clamping member configured to assume an unclamped orientation configured so as not to clamp stomach tissue, and a clamped orientation configured to clamp stomach tissue relative to said instrument.

4. The instrument of claim 2, further comprising means for driving a plurality of connectors from said first elongate end effector, through stomach tissue and to said second elongate end effector.

5. The instrument of claim 4, further comprising means for fixing said connectors to maintain a plication in the stomach.

6. The instrument of claim 4, further provided with a layer of material configured to be placed adjacent or between locations where said connectors from said first elongate end effector are configured to pass through the stomach tissue and to said second elongate end effector.

7. The instrument of claim 1, further comprising a plurality of suture drivers extending along a length of said first elongate end effector.

8. The instrument of claim 7, further comprising a plurality of suture anchors extending along a length of said second elongate end effector and opposing said plurality of suture drivers, respectively.

9. The instrument of claim 8, further comprising a plurality of sutures releasably engaged with said plurality of suture drivers, respectively.

10. The instrument of claim 9, wherein each said suture extends through a suture lock releasably provided on said first elongate end effector.

11. The instrument of claim 9, wherein each said suture comprises an anchor mate mounted on a distal end portion thereof, said anchor mate being configured to engage with and connect to said anchor.

12. The instrument of claim 1, further including an expandable implant configured to be implanted in a plication created by said instrument.

13. A system for use in modifying a patient's stomach by operating on the stomach extragastrically to decrease the effective volume of the patient's stomach, said system comprising:
an engagement instrument comprising:
a first elongate end effector at a distal end portion of said engagement instrument, said first elongate end effector having a first operational surface configured to contact an external surface of the patient's stomach;
a second elongate end effector at a distal end portion of said engagement instrument, said second elongate end effector having a second operational surface configured to contact an external surface of the patient's stomach on a location opposite of where the first elongate end effector is configured to contact the external surface of the stomach, and wherein said second operational surface opposes said first operational surface;
a first plurality of suction ports extending along a length of said first elongate end effector and configured to deliver suction to the external surface of the stomach to engage said first elongate end effector therewith; and
a second plurality of suction ports extending along a length of said second elongate end effector and configured to deliver suction to the external surface of the stomach to engage said second elongate end effector therewith; and
a stitching instrument comprising:
a third end effector at a distal end portion of said stitching instrument, said third end effector having a third operational surface configured to contact an external surface of the patient's stomach;
a fourth end effector at a distal end portion of said stitching instrument, said fourth end effector having a fourth operational surface configured to contact an external surface of the patient's stomach on a location opposite of where the third end effector is configured to contact the external surface of the stomach, and wherein said fourth operational surface opposes said third operational surface;
at least one suture driver on the third end effector; and
at least one suture anchor on said fourth end effector opposing said suture driver.

14. The system of claim 13, wherein:
the third end effector is elongated;
the fourth end effector is elongated;
a plurality of suture drivers are spaced along a length of said third elongate end effector; and
a plurality of suture anchors are spaced along a length of said fourth elongate end effector and opposing said plurality of suture drivers, respectively.

15. The system of claim 14, wherein said first and second pluralities of suction ports are configured to apply suction in an amount sufficient to pull opposite walls of the stomach apart when said first and second elongate end effectors are engaged therewith and said first and second elongate end effectors are moved apart from one another,
wherein at least one of said first and second elongate effectors is configured with a clamping mechanism to mechanically clamp stomach wall tissue, and
wherein the opposite walls are pulled apart without losing engagement of said first and second elongate end effectors therewith.

* * * * *